(12) United States Patent
Kim et al.

(10) Patent No.: US 10,155,773 B2
(45) Date of Patent: Dec. 18, 2018

(54) ORGANIC ELECTROLUMINESCENT COMPOUND AND ORGANIC ELECTROLUMINESCENT DEVICE

(71) Applicant: NANJING TOPTO MATERIALS CO., LTD., Nanjing (CN)

(72) Inventors: Jin Woo Kim, Nanjing (CN); Chao Qian, Nanjing (CN); Penghui Gao, Nanjing (CN); Xiaowei Wang, Nanjing (CN)

(73) Assignee: NANJING TOPTO MATERIALS CO., LTD., Nanjing (CN)

( * ) Notice: Subject to any disclaimer, the term of this patent is extended or adjusted under 35 U.S.C. 154(b) by 0 days.

(21) Appl. No.: 15/826,747

(22) Filed: Nov. 30, 2017

(65) Prior Publication Data

US 2018/0105534 A1    Apr. 19, 2018

(30) Foreign Application Priority Data

Sep. 30, 2016 (CN) .......................... 2016 1 0879539

(51) Int. Cl.
| | |
|---|---|
| *C07D 493/04* | (2006.01) |
| *C09K 11/06* | (2006.01) |
| *H01L 51/50* | (2006.01) |
| *H01L 51/00* | (2006.01) |

(52) U.S. Cl.
CPC ............ *C07D 493/04* (2013.01); *C09K 11/06* (2013.01); *H01L 51/0073* (2013.01); *H01L 51/5012* (2013.01); *C09K 2211/1088* (2013.01)

(58) Field of Classification Search
CPC .......... C07D 493/04; C07D 2211/1088; H01L 51/5012; H01L 51/0073; C09K 11/06; C09K 2211/1088
See application file for complete search history.

(56) References Cited

FOREIGN PATENT DOCUMENTS

JP        2000077186 A   *   3/2000

OTHER PUBLICATIONS

Karaush, N.N., "DFT simulation of the heteroannelated octatetraenes vibronic spectra with the Franck-Condon and Herzberg-Teller approaches including Duschinsky effect." Chemical Physics 459 (2015): 65-71.*
JP 2000-77186 (2000) ProQuest English machine translation p. 1-21.*

* cited by examiner

*Primary Examiner* — John M Mauro
(74) *Attorney, Agent, or Firm* — Gokalp Bayramoglu

(57) ABSTRACT

The present invention provides an organic electroluminescent compound and an organic electroluminescent device using the organic electroluminescent compound, the compound has the following structural formula:

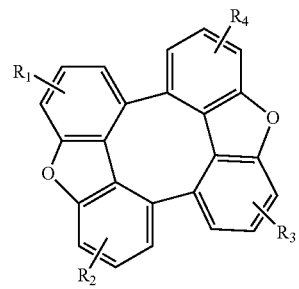

wherein $R_1$, $R_2$ and $R_4$ are, each independently, selected from a group consisting of a hydrogen atom, a C1-C20 linear or branched alkyl group, a substituted or unsubstituted N-(phenylmethyl)imino group, a phenyl group, phenylamine, diphenylamine, phenyl pyridinylamine, bipyridinylamine, phenyl naphthylamine, binaphthylamine, phenyl phenanthrylamine, biphenanthrylamine, phenyl anthrylamine, bianthrylamine, phenanthridine, biphenyl, a pyridyl group, a pyrimidinyl group, a quinolinyl group and a triazinyl group; $R_3$ is selected from a group consisting of hydrogen atom, a C1-C10 linear or branched alkyl group, a substituted or unsubstituted N-(phenylmethyl)imino group, a phenyl group, phenylamine, diphenylamine, phenyl pyridinylamine, bipyridinylamine, phenyl naphthylamine, binaphthylamine, phenyl phenanthrylamine, biphenanthrylamine, phenyl anthrylamine, bianthrylamine, phenanthridine, biphenyl, a pyridyl group, a pyrimidinyl group, a quinolinyl group and a triazinyl group.

12 Claims, No Drawings

ORGANIC ELECTROLUMINESCENT COMPOUND AND ORGANIC ELECTROLUMINESCENT DEVICE

CROSS REFERENCE TO RELATED APPLICATIONS

This application is based upon and claims priority to Chinese Patent Application No. 201610879539.8 filed on Sep. 30, 2016, the entire contents of which are incorporated herein by reference.

TECHNICAL FIELD

The present invention falls within the field of luminescent material technology and it specifically relates to an organic electroluminescent compound which could be used as blue dopant material and an organic electroluminescent device using the organic electroluminescent compound.

BACKGROUND OF THE INVENTION

So far, most of flat panel displays are liquid crystal displays (LCD), however, people around the world have been trying with great efforts to develop a new flat panel display different from LCD, which is more economical and has an outstanding performance. Recently, organic electroluminescent devices, as the next generation of flat panel displays, have attracted much attention. Compared with LCDs, organic electroluminescent devices have many advantages, such as self-luminescence, wide angle of view, low driving voltage, fast response speed, potential of achieving flexible display lamps, etc. Since they were invented in 1980s, organic electroluminescent devices have already been applied in industrial practice, such as manufacturing of cameras, computers, mobile phones, TV displays, etc. Although the technology of organic electroluminescent device has been greatly developed over the years due to continuous investments and unremitting efforts from all over the field, it is still restricted by many problems, such as short life expectancy, low efficiency, etc.

An organic electroluminescent device includes a substrate, an anode, a hole injection layer for accepting holes from the anode, a hole transport layer for transporting holes, an emission layer where holes and electrons are combined to emit lights, an electron blocking layer for preventing electrons entering the hole transport layer from the emission layer, an hole blocking layer for preventing holes entering the electron transport layer from the emission layer, an electron injection layer for accepting electrons from cathode.

The driving mechanism of the organic electroluminescent device is described as follows: when voltage is applied between the anode and the cathode, holes injected from the anode travel via the hole injection layer and the hole transport layer into the emission layer. Meanwhile, electrons injected from the cathode travel via the electron injection layer and electron transport layer into the emission layer. The current carriers and electrons are recombined to generate excitons within the emission layer. Under the current status, the excitons change into the ground state, and accordingly, the fluorescent molecules in the emission layer emit lights to form images. Here, when excitons return to the ground state through a singlet excited state, the lights emitted are called fluorescence; when excitons return to the ground state through a triplet excited state, the lights emitted are called phosphorescence. The probability for excitons to transfer through a singlet excited state to the ground state is 25%, while the probability through a triplet excited state to the ground state is 75%. Therefore, for organic electroluminescent devices emitting fluorescence, the luminous efficiency is limited; however, for organic electroluminescent devices emitting phosphorescence, emissions can be caused by 75% of triplet excitons and 25% of singlet excitons, rendering the internal quantum efficiency up to 100% in theory. The phosphorescent emission layer includes main body material and dopant material. The dopant material accepts energy from the main body material to emit lights. The dopant material may include Iridium compounds, which yet may cause problems such as low luminous efficiency of blue lights and short life expectancy. It is of great urgency, with the enlargement of displays' sizes, to invent a new blue dopant material for solving the above problems.

SUMMARY OF THE INVENTION

Technical Problem to be solved: the present invention provides an organic electroluminescent compound to overcome the deficiencies of prior arts. This organic compound, when used as a blue dopant material for an organic electroluminescent device, may contribute to lower driving voltage, and increase luminous efficiency, brightness, heat stability, color purity and life expectancy of the device.

Technical Solution: the present invention provides an electroluminescent compound of the following structural formula:

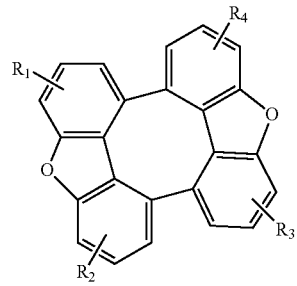

wherein $R_1$, $R_2$ and $R_4$ are, each independently, selected from a group consisting of a hydrogen atom, a C1-C20 linear or branched alkyl group, a substituted or unsubstituted N-(phenylmethyl)imino group, a phenyl group, phenylamine, diphenylamine, phenyl pyridinylamine, bipyridinylamine, phenyl naphthylamine, binaphthylamine, phenyl phenanthrylamine, biphenanthrylamine, phenyl anthrylamine, bianthrylamine, phenanthridine, biphenyl, a pyridyl group, a pyrimidinyl group, a quinolyl group and a triazinyl group;

$R_3$ is selected from a group consisting of a hydrogen atom, a C1-C10 linear or branched alkyl group, a substituted or unsubstituted N-(phenylmethyl)imino group, a phenyl group, phenylamine, diphenylamine, phenyl pyridinylamine, bipyridinylamine, phenyl naphthylamine, binaphthylamine, phenyl phenanthrylamine, biphenanthrylamine, phenyl anthrylamine, bianthrylamine, phenanthridine, biphenyl, a pyridyl group, a pyrimidinyl group, a quinolyl group and a triazinyl group.

The present invention, on the other hand, provides an organic electroluminescent device including the above organic electroluminescent compound.

Advantageous effects: the organic compound provided in the present invention and used as the blue dopant may facilitate lower driving voltage and increase efficiency, brightness, heat stability, color purity, life expectancy, etc. Further, an organic electroluminescent device using the organic compound has excellent performances such as high efficiency and long life expectancy.

DETAILED DESCRIPTION OF THE INVENTION

The following embodiments further describe, yet should not be understood as limitations to, the contents of the present invention. Modifications and alternatives to the methods, steps or conditions of the present invention are intended to fall within the scope of the present invention, without departing from the spirit and substance thereof. All technical means employed in the embodiments are conventional means and are well known to persons skilled in the art, unless specifically stated.

In one respect, the present invention provides an organic electroluminescent compound of the following structural formula:

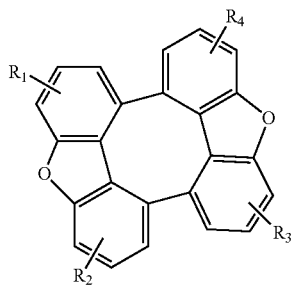

wherein $R_1$, $R_2$ and $R_4$ are, each independently, selected from a group consisting of a hydrogen atom, a C1-C20 linear or branched alkyl group, a substituted or unsubstituted N-(phenylmethyl)imino group, a phenyl group, phenylamine, diphenylamine, phenyl pyridinylamine, bipyridinylamine, phenyl naphthylamine, binaphthylamine, phenyl phenanthrylamine, biphenanthrylamine, phenyl anthrylamine, bianthrylamine, phenanthridine, biphenyl, a pyridyl group, a pyrimidinyl group, a quinolyl group and a triazinyl group;

$R_3$ is selected from a group consisting of a hydrogen atom, a C1-C10 linear or branched alkyl group, a substituted or unsubstituted N-(phenylmethyl)imino group, a phenyl group, phenylamine, diphenylamine, phenyl pyridinylamine, bipyridinylamine, phenyl naphthylamine, binaphthylamine, phenyl phenanthrylamine, biphenanthrylamine, phenyl anthrylamine, bianthrylamine, phenanthridine, biphenyl, a pyridyl group, a pyrimidinyl group, a quinolyl group and a triazinyl group.

Further, when $R_1$ is selected from a group consisting of an N-(phenylmethyl)imino group, a phenyl group, phenylamine, diphenylamine, phenyl pyridinylamine, bipyridinylamine, phenyl naphthylamine, binaphthylamine, phenyl phenanthrylamine, biphenanthrylamine, phenyl anthrylamine, bianthrylamine, phenanthridine, biphenyl, a pyridyl group, a pyrimidinyl group, a quinolyl group and a triazinyl group, at least one hydrogen atom is substituted with a C1-C20 linear or branched alkyl group, a C3-C24 cyclic alkyl group, a C1-C20 alkoxyl group, a halogen atom, CN, $CF_3$, a $Si(CH_3)_3$ group, or a C6-C50 aryl group.

Further, when $R_2$ is selected from a group consisting of an N-(phenylmethyl)imino group, a phenyl group, phenylamine, diphenylamine, phenyl pyridinylamine, bipyridinylamine, phenyl naphthylamine, binaphthylamine, phenyl phenanthrylamine, biphenanthrylamine, phenyl anthrylamine, bianthrylamine, phenanthridine, biphenyl, a pyridyl group, a pyrimidinyl group, a quinolyl group and a triazinyl group, at least one hydrogen atom is substituted with a C1-C20 linear or branched alkyl group, a C3-C24 cyclic alkyl group, a C1-C20 alkoxyl group, a halogen atom, CN, $CF_3$, a $Si(CH_3)_3$ group, a naphthyl group, an anthryl group, a phenanthryl group, dibenzofuran, a fluorenyl group, a carbazolyl group, spiro fluorene, or a heteroaryl group with nuclear number of 5-20.

Further, when $R_3$ is selected from a group consisting of an N-(phenylmethyl)imino group, a phenyl group, phenylamine, diphenylamine, phenyl pyridinylamine, bipyridinylamine, phenyl naphthylamine, binaphthylamine, phenyl phenanthrylamine, biphenanthrylamine, phenyl anthrylamine, bianthrylamine, phenanthridine, biphenyl, a pyridyl group, a pyrimidinyl group, a quinolyl group and a triazinyl group, at least one hydrogen atom is substituted with a C1-C10 linear or branched alkyl group, a C3-C12 cyclic alkyl group, a C1-C10 alkoxyl group, a halogen atom, CN, $CF_3$, a $Si(CH_3)_3$ group, or a C6-C30 aryl group.

Further, when $R_4$ is selected from a group consisting of an N-(phenylmethyl)imino group, a phenyl group, phenylamine, diphenylamine, phenyl pyridinylamine, bipyridinylamine, phenyl naphthylamine, binaphthylamine, phenyl phenanthrylamine, biphenanthrylamine, phenyl anthrylamine, bianthrylamine, phenanthridine, biphenyl, a pyridyl group, a pyrimidinyl group, a quinolyl group and a triazinyl group, at least one hydrogen atom is substituted with a C1-C10 linear or branched alkyl group, a C3-C12 cyclic alkyl group, a C1-C10 alkoxyl group, a halogen atom, CN, $CF_3$, a $Si(CH_3)_3$ group, a naphthyl group, an anthryl group, a phenanthryl group, dibenzofuran, a fluorenyl group, a carbazolyl group, spiro fluorene, or a heteroaryl group with nuclear number of 5-20.

The organic electroluminescent compound in the present invention may be any one of the following compounds:

5
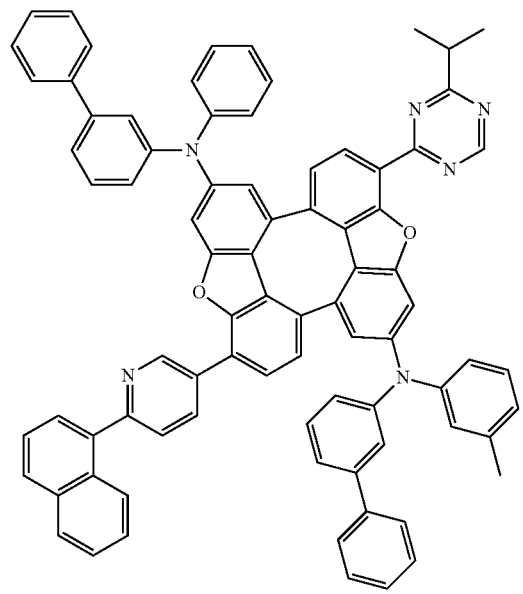
6
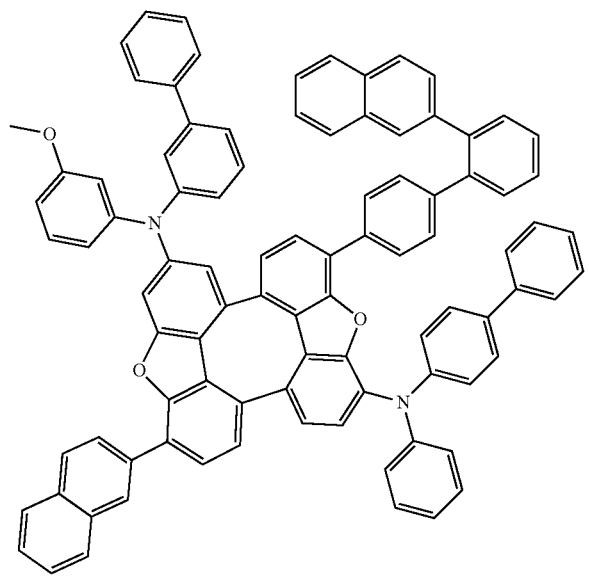
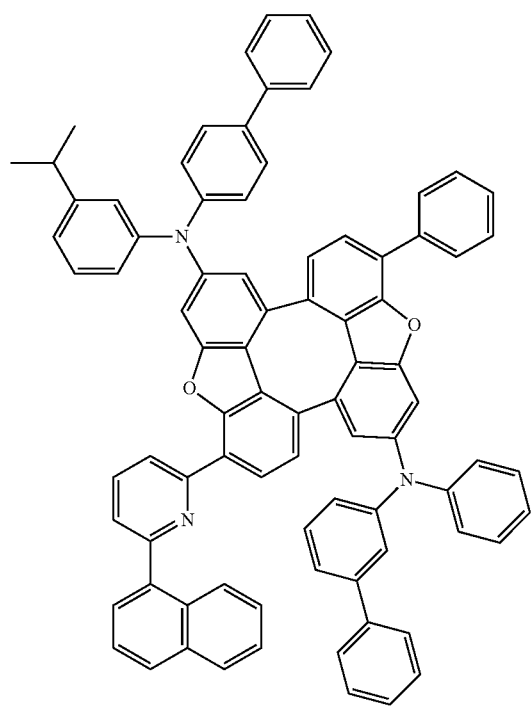
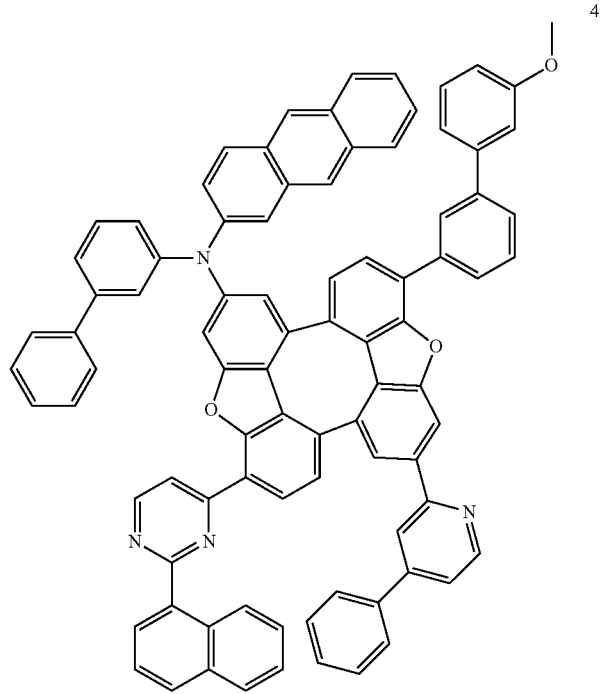

-continued
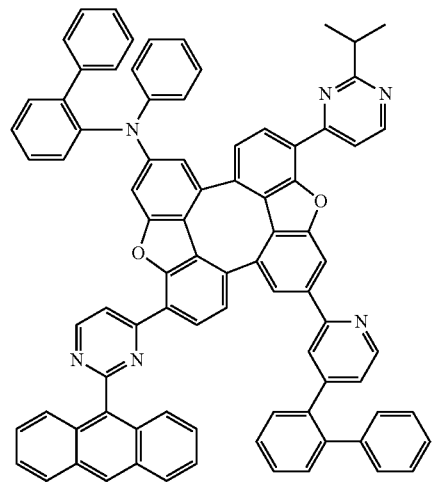
5
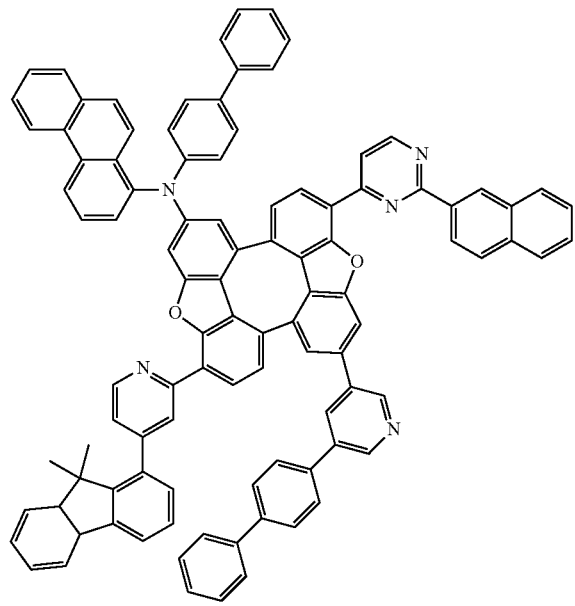
6
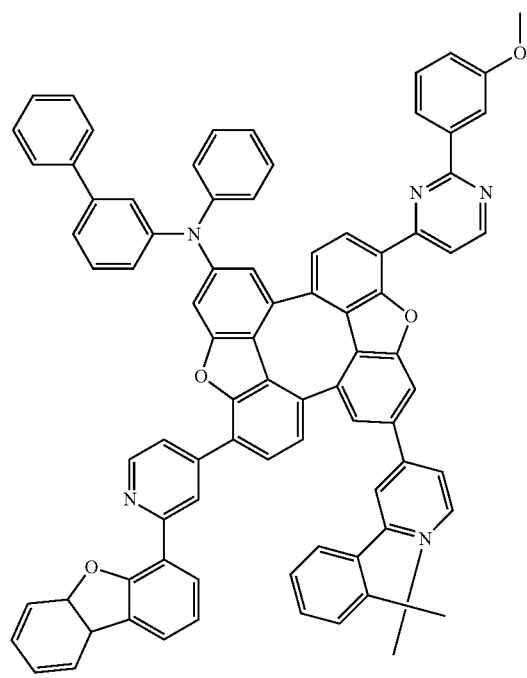
7
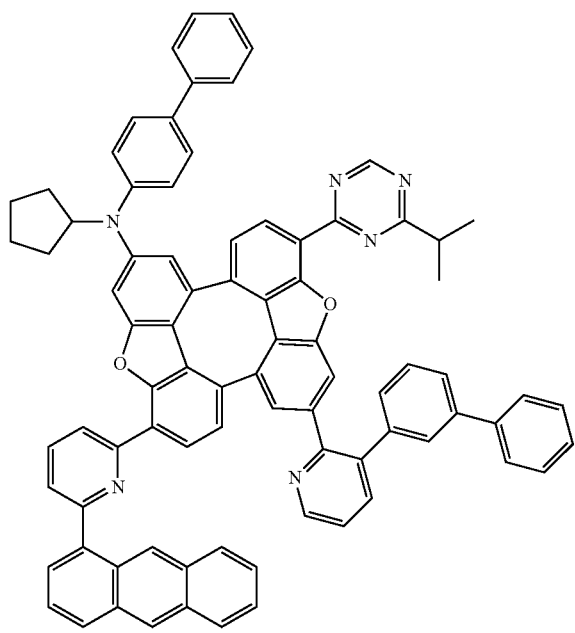
8

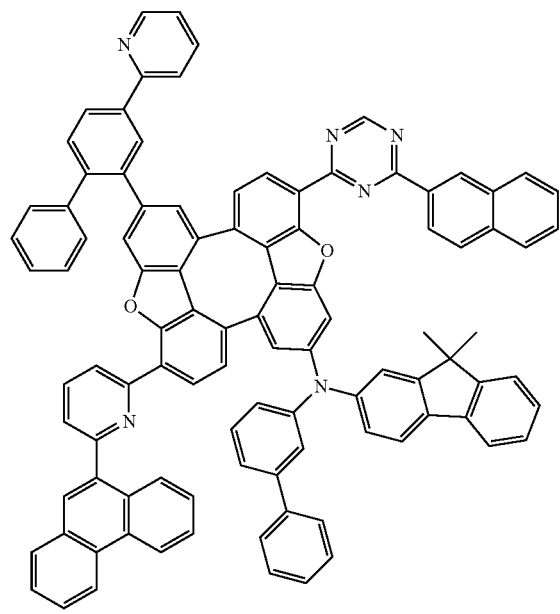
9
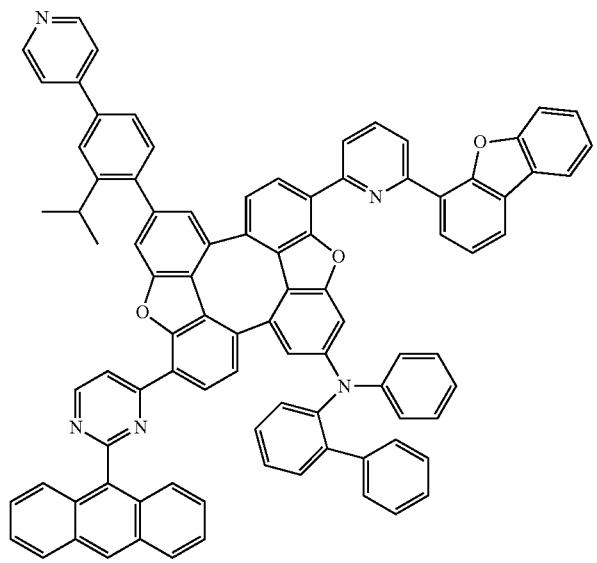
10
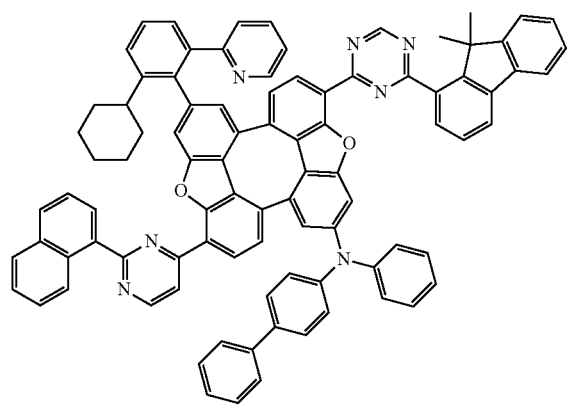
11
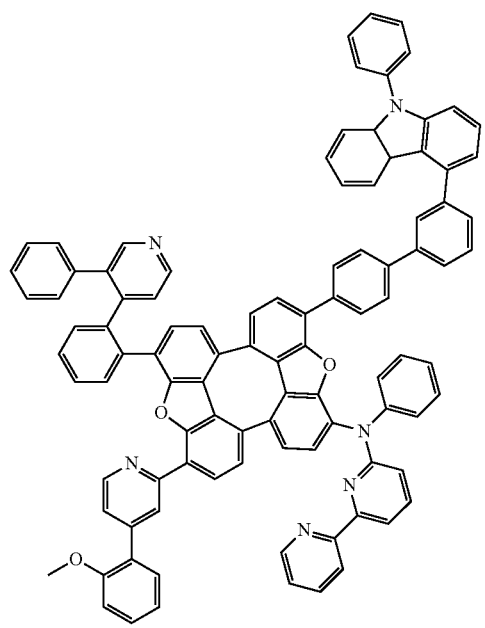
12

13
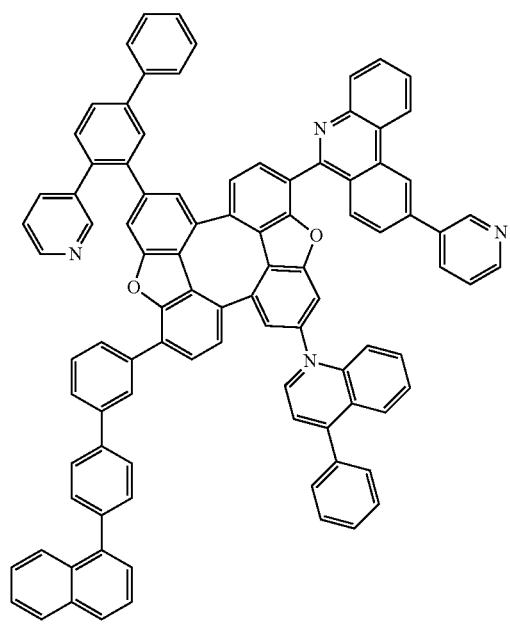
14
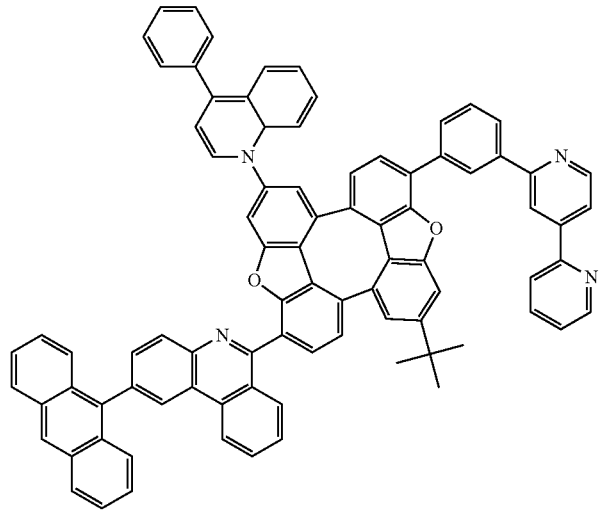
15
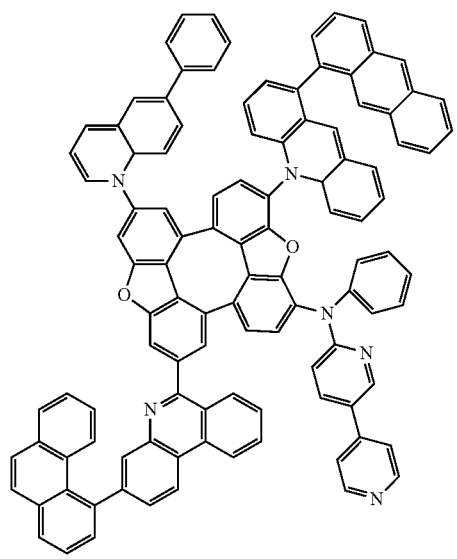
16
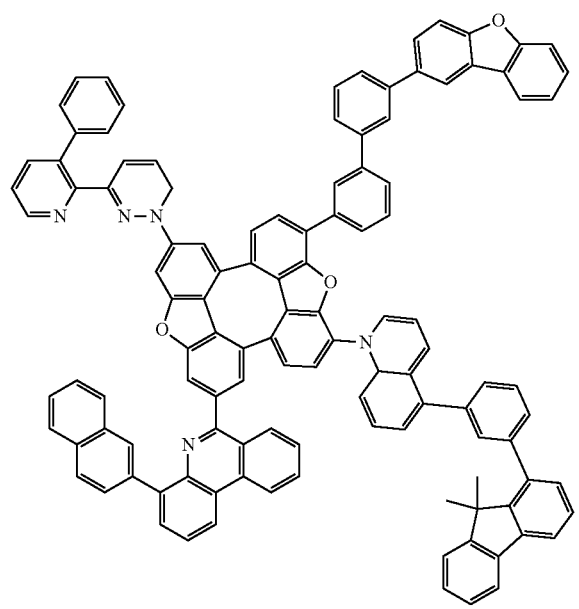

-continued
17
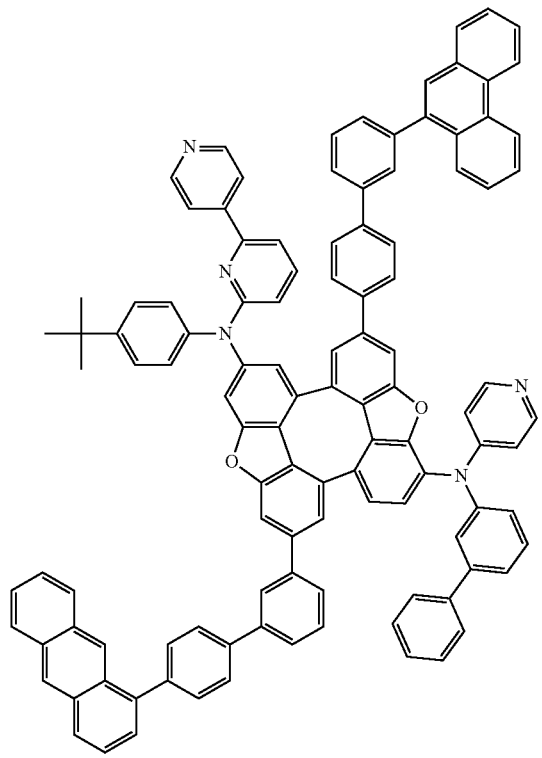
18
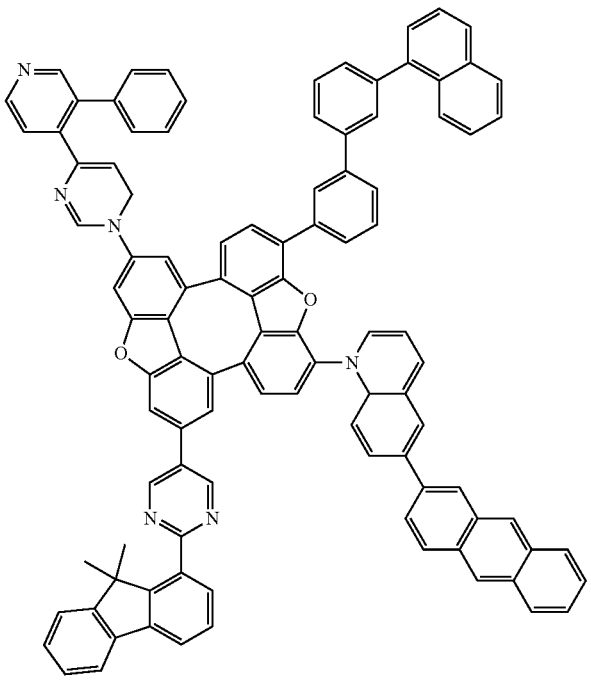
19
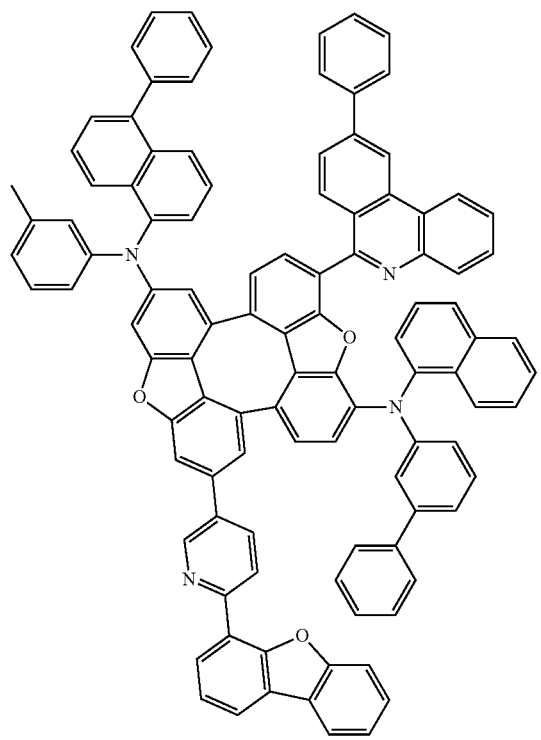
20
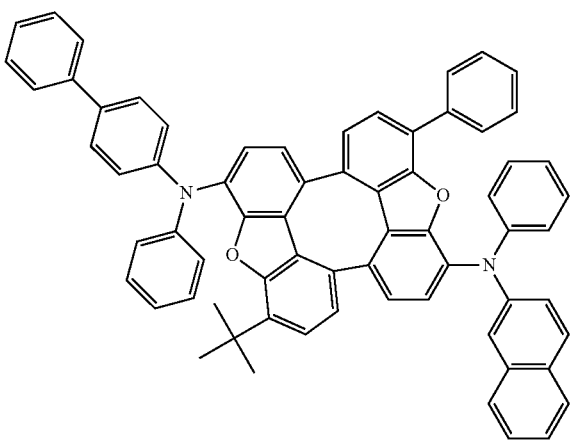

-continued
21
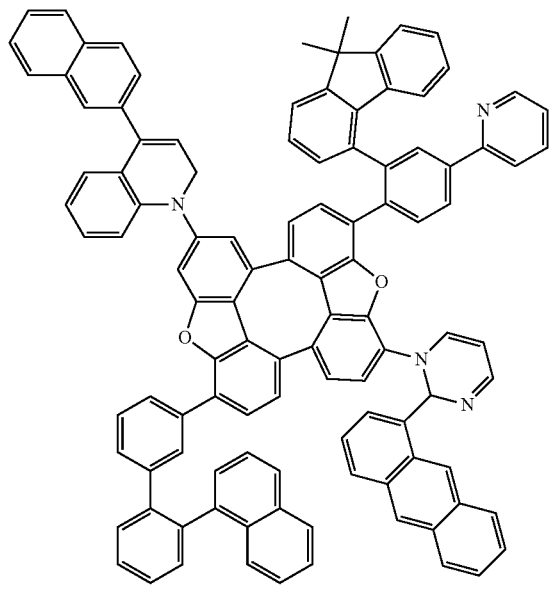
22
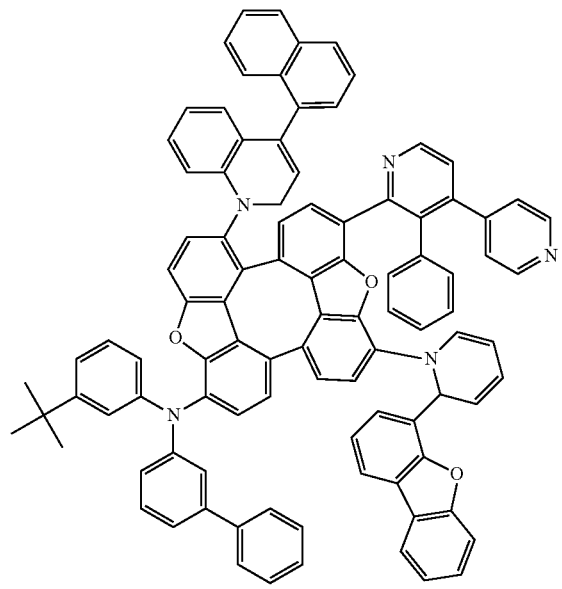
23
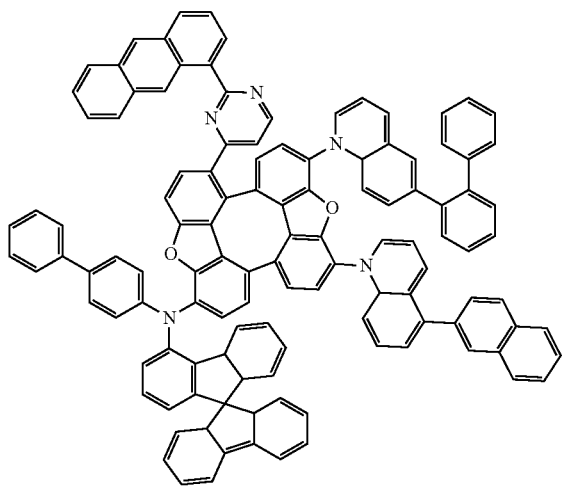
24
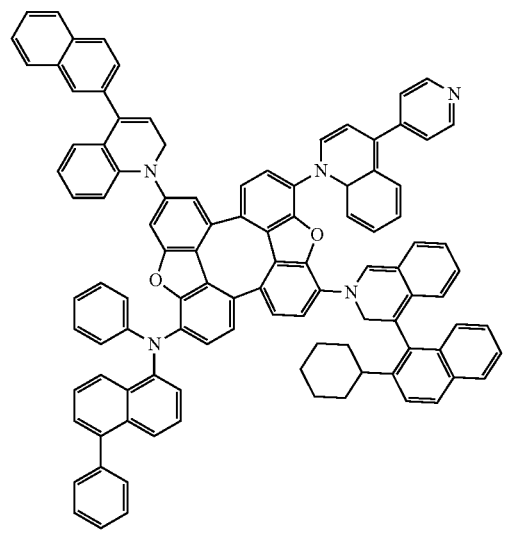

-continued
25
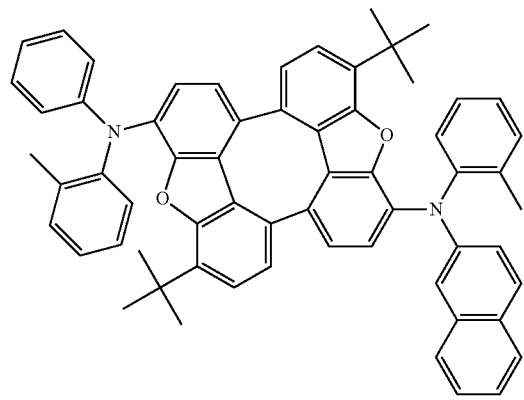
26
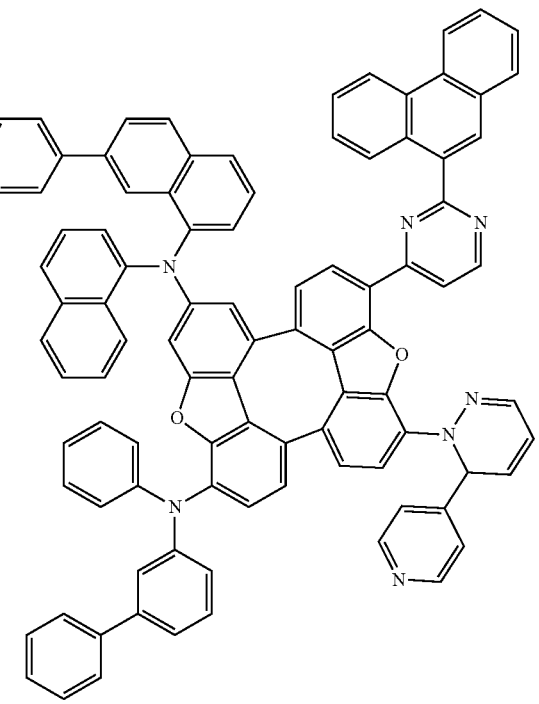
27
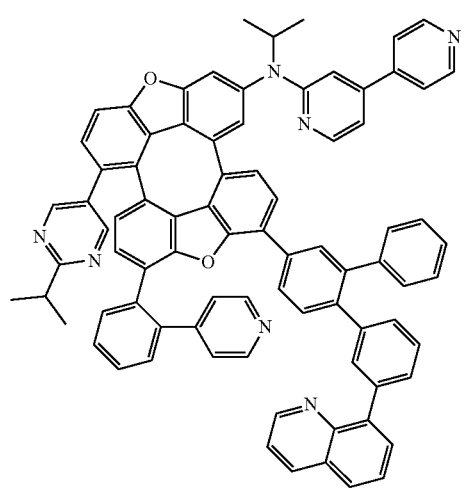
28
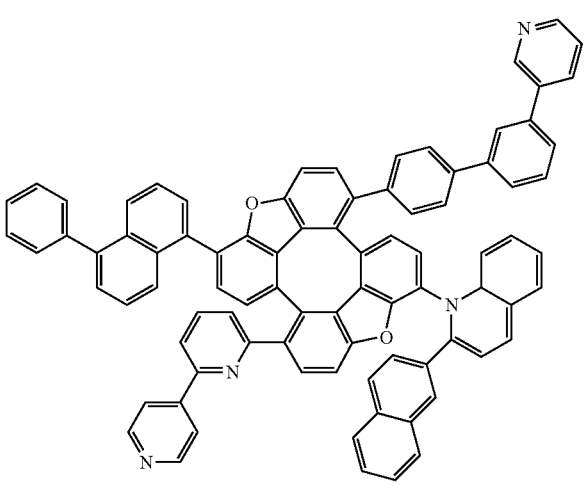

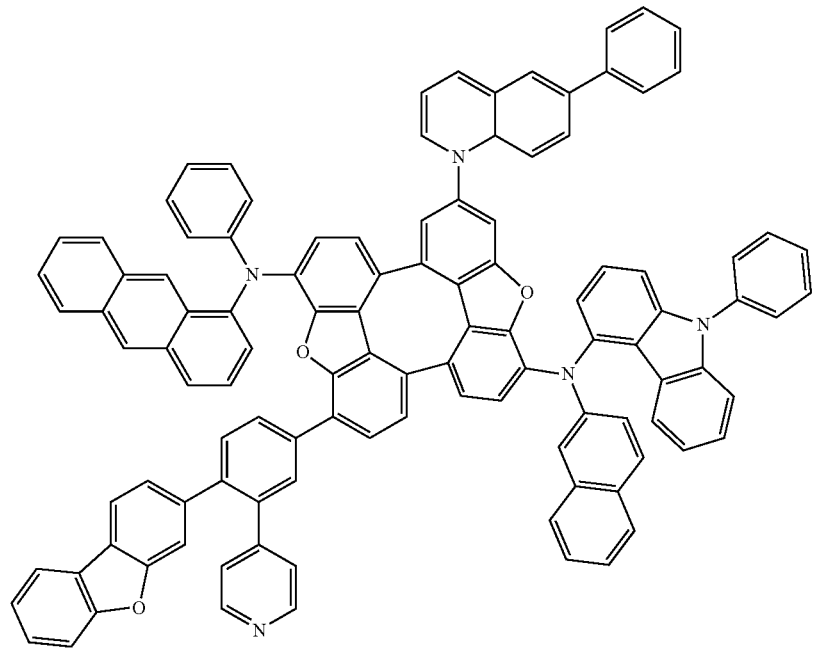
29
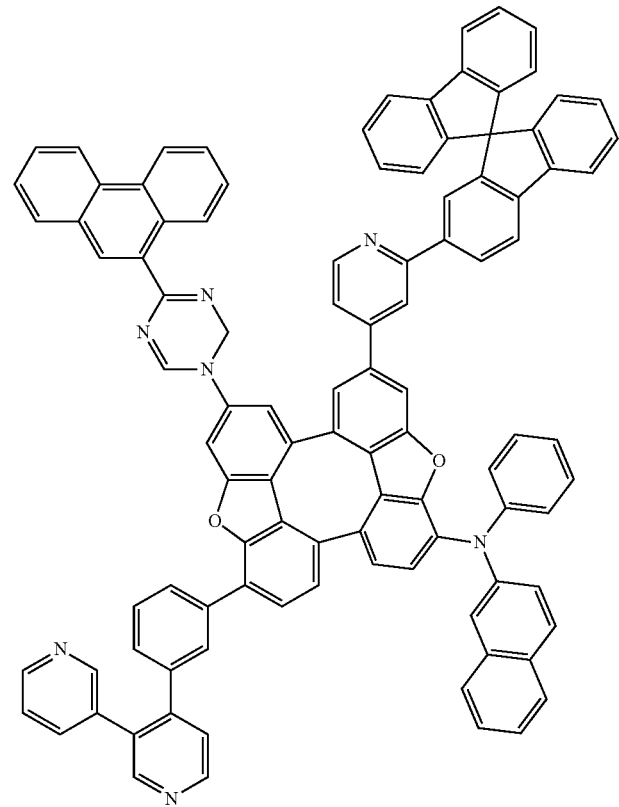
30

-continued
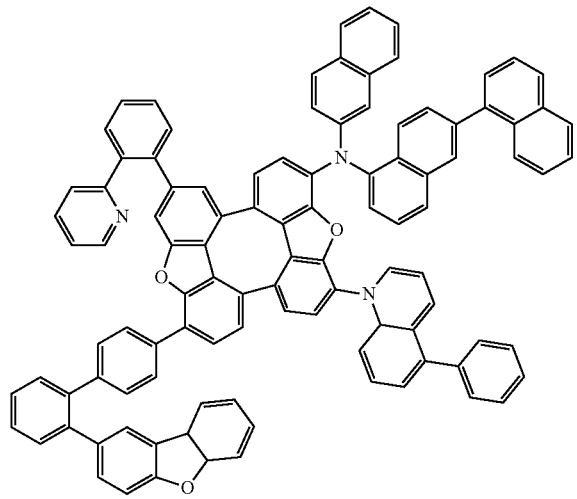
31
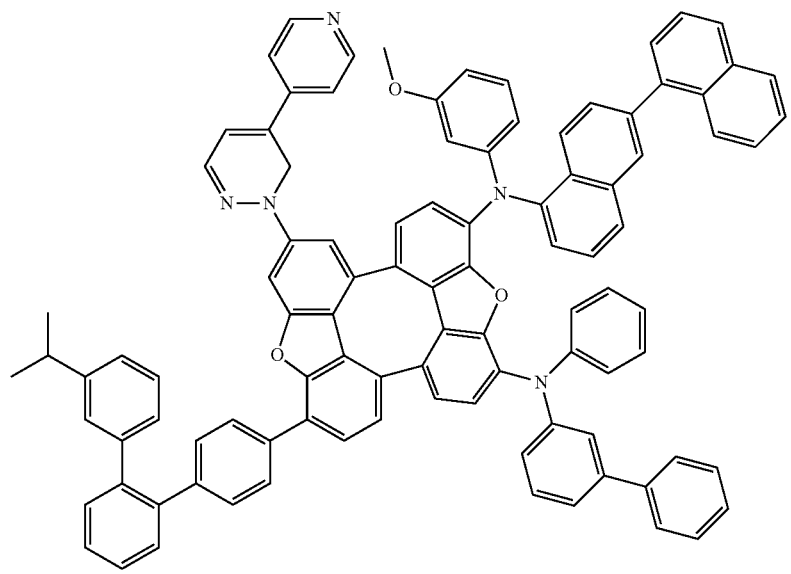
32
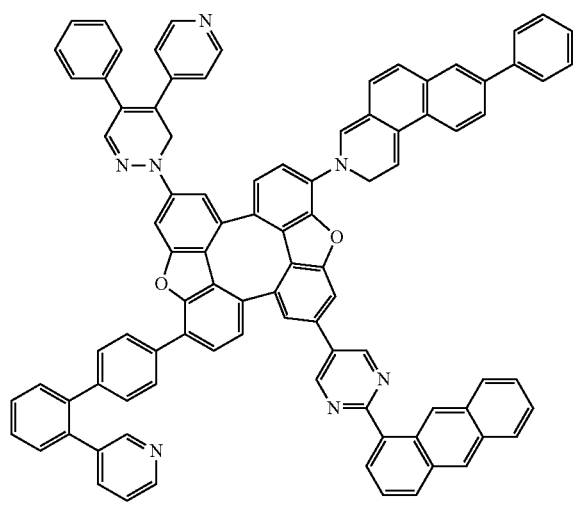
33
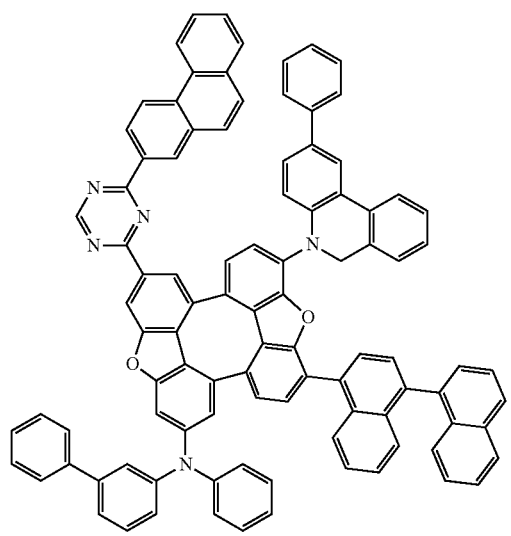
34

-continued
35
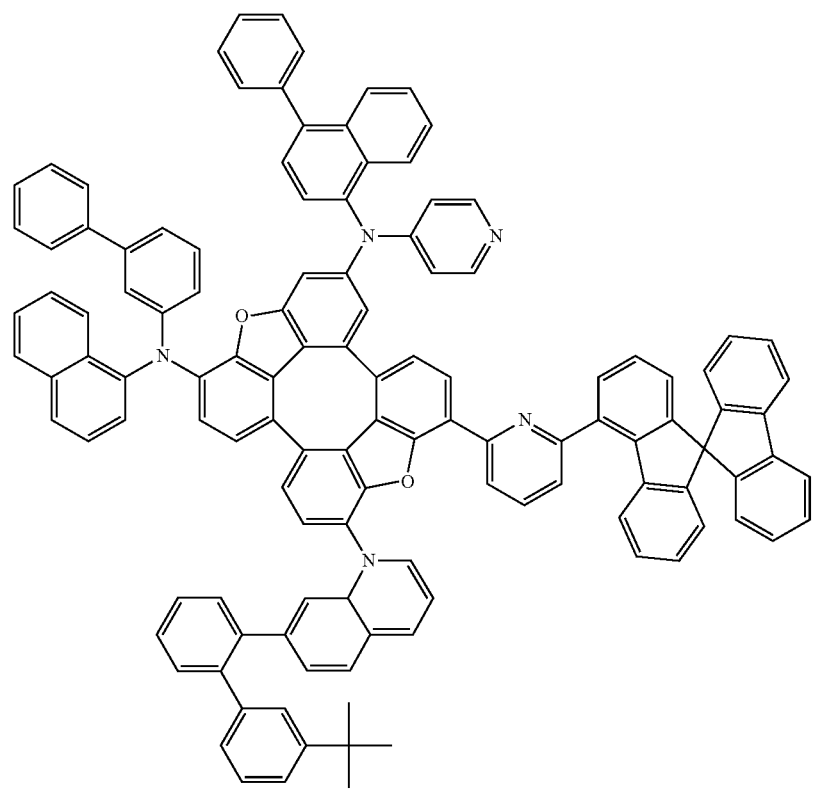
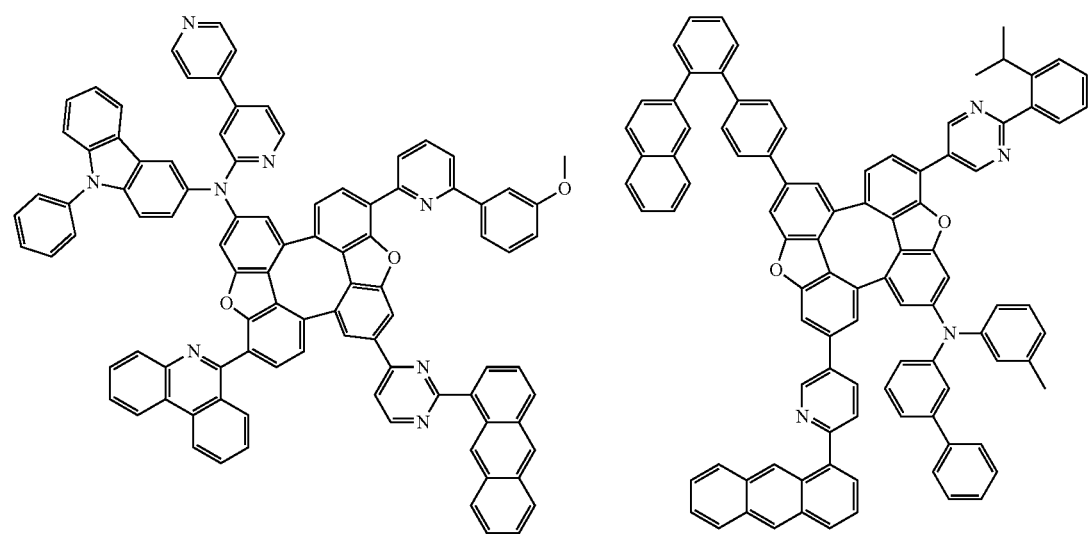

38
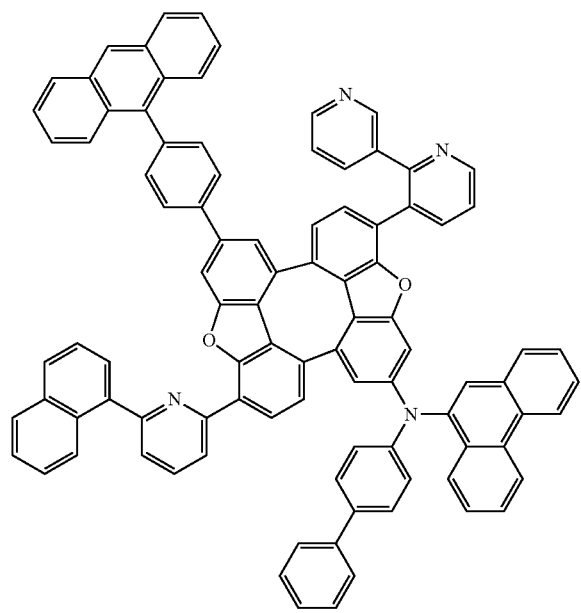
39
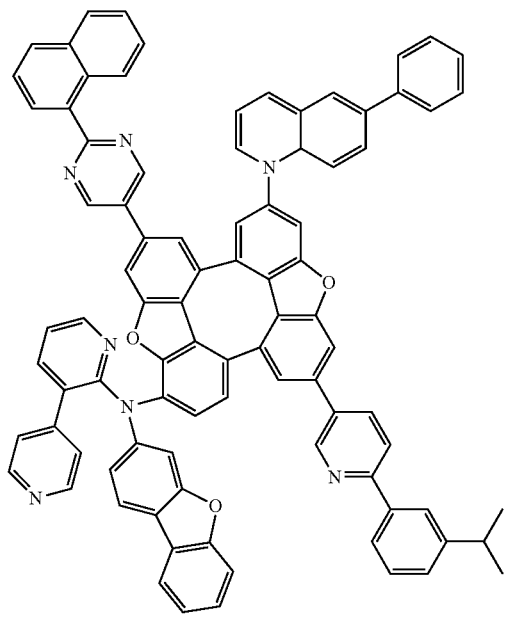
40
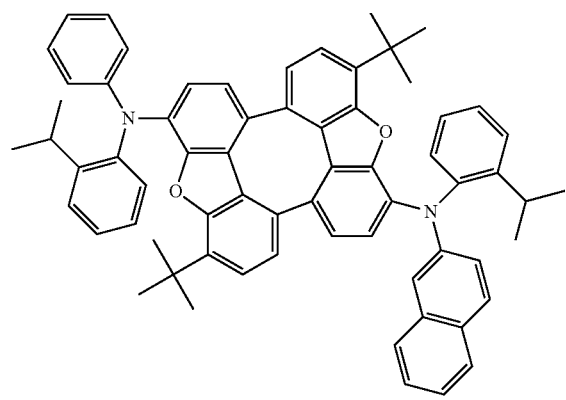
41
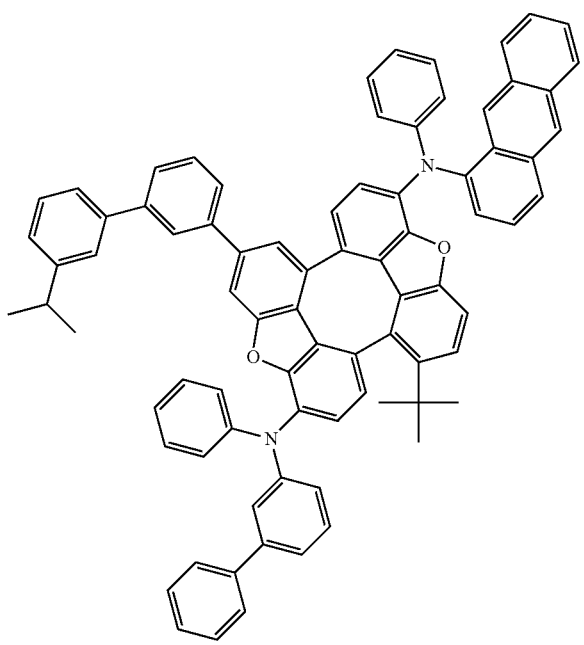

42
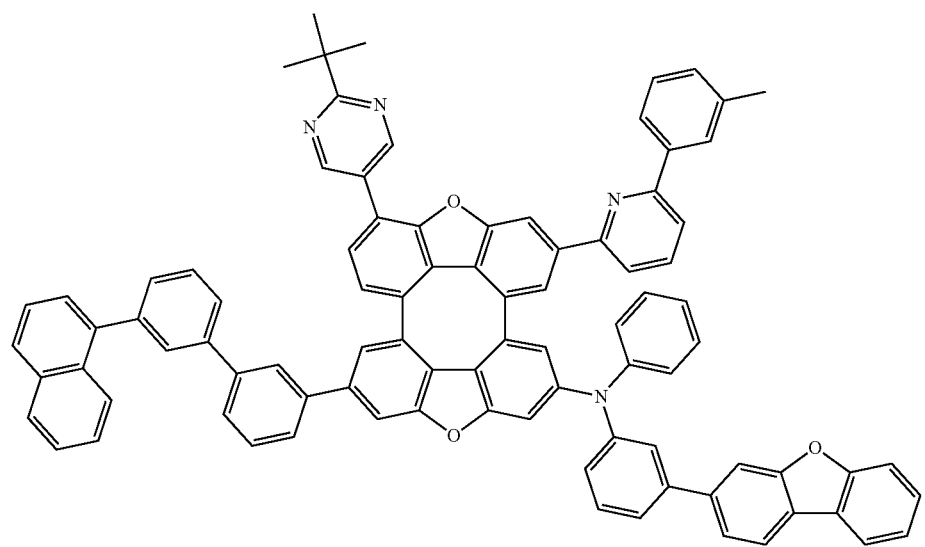
43
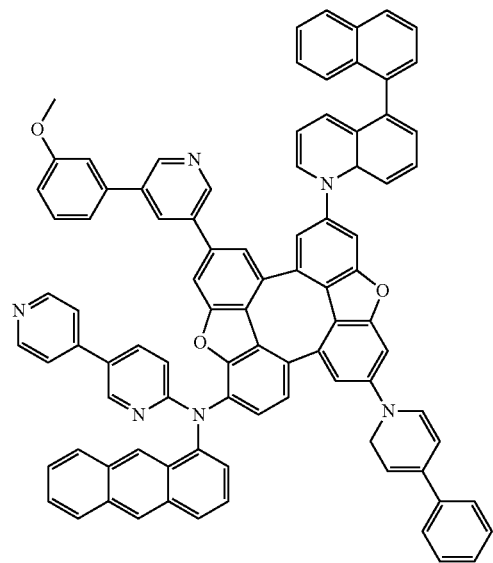
44
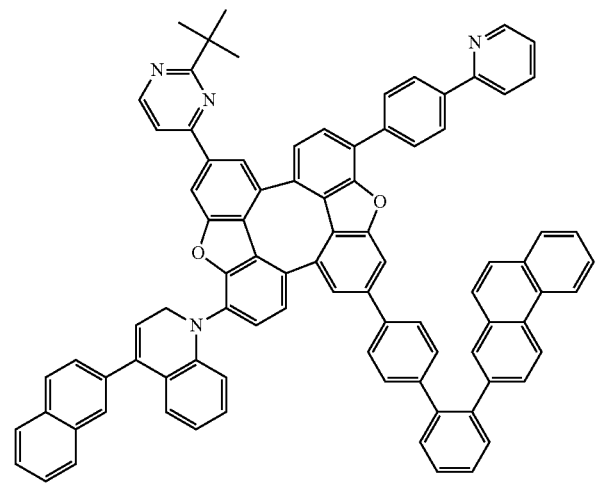

45
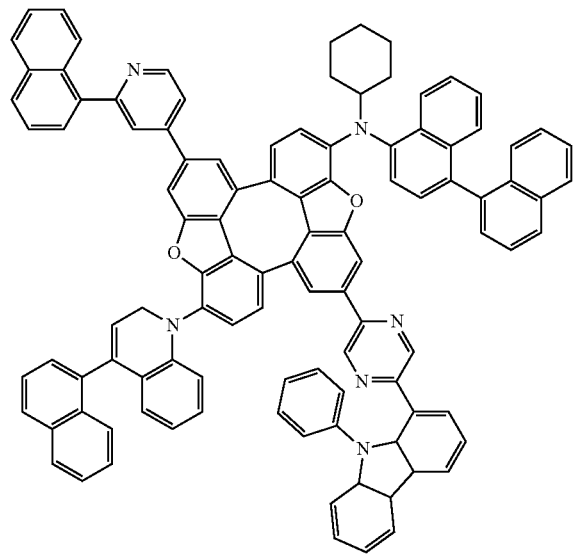
46
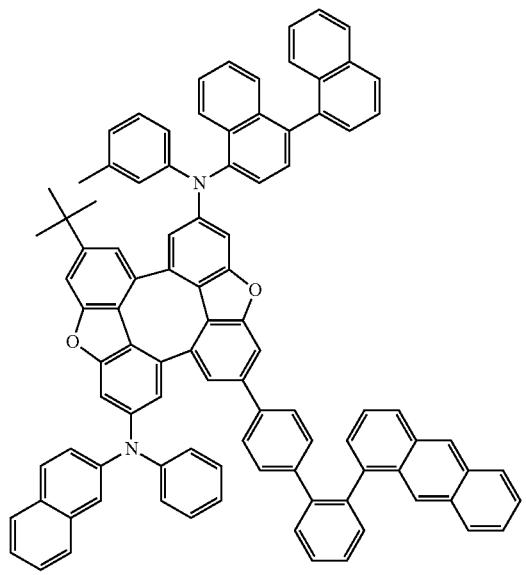
47
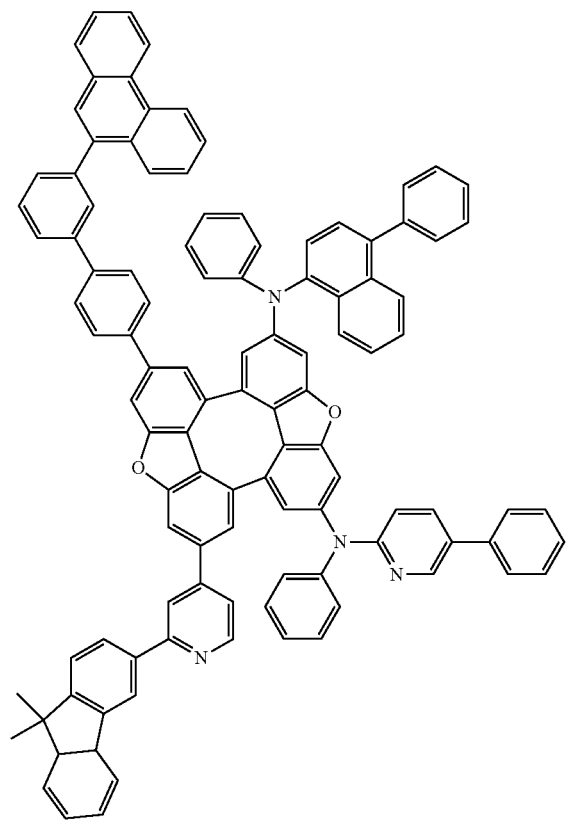

-continued
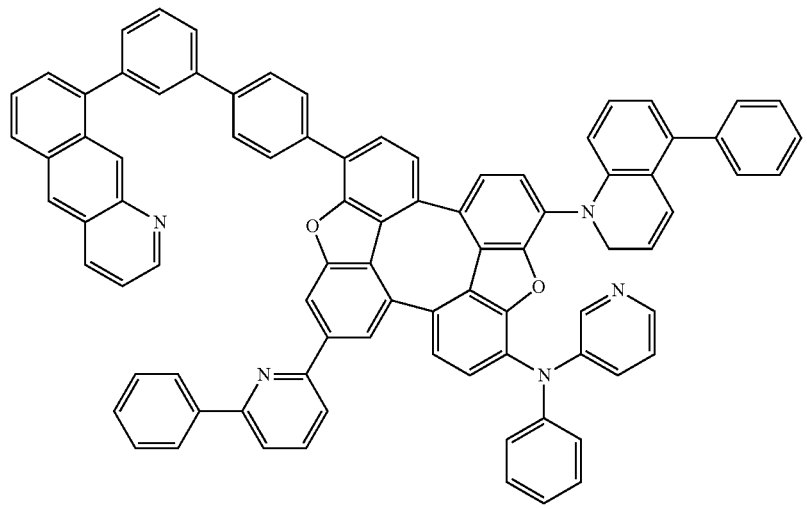
48
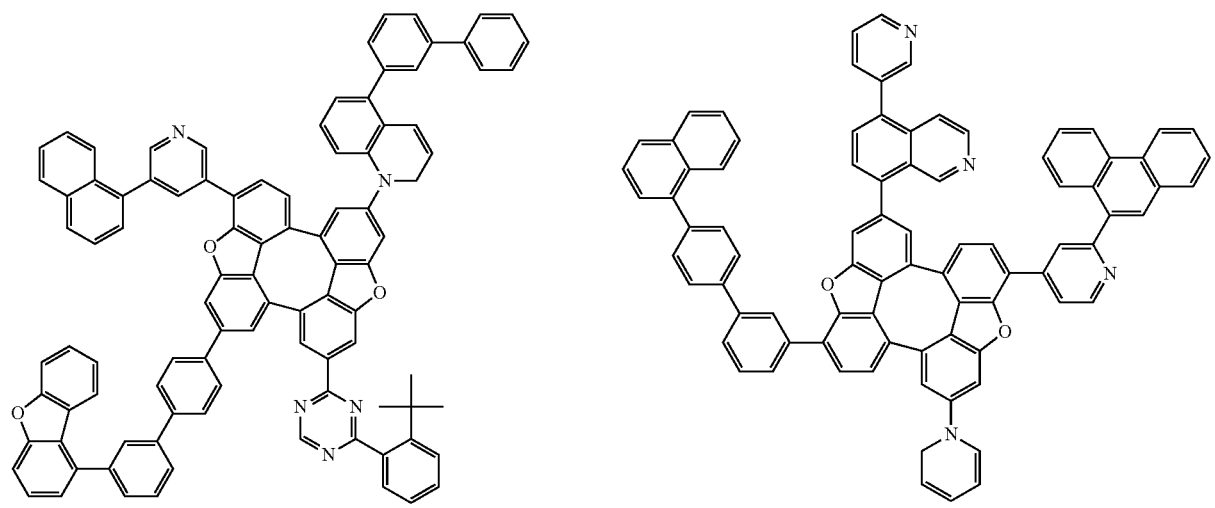
49
50
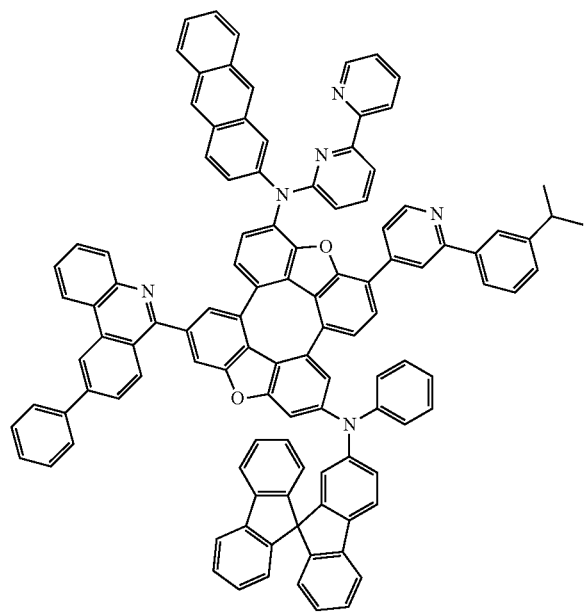
51

-continued
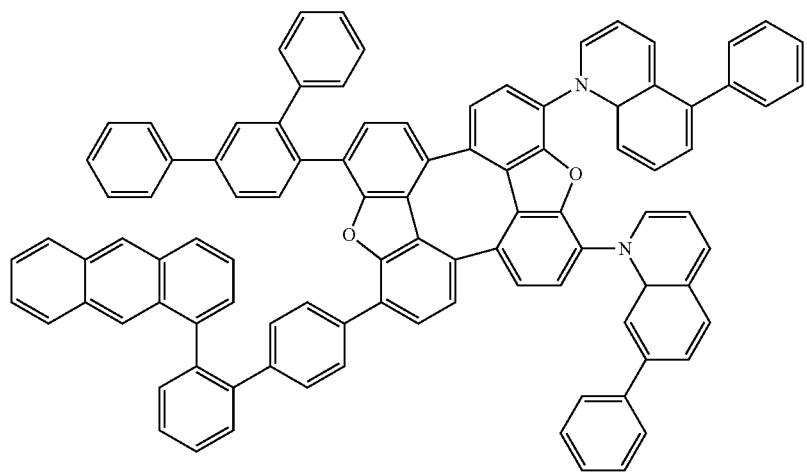
52
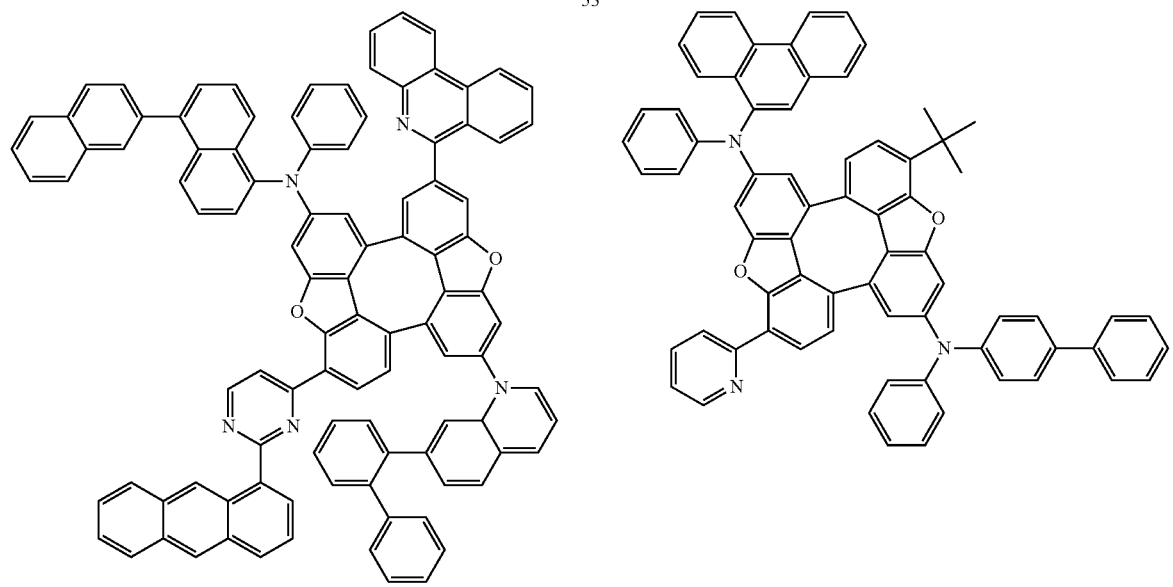
53
54
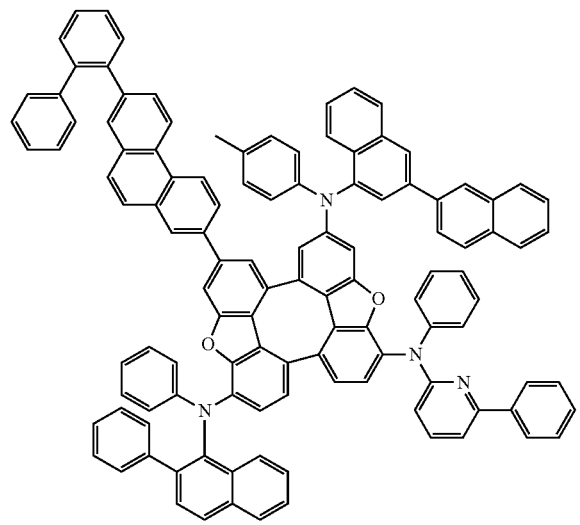
55

56
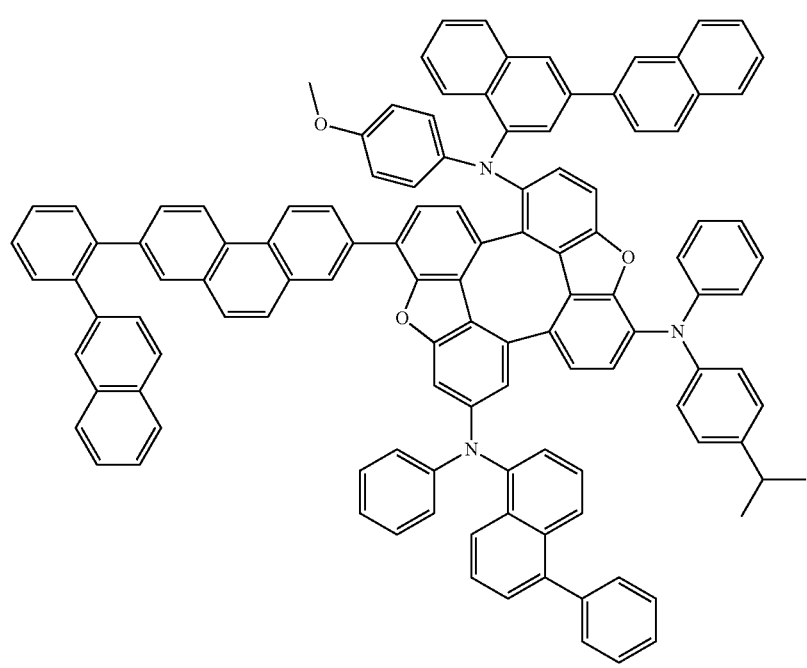
57
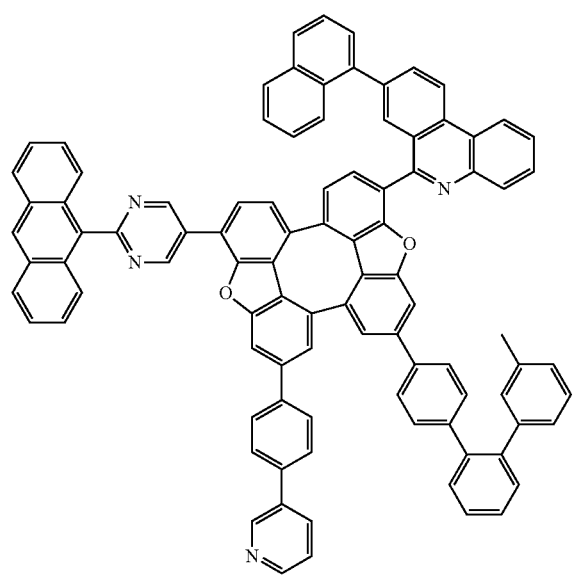

58
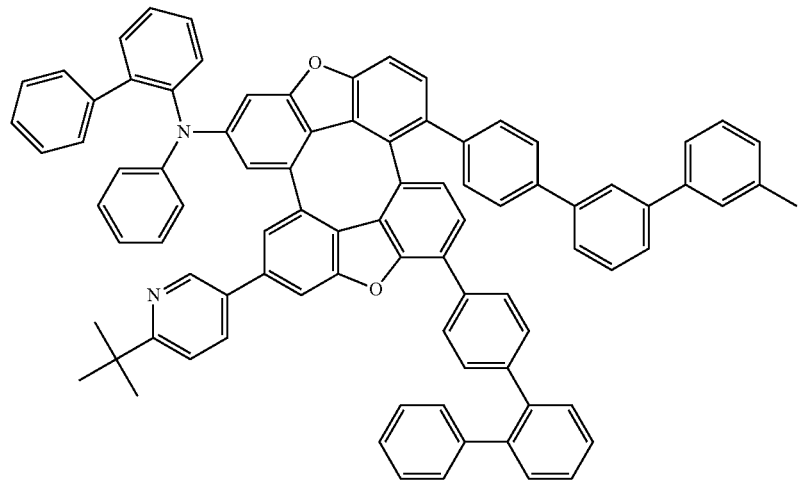
59 60
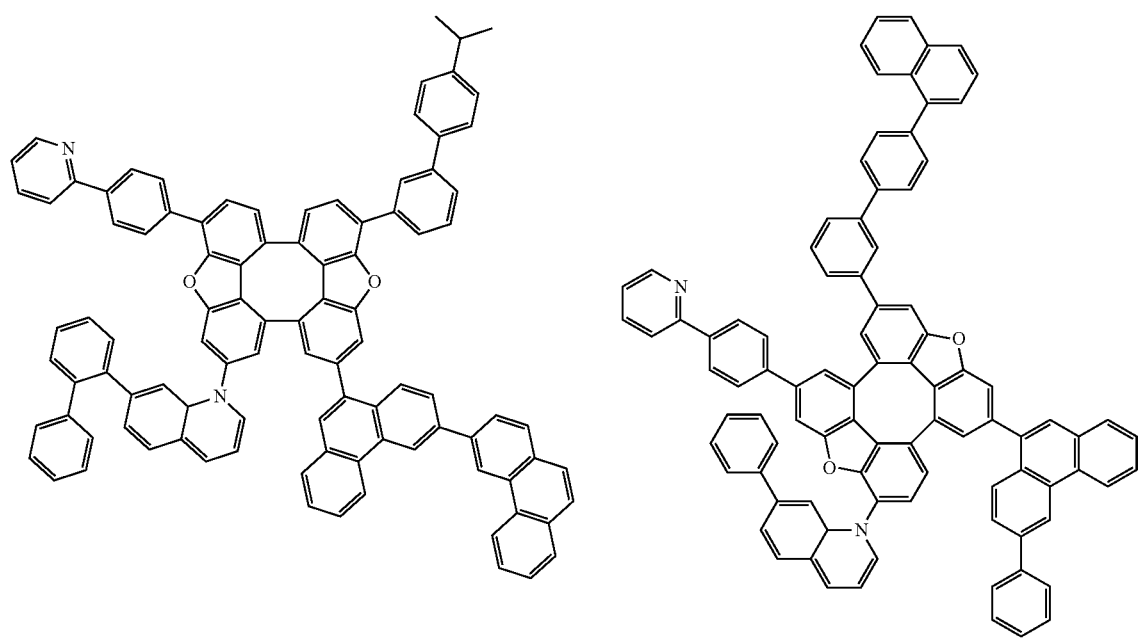

-continued
61
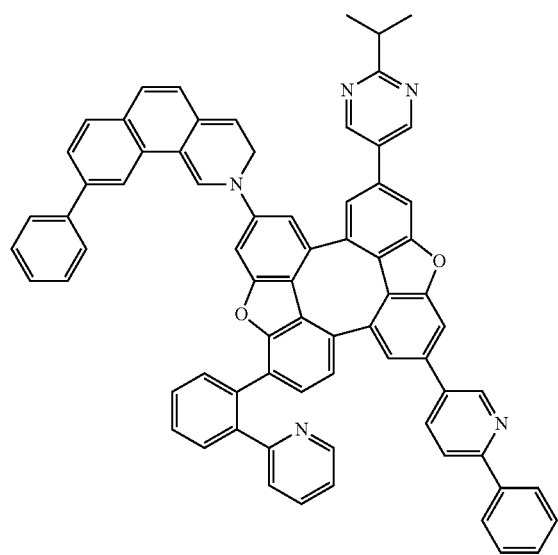
62
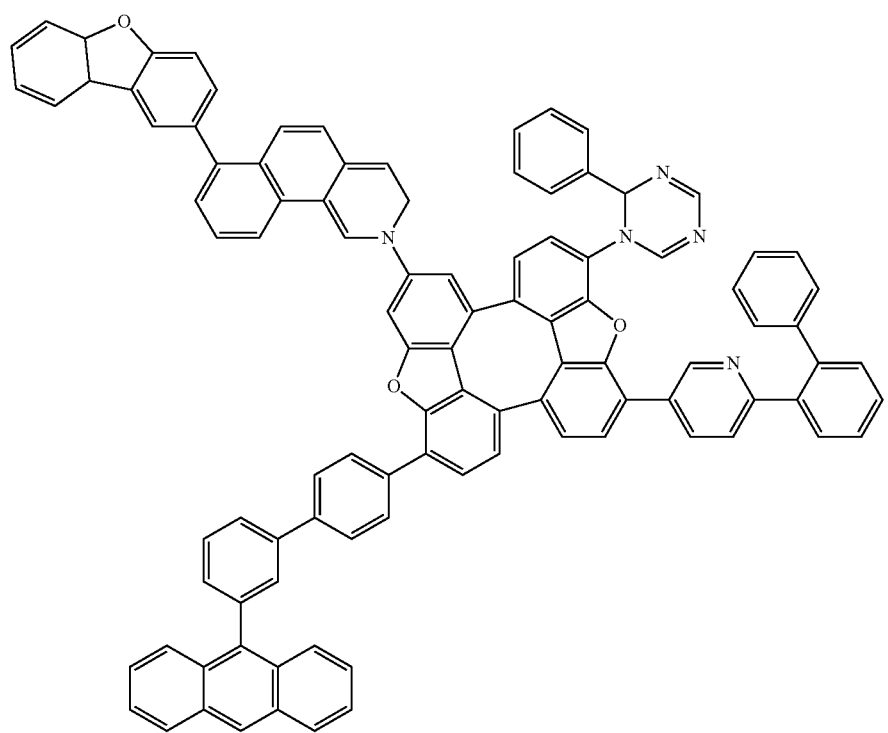

63
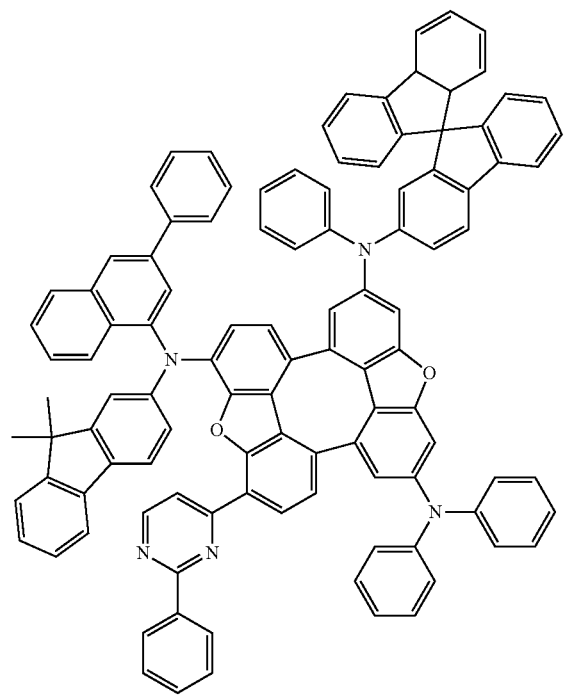
64
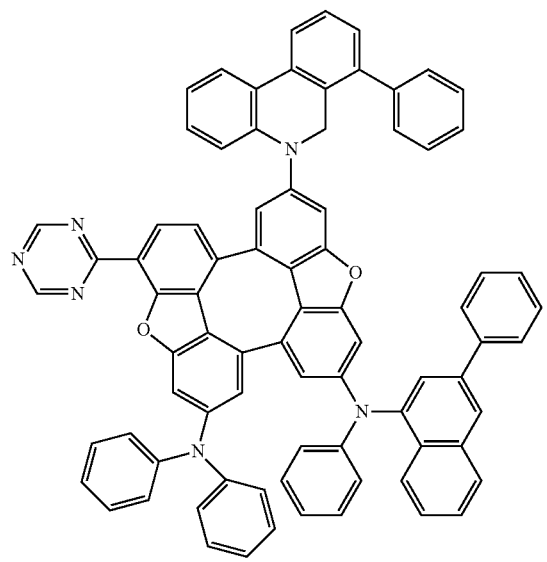
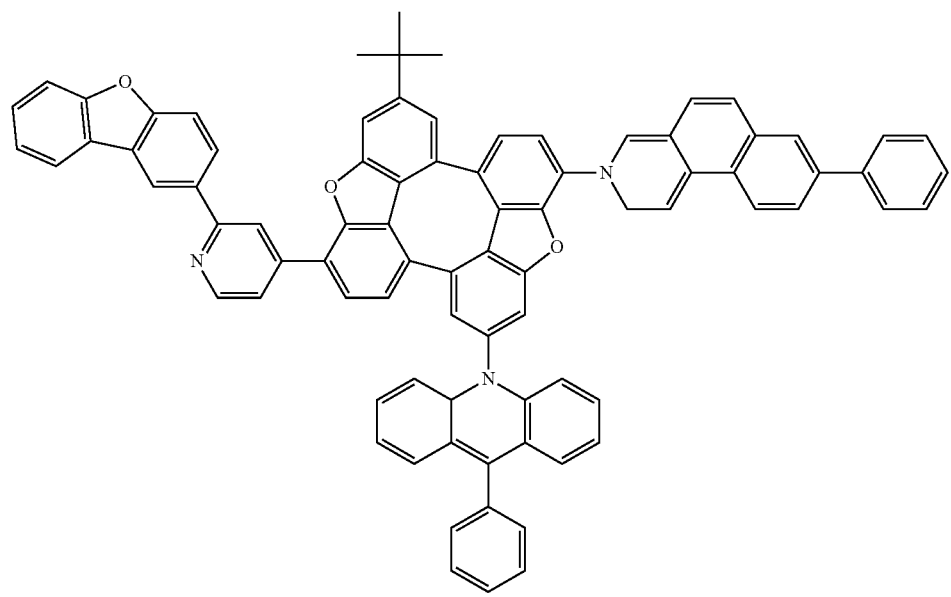

-continued
66
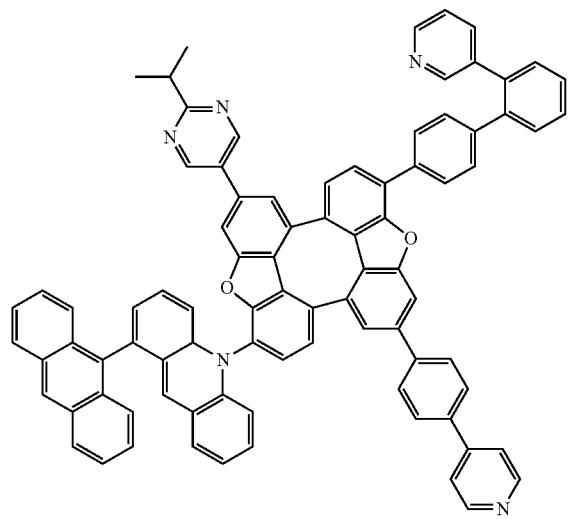
67
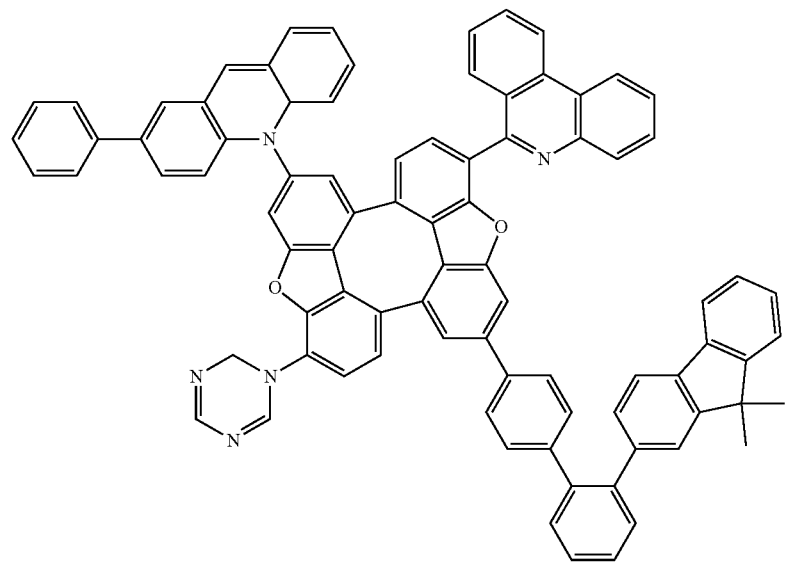

68
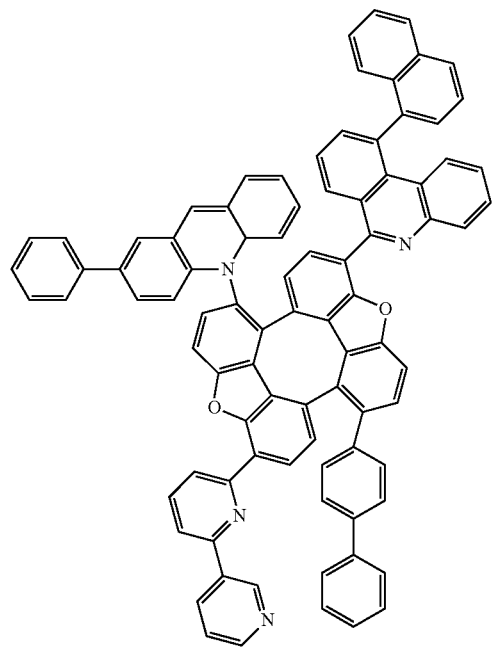
69
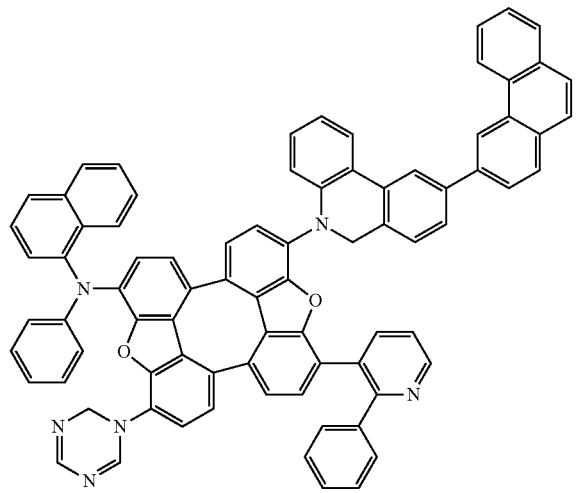
70
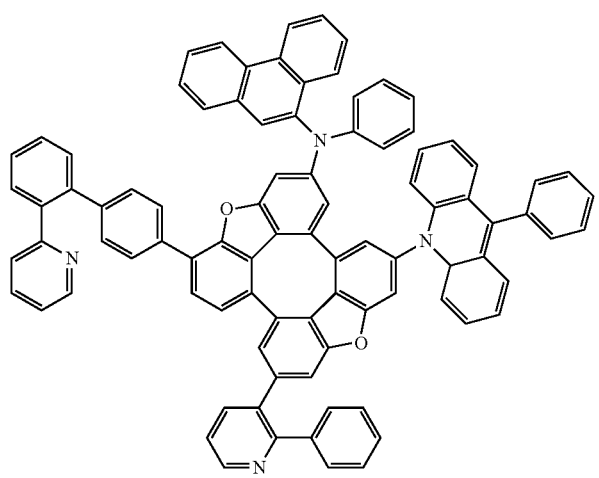

-continued
71
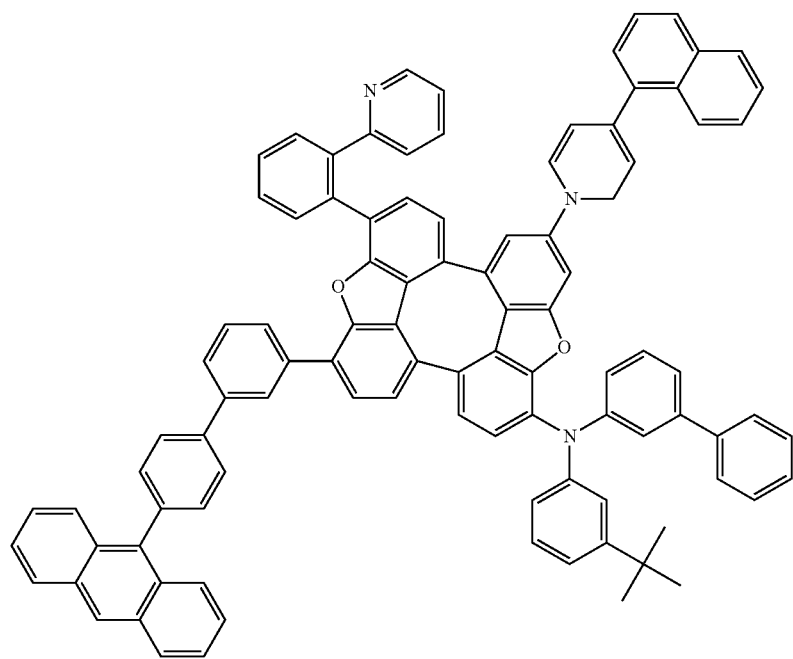
72
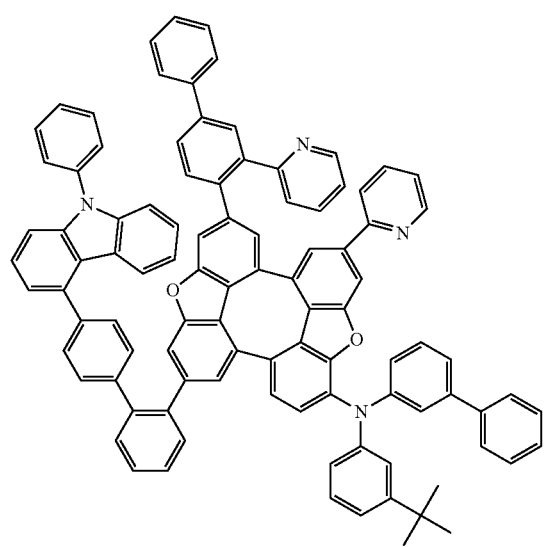

72
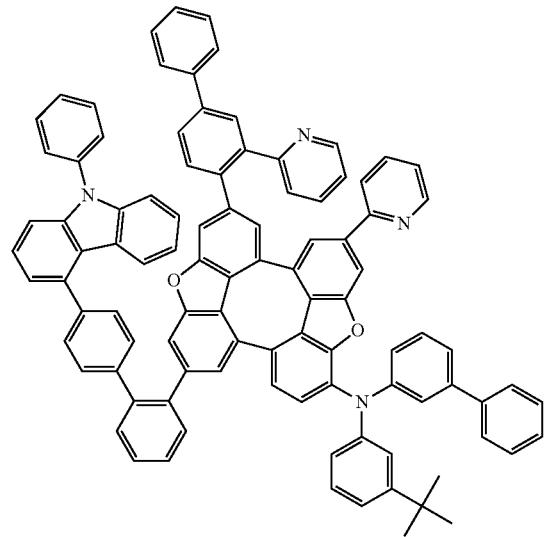
73
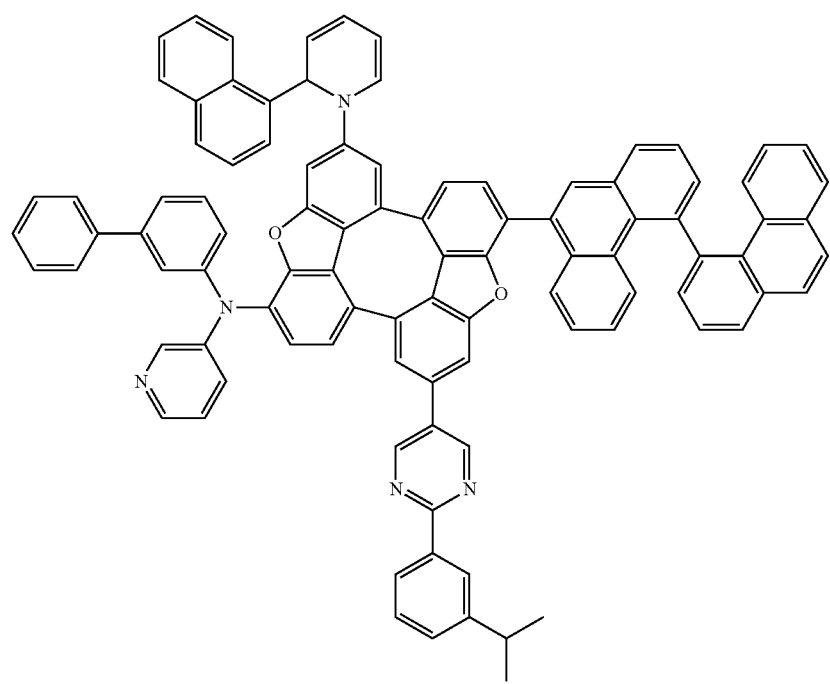

-continued
74
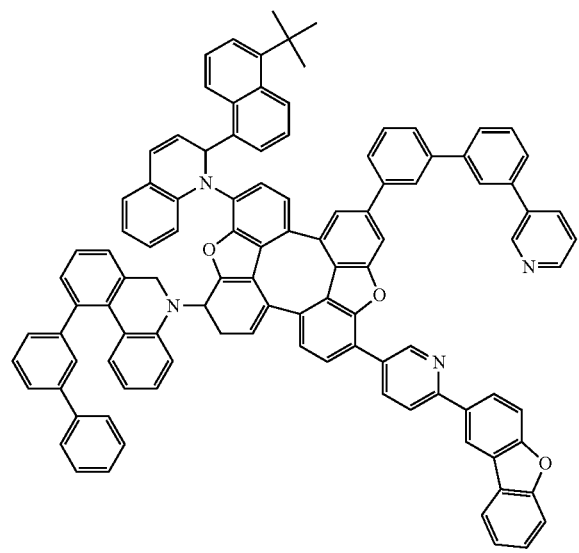
75
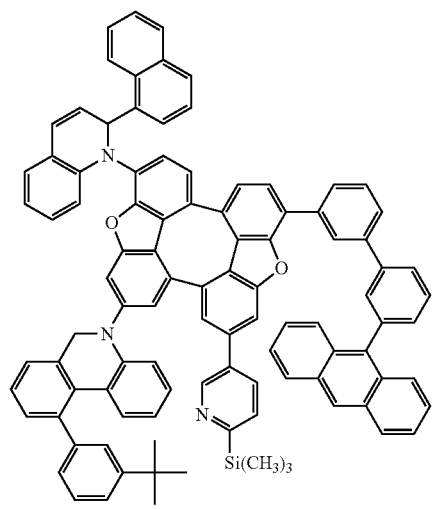
76
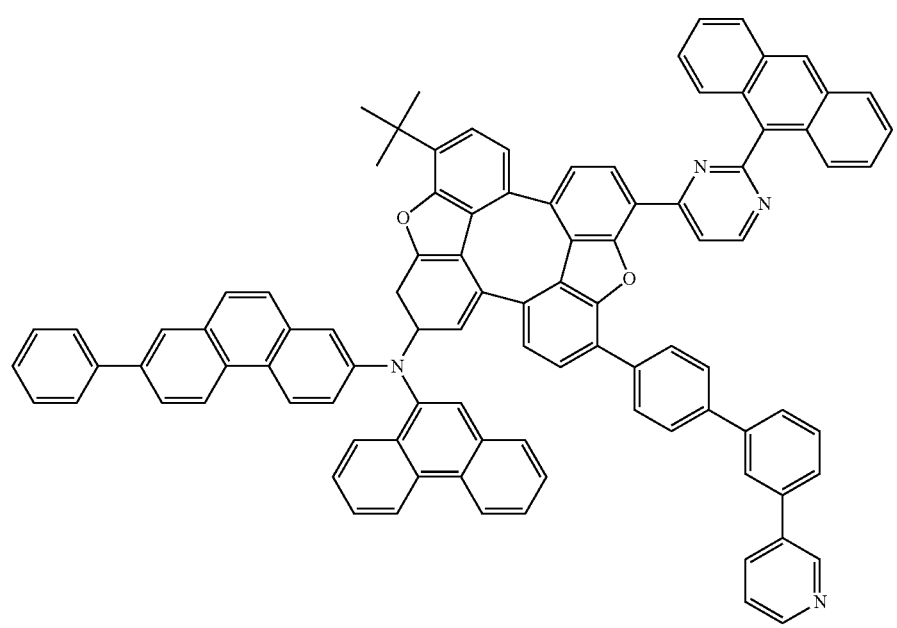
77
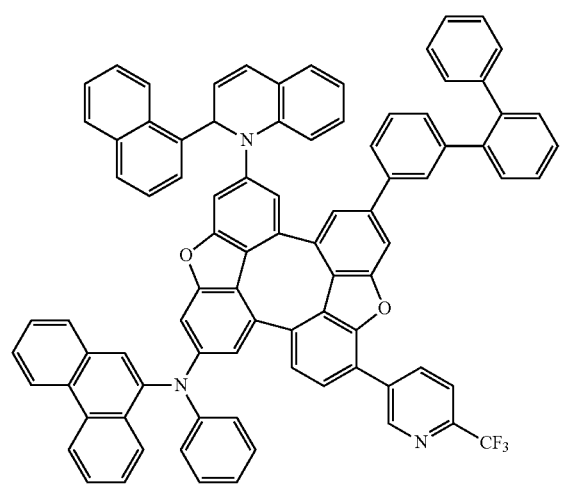

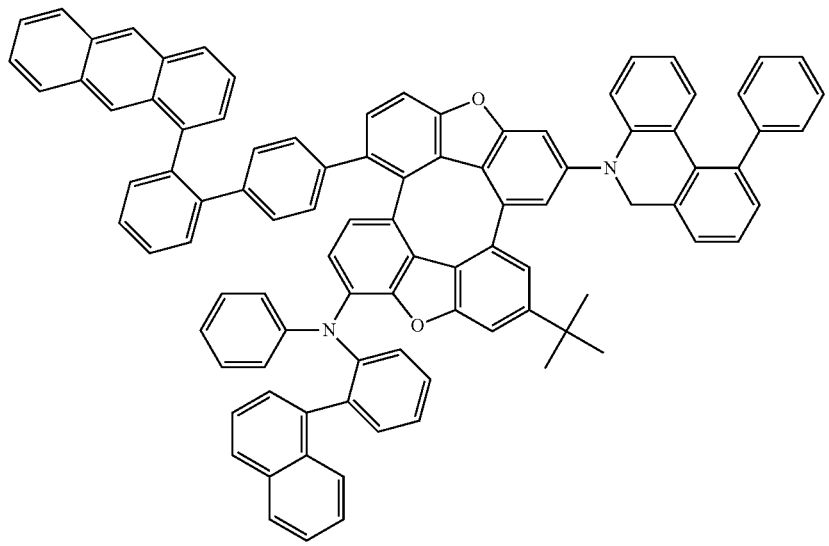
78
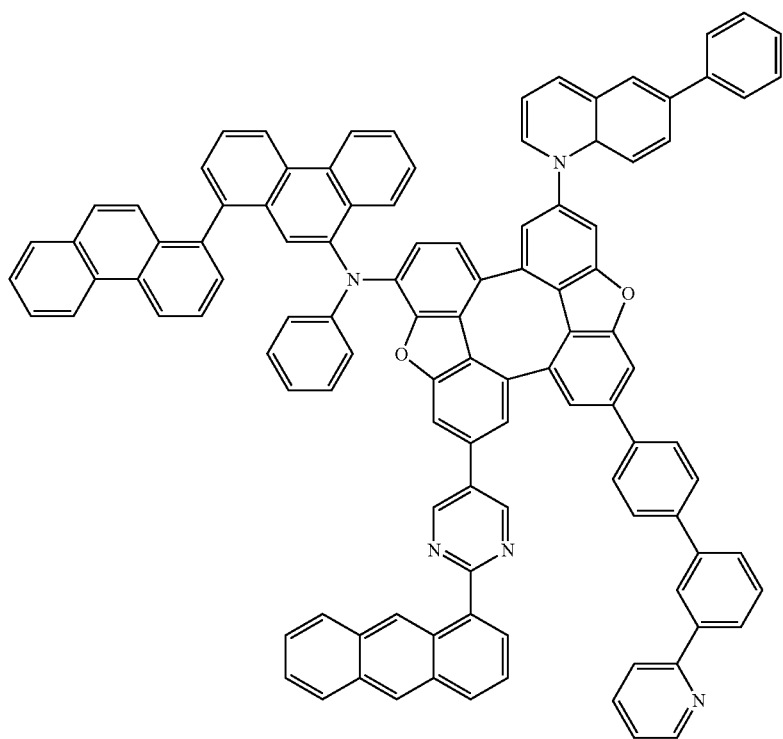
79

-continued
80
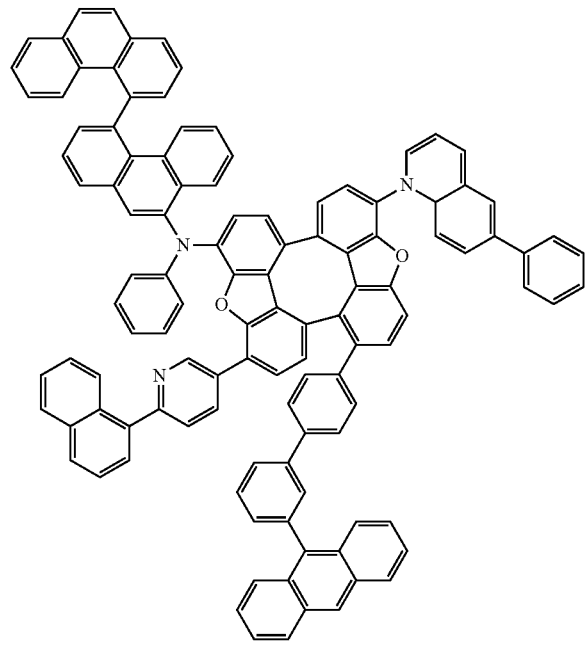
81
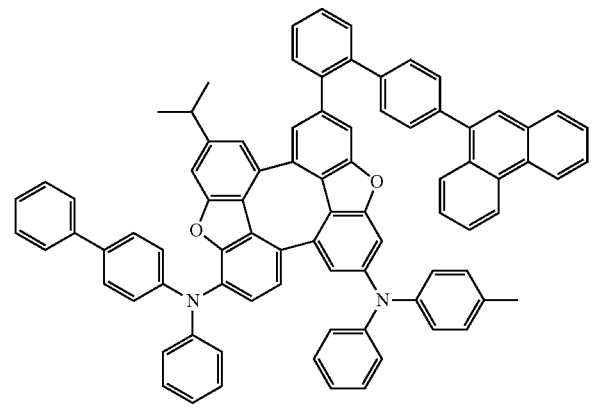
82
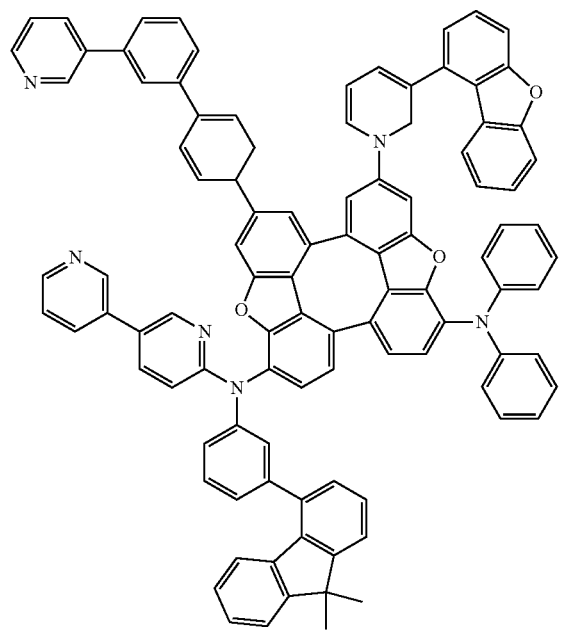
83
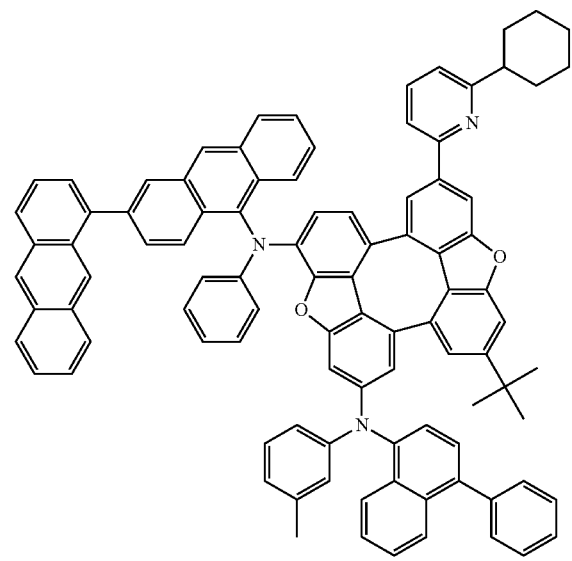

-continued
84
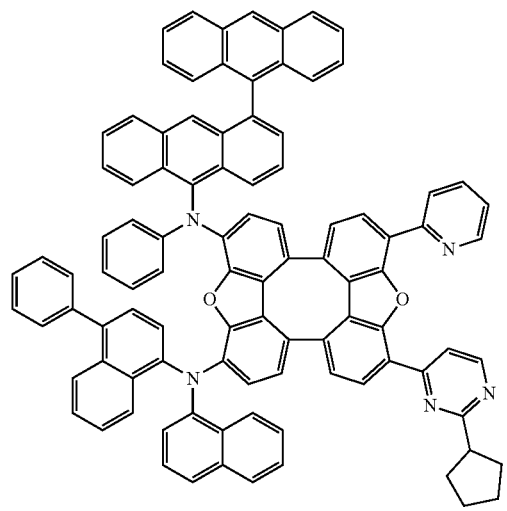
85
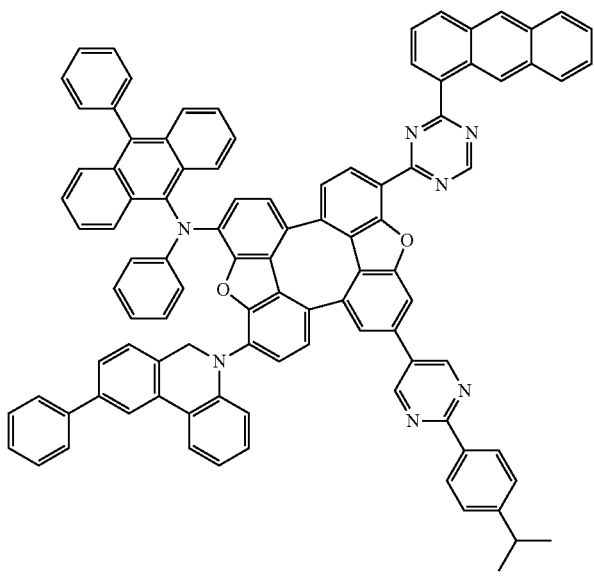
86
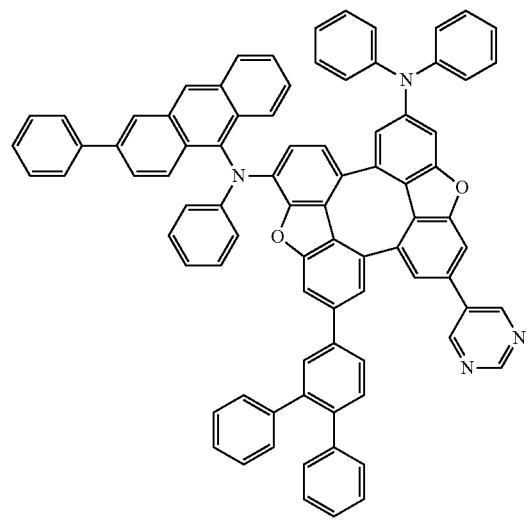
87
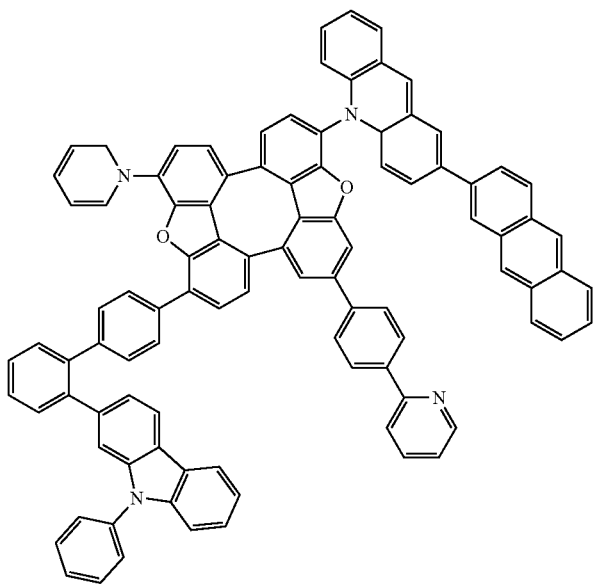

88
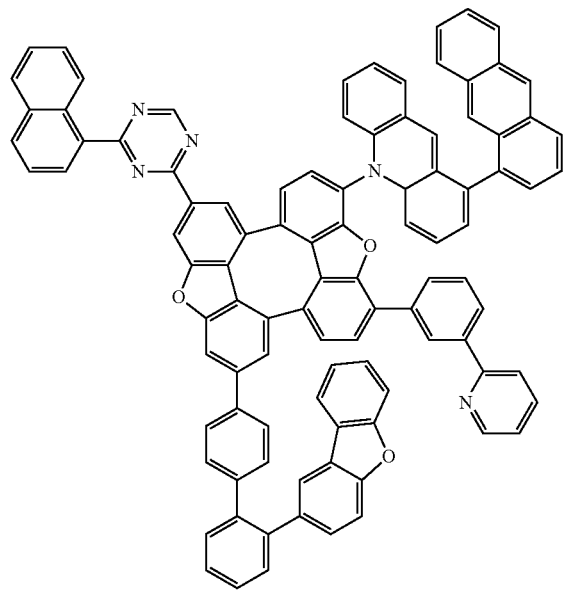
89
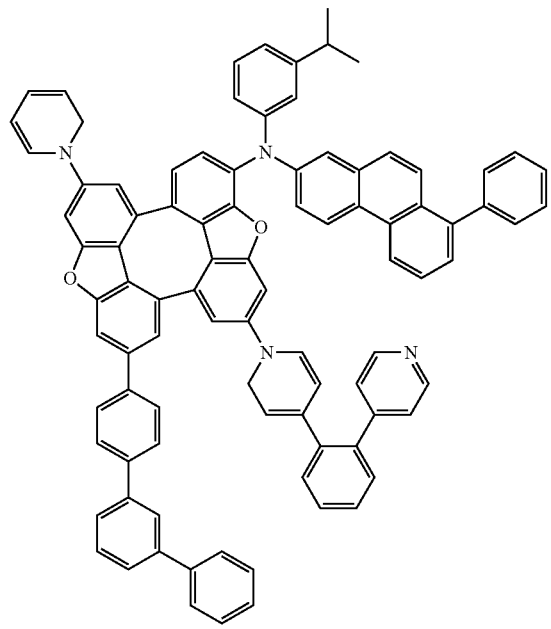
90
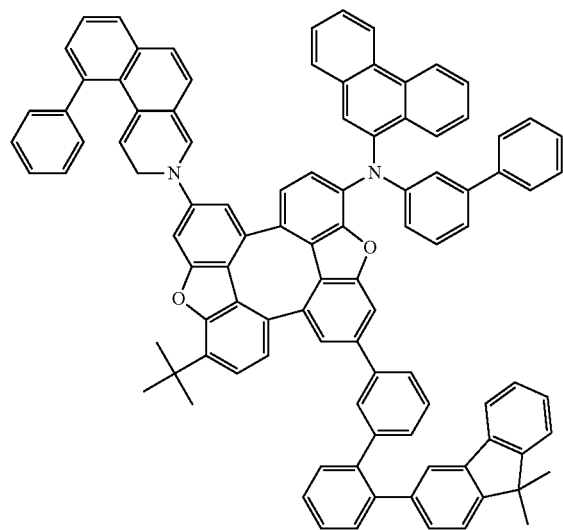
91
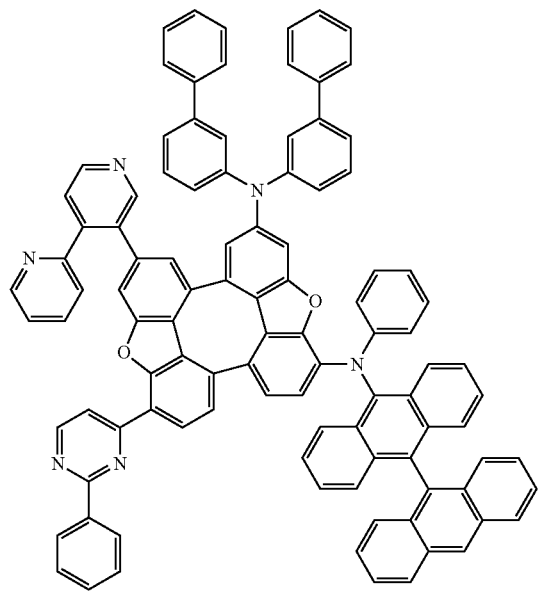

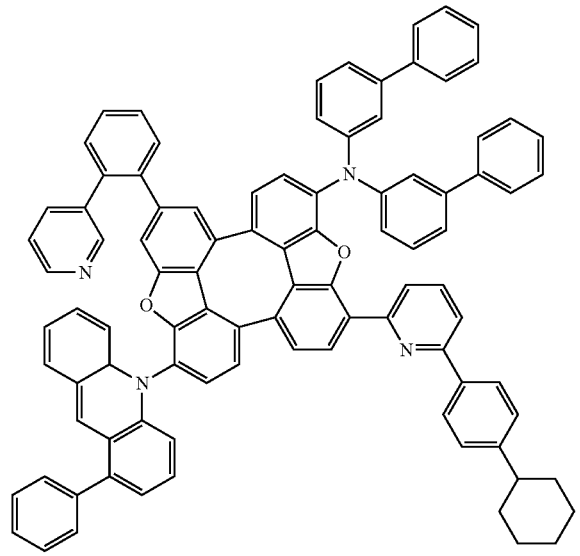
92
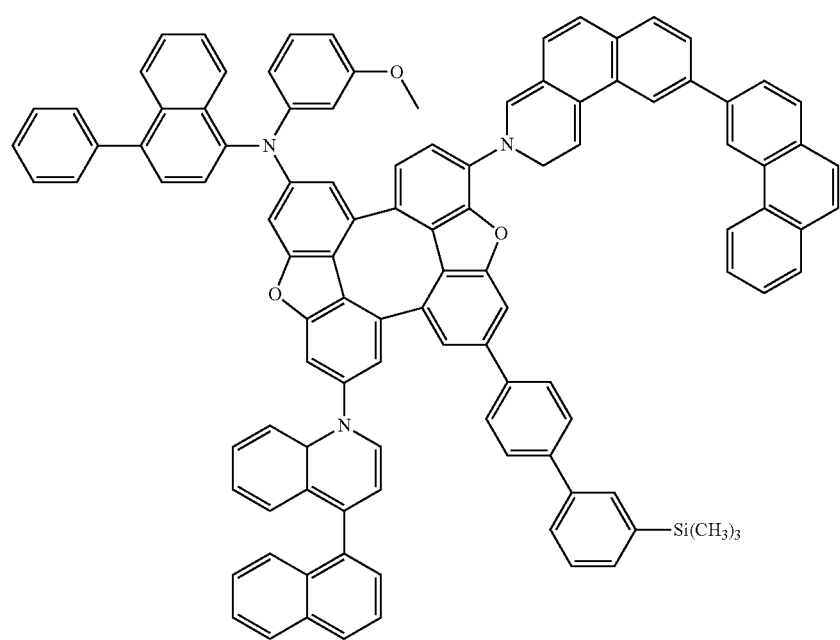
93

94
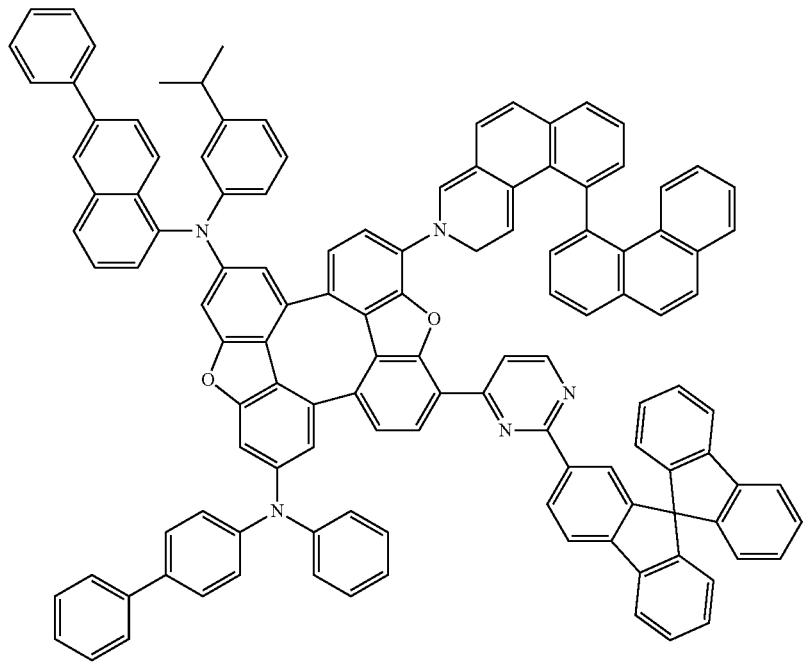
95
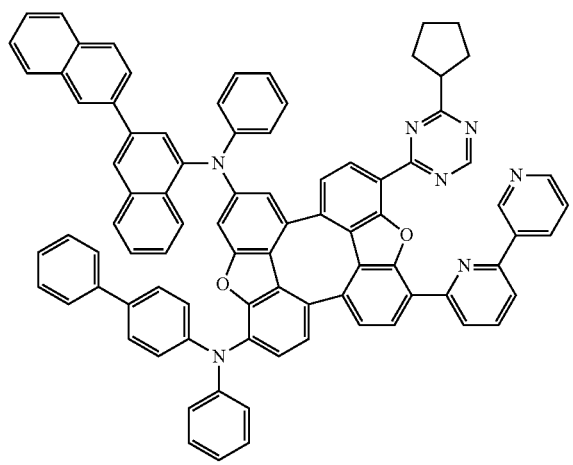
96
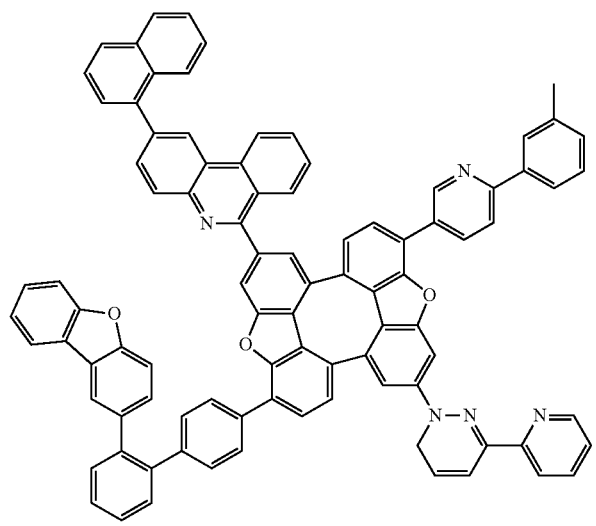

97
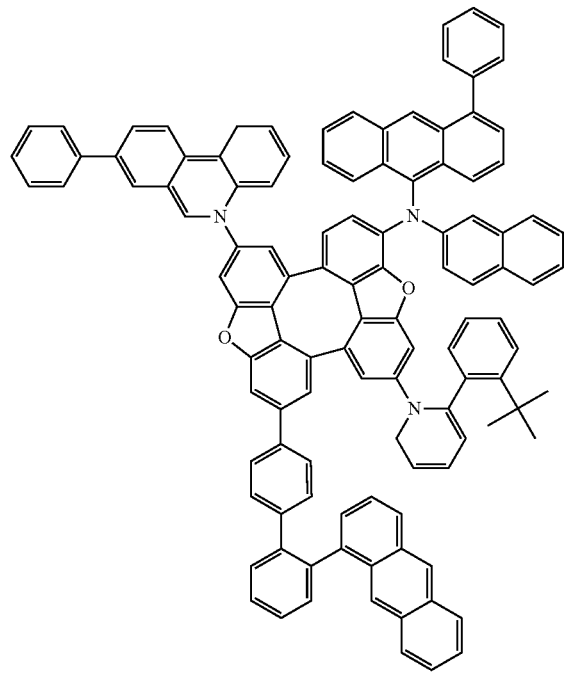
98
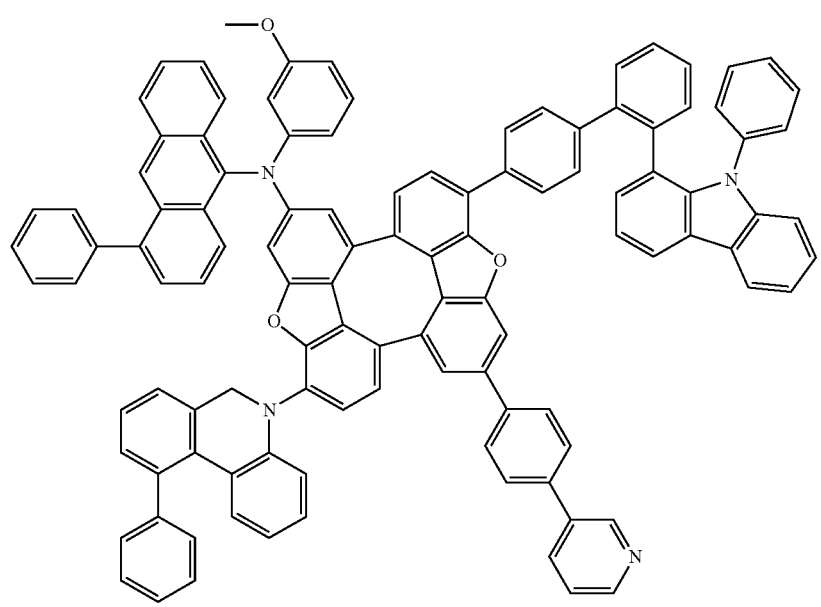

99
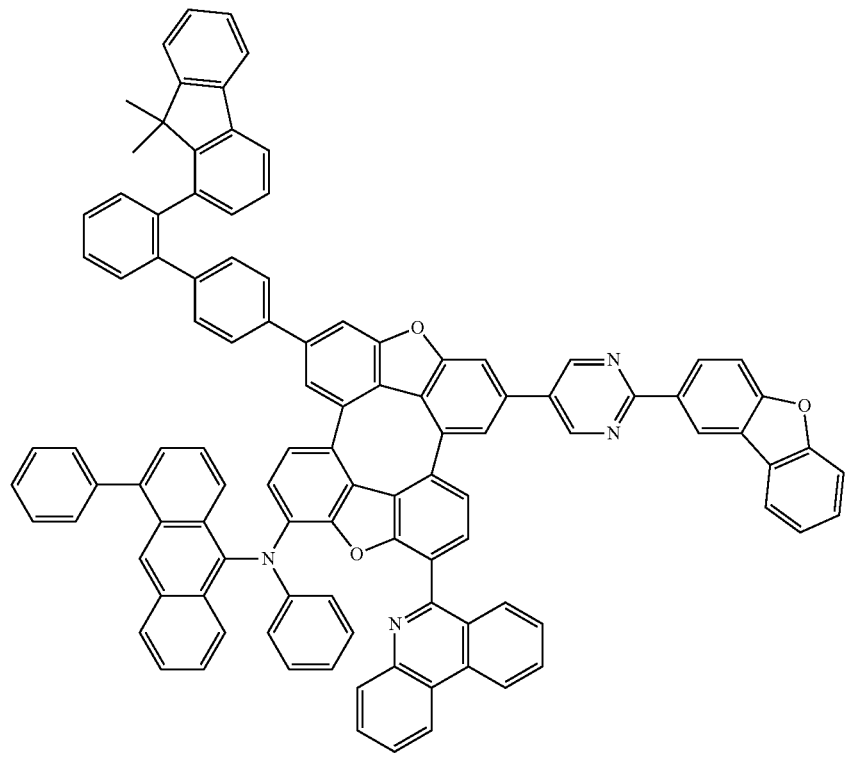
100
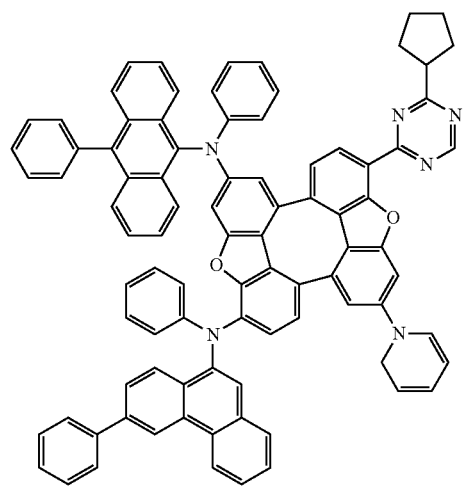
101
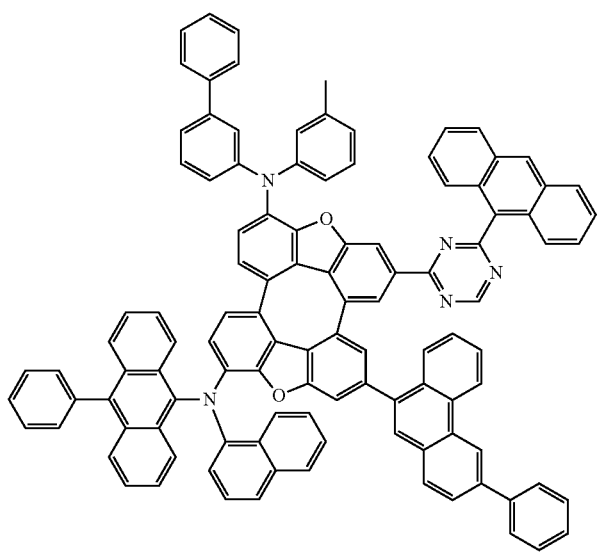

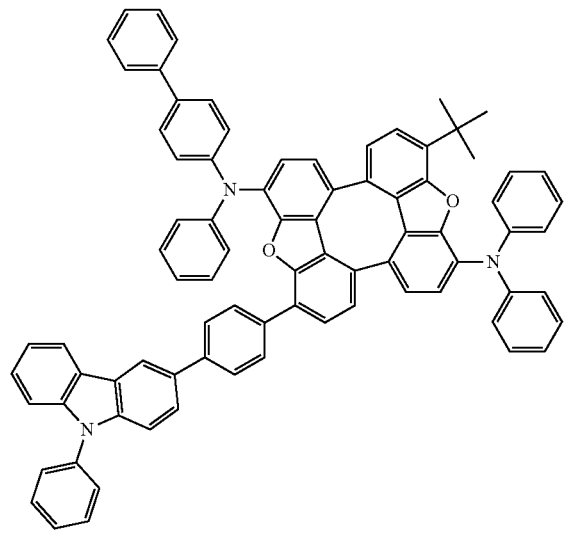
102
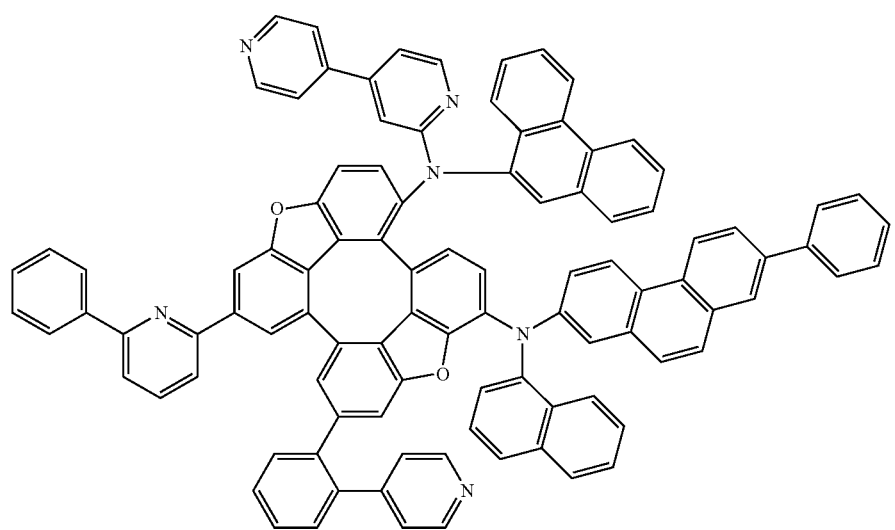
103

104
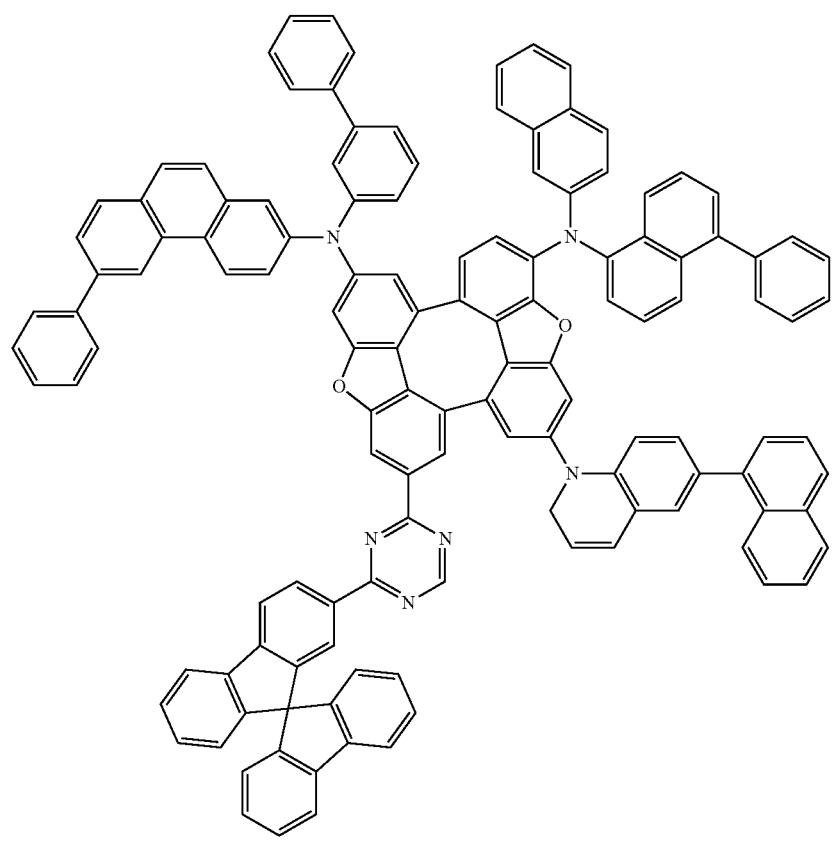
105
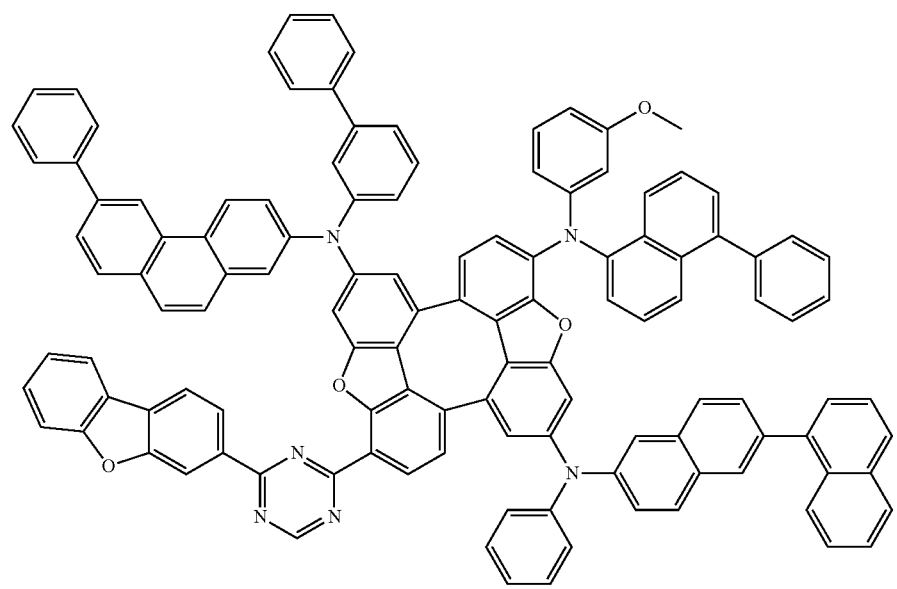

-continued
106
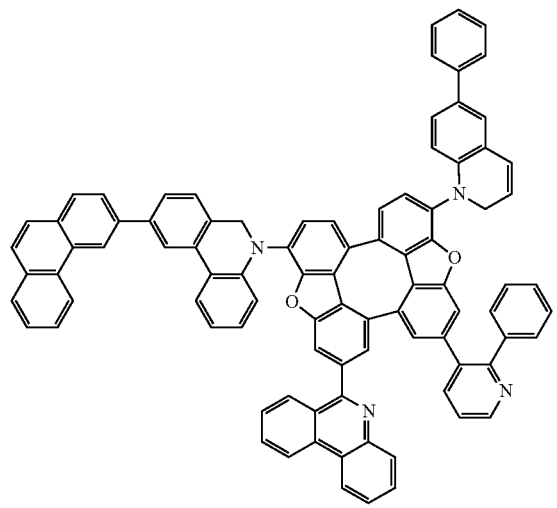
107
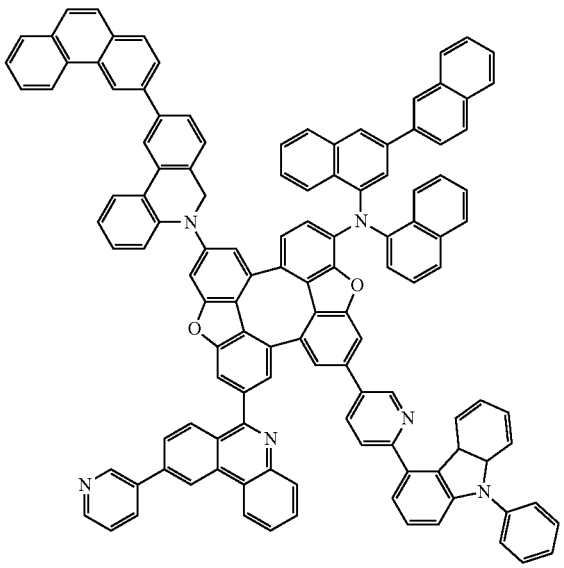
108
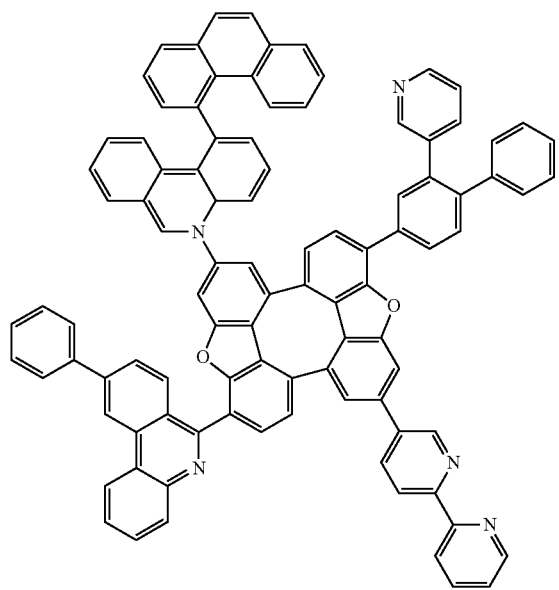
109
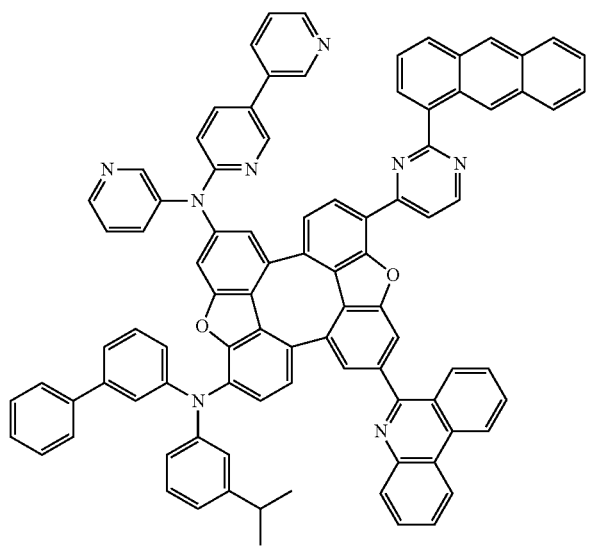

-continued
110
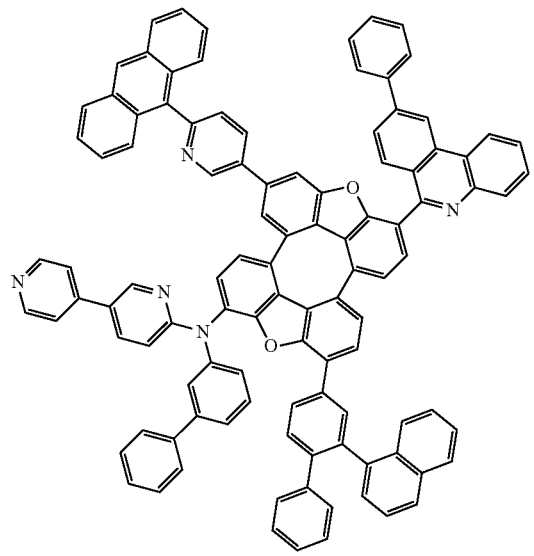
111
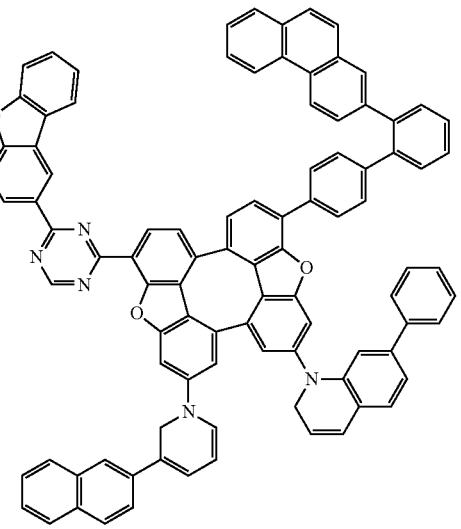
112
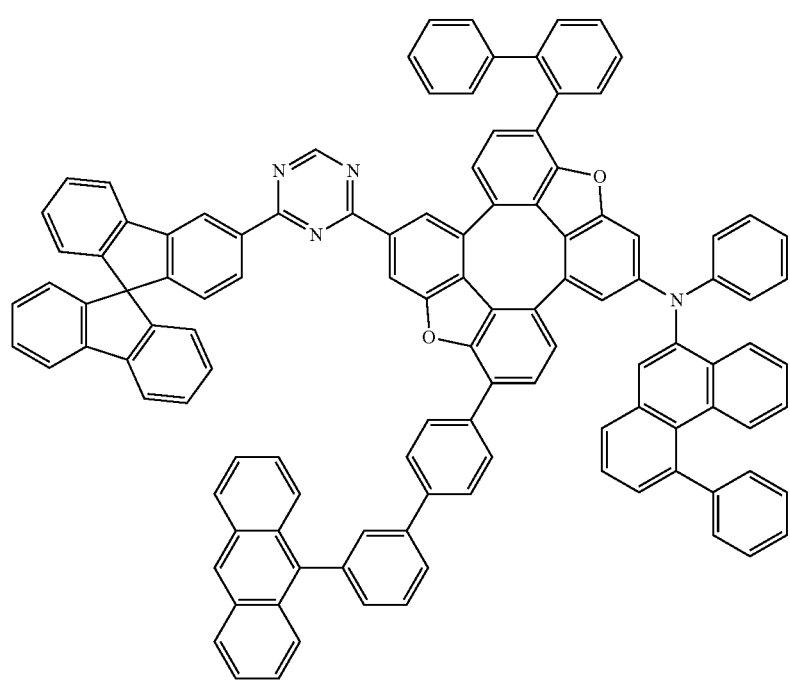

-continued
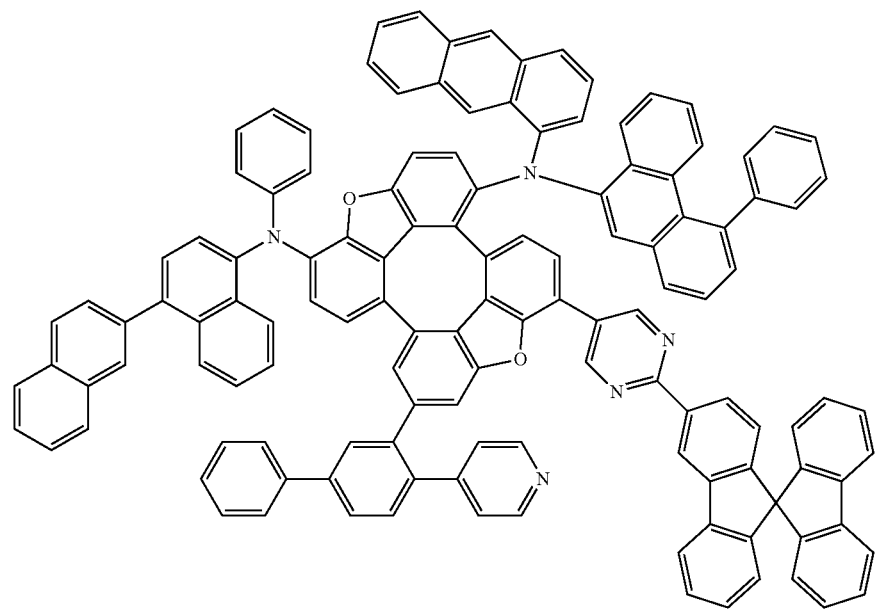
113
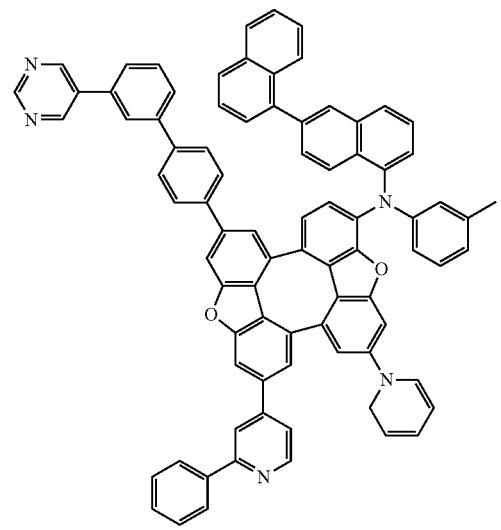
114
115

-continued
116
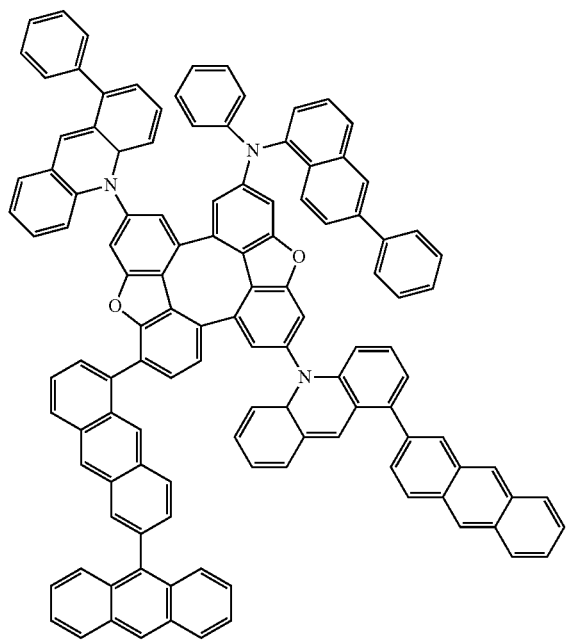
117
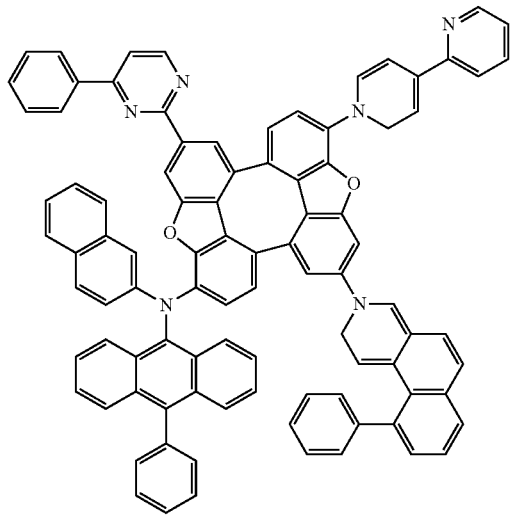
118
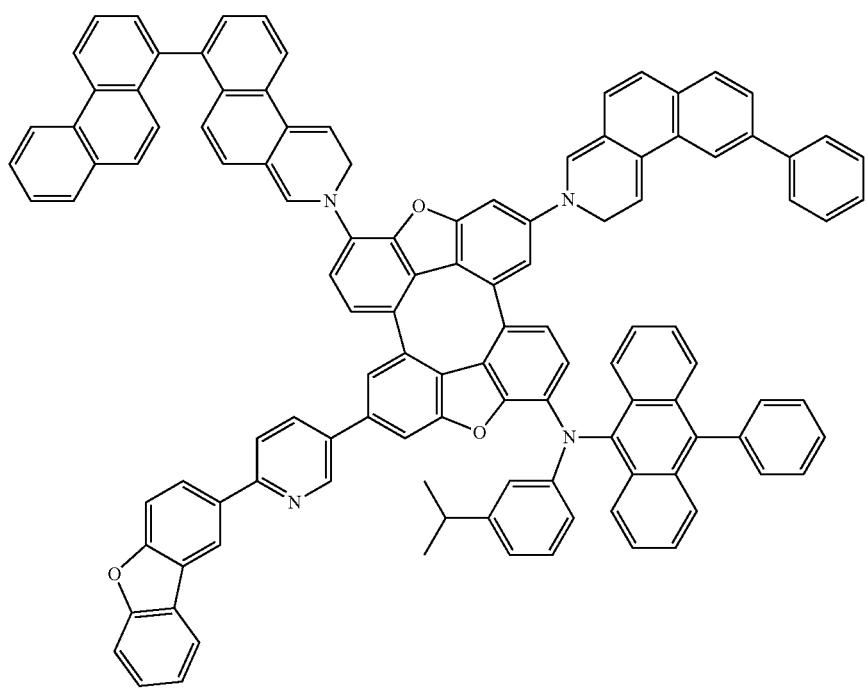

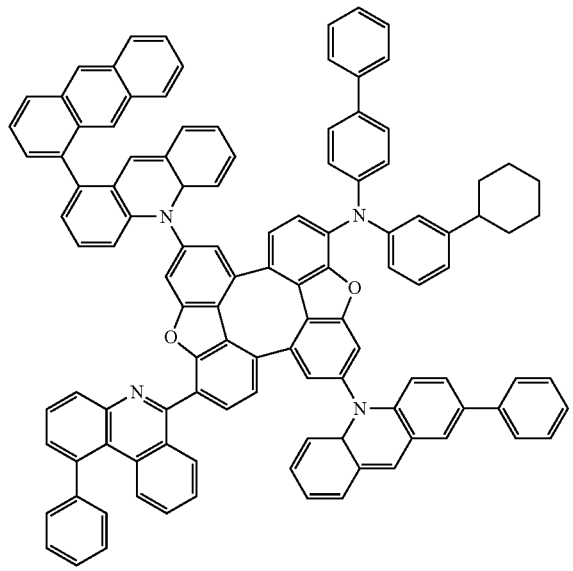

119

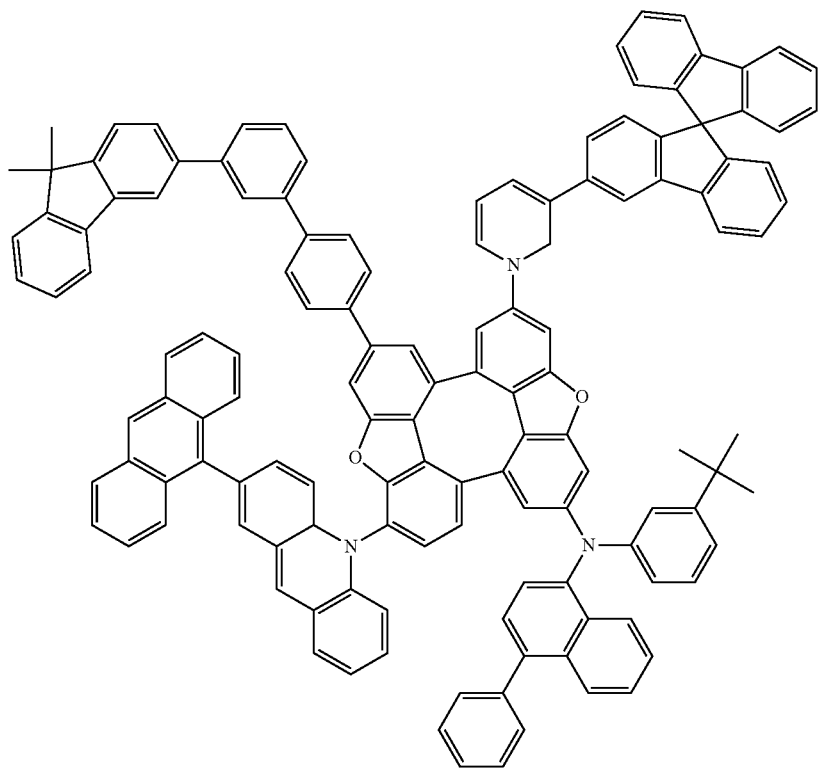

120

The above compound may be used as a blue dopant material.

The present invention also provides an organic electroluminescent device including the above organic electroluminescent compound. The organic electroluminescent device has a structure including an anode (a hole injection electrode), a hole injection layer (HIL), a hole transport layer (HTL), an emission layer (EML), an electron transport layer (ETL), an electron injection layer (EIL) and a cathode (an electron injection electrode) which are sequentially stacked, and if possible, an electron blocking layer (EBL) may be interposed between the anode and the emission layer, a hole blocking layer (HBL) may be interposed between the cathode and the emission layer, and a cathode protecting layer (CPL) may be added onto the surface of the cathode.

A method for manufacturing the organic electroluminescent device includes the following steps:

Step 1, the anode is formed by laminating an anode material on the surface of a substrate using a conventional method, wherein the substrate used is a glass substrate or a transparent plastic substrate with excellent transparency, surface smoothness, operability and water resistance, and the anode material may be materials with excellent transparency and conductivity such as ITO, IZO, $SnO_2$, ZnO, etc.

Step 2, the hole injection layer (HIL) material is vacuum heat deposited or spin-coated on the surface of the anode by a conventional method, wherein the hole injection layer material may be CuPc, m-MTDATA, m-MTDAPB, TCTA, 2-TNATA, or IDE406 which is available from Idemitsu Kosan, etc.

Step 3, the HTL is formed by vacuum heat depositing or spin-coating hole transport layer material on the surface of the hole injection layer using a conventional method, wherein the hole transport layer material may be α-NPD, NPB or TPD.

Step 4, the emission layer is formed by vacuum heat depositing or spin-coating an emission layer material (EML) on the surface of the hole transport layer using a conventional method, wherein the emission layer material used is a mixture of luminescent substance and the organic compound in the present invention.

Step 5, the electron transport layer is formed by vacuum heat depositing or spin-coating an electron transport layer material (ETL) on the surface of the emission layer using a conventional method, wherein the electron transport layer material is not particularly limited and is preferably $Alq_3$.

Step 6, the electron injection layer is formed by vacuum heat depositing or spin-coating an electron injection layer material on the surface of the electron transport layer (EIL) using a conventional method, wherein the electron injection layer material may be LiF, Liq, $Li_2O$, BaO, NaCl, CsF, etc.

Step 7, the cathode is formed by vacuum heat depositing or spin-coating a cathode material on the surface of the electron injection layer using a conventional method, wherein the cathode material may be Li, Al, Al—Li, Ca, Mg, Mg—In, Mg—Ag, etc. Alternatively, a transparent cathode having light transmittance may be formed by using indium tin oxide (ITO) or indium zinc oxide (IZO).

Further, it is effective to prevent diffusion of triplet state excitons or holes into the electron transport layer by interposing a hole blocking layer (HBL) between the emission layer and the electron transport layer along with a use of phosphorescent dopant in the emission layer. The hole blocking layer is formed by a conventional method through vacuum heat depositing or spin-coating hole blocking layer material on the surface of the emission layer. The hole blocking layer material is not particularly limited and is preferably Liq, (2-methyl-8-hydroxyquinoline-4-hydroxybiphenyl) aluminum, BCP or LiF, etc.

Compound Example 1

Synthesis of Compound 2
Synthesis of Intermediate (1)

[Reaction Scheme 1]

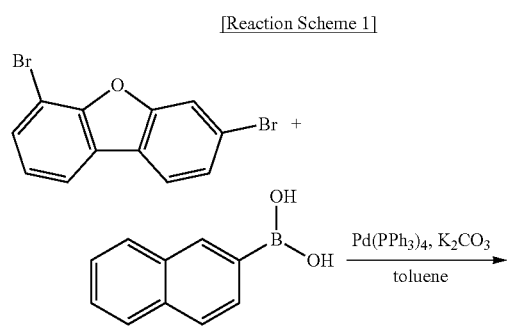

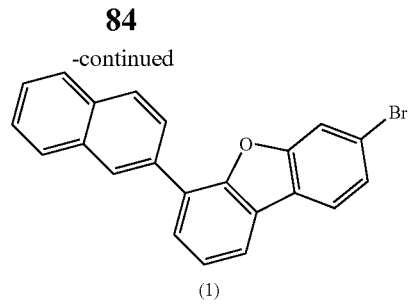

(1)

19.2 g 2-naphthyl boric acid and 32.6 g 3,6-dibromo-diphenylfuran were added into a 2 L three-neck flask, followed by adding 600 mL toluene and 150 mL ethanol to dissolve. The reaction mixture was aerated with nitrogen gas for 15 minutes, then 150 mL aqueous $K_2CO_3$ solution (3.0 eq., 2M) and 2.3 g $Pd(PPh_3)_4$ (2 mol %) were sequentially added. The reaction mixture was heated up to 110° C. and the reaction finished. Afterwards, residual was absorbed by the added activated carbon, filtered by suction filtration, performed with rotated removal of solvent by rotary evaporation, dried and recrystallized with a mixture of toluene and ethanol, to produce 33.6 g Intermediate (1) at a yield of 90%.

Synthesis of Intermediate (2)

[Reaction Scheme 2]

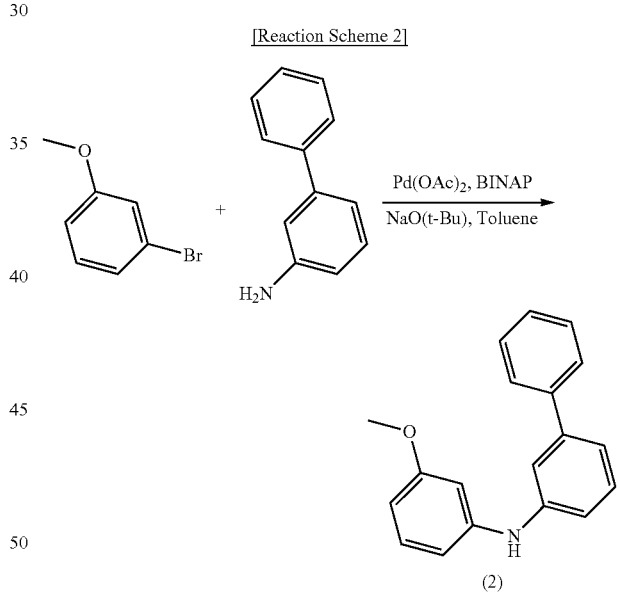

28.1 g 1-bromo-3-methoxylbenzene and 27.9 g 3-amino bibenzene were added into a dry 2 L three-neck flask, followed by 600 mL dry and degassed toluene added to dissolve. Then, 43.2 g sodium tert-butoxide (3 eq.), 0.67 g catalyst palladium diacetate (2% mol) and 3.7 g 1,1'-binaphthyl-2,2'-bis(diphenylphosphino) (BINAP, 4% mol) ligand were added. The reaction mixture was heated up to 110° C. and reacted overnight. After the reaction finished and the reaction mixture was cooled down to room temperature, the residual was absorbed by the added activated carbon, filtered by suction filtration and removed with solvent by rotary evaporation to produce 36.8 g Intermediate (2) at a yield of 89%.

Synthesis of Intermediate (3)

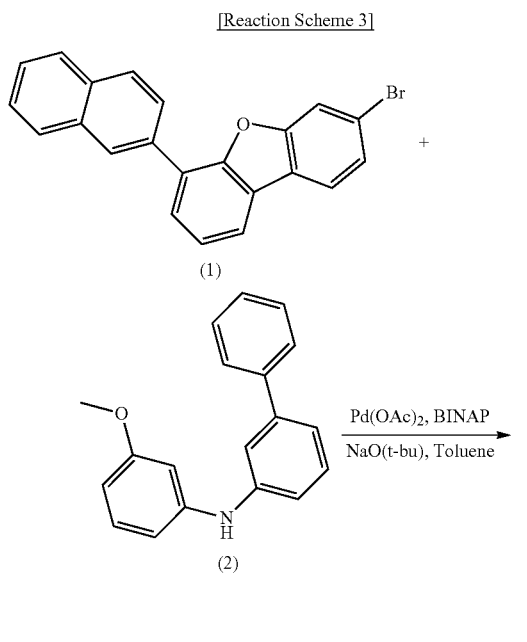

Synthesis of Intermediate (4)

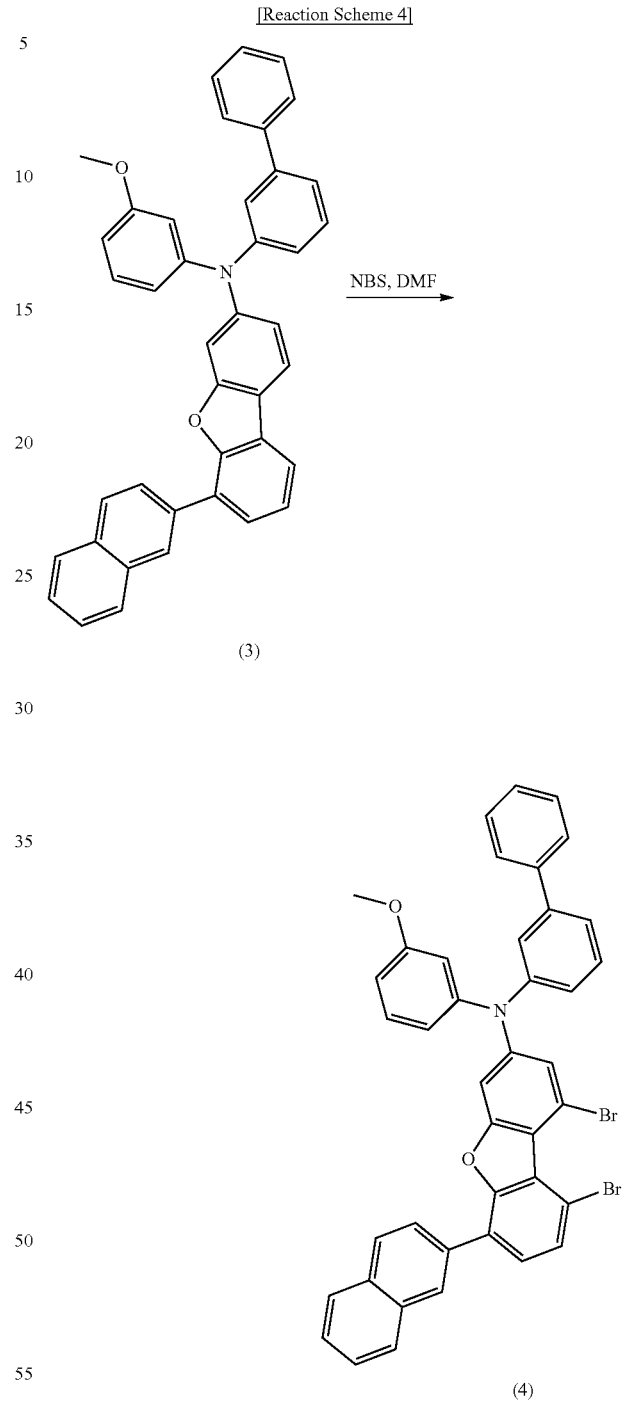

33.6 g Intermediate (1) and 27.3 g Intermediate (2) were added into a dry 2 L three-neck flask, followed by adding 600 mL dry and degassed toluene to dissolve. Then, 25.9 g sodium tert-butoxide (3 eq.), 0.4 g catalyst palladium diacetate (2% mol) and 2.2 g 1,1'-binaphthyl-2,2'-bis(diphenylphosphino) (BINAP, 4% mol) ligand were added. The reaction mixture was heated up to 110° C. and reacted overnight. After the reaction finished and the reaction mixture was cooled down to room temperature. The residual was absorbed by the added activated carbon, filtered by suction filtration and removed with solvent by rotary evaporation and recrystallized with a mixture of toluene and ethanol, to produce 43.4 g Intermediate (3) at a yield of 85%.

43.4 g Intermediate (3) was added into a 2 L three-neck flask, followed by adding 600 mL DMF to dissolve. Then 30.0 g NBS (2.2 eq.) was added and the reaction mixture was stirred overnight at room temperature in the dark. After the reaction finished, a large amount of water was added to separate out solid matter, followed by filtration. The filter cake was washed with water three times, dried and recrystallized with a mixture of toluene and ethanol, to produce 47.7 g Intermediate (4) at a yield of 86%.

Synthesis of Intermediate (5)

Synthesis of Intermediate (6)

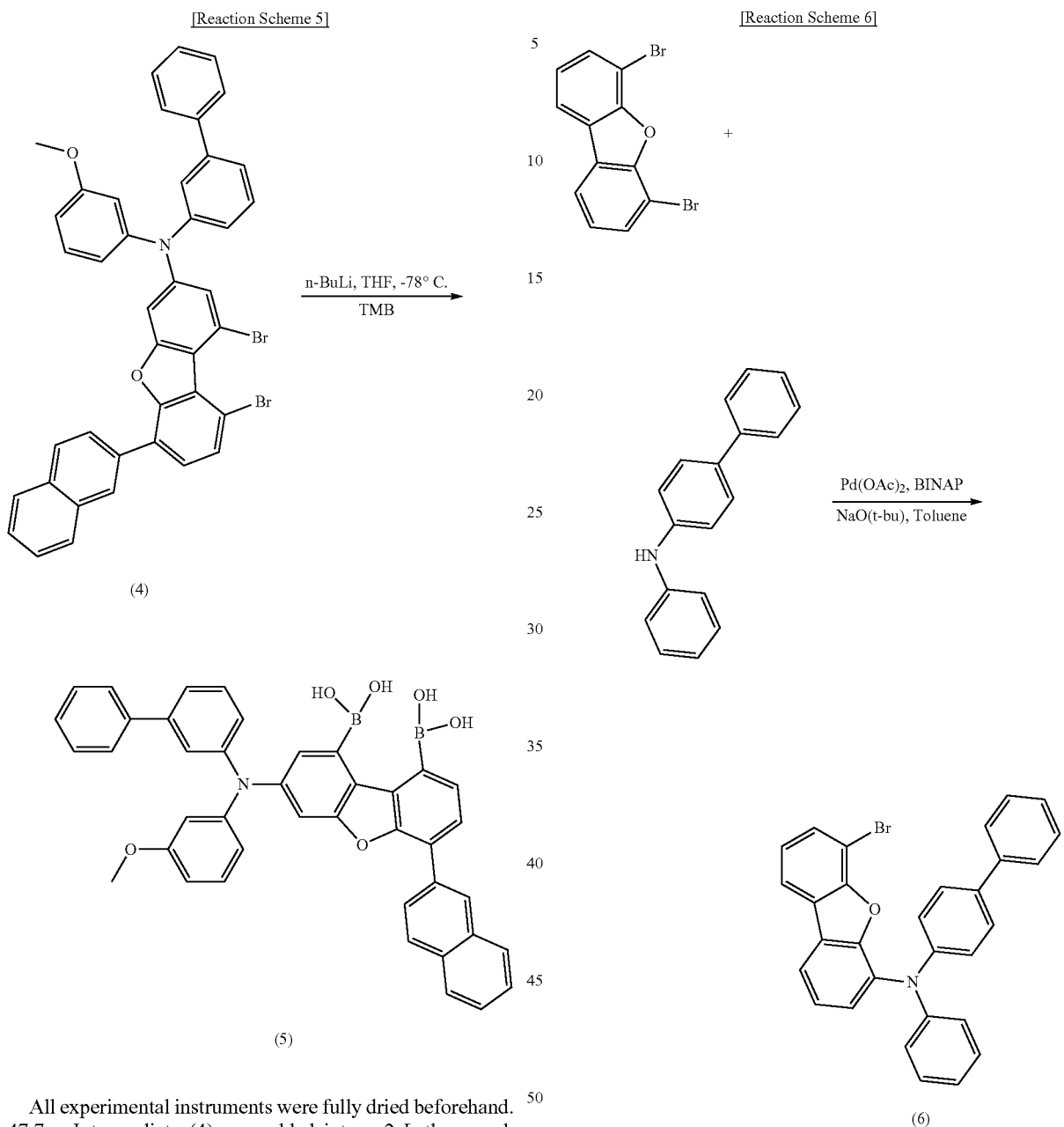

All experimental instruments were fully dried beforehand. 47.7 g Intermediate (4) was added into a 2 L three-neck flask, followed by adding 800 mL dry tetrahydrofuran to dissolve. After the reaction mixture was cooled down to −78° C., 65.8 mL n-BuLi (2.5M) was added dropwise. After the addition the residual was stirred for 1 hour at the above temperature, 20.5 g trimethyl borate (3.0 eq.) was added dropwise. After the addition, the residual was stirred overnight at room temperature. After the reaction finished, hydrochloric acid solution (4M) was added and the reaction mixture was extracted with dichloromethane. The organic phase was washed with saturated aqueous NaCl solution until reaching a neutral state, followed by drying, rotating removal of solvent and boiling with ethyl acetate, to produce a crude product which is then filtered to produce 34.5 g filter cake, i.e. boric acid product Intermediate (5), at a yield of 80%.

32.6 g 3,6-dibromo-diphenylfuran and 27.0 g 4-phenyl-amide bibenzene were added into a dry 2 L three-neck flask, followed by adding 600 mL dry and degassed toluene to dissolve. Then, 28.8 g sodium tert-butoxide (3 eq.), 0.45 g catalyst palladium diacetate (2% mol) and 2.5 g 1,1'-binaphthyl-2,2'-bis(diphenylphosphino) (BINAP, 4% mol) ligand were added. The reaction mixture was heated up to 110° C. and reacted overnight. After the reaction finished and the reaction mixture was cooled down to room temperature, the residual was absorbed by the added activated carbon, filtered by suction filtration and removed with solvent by rotary evaporation and then recrystallized with a mixture of toluene and ethanol, to produce 41.7 g Intermediate (6) at a yield of 85%.

Synthesis of Intermediate (7)

[Reaction Scheme 7]

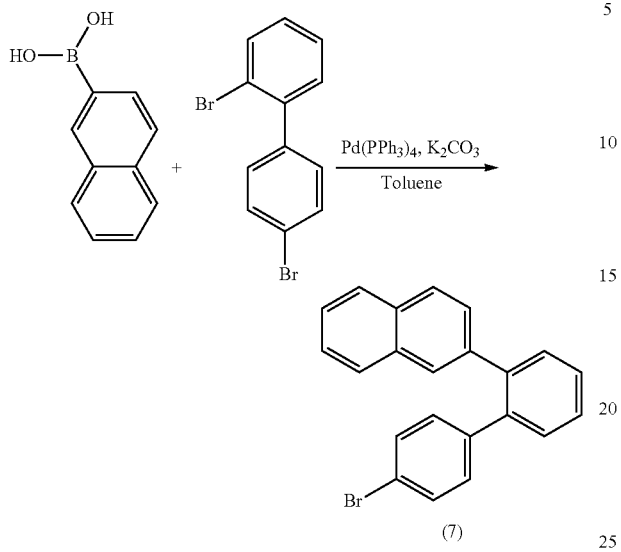

(7)

18.9 g 2-naphthyl boric acid and 31.2 g 2,4-dibromo bibenzene were added into a 2 L three-neck flask, followed by adding 600 mL toluene and 150 mL ethanol to dissolve. The reaction mixture was aerated with nitrogen gas for 15 minutes, then 150 mL aqueous $K_2CO_3$ solution (3.0 eq., 2M) and 2.3 g $Pd(PPh_3)_4$ (2 mol %) were sequentially added. The reaction mixture was heated up to 110° C. and reacted overnight. After the reaction finished, the residual was absorbed by the added activated carbon, filtered by suction filtration and removed with solvent by rotary evaporation, followed by drying and recrystallization with a mixture of toluene and ethanol, to produce 31.6 g Intermediate (7) at a yield of 88%.

Synthesis of Intermediate (8)

All experimental instruments were fully dried beforehand. 31.6 g Intermediate (7) was added into a 2 L three-neck flask, followed by adding 600 mL dry tetrahydrofuran to dissolve. After the reaction mixture was cooled down to −78° C., 38.7 mL n-BuLi (2.5M) was added dropwise. After the addition, the residual was stirred for 1 hour at the above temperature. 11.9 g trimethyl borate (1.3 eq.) was added dropwise, after the addition the residual was stirred overnight at room temperature. After the reaction finished, hydrochloric acid solution (4M) was added and the reaction mixture was extracted with dichloromethane. The organic phase was washed with saturated aqueous NaCl solution until neutral, followed by drying, rotating removal of solvent and boiling with ethyl acetate, to produce a crude product which is then filtered to produce 21.7 g filter cake, i.e. boric acid product Intermediate (8), at a yield of 76%.

Synthesis of Intermediate (9)

[Reaction Scheme 9]

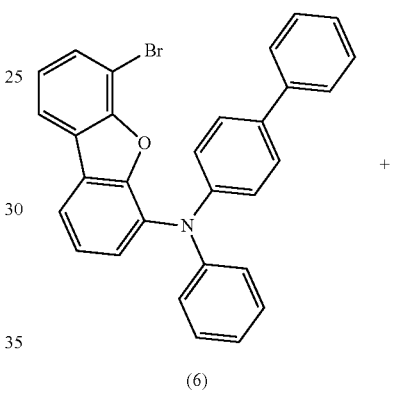

(6)

[Reaction Scheme 8]

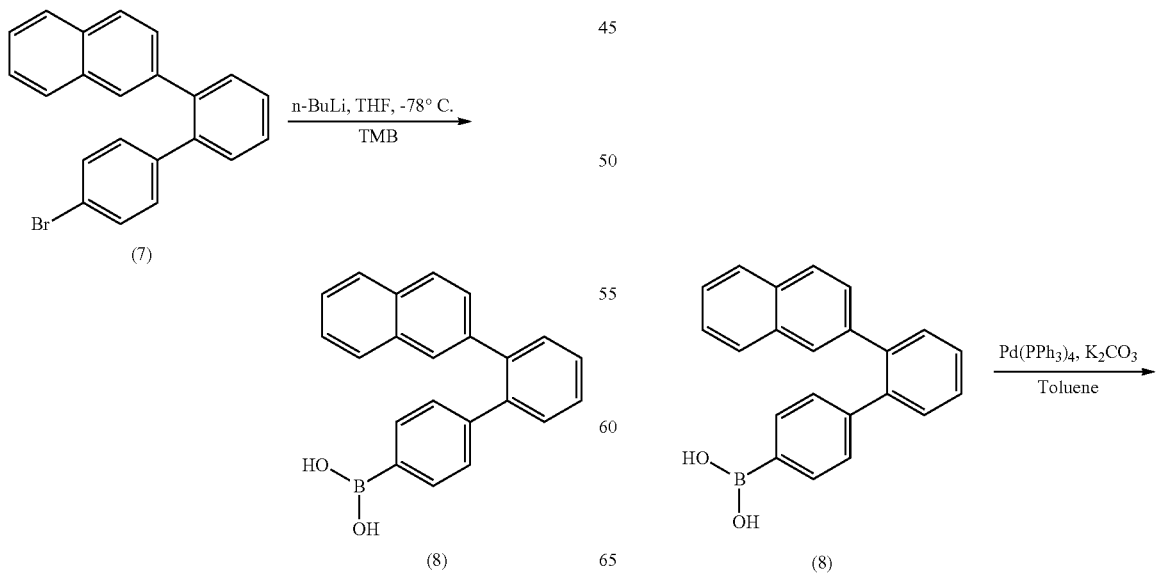

91
-continued

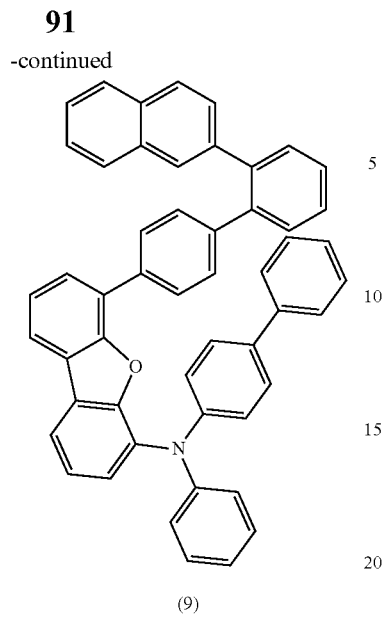

(9)

92
-continued

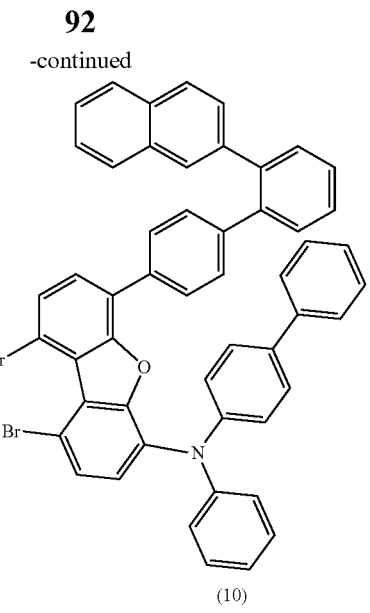

(10)

21.7 g Intermediate (8) and 29.8 g Intermediate (6) were added into a 2 L three-neck flask, followed by adding 600 mL toluene and 150 mL ethanol to dissolve. The reaction mixture was aerated with nitrogen gas for 15 minutes, then 91.4 mL aqueous $K_2CO_3$ solution (3.0 eq., 2M) and 1.4 g $Pd(PPh_3)_4$ (2 mol %) were sequentially added. The reaction mixture was heated up to 110° C. and reacted overnight. After the reaction finished, the residual was absorbed by the added activated carbon, filtered by suction filtration and removed with solvent by rotary evaporation, followed by drying and recrystallization with a mixture of toluene and ethanol, to produce 34.9 g Intermediate (9) at a yield of 83%.

Synthesis of Intermediate J

[Reaction Scheme 10]

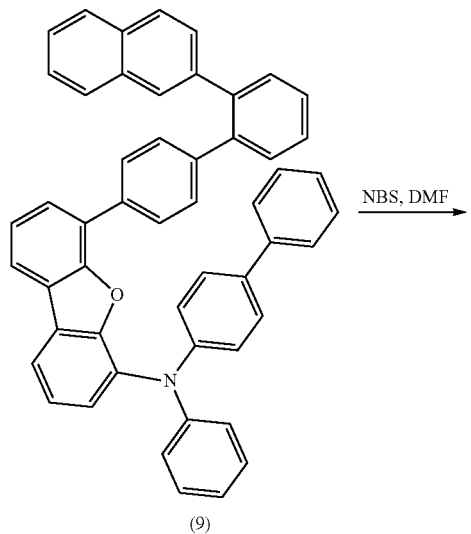

34.9 g Intermediate (9) was added into a 2 L three-neck flask, followed by adding 600 mL DMF to dissolve. Then 19.8 g NBS (2.2 eq.) was added and the reaction mixture was stirred overnight at room temperature in the dark. After the reaction finished, a large amount of water was added to separate out solid matter, followed by filtration. The filter cake was washed with water three times, dried and recrystallized with a mixture of toluene and ethanol, to produce 39.0 g Intermediate (10) at a yield of 91%.

Synthesis of Intermediate K

[Reaction Scheme 11]

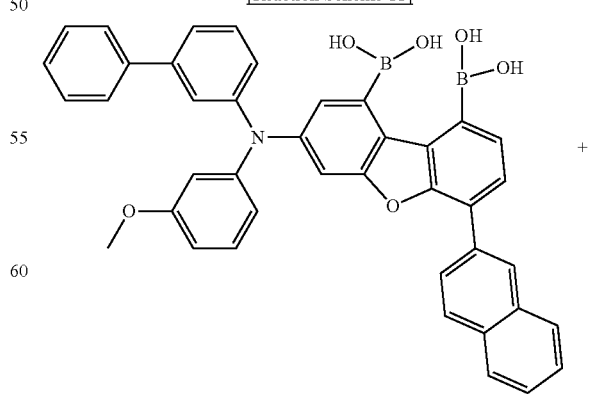

Compound Example 2

Synthesis of Compound 20
Synthesis of Intermediate (11)

[Reaction Scheme 12]

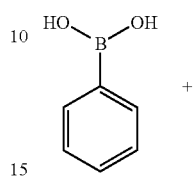
+
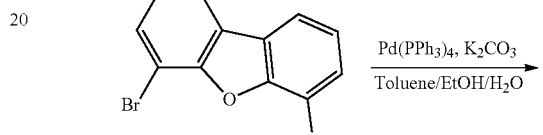

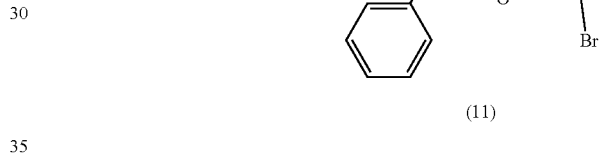

(11)

13.4 g phenyl boric acid and 32.6 g 4,6-dibromo-dibenzofuran were added into a 2 L three-neck flask, followed by adding 700 mL toluene and 150 mL ethanol to dissolve. The reaction mixture was aerated with nitrogen gas for 15 minutes, then 150 mL aqueous $K_2CO_3$ solution (6.0 eq., 2M) and 2.3 g $Pd(PPh_3)_4$ (2 mol %) were sequentially added. The reaction mixture was heated up to 110° C. and reacted overnight. After the reaction finished, the residual was absorbed by the added activated carbon, filtered by suction filtration and removed with solvent by rotary evaporation, then followed by drying and recrystallization with a mixture of toluene and ethanol, to produce 28.1 g Intermediate (11) at a yield of 87%.

Synthesis of Intermediate (12)

[Reaction Scheme 13]

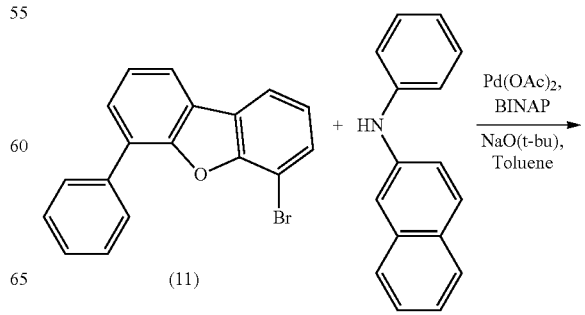

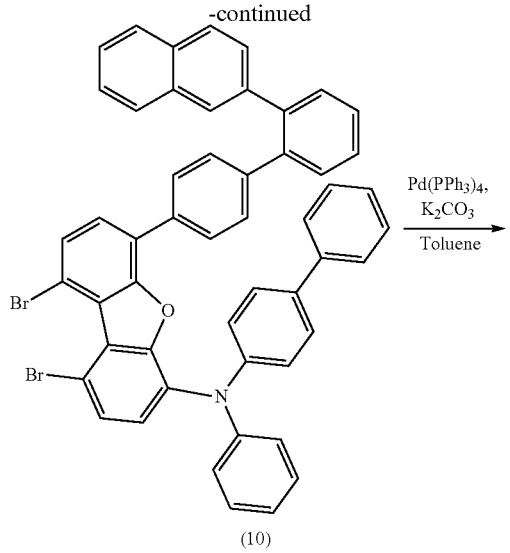

(10)

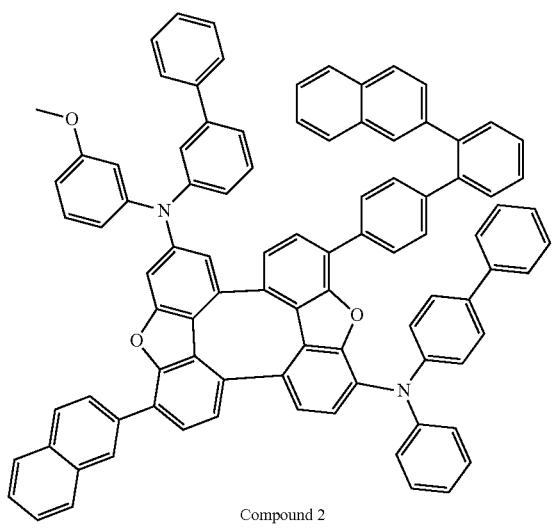

Compound 2

39.0 g Intermediate (10) and 33.2 g Intermediate (5) were added into a 2 L three-neck flask, followed by adding 800 mL toluene and 200 mL ethanol to dissolve. The reaction mixture was aerated with nitrogen gas for 15 minutes, then 138 mL aqueous $K_2CO_3$ solution (6.0 eq., 2M) and 2.1 g $Pd(PPh_3)_4$ (4 mol %) were sequentially added. The reaction mixture was heated up to 110° C. and reacted overnight. After the reaction finished, the residual was absorbed by the added activated carbon, filtered by suction filtration and removed with solvent by rotary evaporation, followed by drying and recrystallization with a mixture of toluene and ethanol, to produce 47.3 g Compound 2 in 82% yield.

1H NMR (DMSO, 300 Hz): δ(ppm)=8.34-7.82 (m, 12H), 7.78-7.38 (m, 28H), 7.36-7.12 (m, 10H), 7.10-6.87 (m, 4H), 6.82-6.68 (m, 2H), 6.60-6.45 (d, 1H), 4.03-3.46 (s, 3H)

MS(FAB): 1253 (M+)

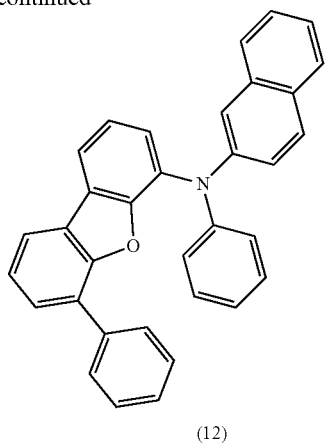

(12)

28.1 g Intermediate (11) and 21 g N-phenyl-2-naphthylamine were added into a dry 2 L three-neck flask, followed by adding 600 mL dry and degassed toluene to dissolve. Then, 25.1 g sodium tert-butoxide, 2.0 g catalyst palladium diacetate (2% mol) and 2.2 g 1,1'-binaphthyl-2,2'-bis(diphenylphosphino) (BINAP, 4% mol) ligand were added. The reaction mixture was heated up to 110° C. and reacted overnight. After the reaction finished and the reaction mixture was cooled down to room temperature, the residual was absorbed by the added activated carbon, filtered by suction filtration and removed with solvent by rotary evaporation followed by recrystallization with a mixture of toluene and ethanol, to produce 36.1 g Intermediate (12) at a yield of 90%.

Synthesis of Intermediate (13)

[Reaction Scheme 14]

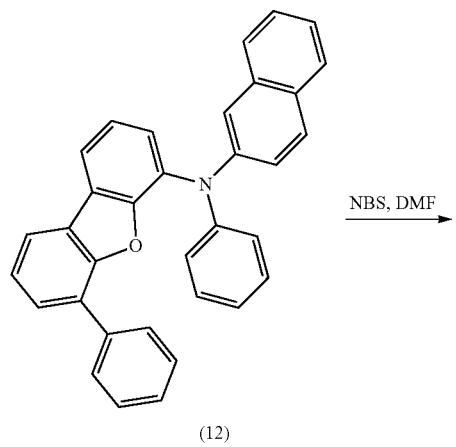

36.1 g Intermediate (12) was added into a 2 L three-neck flask, followed by adding 600 mL DMF to dissolve. Then 30.6 g NBS (2.2 eq.) was added and the reaction mixture was stirred overnight at room temperature in the dark. After the reaction finished, a large amount of water was added to separate out solid matter, followed by filtration. The filter cake was washed with water three times, dried and recrystallized with a mixture of toluene and ethanol, to produce 45.1 g Intermediate (13) at a yield of 93%.

Synthesis of Intermediate (14)

[Reaction Scheme 15]

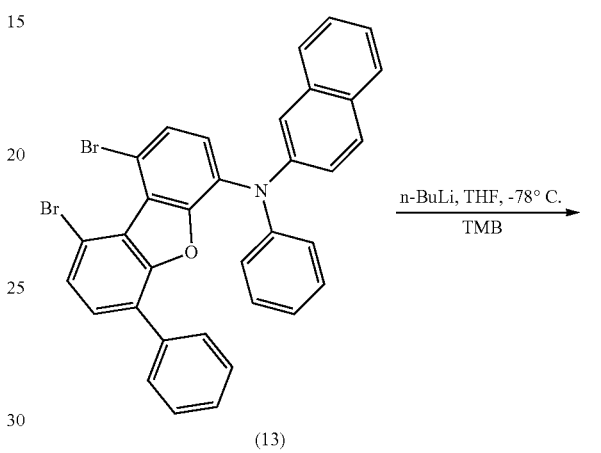

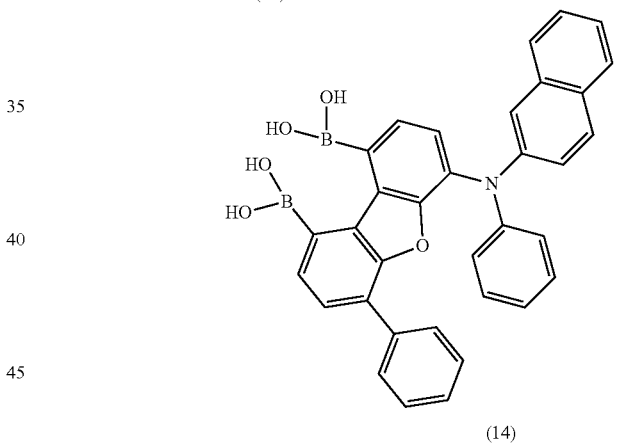

(14)

All experimental instruments were fully dried beforehand. 45.1 g Intermediate (13) was added into a 2 L three-neck flask, followed by adding 700 mL dry tetrahydrofuran to dissolve. After the reaction mixture was cooled down to −78° C., 72.8 mL n-BuLi (2.5 eq., 2.5M) was added dropwise. After the addition, the residual was stirred for 1 hour at the above temperature. 22.7 g trimethyl borate (3 eq.) was added dropwise. After the addition, the residual was stirred overnight at room temperature. After the reaction finished, hydrochloric acid solution (4M) was added and the reaction mixture was extracted with dichloromethane. The organic phase was washed with saturated aqueous NaCl solution until reaching a neutral state, followed by drying, rotating removal of solvent and boiling with ethyl acetate, to produce a crude product which is then filtered to produce 30.4 g filter cake, i.e. boric acid product Intermediate (14), at a yield of 76%.

Synthesis of Intermediate (15)

[Reaction Scheme 16]

32.6 g 4,6-dibromo dibenzofuran and 24.4 g N-phenyl-2-naphthylamine (1.05 eq.) were added into a dry 2 L three-neck flask, followed by adding 600 mL dry and degassed toluene to dissolve. Then, 28.8 g sodium tert-butoxide, 0.45 g catalyst palladium diacetate (2% mol) and 2.5 g 1,1'-binaphthyl-2,2'-bis(diphenylphosphino) (BINAP, 4% mol) ligand were added. The reaction mixture was heated up to 110° C. and reacted overnight. After the reaction finished and the reaction mixture was cooled down to room temperature, the residual was absorbed by the added activated carbon, filtered by suction filtration and removed with solvent by rotary evaporation, followed by recrystallization with a mixture of toluene and ethanol, to produce 40.9 g Intermediate (15) at a yield of 88%.

Synthesis of Intermediate (16)

3.2 g Mg (1.5 eq.), 15 mL THF, and 0.32 g I2 were added into a dry 2 L three-neck flask. The reaction mixture was heated to trigger reaction. Then a solution of 15.7 g tert-butyl bromide (1.3 eq.) in 300 mL THF was added dropwise at room temperature. After the dropwise addition, the reaction mixture was reacted at 51° C. for 2 hours and was thereafter left to stand for 5 minutes. The supernatant was added dropwise to a solution of 40.9 g Intermediate (15) in 600 mL THF, followed by refluxing overnight for 15 hours. After the reaction finished, the reaction mixture was cooled down to room temperature, followed by quenching with drops of water, extraction with a mixture of dichloromethane and water, washing with water, drying, rotating removal of solvent and purification by chromatography column, to produce 31.5 g Intermediate (16) at a yield of 81%.

Synthesis of Intermediate (17)

[Reaction Scheme 17]

[Reaction Scheme 18]

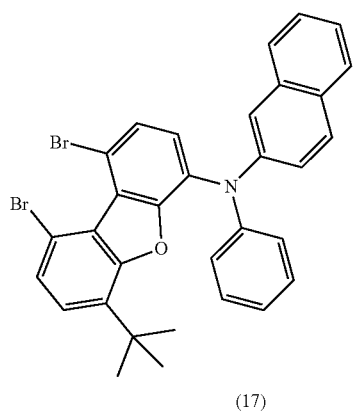

(17)

31.5 g Intermediate (16) was added into a 2 L three-neck flask, followed by adding 600 mL DMF to dissolve. Then 27.9 g NBS (2.2 eq.) was added and the reaction mixture was stirred overnight at room temperature in the dark. After the reaction finished, a large amount of water was added to separate out solid matter, followed by filtration. The filter cake was washed with water three times, dried and recrystallized with a mixture of toluene and ethanol, to produce 35.5 g Intermediate (17) at a yield of 83%.

Synthesis of Intermediate (18)

[Reaction Scheme 19]

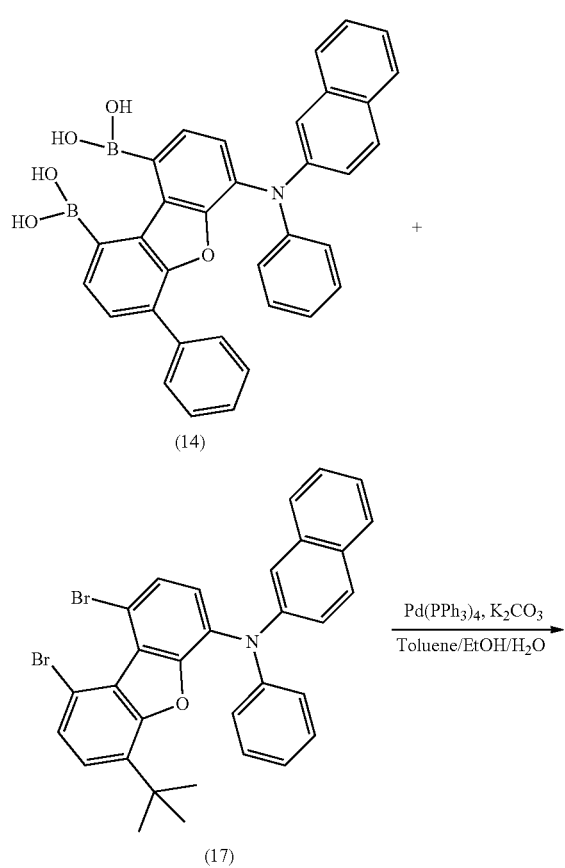

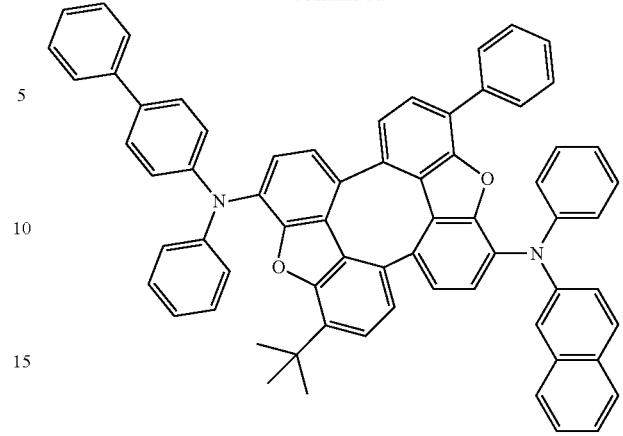

Compound 20

30.4 g Intermediate (14) and 30.2 g Intermediate (17) were added into a 2 L three-neck flask, followed by adding 600 mL toluene and 150 mL ethanol to dissolve. The reaction mixture was aerated with nitrogen gas for 15 minutes, then 151 mL aqueous $K_2CO_3$ solution (6.0 eq., 2M) and 2.4 g $Pd(PPh_3)_4$ (4 mol %) were sequentially added. The reaction mixture was heated up to 110° C. and reacted overnight. After the reaction finished, the residual was absorbed by the added activated carbon, filtered by suction filtration and removed with solvent by rotary evaporation, followed by dry and recrystallization with a mixture of toluene and ethanol, to produce 40 g Compound 20 at a yield of 81%.

1H NMR (DMSO, 300 Hz): δ(ppm)=8.14-7.88 (d, 1H), 7.86-7.63 (m, 5H), 7.61-7.35 (m, 19H), 7.33-7.20 (d, 5H), 7.18-6.75 (m, 9H), 1.68-1.55 (s, 9H)

MS(FAB): 925 (M+)

Compound Example 3

Synthesis of Compound 40
Synthesis of Intermediate (18)

[Reaction Scheme 20]

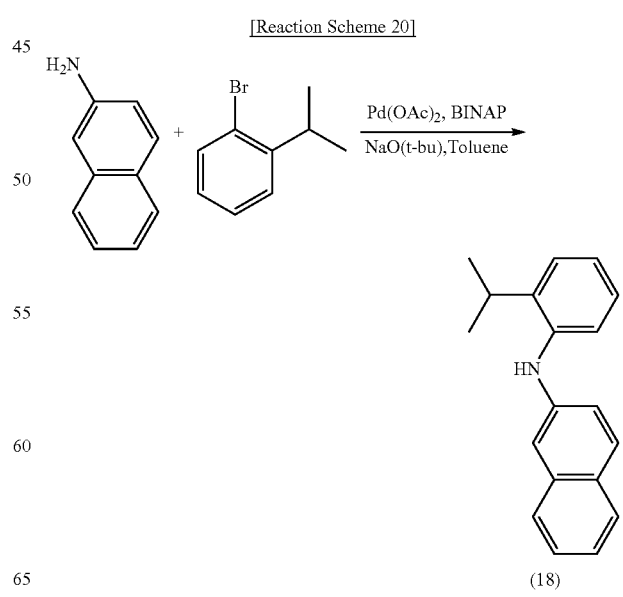

29.87 g 1-bromo-2-isopropyl benzene and 23.6 g 2-naphthylamine were added into a dry 2 L three-neck flask, followed by adding 600 mL dry and degassed toluene to dissolve. Then, 43.2 g sodium tert-butoxide (3.0 eq.), 0.7 g catalyst palladium diacetate (2% mol) and 3.7 g 1,1'-binaphthyl-2,2'-bis(diphenylphosphino) (BINAP, 4% mol) ligand were added. The reaction mixture was heated up to 110° C. and reacted overnight. After the reaction finished and the reaction mixture was cooled down to room temperature. The residual was absorbed by the added activated carbon, filtered by suction filtration and removed with solvent by rotary evaporation, followed by recrystallization with a mixture of toluene and ethanol, to produce 34.5 g Intermediate (18) at a yield of 88%.

Synthesis of Intermediate (19)

[Reaction Scheme 21]

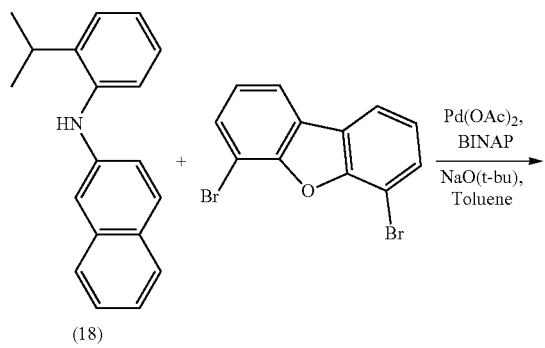

(18)

(19)

34.5 g Intermediate (18) and 39.1 g 4,6-dibromo dibenzofuran were added into a dry 2 L three-neck flask, followed by adding 800 mL dry and degassed toluene to dissolve. Then, 34.6 g sodium tert-butoxide (3.0 eq.), 0.554 g catalyst palladium diacetate (2% mol) and 3.0 g 1,1'-binaphthyl-2,2'-bis(diphenylphosphino) (BINAP, 4% mol) ligand were added. The reaction mixture was heated up to 110° C. and reacted overnight. After the reaction finished and the reaction mixture was cooled down to room temperature. The residual was absorbed by the added activated carbon, filtered by suction filtration and removed with solvent by rotary evaporation, followed by recrystallization with a mixture of toluene and ethanol, to produce 52.8 g Intermediate (19) at a yield of 87%.

Synthesis of Intermediate (20)

[Reaction Scheme 22]

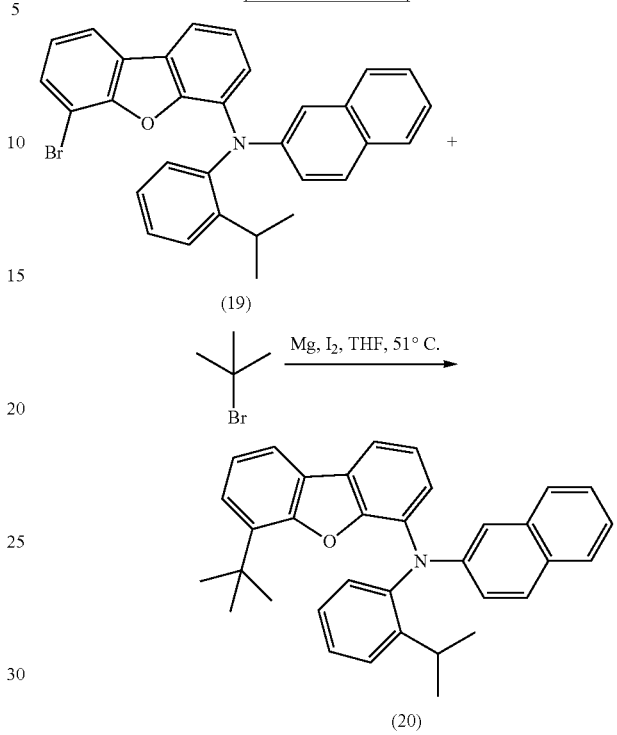

(19)

(20)

3.8 g Mg (1.5 eq.), 20 mL THF, and 0.38 g I2 were added into a dry 2 L three-neck flask. The reaction mixture was heated to trigger reaction. Then a solution of 18.6 g tert-butyl bromide (1.3 eq.) in 180 mL THF was added dropwise at room temperature. After the dropwise addition, the reaction mixture was reacted at 51° C. for 2 hours and was thereafter left to stand for 5 minutes. The supernatant was added dropwise to a solution of 52.8 g Intermediate (19) in 800 mL THF, followed by refluxing overnight for 15 hours. After the reaction finished, the reaction mixture was cooled down to room temperature, followed by quenching with drops of water, extraction with a mixture of dichloromethane and water, washing with water, drying, rotating removal of solvent and purification by chromatography column, to produce 42.9 g Intermediate (20) at a yield of 85%.

Synthesis of Intermediate (21)

[Reaction Scheme 23]

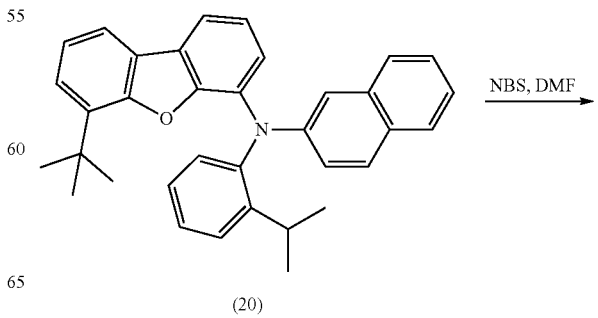

(20)

103

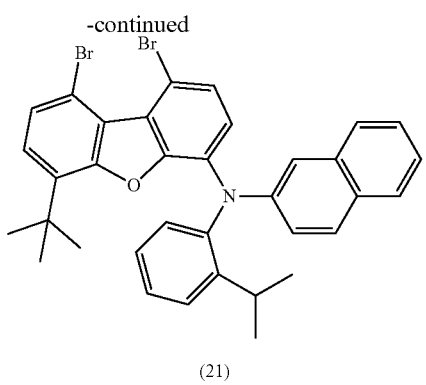

(21)

42.9 g Intermediate (20) was added into a 2 L three-neck flask, followed by adding 600 mL DMF to dissolve. Then 33.2 g NBS (2.1 eq.) was added and the reaction mixture was stirred overnight at room temperature in the dark. After the reaction finished, a large amount of water was added to separate out solid matter, followed by filtration. The filter cake was washed with water three times, dried and recrystallized with a mixture of toluene and ethanol, to produce 48.9 g Intermediate (21) at a yield of 86%.

Synthesis of Intermediate (22)

[Reaction Scheme 24]

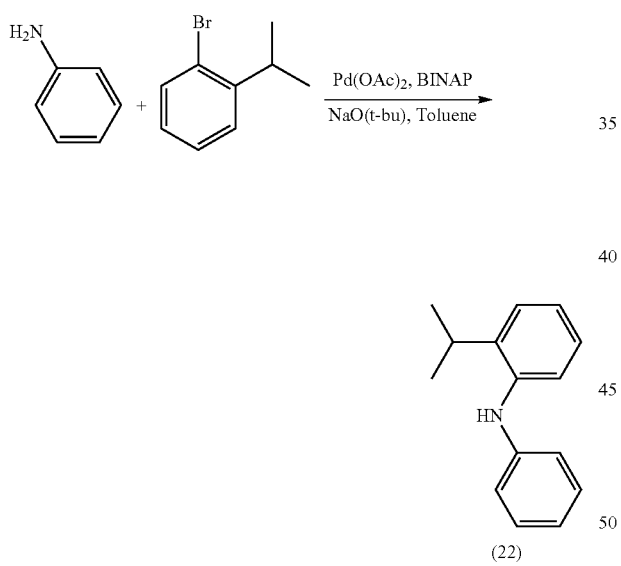

(22)

29.87 g 1-bromo-2-isopropyl benzene and 15.4 g phenyl naphthylamine were added into a dry 2 L three-neck flask, followed by adding 600 mL dry and degassed toluene to dissolve. Then, 43.2 g sodium tert-butoxide (3.0 eq.), 0.7 g catalyst palladium diacetate (2% mol) and 3.7 g 1,1'-binaphthyl-2,2'-bis(diphenylphosphino) (BINAP, 4% mol) ligand were added. The reaction mixture was heated up to 110° C. and reacted overnight. After the reaction finished and the reaction mixture was cooled down to room temperature. The residual was absorbed by the added activated carbon, filtered by suction filtration and removed with solvent by rotary evaporation, followed by recrystallization with a mixture of toluene and ethanol, to produce 26.9 g Intermediate (22) at a yield of 85%.

104

Synthesis of Intermediate (23)

[Reaction Scheme 25]

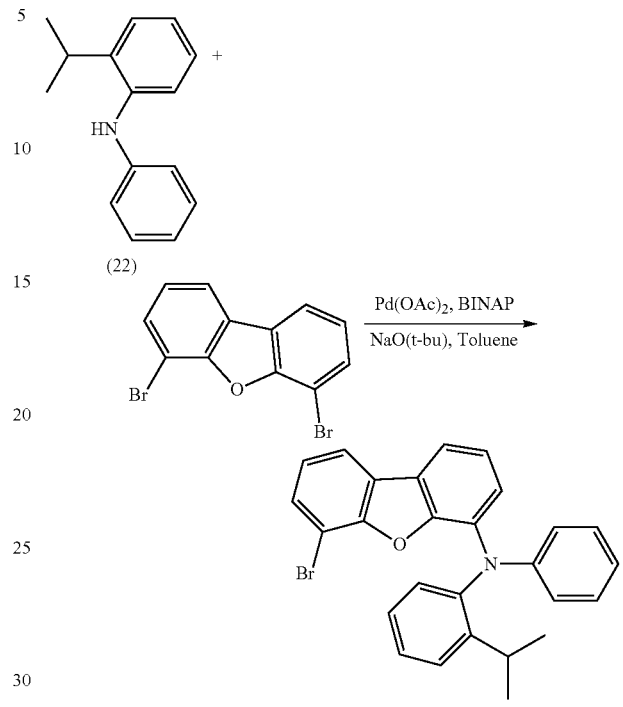

(23)

26.9 g Intermediate (22) and 37.8 g 4,6-dibromo dibenzofuran were added into a dry 2 L three-neck flask, followed by adding 800 mL dry and degassed toluene to dissolve. Then, 33.4 g sodium tert-butoxide (3.0 eq.), 0.52 g catalyst palladium diacetate (2% mol) and 2.9 g 1,1'-binaphthyl-2,2'-bis(diphenylphosphino) (BINAP, 4% mol) ligand were added. The reaction mixture was heated up to 110° C. and reacted overnight. After the reaction finished and the reaction mixture was cooled down to room temperature. The residual was absorbed by the added activated carbon, filtered by suction filtration and removed with solvent by rotary evaporation, followed by recrystallization with a mixture of toluene and ethanol, to produce 47.6 g Intermediate (23) at a yield of 90%.

Synthesis of Intermediate (24)

[Reaction Scheme 26]

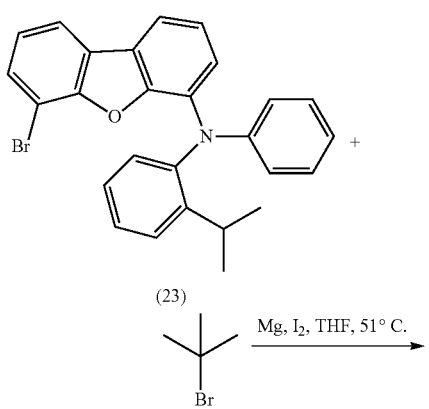

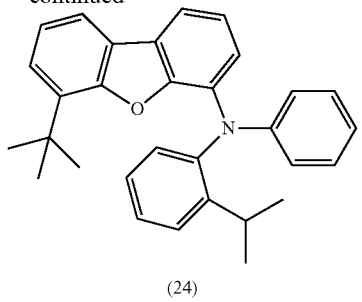

(24)

3.8 g Mg (1.5 eq.), 20 mL THF, and 0.38 g I$_2$ were added into a dry 2 L three-neck flask. The reaction mixture was heated to trigger reaction. Then a solution of 18.6 g tert-butyl bromide (1.3 eq.) in 180 mL THF was added dropwise at room temperature. After the dropwise addition, the reaction mixture was reacted at 51° C. for 2 hours and was thereafter left to stand for 5 minutes. The supernatant was added dropwise to a solution of 47.6 g Intermediate (23) in 800 mL THF, followed by refluxing overnight for 15 hours. After the reaction finished, the reaction mixture was cooled down to room temperature, followed by quenching with drops of water, extraction with a mixture of dichloromethane and water, washing with water, drying, rotating removal of solvent and purification by chromatography column, to produce 37.1 g Intermediate (24) at a yield of 82%.

Synthesis of Intermediate (25)

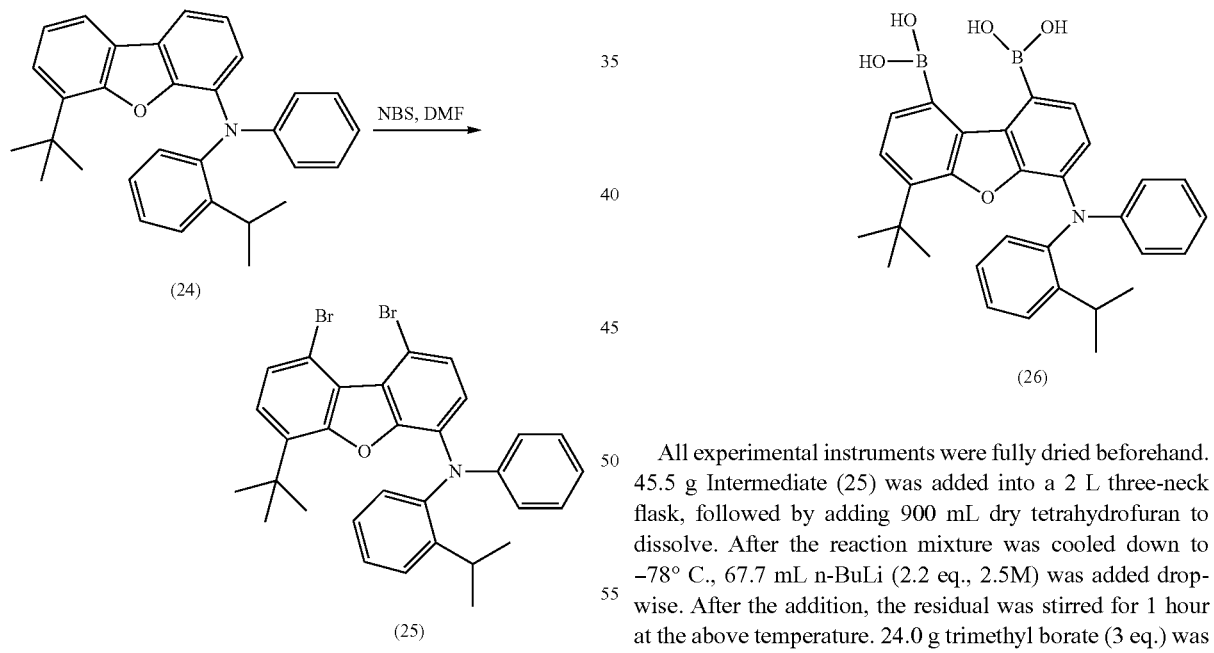

37.1 g Intermediate (24) was added into a 2 L three-neck flask, followed by adding 600 mL DMF to dissolve. Then 32 g NBS (2.1 eq.) was added and the reaction mixture was stirred overnight at room temperature in the dark. After the reaction finished, a large amount of water was added to separate out solid matter, followed by filtration. The filter cake was washed with water three times, dried and recrystallized with a mixture of toluene and ethanol, to produce 45.5 g Intermediate (25) at a yield of 90%.

Synthesis of Intermediate (26)

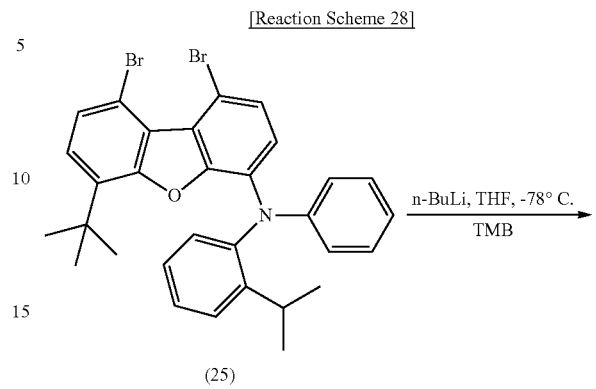

All experimental instruments were fully dried beforehand. 45.5 g Intermediate (25) was added into a 2 L three-neck flask, followed by adding 900 mL dry tetrahydrofuran to dissolve. After the reaction mixture was cooled down to −78° C., 67.7 mL n-BuLi (2.2 eq., 2.5M) was added dropwise. After the addition, the residual was stirred for 1 hour at the above temperature. 24.0 g trimethyl borate (3 eq.) was added dropwise, followed by stirring overnight at room temperature. After the reaction finished, hydrochloric acid solution (4M) was added and the reaction mixture was extracted with dichloromethane. The organic phase was washed with saturated aqueous NaCl solution until reaching a neutral state, followed by drying, rotating removal of solvent and boiling with ethyl acetate, to produce a crude product which is then filtered to produce 30.5 g filter cake, i.e. boric acid product Intermediate (26), at a yield of 76%.

Synthesis of Compound 40

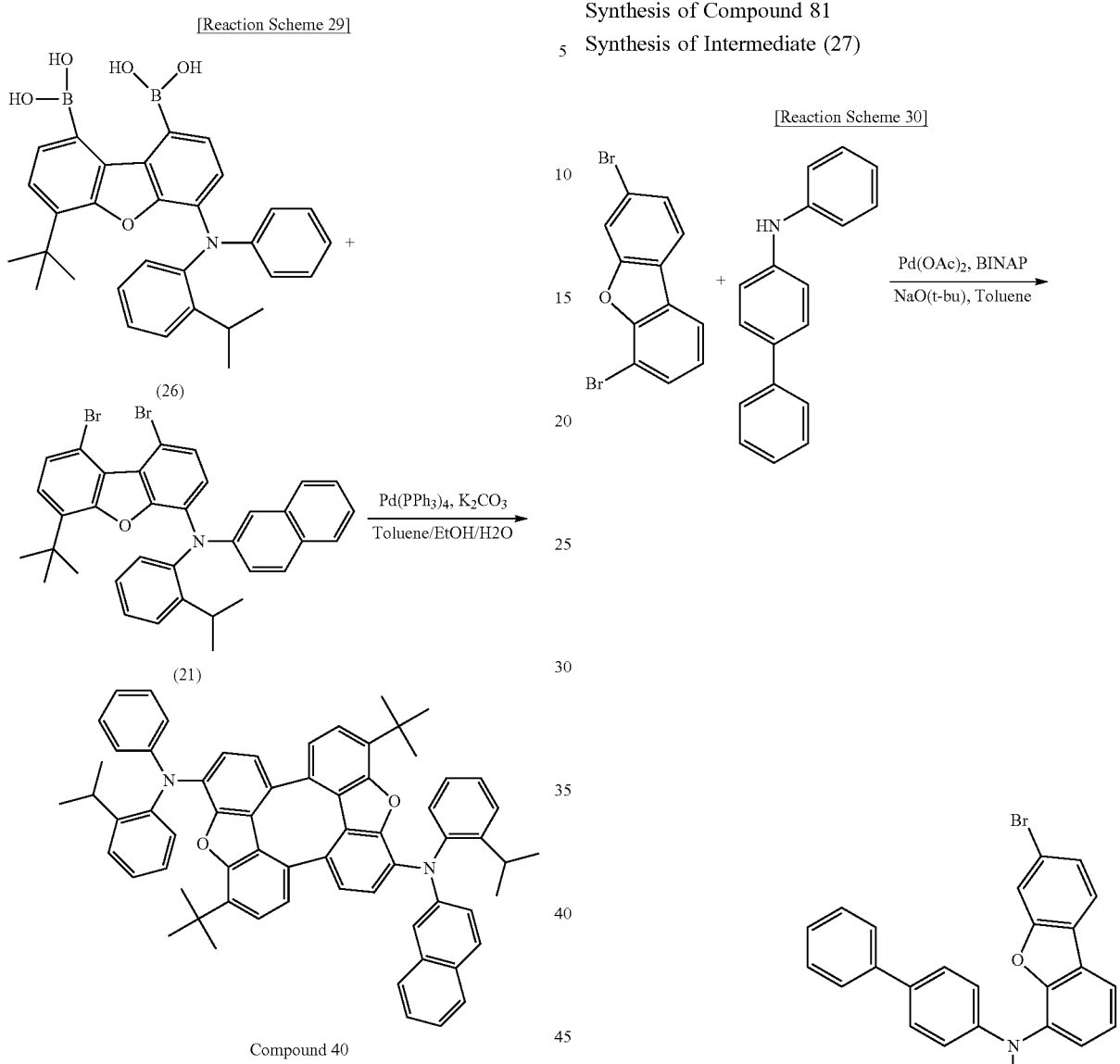

30.5 g Intermediate (26) (1.1 eq.) and 34.1 g Intermediate (21) were added into a 2 L three-neck flask, followed by adding 600 mL toluene and 150 mL ethanol to dissolve. The reaction mixture was aerated with nitrogen gas for 15 minutes, then 160 mL aqueous $K_2CO_3$ solution (6.0 eq., 2M) and 2.5 g $Pd(PPh_3)_4$ (4 mol %) were sequentially added. The reaction mixture was heated up to 110° C. and reacted overnight. After the reaction finished, the residual was absorbed by the added activated carbon, filtered by suction filtration and removed with solvent by rotary evaporation followed by drying and recrystallization with a mixture of toluene and ethanol, to produce 35.4 g Compound 40 at a yield of 73%.

1H NMR (DMSO, 300 Hz): δ(ppm)=8.10-7.75 (d, 1H), 7.73-7.62 (d, 1H), 7.60-7.51 (d, 1H), 7.49-7.43 (m, 7H), 7.40-7.20 (m, 10H), 7.18-7.03 (m, 3H), 7.01-6.75 (m, 5H), 3.01-2.52 (q, 2H), 1.68-1.55 (s, 18H), 1.38-1.03 (d, 12H)

MS(FAB): 913 (M+)

Compound Example 4

Synthesis of Compound 81

Synthesis of Intermediate (27)

32.6 g 3,6-dibromo dibenzofuran and 27 g N-phenyl-4-biphenylamine were added into a dry 2 L three-neck flask, followed by adding 600 mL dry and degassed toluene to dissolve. Then, 28.8 g sodium tert-butoxide (3 eq.), 0.45 g catalyst palladium diacetate (2% mol) and 2.5 g 1,1'-binaphthyl-2,2'-bis(diphenylphosphino) (BINAP, 4% mol) ligand were added. The reaction mixture was heated up to 110° C. and reacted overnight. After the reaction finished and the reaction mixture was cooled down to room temperature, the residual was absorbed by the added activated carbon, filtered by suction filtration and removed with solvent by rotary evaporation, followed by recrystallization with a mixture of toluene and ethanol, to produce 43.6 g Intermediate (27) at a yield of 89%.

Synthesis of Intermediate (28)

[Reaction Scheme 31]

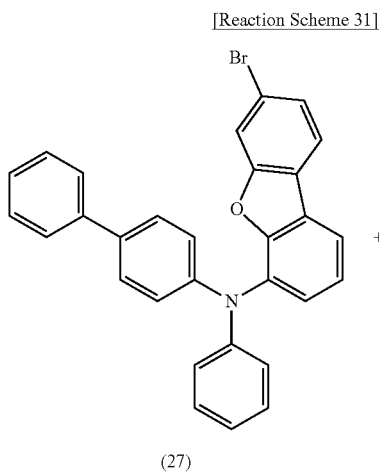

(27)

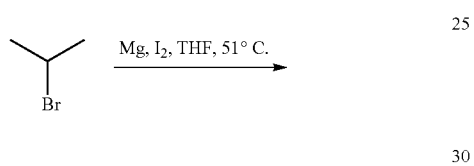

(28)

Synthesis of Intermediate (29)

[Reaction Scheme 32]

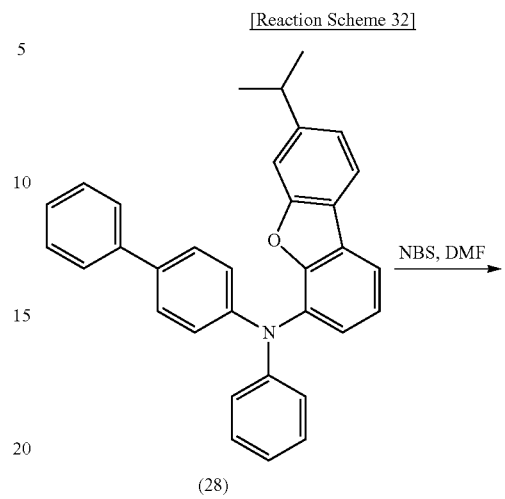

(28)

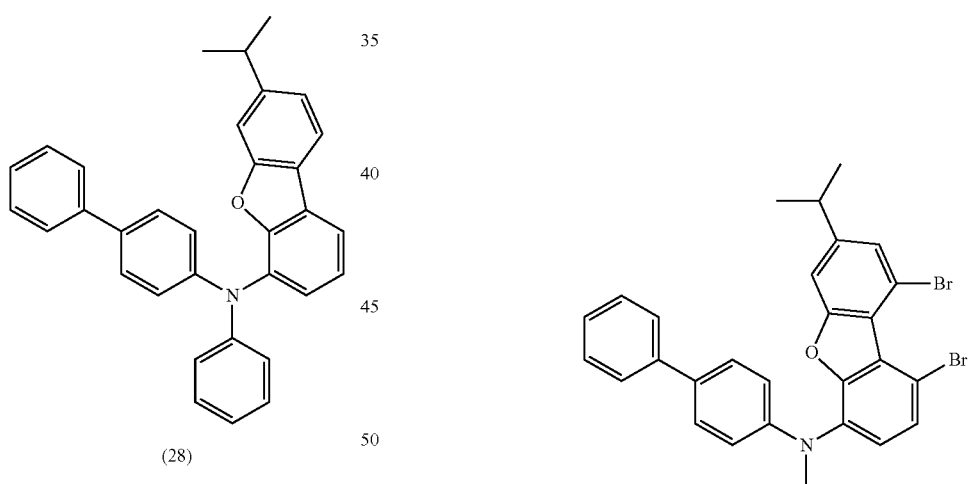

(29)

2.4 g Mg (1.5 eq.), 12 mL THF, and 0.24 g $I_2$ were added into a dry 2 L three-neck flask. The reaction mixture was heated to trigger reaction. Then a solution of 14.2 g 2-bromopropyl (1.3 eq.) in 140 mL THF was added dropwise at room temperature. After the dropwise addition, the reaction mixture was reacted at 51° C. for 2 hours and was thereafter left to stand for 5 minutes. The supernatant was added dropwise to a solution of 43.6 g Intermediate (27) in 600 mL THF, followed by refluxing overnight for 15 hours. After the reaction finished, the reaction mixture was cooled down to room temperature, followed by quenching with drops of water, extraction with a mixture of dichloromethane and water, washing with water, drying, rotating removal of solvent and purification by chromatography column, to produce 32.3 g Intermediate (28) at a yield of 80%.

32.3 g Intermediate (28) was added into a 2 L three-neck flask, followed by adding 600 mL DMF to dissolve. Then 27.8 g NBS (2.2 eq.) was added and the reaction mixture was stirred overnight at room temperature in the dark. After the reaction finished, a large amount of water was added to separate out solid matter, followed by filtration. The filter cake was washed with water three times, dried and recrystallized with a mixture of toluene and ethanol, to produce 39.6 g Intermediate (29) at a yield of 91%.

Synthesis of Intermediate (30)

[Reaction Scheme 33]

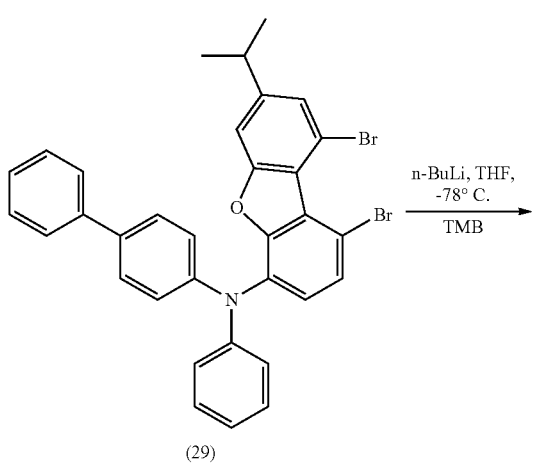

(29)

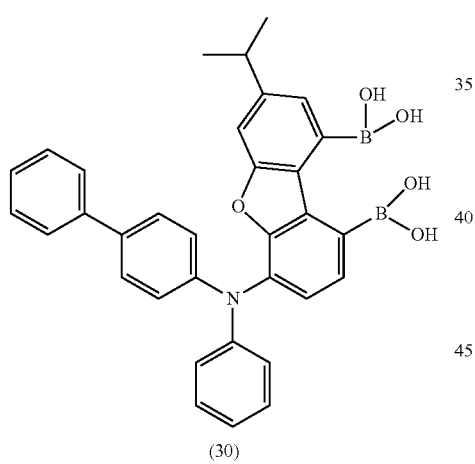

(30)

All experimental instruments were fully dried beforehand. 39.6 g Intermediate (29) was added into a 2 L three-neck flask, followed by adding 600 mL dry tetrahydrofuran to dissolve. After the reaction mixture was cooled down to −78° C., 64.8 mL n-BuLi (2.5 eq., 2.5M) was added dropwise. After the addition, the residual was stirred for 1 hour at the above temperature. 20.2 g trimethyl borate (3 eq.) was added dropwise, after the addition, the residual was stirred overnight at room temperature. After the reaction finished, hydrochloric acid solution (4M) was added and the reaction mixture was extracted with dichloromethane. The organic phase was washed with saturated aqueous NaCl solution until reaching a neutral state, followed by drying, rotating removal of solvent and boiling with ethyl acetate, to produce a crude product which is then filtered to produce 28.8 g filter cake, i.e. boric acid product Intermediate (30) at a yield of 82%.

Synthesis of Intermediate (31)

[Reaction Scheme 34]

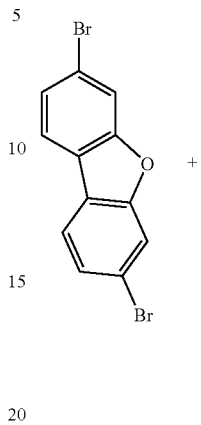

+

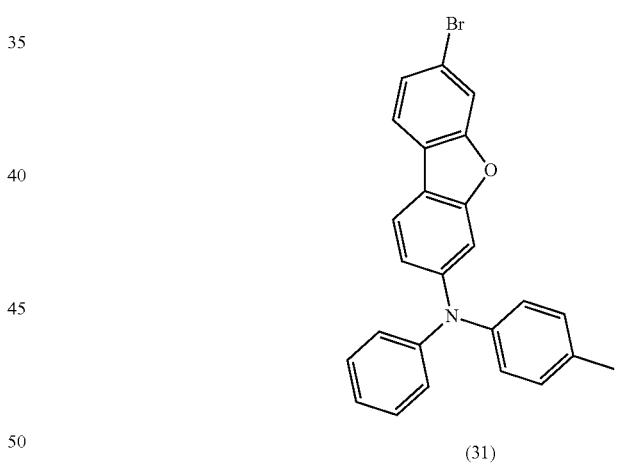

(31)

32.6 g 3,7-dibromo dibenzofuran and 20.2 g 4-methyl-N-phenyl phenylamine were added into a dry 2 L three-neck flask, followed by adding 600 mL dry and degassed toluene to dissolve. Then, 28.3 g sodium tert-butoxide (3 eq.), 0.45 g catalyst palladium diacetate (2% mol) and 2.5 g 1,1'-binaphthyl-2,2'-bis(diphenylphosphino) (BINAP, 2% mol) ligand were added. The reaction mixture was heated up to 110° C. and reacted overnight. After the reaction finished and the reaction mixture was cooled down to room temperature. The residual was absorbed by the added activated carbon, filtered by suction filtration and removed with solvent by rotary evaporation, followed by recrystallization with a mixture of toluene and ethanol, to produce 37.3 g Intermediate (31) at a yield of 87%.

Synthesis of Intermediate (32)

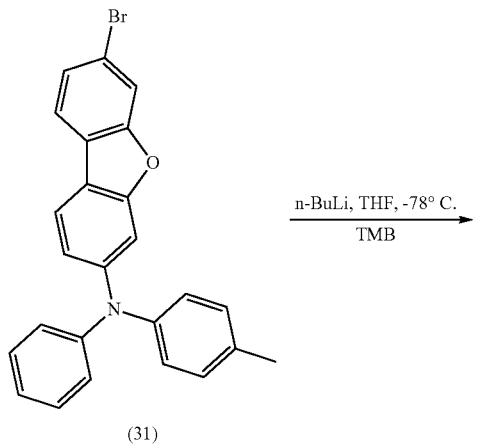

(31)

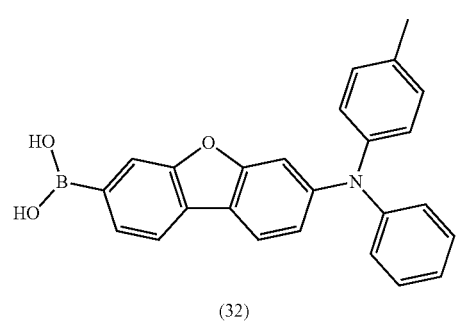

(32)

All experimental instruments were fully dried beforehand. 37.3 g Intermediate (31) was added into a 2 L three-neck flask, followed by adding 800 mL dry tetrahydrofuran to dissolve. After the reaction mixture was cooled down to −78° C., 38.3 mL n-BuLi (1.1 eq., 2.5M) was added dropwise, followed by stirring for 1 hour at the above temperature. 11.8 g trimethyl borate (1.3 eq.) was added dropwise, followed by stirring overnight at room temperature. After the reaction finished, hydrochloric acid solution (4M) was added and the reaction mixture was extracted with dichloromethane. The organic phase was washed with saturated aqueous NaCl solution until reaching a neutral state, followed by drying, rotating removal of solvent and boiling with ethyl acetate, to produce a crude product which is then filtered to produce 29.5 g filter cake, i.e. boric acid product Intermediate (32) at a yield of 86%.

Synthesis of Intermediate (33)

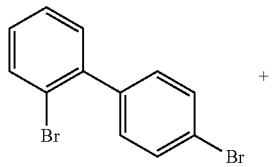

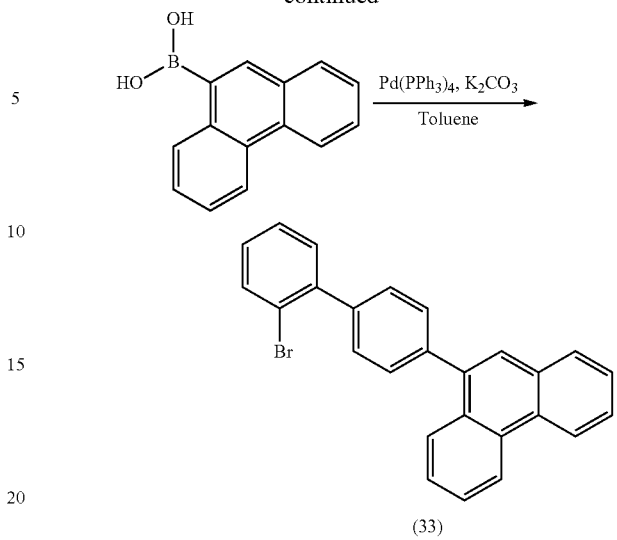

(33)

31.2 g 2,4-dibromo bibenzene and 24.4 g 9-phenanthrenyl boric acid were added into a 2 L three-neck flask, followed by adding 600 mL toluene and 150 mL ethanol to dissolve. The reaction mixture was aerated with nitrogen gas for 15 minutes, then 150 mL aqueous $K_2CO_3$ solution (3.0 eq., 2M) and 2.3 g $Pd(PPh_3)_4$ (2 mol %) were sequentially added. The reaction mixture was heated up to 110° C. and reacted overnight. After the reaction was completed, the residual was absorbed by the added activated carbon, filtered by suction filtration and removed with solvent by rotary evaporation, followed by drying and recrystallization with a mixture of toluene and ethanol, to produce 37.2 g Intermediate (33) at a yield of 91%.

Synthesis of Intermediate (34)

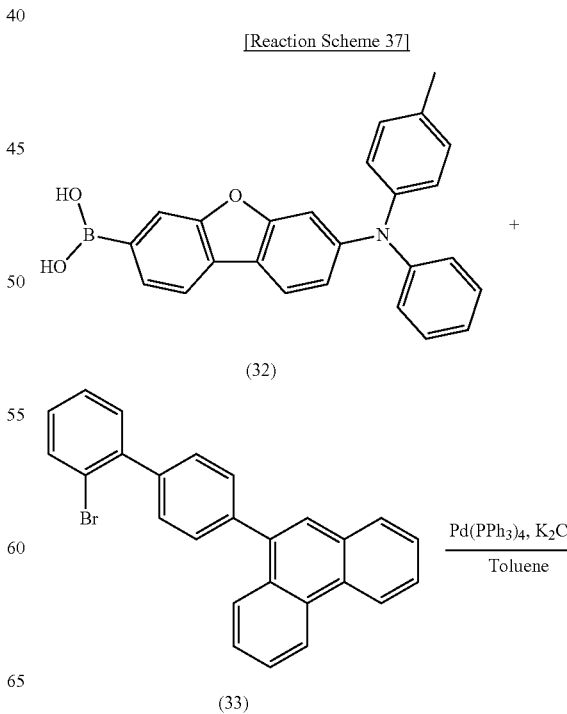

115

-continued

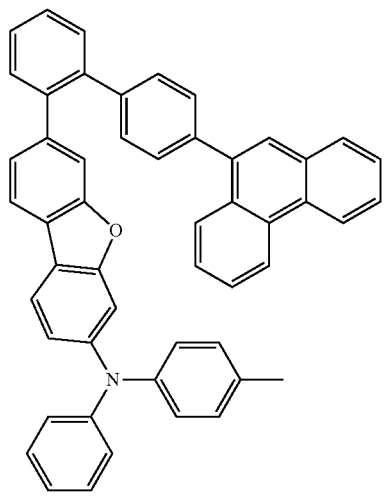

(34)

116

-continued

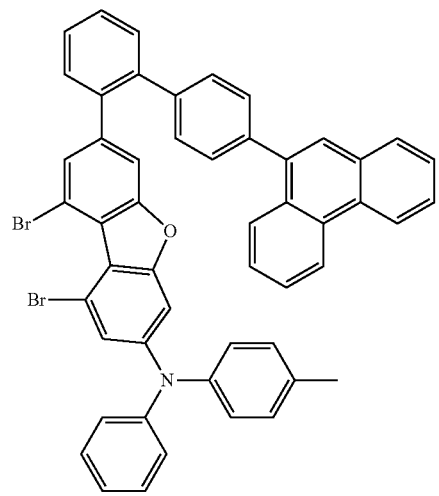

(35)

27.9 g Intermediate (32) and 29.5 g Intermediate (33) were added into a 2 L three-neck flask, followed by adding 600 mL toluene and 150 mL ethanol to dissolve. The reaction mixture was aerated with nitrogen gas for 15 minutes, then 102 mL aqueous $K_2CO_3$ solution (3.0 eq., 2M) and 1.6 g $Pd(PPh_3)_4$ (2 mol %) were sequentially added. The reaction mixture was heated up to 110° C. and reacted overnight. After the reaction finished, the residual was absorbed by the added activated carbon, filtered by suction filtration and removed with solvent by rotary evaporation followed by drying and recrystallization with a mixture of toluene and ethanol, to produce 41.1 g Intermediate (34) at a yield of 89%.

Synthesis of Intermediate (35)

41.1 g Intermediate (34) was added into a 2 L three-neck flask, followed by adding 600 mL DMF to dissolve. Then 23.7 g NBS (2.2 eq.) was added and the reaction mixture was stirred overnight at room temperature in the dark. After the reaction finished, a large amount of water was added to separate out solid matter, followed by filtration. The filter cake was washed with water three times, dried and recrystallized with a mixture of toluene and ethanol, to produce 44.6 g Intermediate (35) at a yield of 88%.

Synthesis of Compound 81

[Reaction Scheme 38]

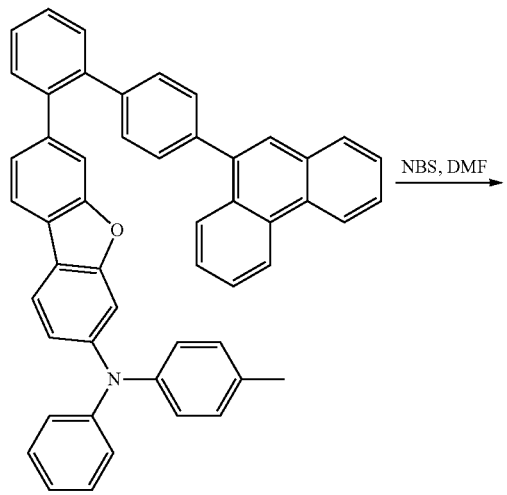

(34)

[Reaction Scheme 39]

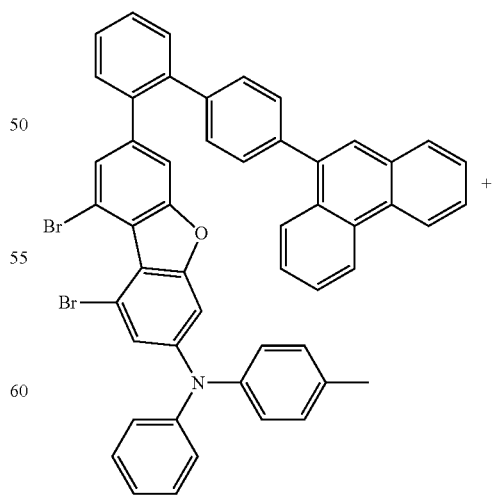

(35)

-continued

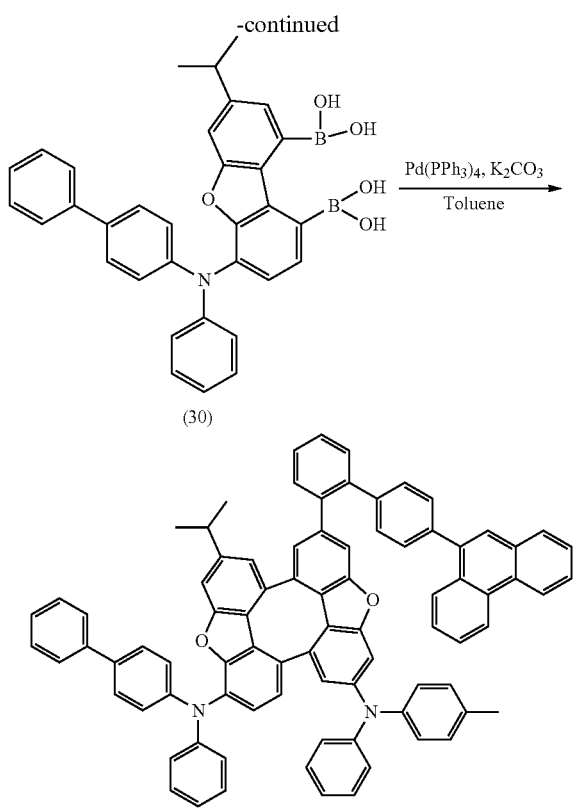

(30)

Compound 81

40.4 g Intermediate (35) and 28.8 g Intermediate (30) were added into a 2 L three-neck flask, followed by adding 800 mL toluene and 200 mL ethanol to dissolve. The reaction mixture was aerated with nitrogen gas for 15 minutes, then 145 mL aqueous K$_2$CO$_3$ solution (6.0 eq., 2M) and 2.2 g Pd(PPh$_3$)$_4$ (4 mol %) were sequentially added. The reaction mixture was heated up to 110° C. and reacted overnight. After the reaction finished, the residual was absorbed by the added activated carbon, filtered by suction filtration and removed with solvent by rotary evaporation followed by drying and recrystallization with a mixture of toluene and ethanol, to produce 46.4 g Compound 81 at a yield of 85%.

1H NMR (DMSO, 300 Hz): δ(ppm)=9.23-9.04 (d, 1H), 8.95-8.72 (d, 1H), 8.36-8.16 (d, 1H) 8.10-7.75 (m, 6H), 7.73-7.62 (d, 19H), 7.40-6.85 (m, 20H), 3.01-2.52 (q, 1H), 2.45-2.23 (s, 3H), 1.38-1.03 (d, 6H)

MS(FAB): 1127 (M+)

Compound Example 5

Synthesis of Compound 92
Synthesis of Intermediate (36)

[Reaction Scheme 40]

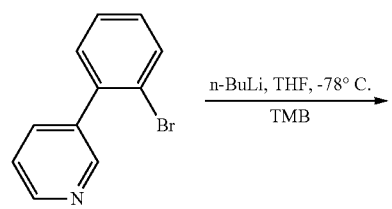

-continued

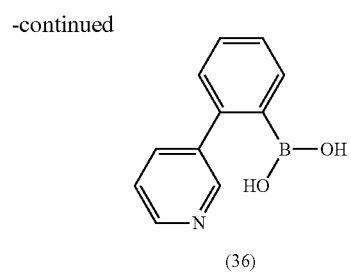

(36)

All experimental instruments were fully dried beforehand. 35.1 g 3-(2-bromophenyl) pyridine was added into a 2 L three-neck flask, followed by adding 700 mL dry tetrahydrofuran to dissolve. After the reaction mixture was cooled down to −78° C., 66 mL n-BuLi (2.5M) was added dropwise, followed by stirring for 1 hour at the above temperature. 20.3 g trimethyl borate (1.3 eq.) was added dropwise, followed by stirring overnight at room temperature. After the reaction finished, hydrochloric acid solution (4M) was added and the reaction mixture was extracted with dichloromethane. The organic phase was washed with saturated aqueous NaCl solution until reaching a neutral state, followed by drying, rotating removal of solvent and boiling with ethyl acetate, to produce a crude product which is then filtered to produce 25.4 g filter cake, i.e. boric acid product Intermediate (36) at a yield of 85%.

Synthesis of Intermediate (37)

[Reaction Scheme 41]

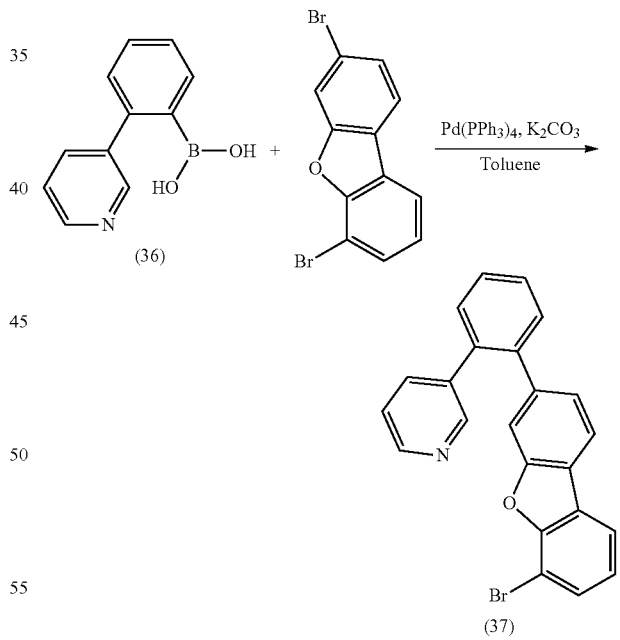

25.4 g Intermediate (36) and 37.8 g 3,6-dibromo-dibenzofuran were added into a 2 L three-neck flask, followed by adding 800 mL toluene and 200 mL ethanol to dissolve. The reaction mixture was aerated with nitrogen gas for 15 minutes, then 174 mL aqueous K$_2$CO$_3$ solution (3.0 eq., 2M) and 2.7 g Pd(PPh$_3$)$_4$ (2 mol %) were sequentially added. The reaction mixture was heated up to 110° C. and reacted overnight. After the reaction finished, the residual was absorbed by the added activated carbon, filtered by suction filtration and removed with solvent by rotary evaporation followed by drying and recrystallization with a mixture of toluene and ethanol, to produce 39.5 g Intermediate (37) at a yield of 85%.

Synthesis of Intermediate (38)

[Reaction Scheme 42]

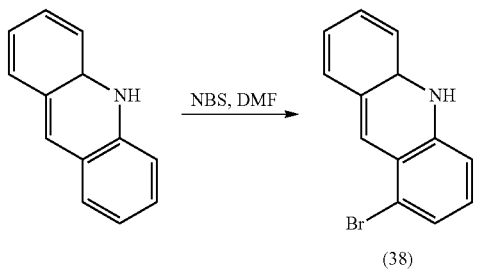

(38)

36.2 g 4a,10-dihydro-10-naphthazine was added into a 2 L three-neck flask, followed by adding 600 mL DMF to dissolve. Then 39.2 g NBS (1.1 eq.) was added and the reaction mixture was stirred overnight at room temperature in the dark. After the reaction finished, a large amount of water was added to separate out solid matter, followed by filtration. The filter cake was washed with water three times, dried and recrystallized with a mixture of toluene and ethanol, to produce 46.3 g Intermediate (38) at a yield of 89%.

Synthesis of Intermediate (39)

[Reation Scheme 43]

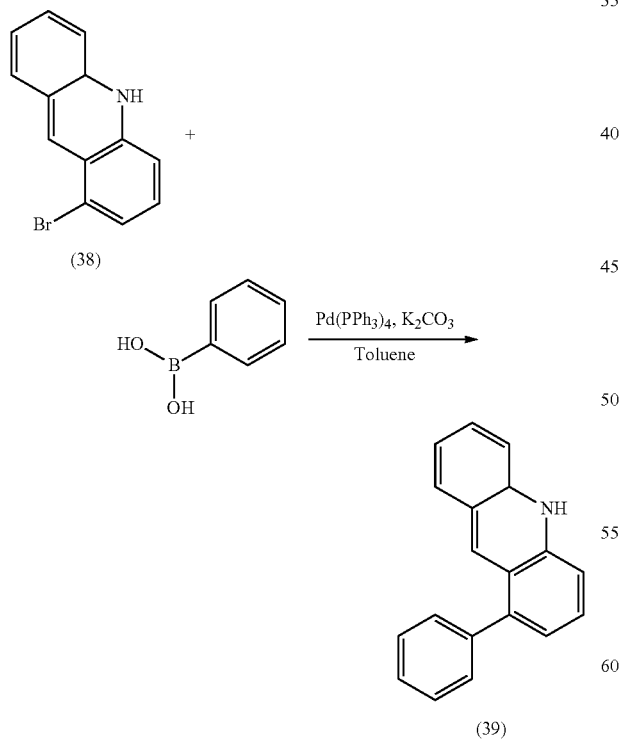

(39)

46.3 g Intermediate (38) and 23.9 g phenyl boric acid were added into a 2 L three-neck flask, followed by adding 1000 mL toluene and 250 mL ethanol to dissolve. The reaction mixture was aerated with nitrogen gas for 15 minutes, then 267 mL aqueous $K_2CO_3$ solution (3.0 eq., 2M) and 4.1 g $Pd(PPh_3)_4$ (2 mol %) were sequentially added. The reaction mixture was heated up to 110° C. and reacted overnight. After the reaction finished, the residual was absorbed by the added activated carbon, filtered by suction filtration and removed with solvent by rotary evaporation followed by drying and recrystallization with a mixture of toluene and ethanol, to produce 41.2 g Intermediate (39) at a yield of 90%.

Synthesis of Intermediate (40)

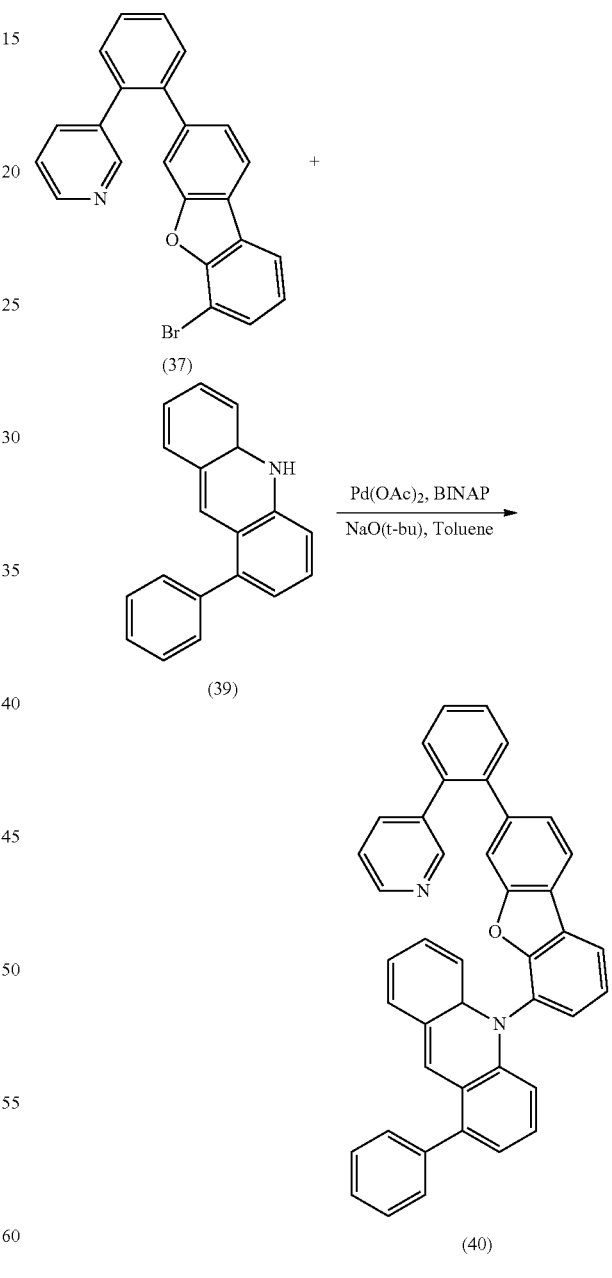

39.5 g Intermediate (37) and 27.9 g Intermediate (39) were added into a dry 2 L three-neck flask, followed by adding 800 mL dry and degassed toluene to dissolve. Then, 28.5 g sodium tert-butoxide, 0.44 g catalyst palladium diacetate (2% mol) and 2.5 g 1,1'-binaphthyl-2,2'-bis(diphenylphosphino) (BINAP, 4% mol) ligand were added. The reaction mixture was heated up to 110° C. and reacted overnight. After the reaction finished and the reaction mixture was cooled down to room temperature, the residual was absorbed by the added activated carbon, filtered by suction filtration and removed with solvent by rotary evaporation, followed by recrystallization with a mixture of toluene and ethanol, to produce 48.4 g Intermediate (40) at a yield of 85%.

Synthesis of Intermediate (41)

Synthesis of Intermediate (42)

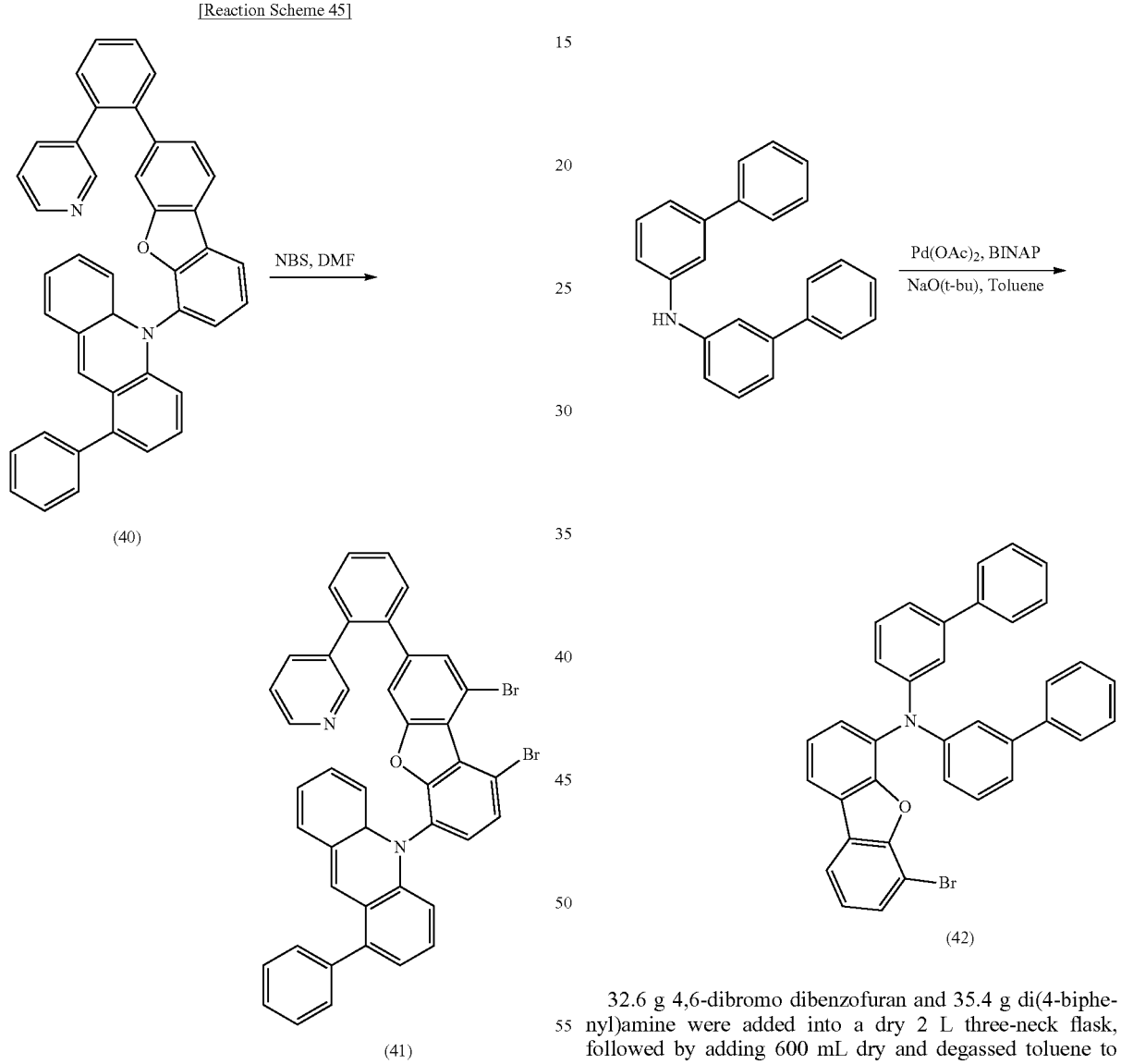

48.4 g Intermediate (40) was added into a 2 L three-neck flask, followed by adding 800 mL DMF to dissolve. Then 32.9 g NBS (2.2 eq.) was added and the reaction mixture was stirred overnight at room temperature in the dark. After the reaction finished, a large amount of water was added to separate out solid matter, followed by filtration. The filter cake was washed with water three times, dried and recrystallized with a mixture of toluene and ethanol, to produce 50.5 g Intermediate (41) at a yield of 82%.

32.6 g 4,6-dibromo dibenzofuran and 35.4 g di(4-biphenyl)amine were added into a dry 2 L three-neck flask, followed by adding 600 mL dry and degassed toluene to dissolve. Then, 28.8 g sodium tert-butoxide, 0.45 g catalyst palladium diacetate (2% mol) and 2.5 g 1,1'-binaphthyl-2,2'-bis(diphenylphosphino) (BINAP, 4% mol) ligand were added. The reaction mixture was heated up to 110° C. and reacted overnight. After the reaction finished and the reaction mixture was cooled down to room temperature. The residual was absorbed by the added activated carbon, filtered by suction filtration and removed with solvent by rotary evaporation, followed by recrystallization with a mixture of toluene and ethanol, to produce 45.9 g Intermediate (42) at a yield of 81%.

Synthesis of Intermediate (43)

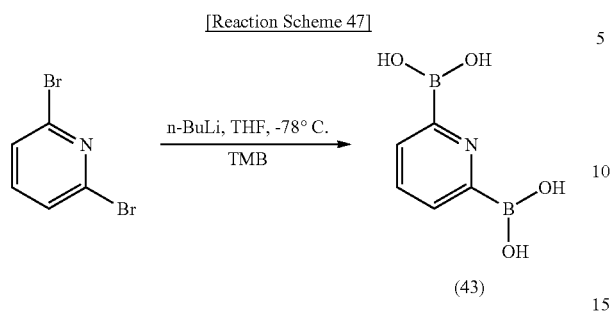

All experimental instruments were fully dried beforehand. 35.5 g 2,6-dibromo pyridine was added into a 2 L three-neck flask, followed by adding 700 mL dry tetrahydrofuran to dissolve. After the reaction mixture was cooled down to −78° C., 150 mL n-BuLi (2.5 eq., 2.5M) was added dropwise, followed by stirring for 1 hour at the above temperature. 46.8 g trimethyl borate (3.0 eq.) was added dropwise, followed by stirring overnight at room temperature. After the reaction finished, hydrochloric acid solution (4M) was added and the reaction mixture was extracted with dichloromethane. The organic phase was washed with saturated aqueous NaCl solution until neutral, followed by drying, rotating removal of solvent and boiling with ethyl acetate, to produce a crude product which is then filtered to produce 20 g filter cake, i.e. boric acid product Intermediate (43) at a yield of 80%.

Synthesis of Intermediate (44)

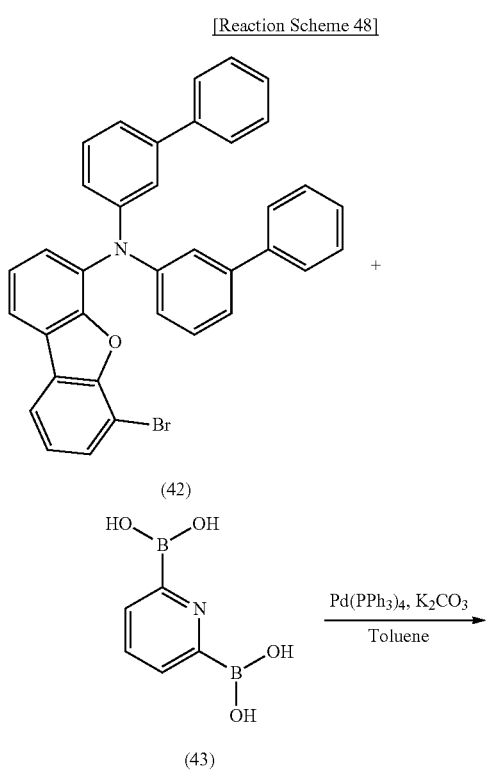

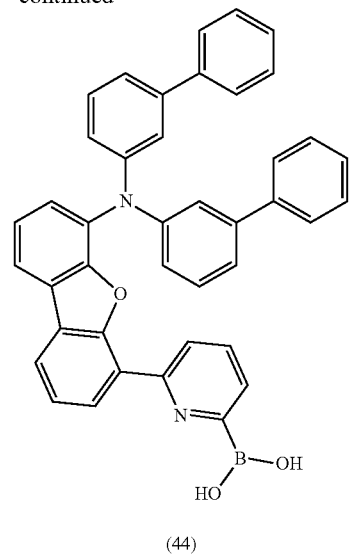

20 g Intermediate (42) and 61.8 g Intermediate (43) were added into a 2 L three-neck flask, followed by adding 1.2 L toluene and 300 mL ethanol to dissolve. The reaction mixture was aerated with nitrogen gas for 15 minutes, then 164 mL aqueous $K_2CO_3$ solution (3.0 eq., 2M) and 2.5 g Pd(PPh$_3$)$_4$ (2 mol %) were sequentially added. The reaction mixture was heated up to 110° C. and reacted overnight. After the reaction finished, the residual was absorbed by the added activated carbon, filtered by suction filtration and removed with solvent by rotary evaporation, followed by dry and recrystallization with a mixture of toluene and ethanol, to produce 55.1 g Intermediate (44) at a yield of 83%.

Synthesis of Intermediate (45)

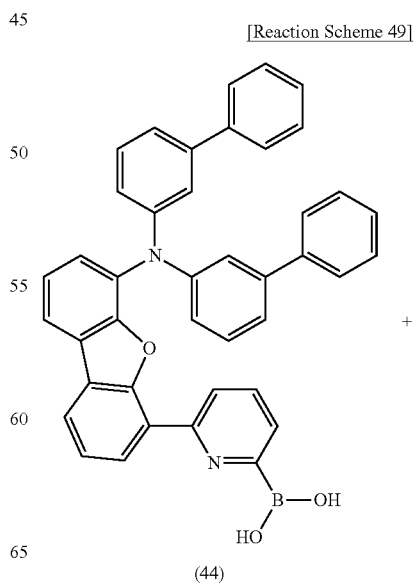

Synthesis of Intermediate (46)

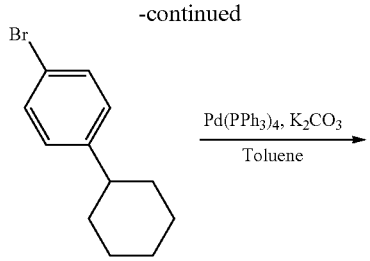

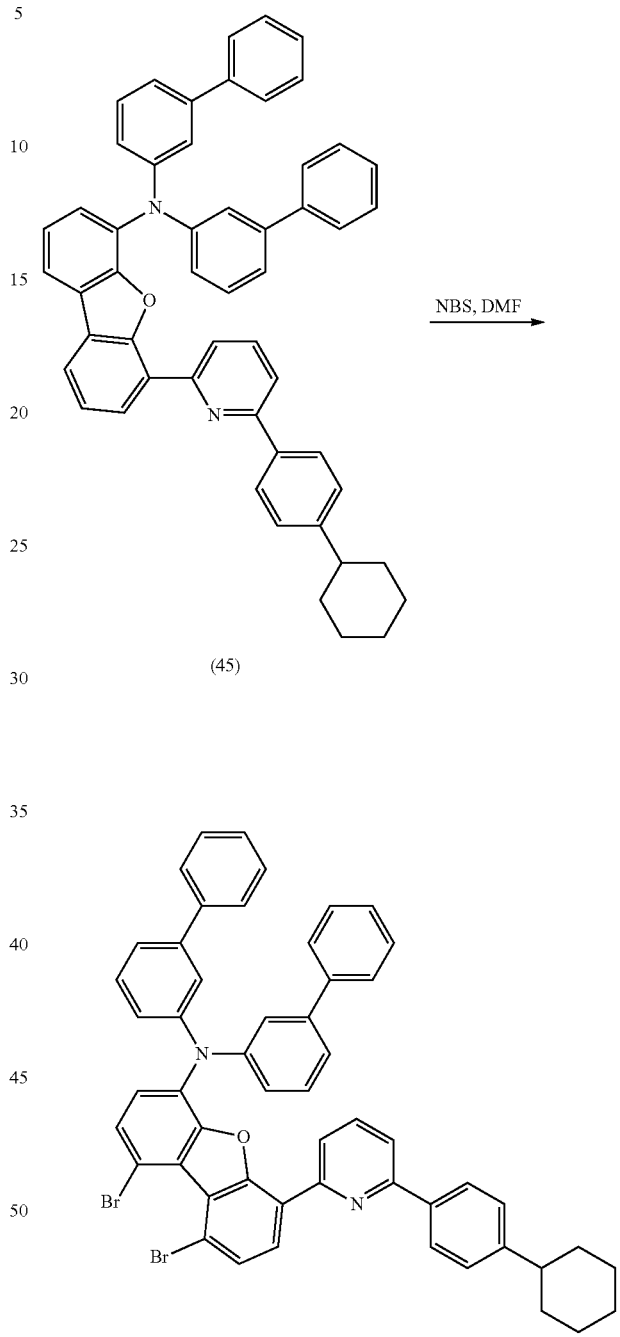

55.1 g Intermediate (44) and 19.7 g 1-bromo-4-cyclohexyl benzene were added into a 2 L three-neck flask, followed by adding 1.1 L toluene and 300 mL ethanol to dissolve. The reaction mixture was aerated with nitrogen gas for 15 minutes, then 123 mL aqueous $K_2CO_3$ solution (3.0 eq., 2M) and 1.9 g Pd(PPh$_3$)$_4$ (2 mol %) were sequentially added. The reaction mixture was heated up to 110° C. and reacted overnight. After the reaction finished, the residual was absorbed by the added activated carbon, filtered by suction filtration and removed with solvent by rotary evaporation, followed by dry and recrystallization with a mixture of toluene and ethanol, to produce 53.5 g Intermediate (45) at a yield of 90%.

53.5 g Intermediate (45) was added into a 2 L three-neck flask, followed by adding 1000 mL DMF to dissolve. Then 29.0 g NBS (2.2 eq.) was added and the reaction mixture was stirred overnight at room temperature in the dark. After the reaction finished, a large amount of water was added to separate out solid matter, followed by filtration. The filter cake was washed with water three times, dried and recrystallized with a mixture of toluene and ethanol, to produce 56.7 g Intermediate (46) at a yield of 87%.

Synthesis of Intermediate (47)

[Reaction Scheme 51]

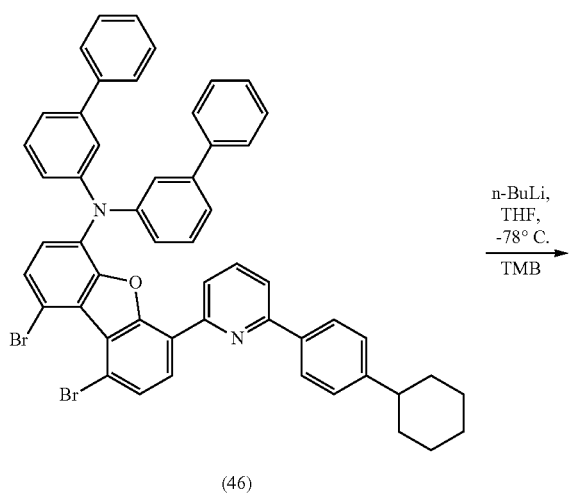

(46)

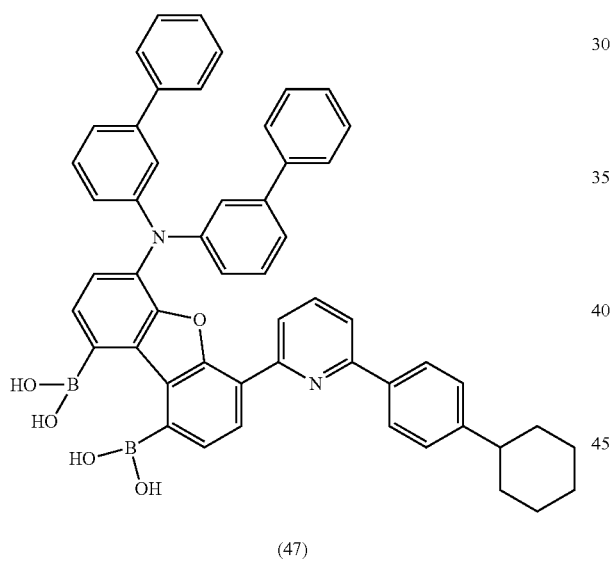

(47)

All experimental instruments were fully dried beforehand. 56.7 g Intermediate (46) was added into a 2 L three-neck flask, followed by adding 1000 mL dry tetrahydrofuran to dissolve. After the reaction mixture was cooled down to −78° C., 64.4 mL n-BuLi (2.5 eq., 2.5M) was added dropwise, followed by stirring for 1 hour at the above temperature; 20.1 g trimethyl borate (3.0 eq.) was added dropwise, followed by stirring overnight at room temperature. After the reaction finished, hydrochloric acid solution (4M) was added and the reaction mixture was extracted with dichloromethane. The organic phase was washed with saturated aqueous NaCl solution until reaching a neutral state, followed by drying, rotating removal of solvent and boiling with ethyl acetate, to produce a crude product which is then filtered to produce 37.6 g filter cake, i.e. boric acid product Intermediate (47) at a yield of 72%.

Synthesis of Compound 92

[Reaction Scheme 52]

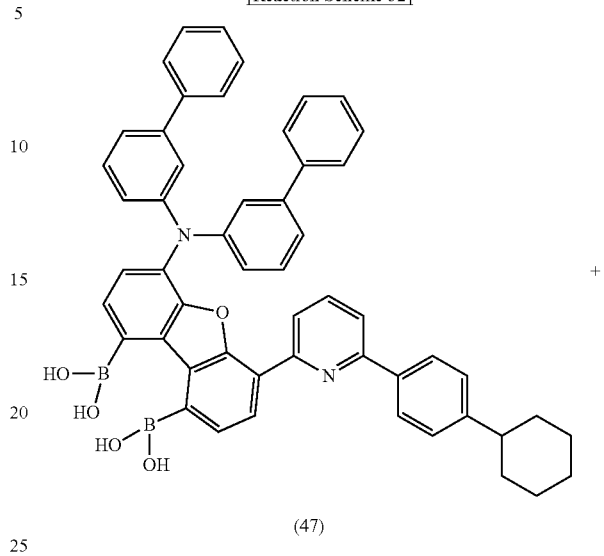

(47)

+

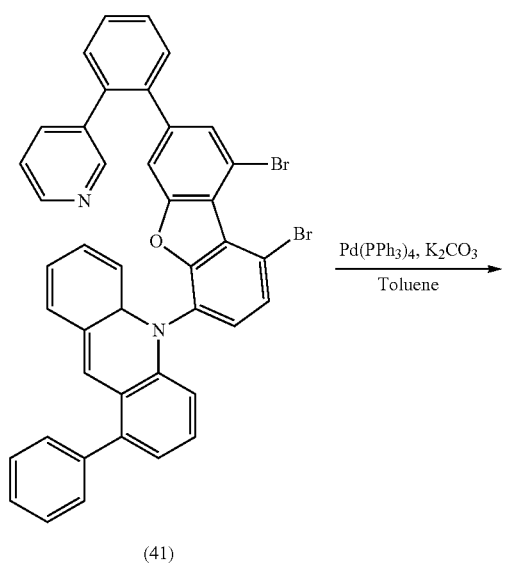

(41)

-continued

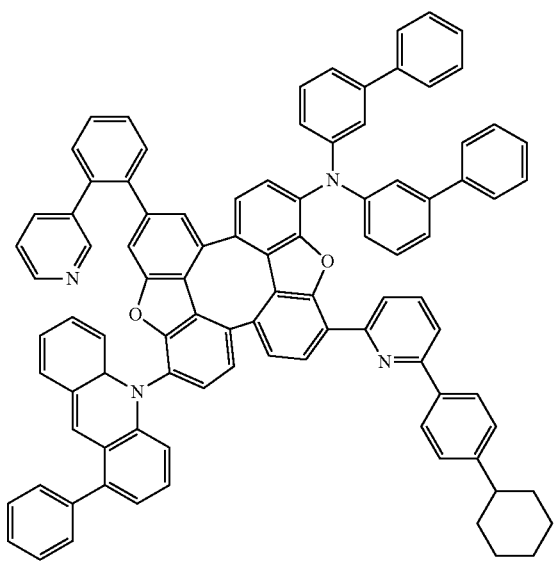

Compound 92

37.6 g Intermediate (47) and 31.0 g Intermediate (41) were added into a 2 L three-neck flask, followed by adding 800 mL toluene and 200 mL ethanol to dissolve. The reaction mixture was aerated with nitrogen gas for 15 minutes, then 127 mL aqueous $K_2CO_3$ solution (6.0 eq., 2M) and 2.0 g $Pd(PPh_3)_4$ (4 mol %) were sequentially added. The reaction mixture was heated up to 110° C. and reacted overnight. After the reaction finished, the residual was absorbed by the added activated carbon, filtered by suction filtration and removed with solvent by rotary evaporation, followed by dry and recrystallization with a mixture of toluene and ethanol, to produce 43.2 g Compound 92 at a yield of 79%.

1H NMR (DMSO, 300 Hz): δ(ppm)=9.45-9.25 (s, 1H), 8.84-8.65 (d, 1H), 8.50-8.39 (d, 1H), 8.32-8.19 (d, 1H), 8.13-7.89 (m, 6H), 7.53-7.40 (m, 28H), 7.32-7.12 (m, 8H), 7.04-6.89 (m, 2H), 6.85-6.68 (m, 3H), 6.51-6.36 (m, 2H), 5.86-5.67 (m, 1H), 4.03-3.89 (m, 1H), 2.81-2.58 (m, 1H), 1.92-1.78 (m, 4H), 1.75-1.41 (d, 6H)

MS(FAB): 1295 (M+)

Compound Example 6

Synthesis of Compound 102
Synthesis of Intermediate (48)

[Reaction Scheme 53]

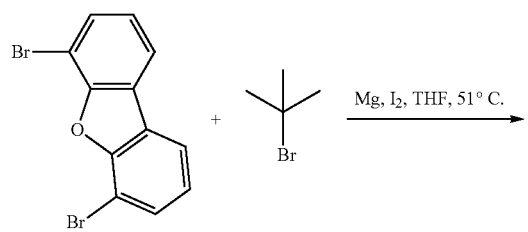

-continued

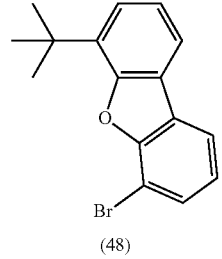

(48)

3.6 g Mg (1.5 eq.), 18 mL THF, and 0.36 g $I_2$ were added into a dry 2 L three-neck flask. The reaction mixture was heated to trigger reaction. Then a solution of 17.8 g tert-butyl bromide (1.3 eq.) in 180 mL THF was added dropwise at room temperature. After the dropwise addition, the reaction mixture was reacted at 51° C. for 2 hours and was thereafter left to stand for 5 minutes. The supernatant was added dropwise to a solution of 32.6 g 4,6-dibromo dibenzofuran in 600 mL THF, followed by refluxing overnight for 15 hours. After the reaction finished, the reaction mixture was cooled down to room temperature, followed by quenching with drops of water, extraction with a mixture of dichloromethane and water, washing with water, drying, rotating removal of solvent and purification by chromatography column, to produce 25.2 g Intermediate (48) at a yield of 83%.

Synthesis of Intermediate (49)

[Reaction Scheme 54]

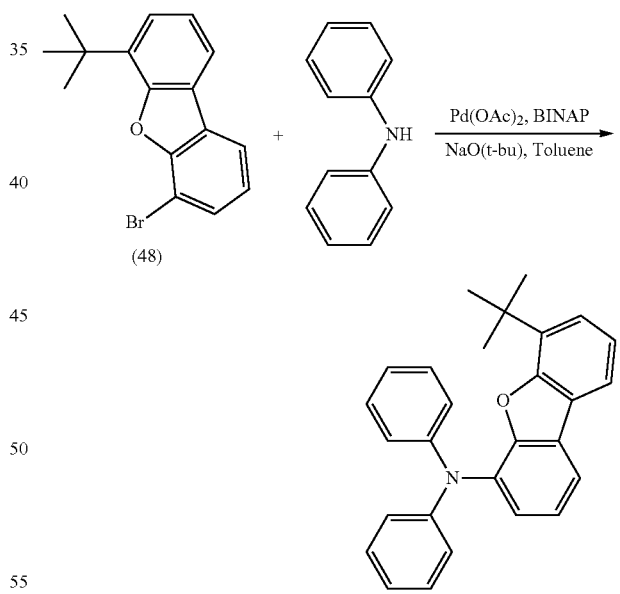

25.2 g Intermediate (48) and 15.5 g diphenylamine were added into a dry 2 L three-neck flasks, followed by adding 500 mL dry and degassed toluene to dissolve. Then, 24.0 g sodium tert-butoxide, 0.37 g catalyst palladium diacetate (2% mol) and 2.1 g 1,1'-binaphthyl-2,2'-bis(diphenylphosphino) (BINAP, 4% mol) ligand were added. The reaction mixture was heated up to 110° C. and reacted overnight. After the reaction finished and the reaction mixture was cooled down to room temperature, the residual was absorbed by the added activated carbon, filtered by suction filtration and removed with solvent by rotary evaporators, followed by recrystallization with a mixture of toluene and ethanol, to produce 30.0 g Intermediate (49) at a yield of 92%.

Synthesis of Intermediate (50)

[Reaction Scheme 55]

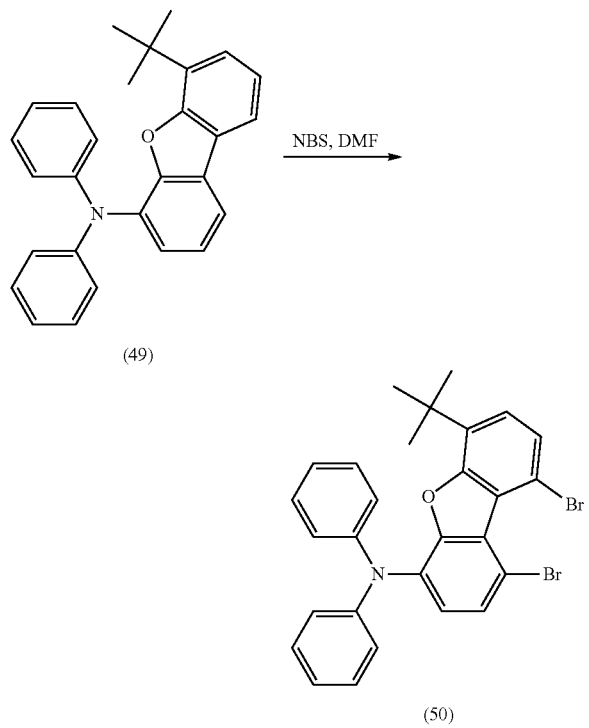

30.0 g Intermediate (49) was added into a 2 L three-neck flask, followed by adding 400 mL DMF to dissolve. Then 30.0 g NBS (2.2 eq.) was added and the reaction mixture was stirred overnight at room temperature in the dark. After the reaction finished, a large amount of water was added to separate out solid matter, followed by filtration. The filter cake was washed with water three times, dried and recrystallized with a mixture of toluene and ethanol, to produce 37.4 g Intermediate (50) at a yield of 89%.

Synthesis of Intermediate (51)

[Reaction Scheme 56]

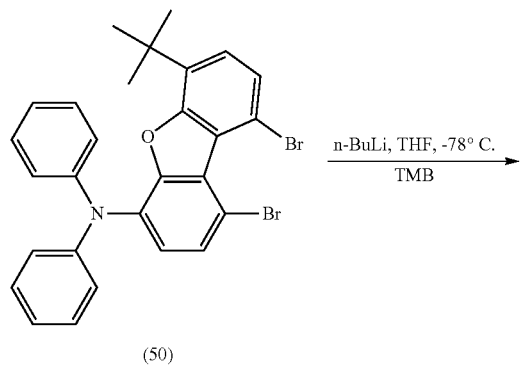

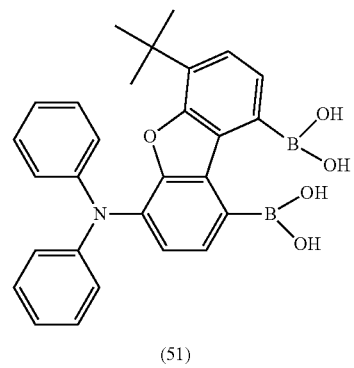

(51)

All experimental instruments were fully dried beforehand. 37.4 g Intermediate (50) was added into a 2 L three-neck flask, followed by adding 800 mL dry tetrahydrofuran to dissolve. After the reaction mixture was cooled down to −78° C., 68.1 mL n-BuLi (2.5 eq., 2.5M) was added dropwise, followed by stirring for 1 hour at the above temperature; 21.2 g trimethyl borate (3.0 eq.) was added dropwise, followed by stirring overnight at room temperature. After the reaction finished, hydrochloric acid solution (4M) was added and the reaction mixture was extracted with dichloromethane. The organic phase was washed with saturated aqueous NaCl solution until reaching a neutral state, followed by drying, rotating removal of solvent and boiling with ethyl acetate, to produce a crude product which is then filtered to produce 30.2 g filter cake, i.e. boric acid product Intermediate (51) at a yield of 81%.

Synthesis of Intermediate (52)

[Reaction Scheme 57]

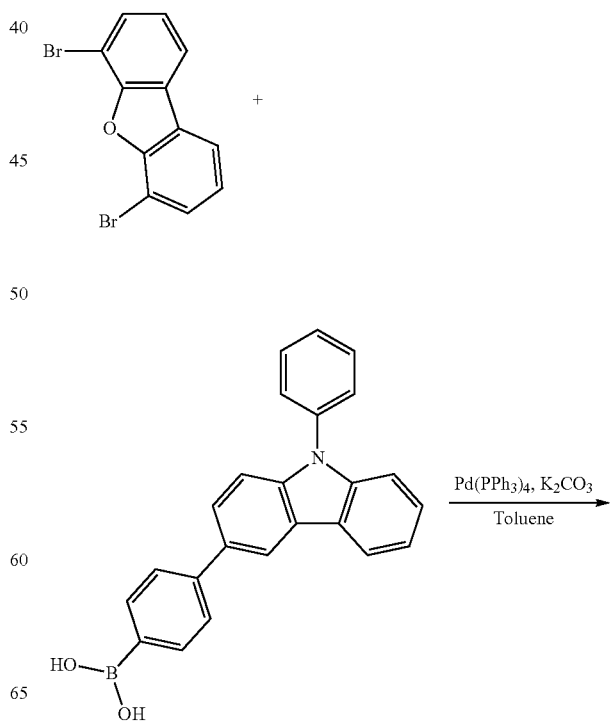

-continued

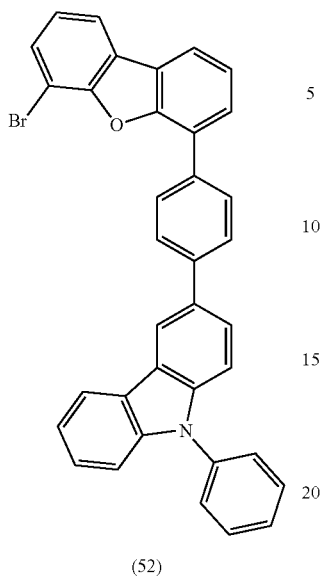

(52)

40.0 g (4-(9-phenyl-9H-carbazole-3-)phenyl) boric acid and 32.6 g 4,6-dibromo-dibenzofuran were added into a 2 L three-neck flask, followed by adding 700 mL toluene and 150 mL ethanol to dissolve. The reaction mixture was aerated with nitrogen gas for 15 minutes, then 150 mL aqueous $K_2CO_3$ solution (3.0 eq., 2M) and 2.3 g $Pd(PPh_3)_4$ (2 mol %) were sequentially added. The reaction mixture was heated up to 110° C. and reacted overnight. After the reaction finished, the residual was absorbed by the added activated carbon, filtered by suction filtration and removed with solvent by rotary evaporation, followed by drying and recrystallization with a mixture of toluene and ethanol, to produce 48.0 g Intermediate (52) at a yield of 85%.

Synthesis of Compound 83

[Reaction Scheme 58]

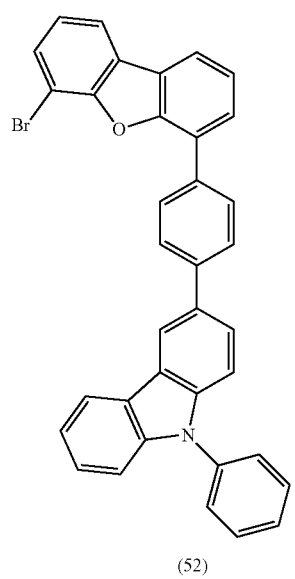

(52)

+

-continued

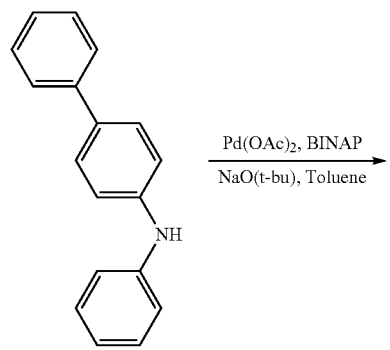

$Pd(OAc)_2$, BINAP
NaO(t-bu), Toluene

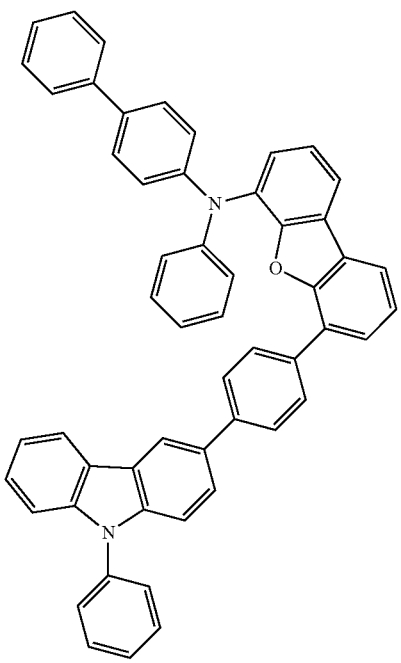

(53)

48.0 g Intermediate (52) and 22.9 g 4-phenylamide bibenzene were added into a dry 2 L three-neck flask, followed by adding 1000 mL dry and degassed toluene to dissolve. Then, 24.5 g sodium tert-butoxide, 0.38 g catalyst palladium diacetate (2% mol) and 2.11 g 1,1'-binaphthyl-2,2'-bis(diphenylphosphino) (BINAP, 4% mol) ligand were added. The reaction mixture was heated up to 110° C. and reacted overnight. After the reaction finished and the reaction mixture was cooled down to room temperature, the residual was absorbed by the added activated carbon, filtered by suction filtration and removed with solvent by rotary evaporation, followed by recrystallization with a mixture of toluene and ethanol, to produce 55.8 g Intermediate (53) at a yield of 90%.

Synthesis of Intermediate (54)

[Reaction Scheme 59]

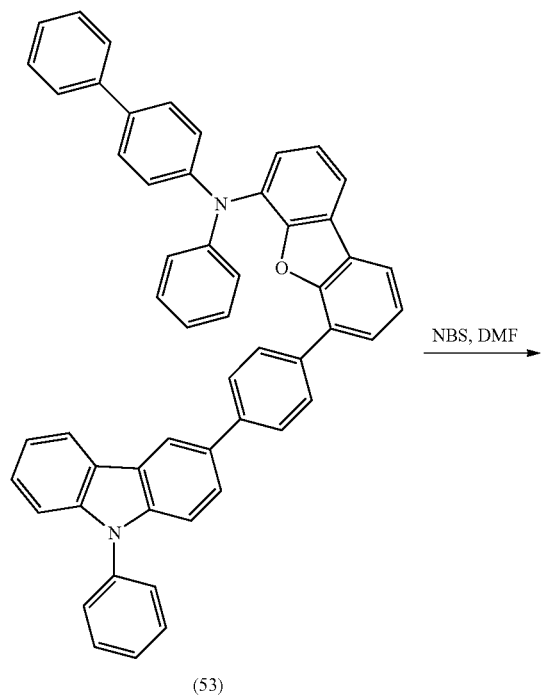

(53)

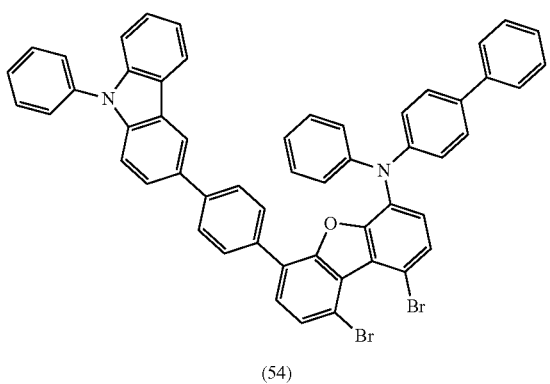

(54)

55.8 g Intermediate (53) was added into a 2 L three-neck flask, followed by adding 400 mL DMF to dissolve. Then 30.0 g NBS (2.2 eq.) was added and the reaction mixture was stirred overnight at room temperature in the dark. After the reaction finished, a large amount of water was added to separate out solid matter, followed by filtration. The filter cake was washed with water three times, dried and recrystallized with a mixture of toluene and ethanol, to produce 56.4 g Intermediate (54) at a yield of 83%.

Synthesis of Compound 102

[Reaction Scheme 60]

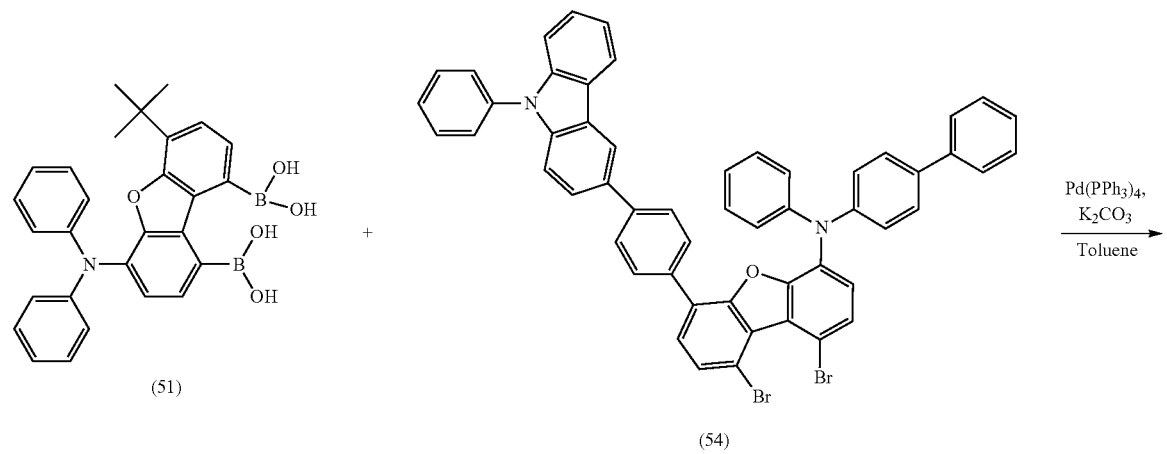

-continued

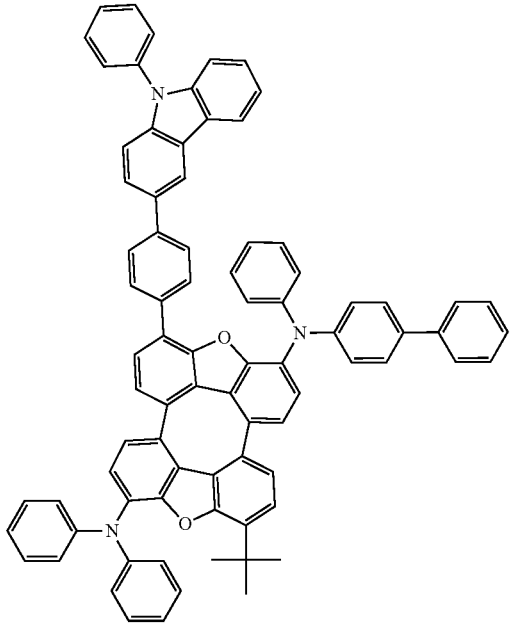

Compound 102

44.4 g Intermediate (54) and 30.2 g Intermediate (51) were added into a 2 L three-neck flask, followed by adding 800 mL toluene and 200 mL ethanol to dissolve. The reaction mixture was aerated with nitrogen gas for 15 minutes, then 150 mL aqueous $K_2CO_3$ solution (6.0 eq., 2M) and 2.3 g $Pd(PPh_3)_4$ (4 mol %) were sequentially added. The reaction mixture was heated up to 110° C. and reacted overnight. After the reaction finished, the residual was absorbed by the added activated carbon, filtered by suction filtration and removed with solvent by rotary evaporation, followed by drying and recrystallization with a mixture of toluene and ethanol, to produce 45.3 g Compound 102 at a yield of 81%.

1H NMR (DMSO, 300 Hz): δ(ppm)=8.62-8.48 (d, 1H), 8.14-7.88 (m, 4H), 7.86-7.63 (m, 3H), 7.61-7.38 (m, 17H), 7.36-6.85 (m, 23H), 1.68-1.55 (s, 9H)

MS(FAB): 1116 (M+)

Compounds in the present invention can be synthesized following Reaction Schemes 1-60.

Manufacturing of Organic Electroluminescent Device

Device Example 1

ITO was used as an anode substrate material of reflecting layer and the surface of the ITO anode was treated with $N_2$ plasma or UV-Ozone. On top of the anode, a 10 nm-thick HAT-CN was vapor deposited to form the hole injection layer (HIL) and a 120 nm-thick NPD was vapor deposited to form the hole transport layer (HTL). On top of the hole transport layer as described above, an emission layer (EML) was formed by vapor deposition of a 25 nm-thick 9,10-di (2-naphthyl) anthraces (ADN) which could produce blue EML mixed with 5 wt % Compound 2 in the present invention.

On top of the emission layer, an electron transport layer (ETL) was formed by vapor deposition of a 35 nm-thick mixture of anthracene derivatives (50 wt %) and Liq (50 wt %); and an electron injection layer (EIL) was formed thereon, by a 2 nm-thick Liq. Finally, a cathode was formed, by vapor deposition of a 15 nm-thick mixture of Magnesium (90 wt %) and Argentine (10 wt %), and covering and protecting layer (CPL) was formed thereon, to a thickness of 65 nm, by yap or depositing N4,N4'-bis[4-[bis(3-methyl-phenyl)amino]phenyl]-N4,N4'-diphenyl-[1,1'-biphenyl]-4,4'-biamine (DNTPD). In addition, a water absorbent material containing UV hardening adhesive was applied to the surface of the cathode to protect the organic electroluminescent device from being affected by the oxygen and water in the atmosphere.

The compound mentioned in this example is of the following structural formula:

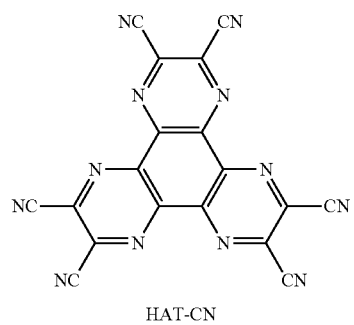

HAT-CN

-continued

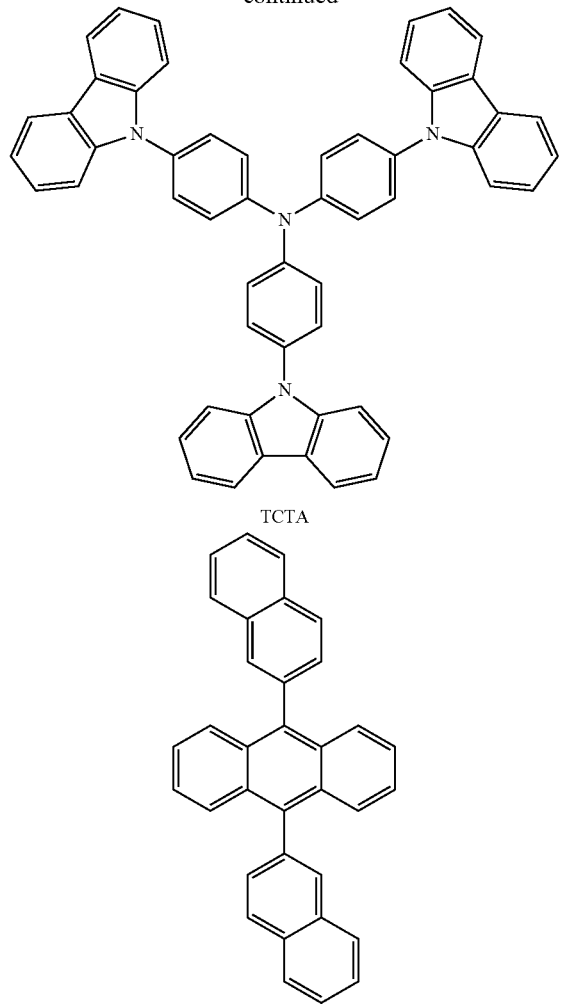

TCTA

ADN

T-Bu-Perylene

-continued

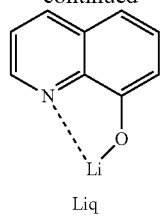

Liq

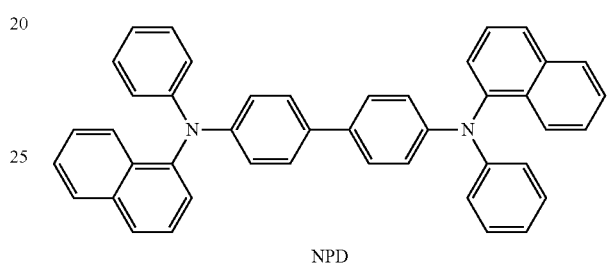

NPD

Device Examples 2-10

Device Examples 2-10 were prepared as described for Device Example 1 that the Compounds 20, 25, 31, 40, 56, 81, 92, 102 and 118 were mixed into the EML respectively as the blue dopant material.

Comparative Device Example 1

An organic electroluminescent device was prepared as described for Device Example 1 except that 2,5,8,11-tetra-butyl-Perylene (t-Bu-Perylene) was mixed into the EML as the blue dopant material.

The Property Evaluation of the Organic Electroluminescent Devices

Under a current density of 10 mA/cm$^2$, performances of organic electroluminescent devices prepared as described for Device Examples and Comparative Device Example were tested. Results are given in the following Table.

|  | Material Name | Current Density (mA/cm$^2$) | Voltage (V) | Efficiency (Cd/A) | CIE (X Y) |
|---|---|---|---|---|---|
| Comparative Device Example 1 | t-Bu-Perylene | 10 | 4.8 | 4.1 | (0.135 0.058) |
| Device Examples 1 | Compound 2 | 10 | 4.4 | 6.1 | (0.136 0.056) |
| Device Examples 2 | Compound 20 | 10 | 4.2 | 6.5 | (0.136 0.049) |
| Device Examples 3 | Compound 25 | 10 | 4.1 | 6.4 | (0.137 0.047) |

-continued

| | Material Name | Current Density (mA/cm$^2$) | Voltage (V) | Efficiency (Cd/A) | CIE (X Y) |
|---|---|---|---|---|---|
| Device Examples 4 | Compound 31 | 10 | 4.1 | 5.9 | (0.136 0.049) |
| Device Examples 5 | Compound 40 | 10 | 4.2 | 6.4 | (0.137 0.048) |
| Device Examples 6 | Compound 56 | 10 | 4.4 | 6.3 | (0.136 0.055) |
| Device Examples 7 | Compound 81 | 10 | 4.3 | 6.2 | (0.136 0.056) |
| Device Examples 8 | Compound 92 | 10 | 4.4 | 6.0 | (0.136 0.057) |
| Device Examples 9 | Compound 102 | 10 | 4.3 | 6.3 | (0.137 0.049) |
| Device Examples 10 | Compound 118 | 10 | 4.0 | 5.8 | (0.136 0.056) |

As shown in the above table, compared with those prepared as described for Comparative Device Example 1, organic electroluminescent devices prepared as described for Device Examples 1-10 using Compounds in the present invention, present higher efficiency and an outstanding voltage performance.

Further, the results of CIE chromaticity coordinates (CIE x, y) have showed that, compared with those prepared as described for Comparative Device Example 1, the CIE y values of organic electroluminescent devices prepared as described for Device Examples 1-10 are lower, thus it can be inferred as having deep blue performance, especially for the devices prepared as described for Device Examples 2, 3, 4, 5 and 9, which have more an obvious deep blue performance.

Therefore, organic electroluminescent devices using compounds in the present invention as the dopant are advantageous in terms of the device efficiency, voltage and deep blue performance.

We claim:
1. An organic electroluminescent compound having the following structural formula:

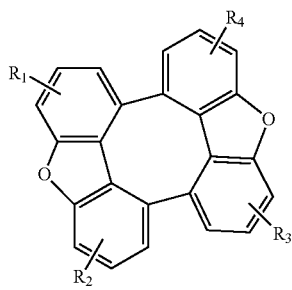

wherein $R_1$, $R_2$ and $R_4$ are, each independently, selected from a group consisting of hydrogen, a C1-C20 linear or branched alkyl group, a substituted or unsubstituted N-(phenylmethyl)imino group, a phenyl group, phenylamine, diphenylamine, phenyl pyridinylamine, bipyridinylamine, phenyl naphthylamine, binaphthylamine, phenyl phenanthrylamine, biphenanthrylamine, phenyl anthrylamine, bianthrylamine, phenanthridine, biphenyl, a pyridyl group, a pyrimidinyl group, a quinolyl group and a triazinyl group;
$R_3$ is selected from a group consisting of hydrogen, a C1-C10 linear or branched alkyl group, a substituted or unsubstituted N-(phenylmethyl)imino group, a phenyl group, phenylamine, diphenylamine, phenyl pyridinylamine, bipyridinylamine, phenyl naphthylamine, binaphthylamine, phenyl phenanthrylamine, biphenanthrylamine, phenyl anthrylamine, bianthrylamine, phenanthridine, biphenyl, a pyridyl group, a pyrimidinyl group, a quinolyl group and a triazinyl group;
wherein $R_1$, $R_2$, $R_3$ and $R_4$ being all hydrogen or C4 branched alkyl group is excluded.

2. The organic electroluminescent compound according to claim 1, wherein among $R_1$, the N-(phenylmethyl)imino group, the phenyl group, phenylamine, diphenylamine, phenyl pyridinylamine, bipyridinylamine, phenyl naphthylamine, binaphthylamine, phenyl phenanthrylamine, biphenanthrylamine, phenyl anthrylamine, bianthrylamine, phenanthridine, biphenyl, the pyridyl group, the pyrimidinyl group, the quinolyl group or the triazinyl group, at least one hydrogen atom thereof is substituted with a C1-C20 linear or branched alkyl group, a C3-C24 cyclic alkyl group, a C1-C20 alkoxyl group, halogen, CN, $CF_3$, $Si(CH_3)_3$, or a C6-C50 aryl group.

3. The organic electroluminescent compound according to claim 1, wherein among $R_2$, the N-(phenylmethyl)imino group, the phenyl group, phenylamine, diphenylamine, phenyl pyridinylamine, bipyridinylamine, phenyl naphthylamine, binaphthylamine, phenyl phenanthrylamine, biphenanthrylamine, phenyl anthrylamine, bianthrylamine, phenanthridine, biphenyl, the pyridyl group, the pyrimidinyl group, the quinolyl group and the triazinyl group, at least one hydrogen atom thereof is substituted with a C1-C20 linear or branched alkyl group, a C3-C24 cyclic alkyl group, a C1-C20 alkoxyl group, halogen, CN, $CF_3$, $Si(CH_3)_3$, a naphthyl group, an anthryl group, a phenanthryl group, dibenzofuran, a fluorenyl group, a carbazolyl group, spiro fluorene, or a heteroaryl group having 5-20 non-H atoms.

4. The organic electroluminescent compound according to claim 1, wherein among $R_3$, the N-(phenylmethyl)imino group, the phenyl group, phenylamine, diphenylamine, phenyl pyridinylamine, bipyridinylamine, phenyl naphthylamine, binaphthylamine, phenyl phenanthrylamine, biphenanthrylamine, phenyl anthrylamine, bianthrylamine, phenanthridine, biphenyl, the pyridyl group, the pyrimidinyl group, the quinolyl group or the triazinyl group, at least one hydrogen atom thereof is substituted with a C1-C10 linear or branched alkyl group, a C3-C12 cyclic alkyl group, a C1-C10 alkoxyl group, halogen, CN, $CF_3$, $Si(CH_3)_3$, or a C6-C30 aryl group.

5. The organic electroluminescent compound according to claim 1, wherein among $R_4$, the N-(phenylmethyl)imino group, the phenyl group, phenylamine, diphenylamine, phenyl pyridinylamine, bipyridinylamine, phenyl naphthylamine, binaphthylamine, phenyl phenanthrylamine, biphenanthrylamine, phenyl anthrylamine, bianthrylamine, phenanthridine, biphenyl, the pyridyl group, the pyrimidinyl group, the quinolyl group and the triazinyl group, at least one hydrogen atom thereof is substituted with a C1-C10 linear or branched alkyl group, a C3-C12 cyclic alkyl group, a C1-C10 alkoxyl group, halogen, CN, $CF_3$, $Si(CH_3)_3$, a naphthyl group, an anthryl group, a phenanthryl group, dibenzofuran, a fluorenyl group, a carbazolyl group, spiro fluorene, or a heteroaryl group having 5-20 non-H atoms.

6. The organic electroluminescent compound according to claim 1, wherein the organic electroluminescent compound is any one of following compounds:

1

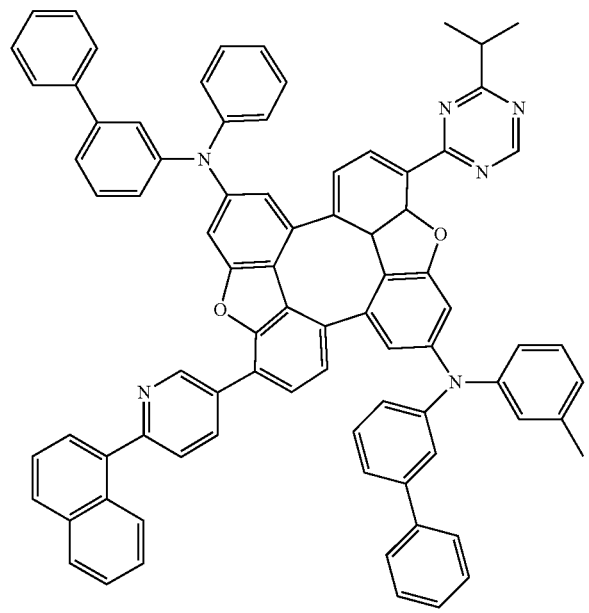

2

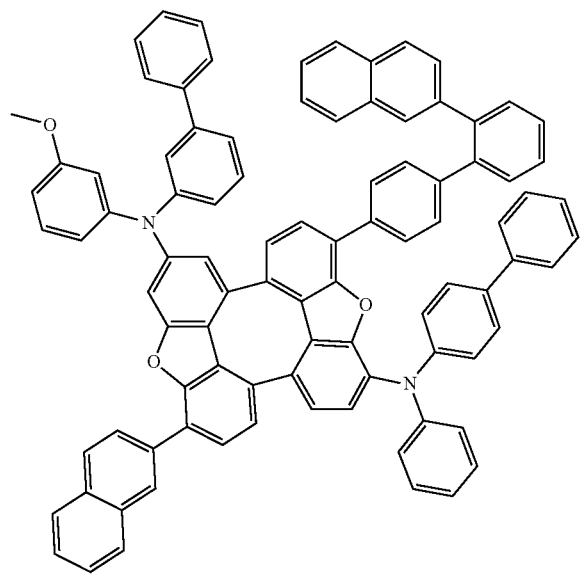

3

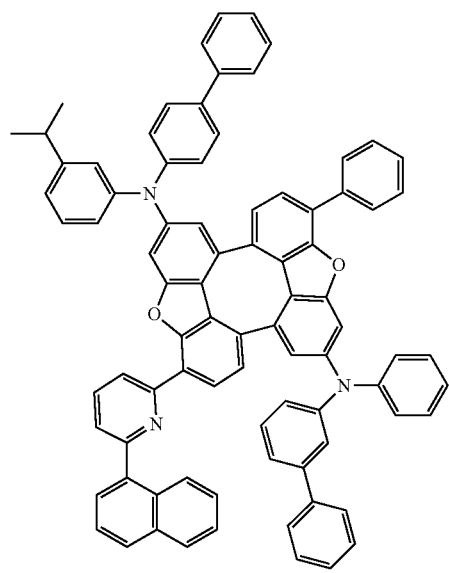

4

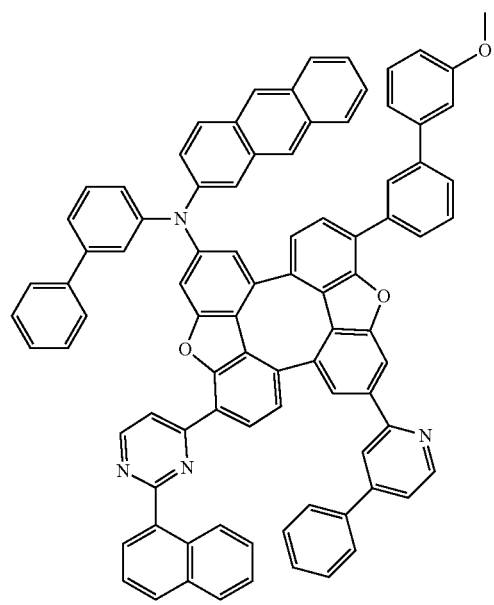

145
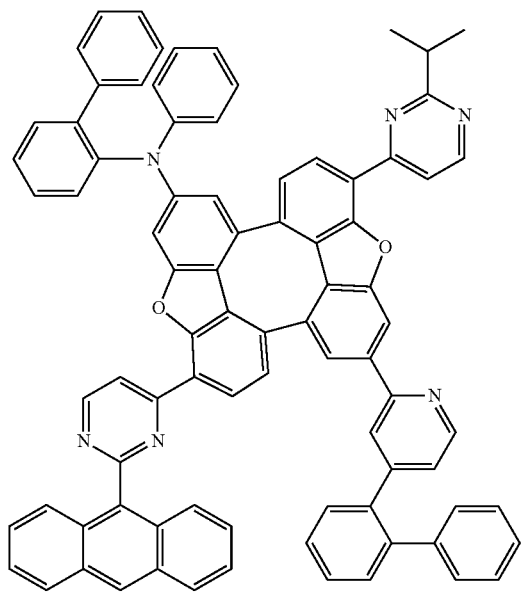
146
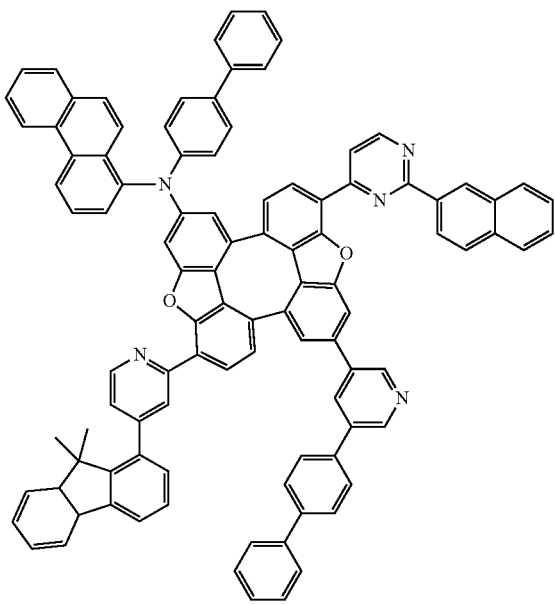
7
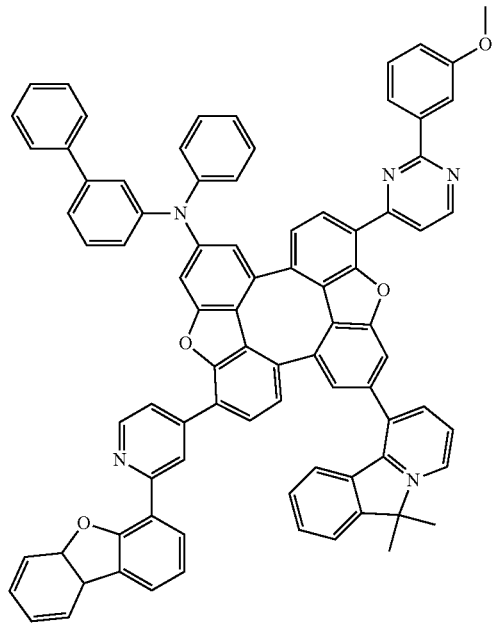
8
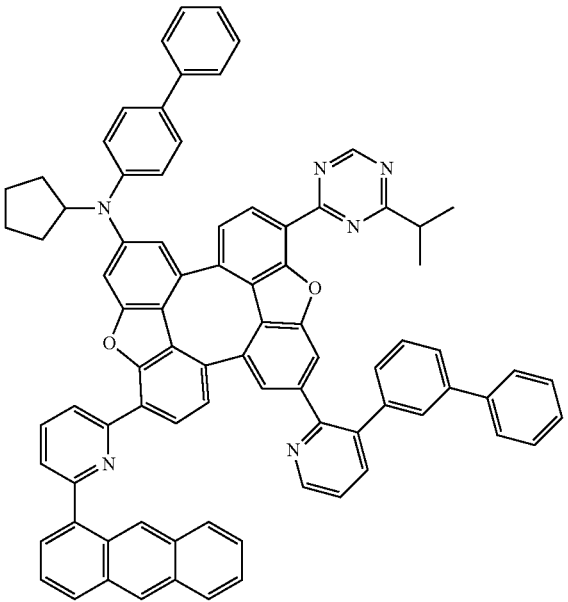

-continued
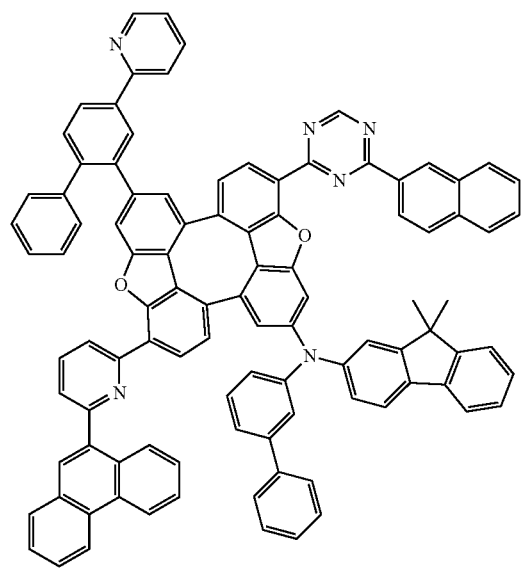
9
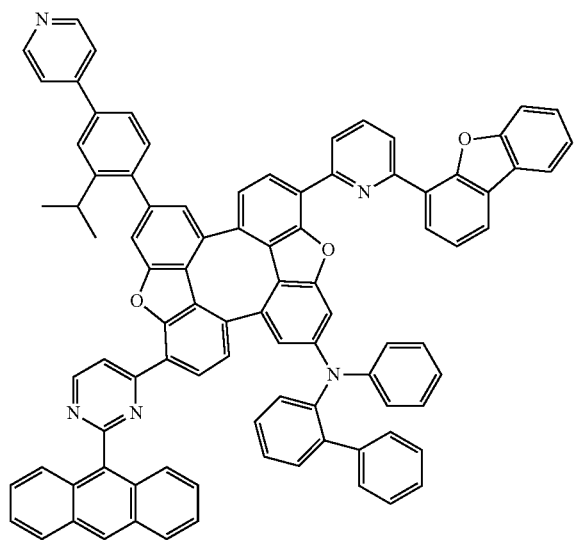
10
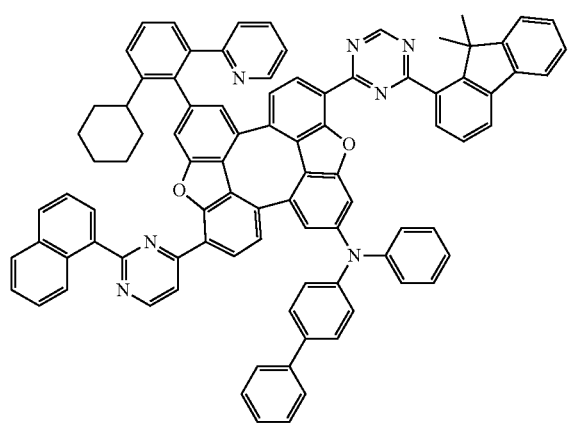
11
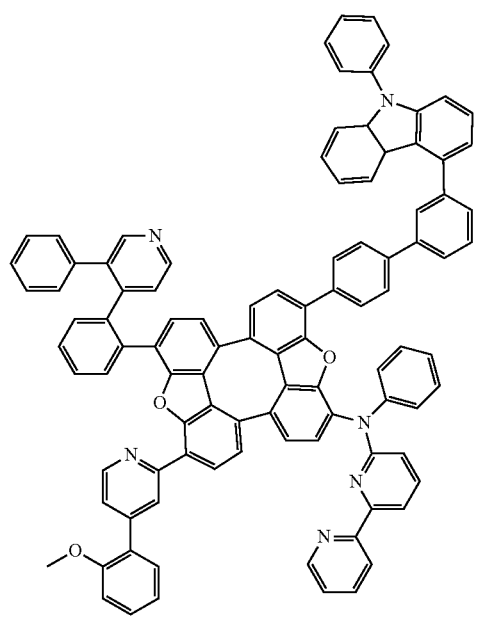
12

13
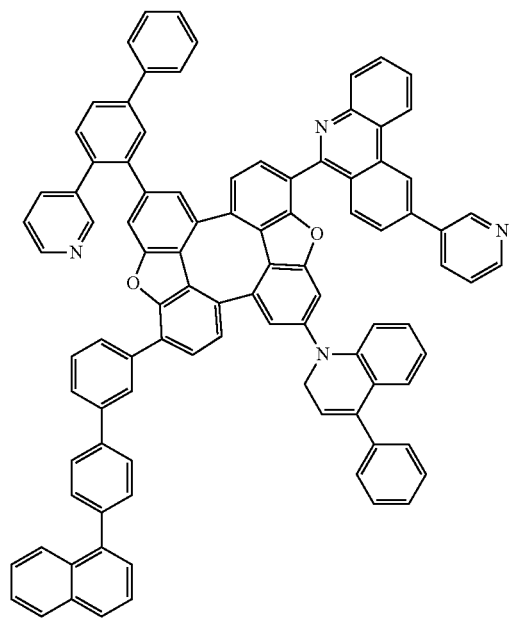
14
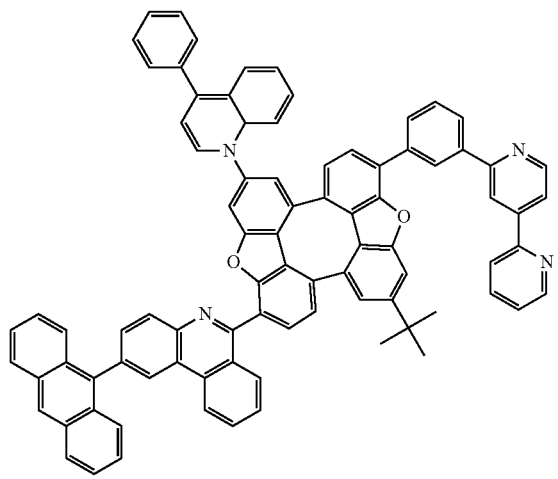
15
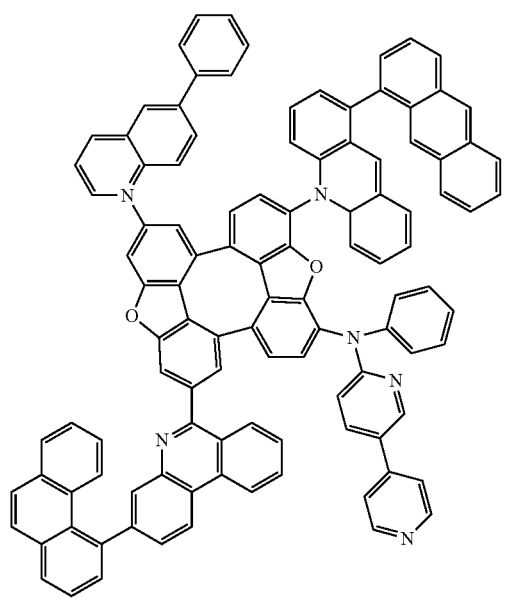
16
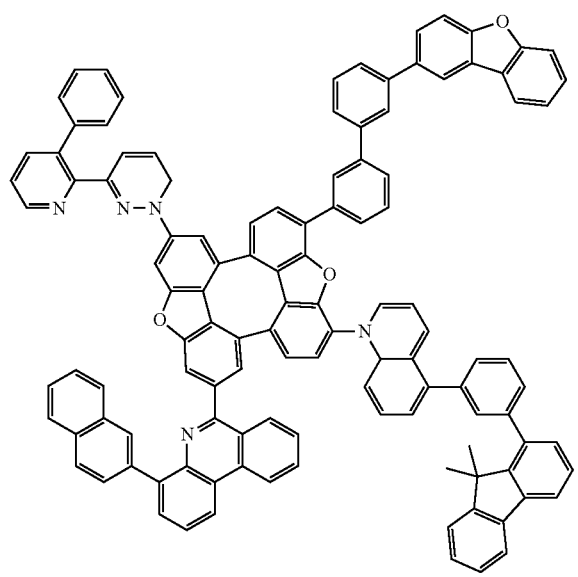

-continued
17
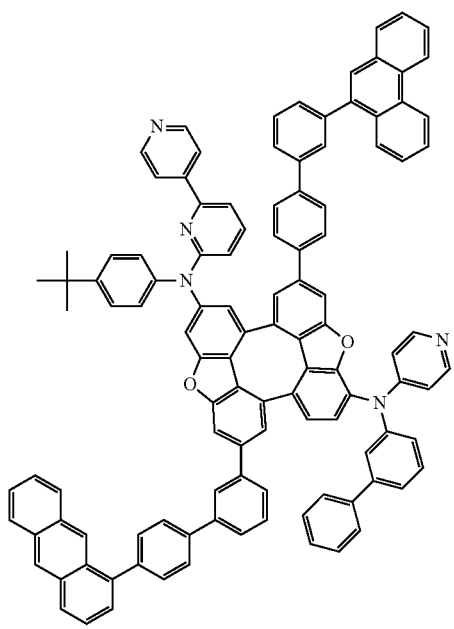
18
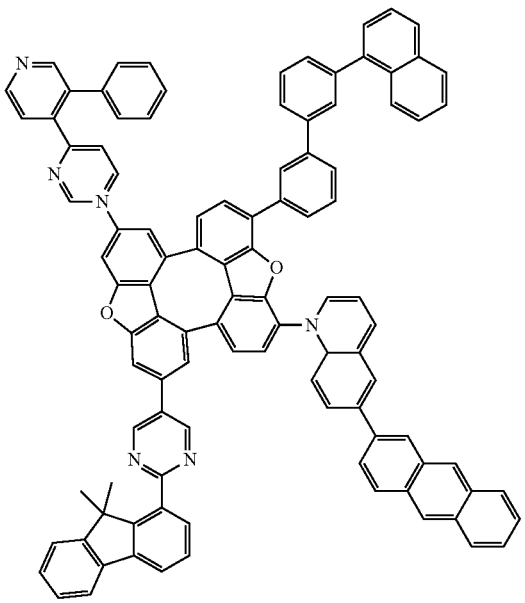
19
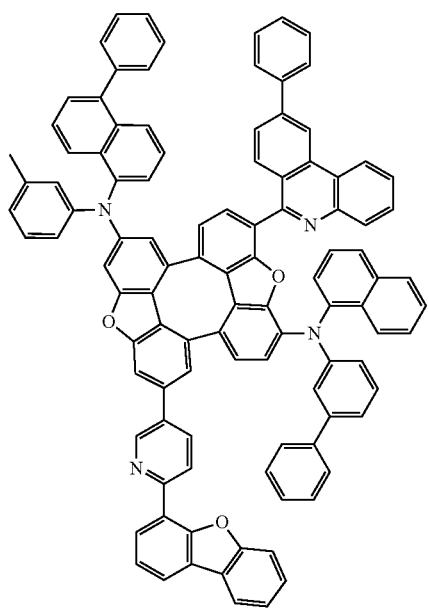
20
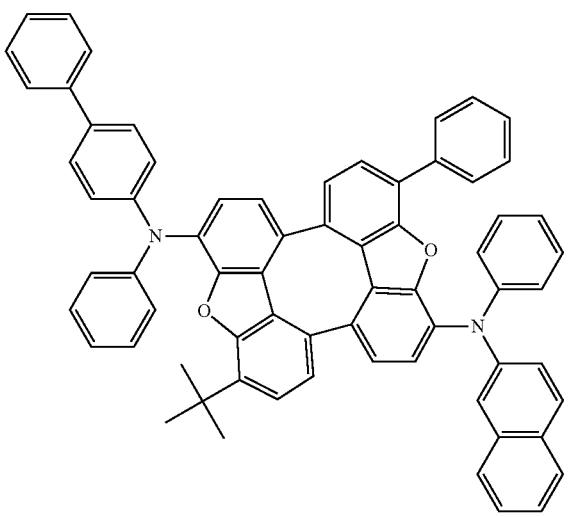

153
154
-continued
21
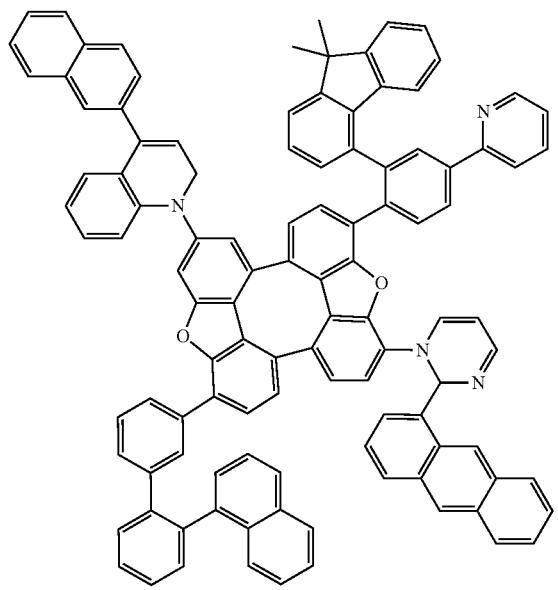
22
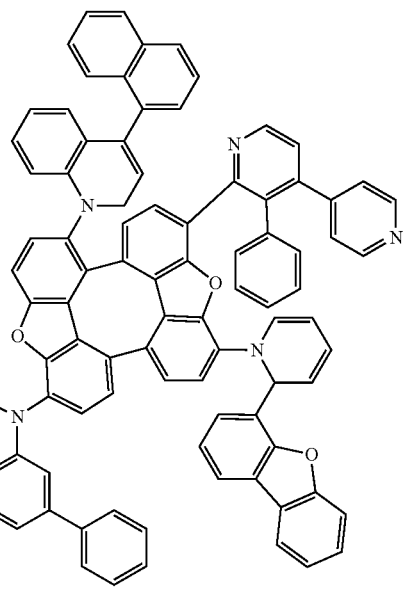
23
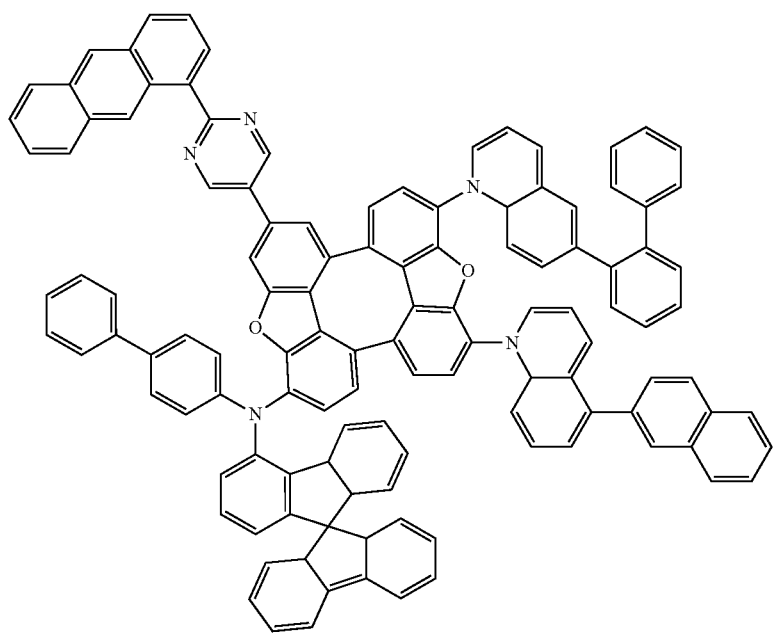

-continued
24
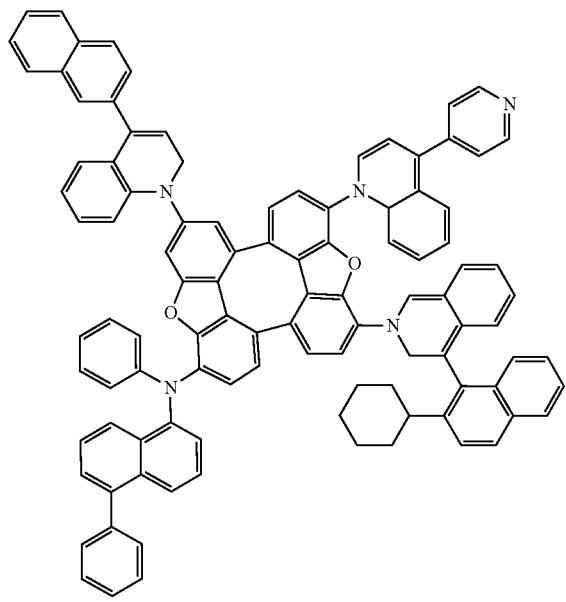
25
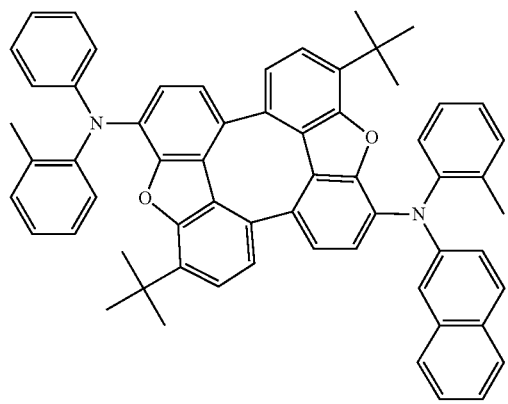
26
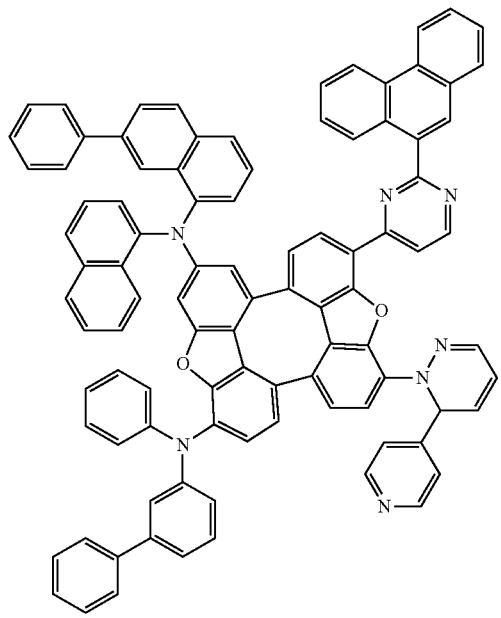
27
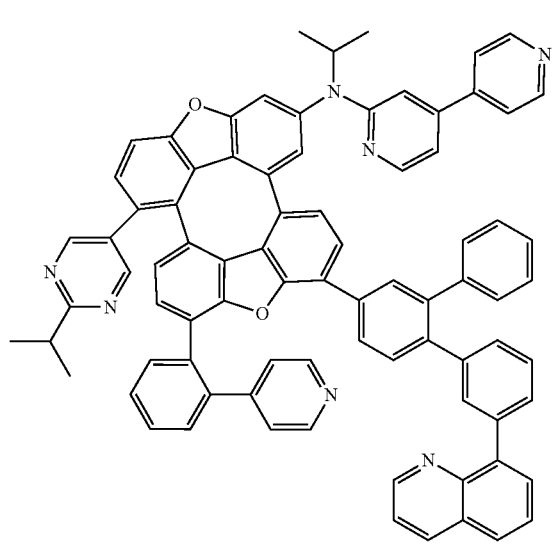

-continued
28
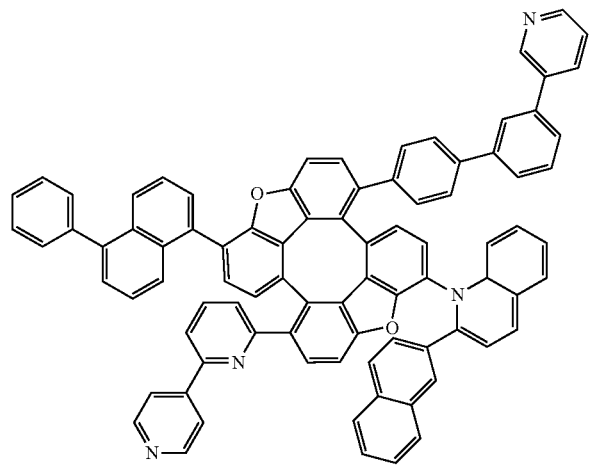
29
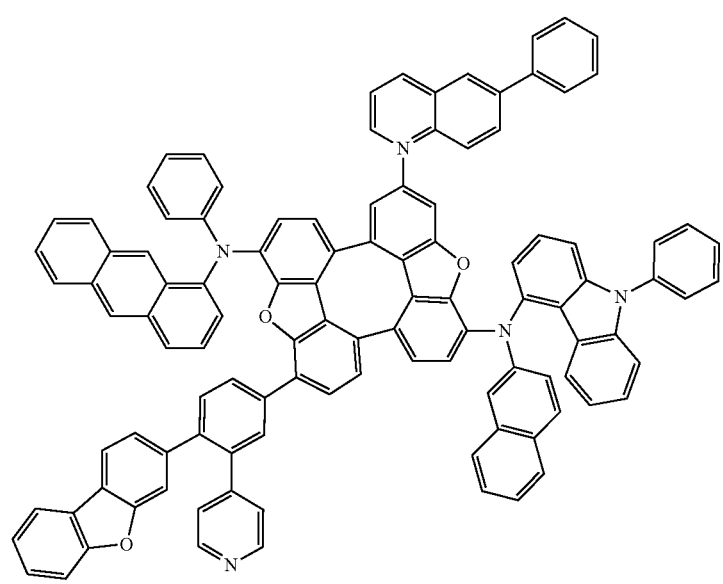
30
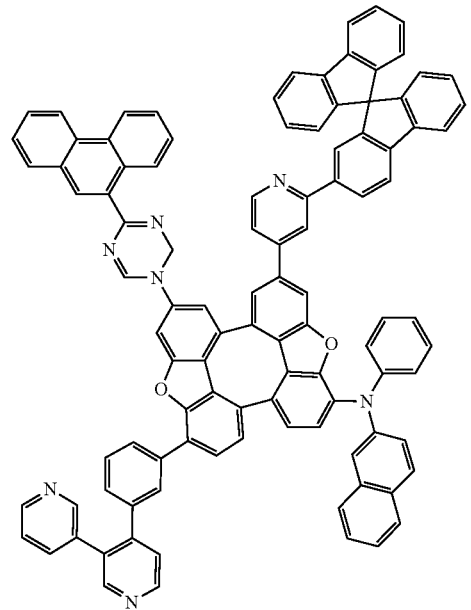
31
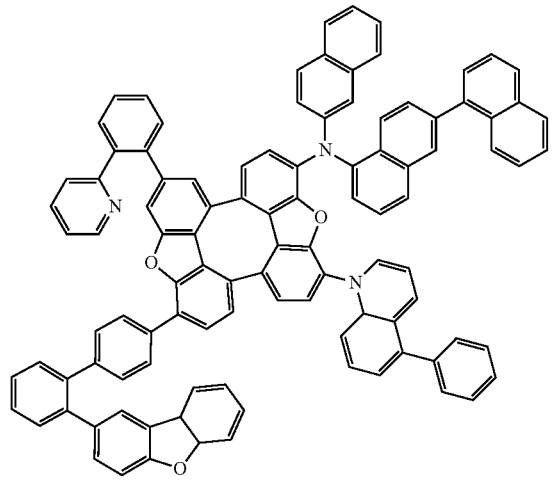

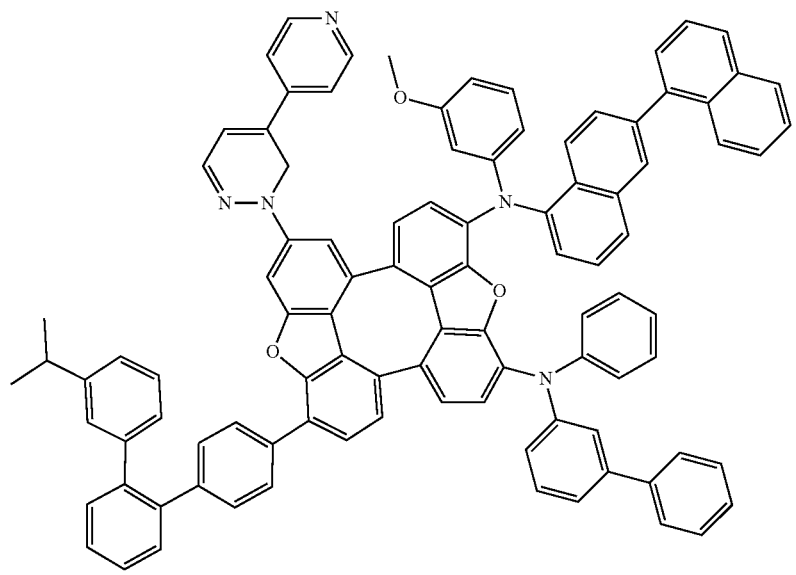
32
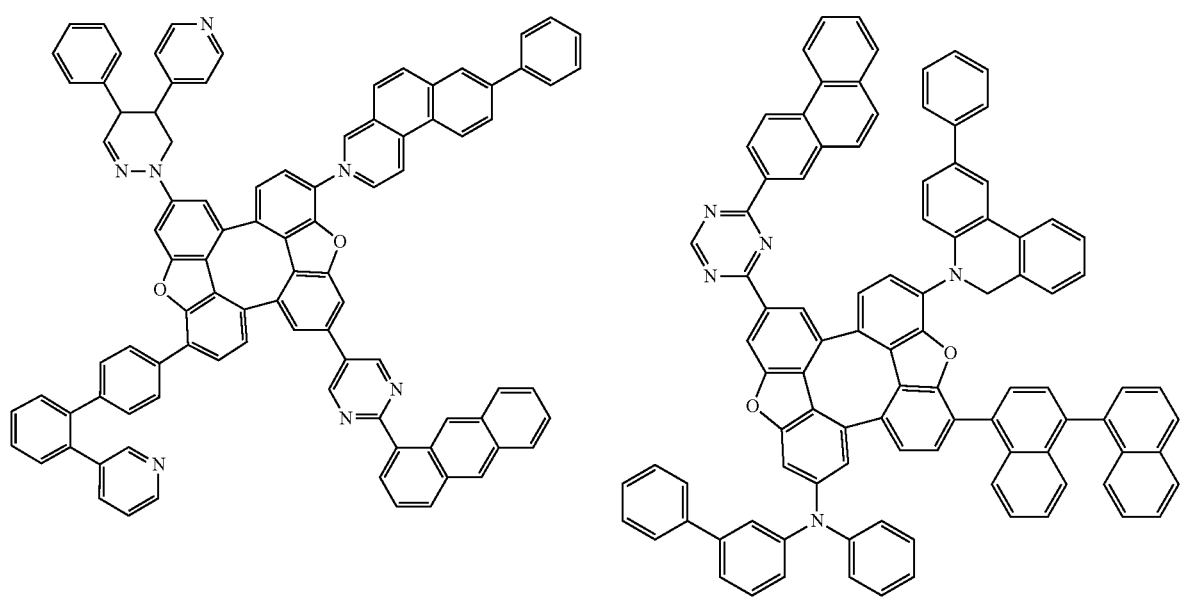
33
34

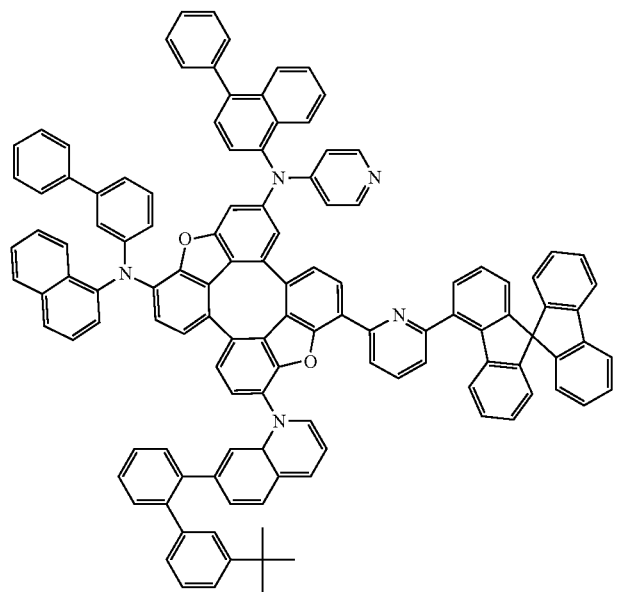
35
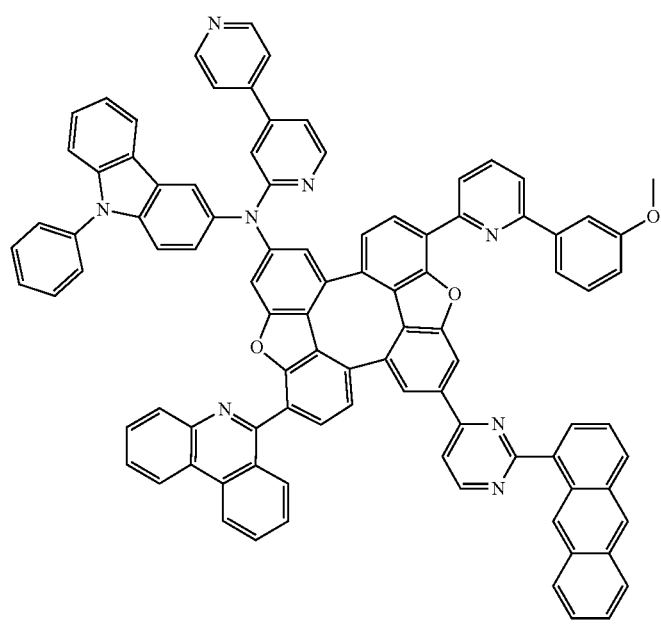
36

-continued
37
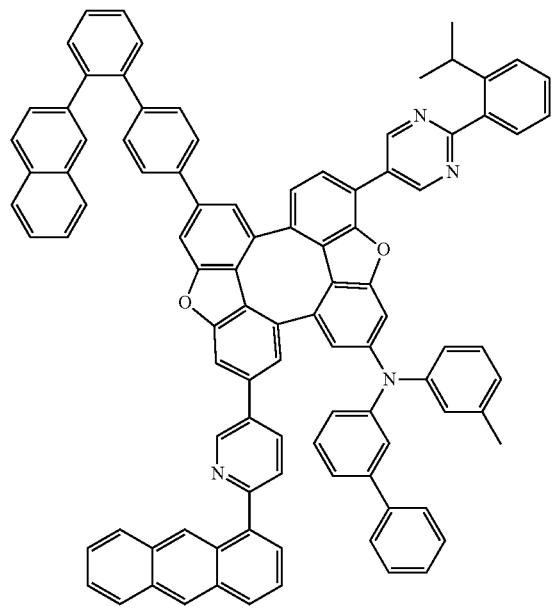
38
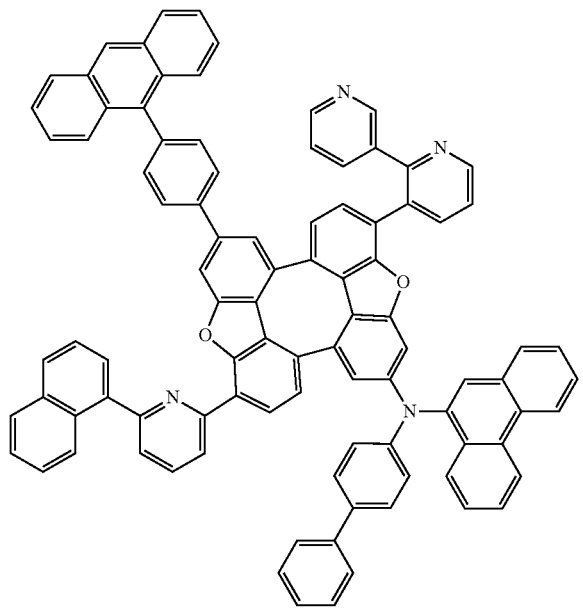
39
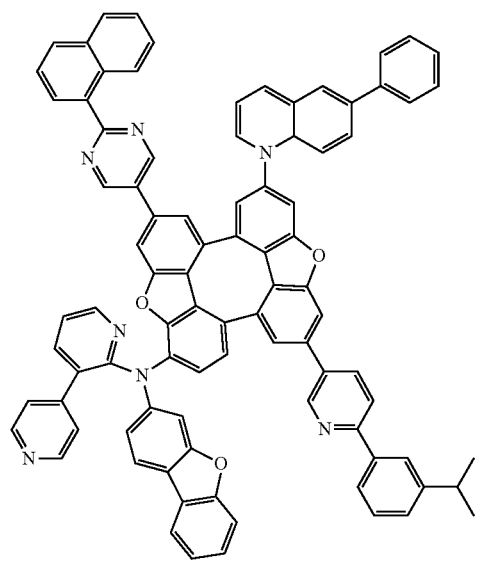
40
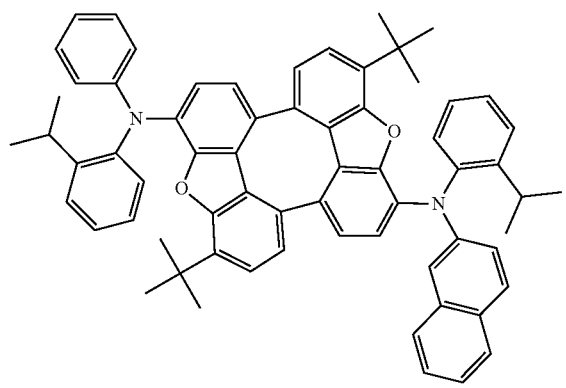

-continued
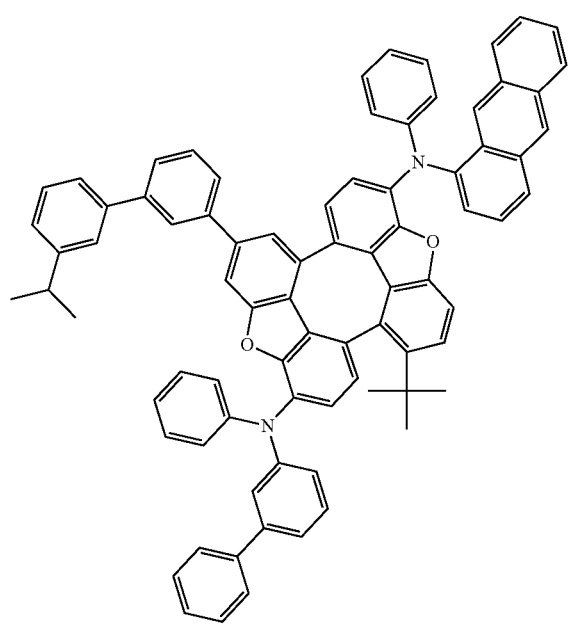
41
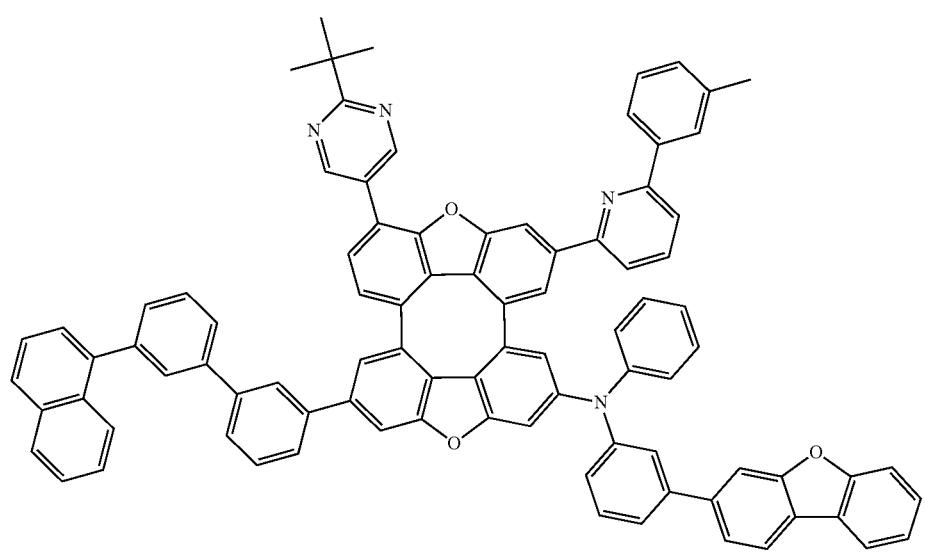
42

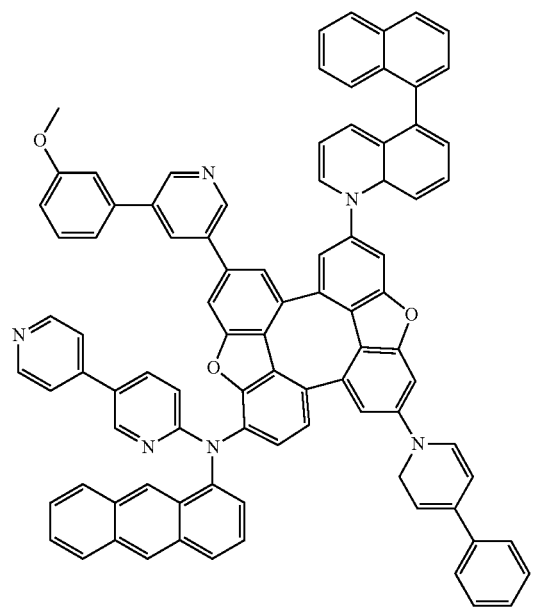
43
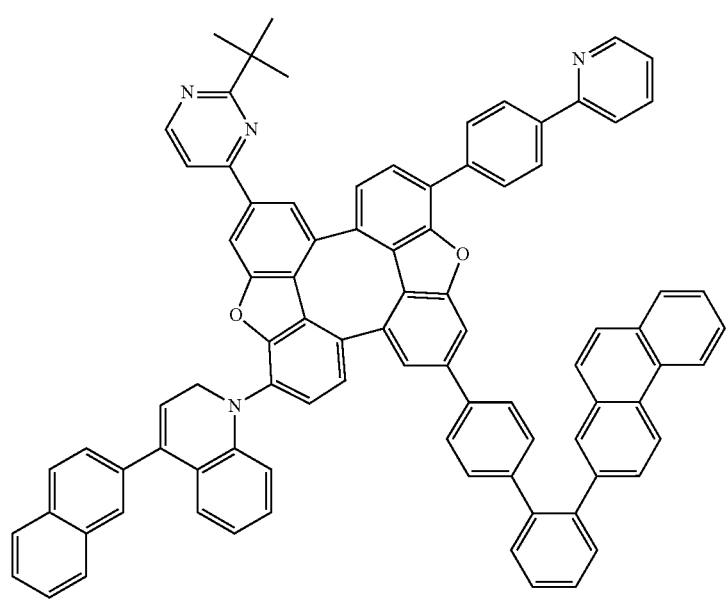
44

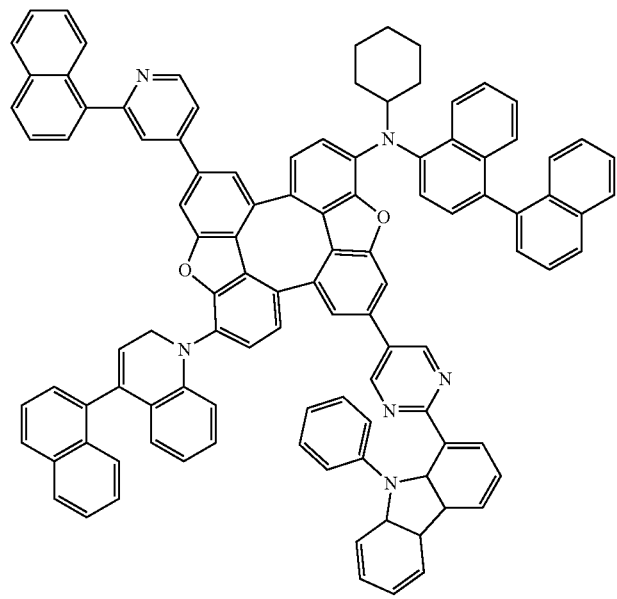
45
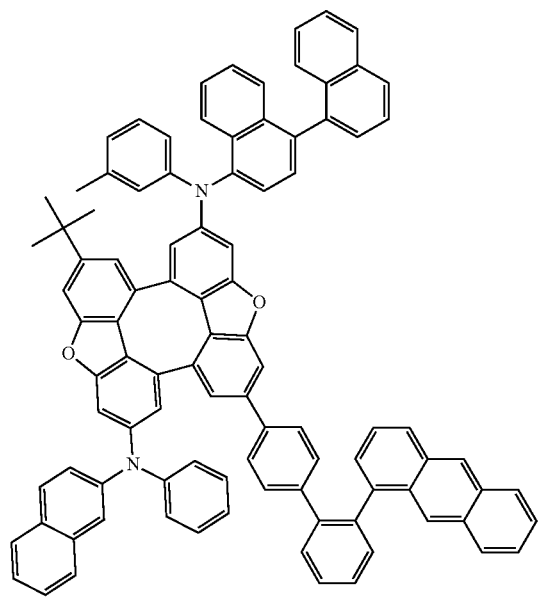
46
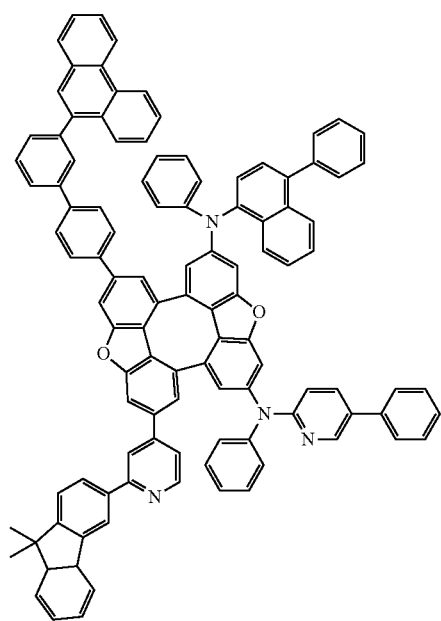
47

-continued
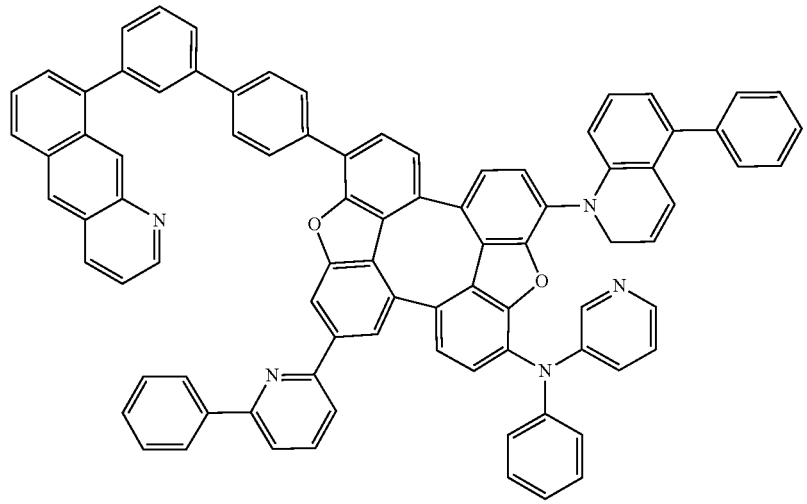
48
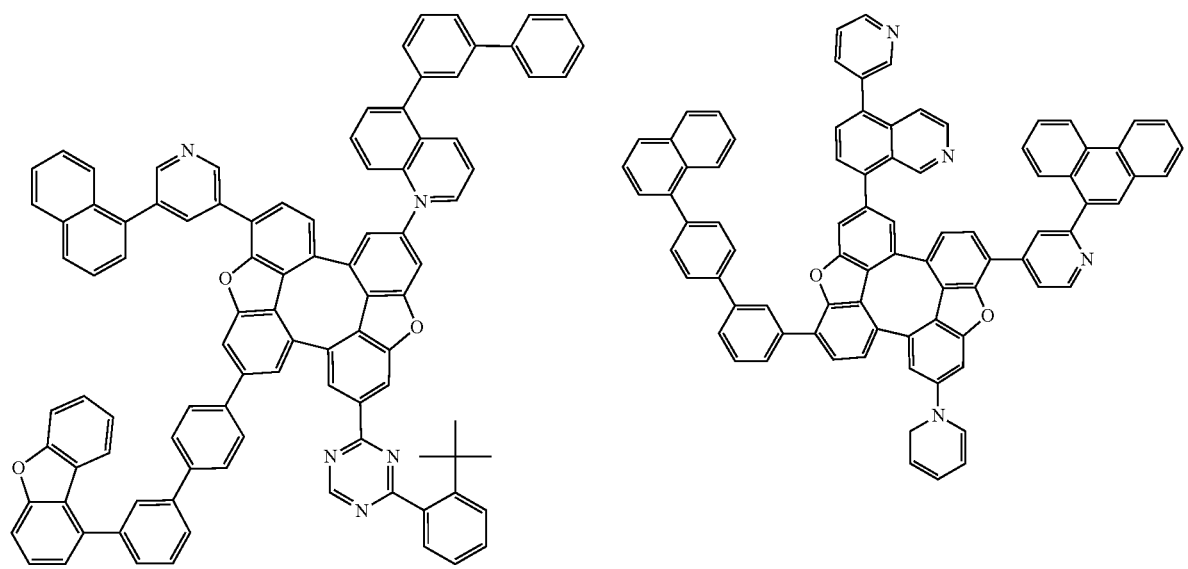
49
50
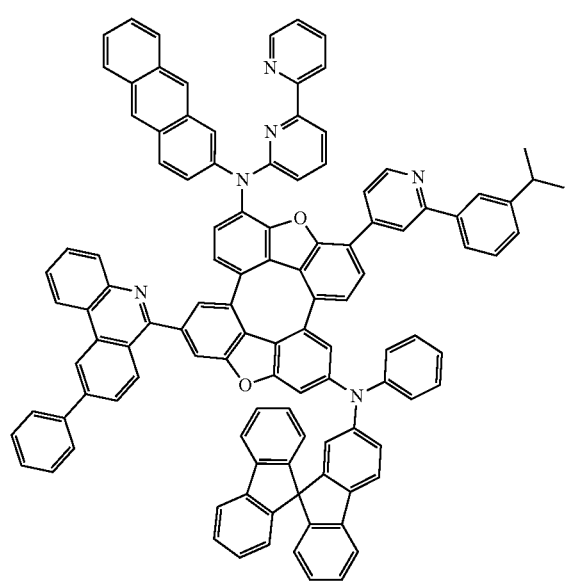
51

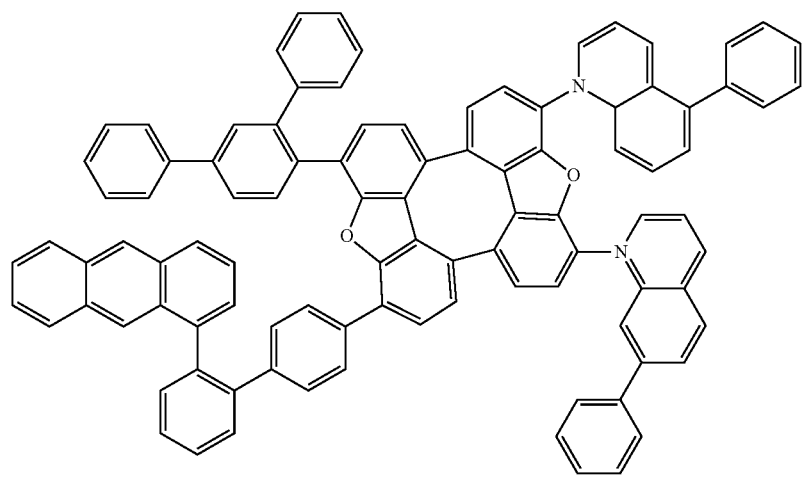
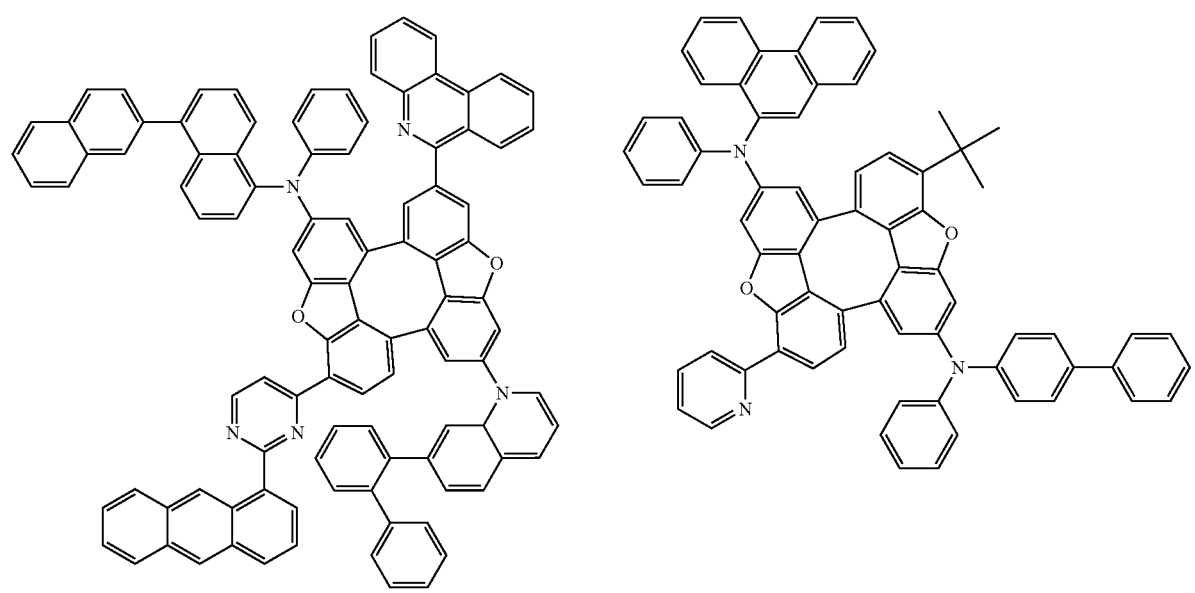

55
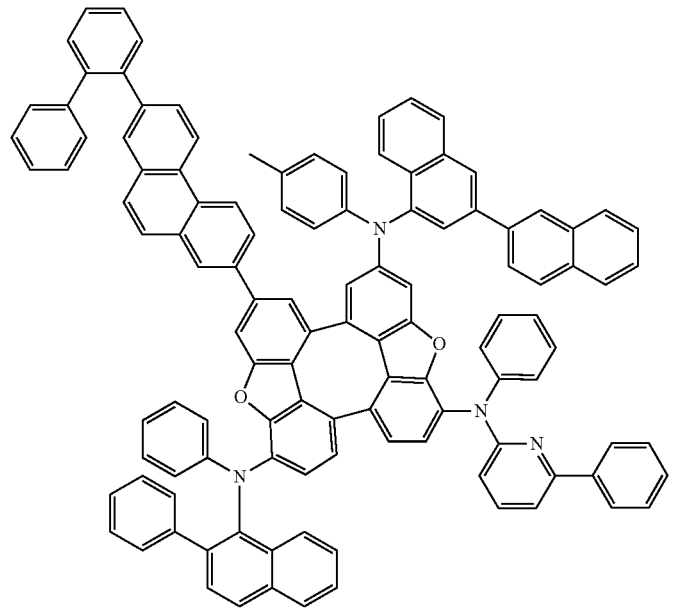
56
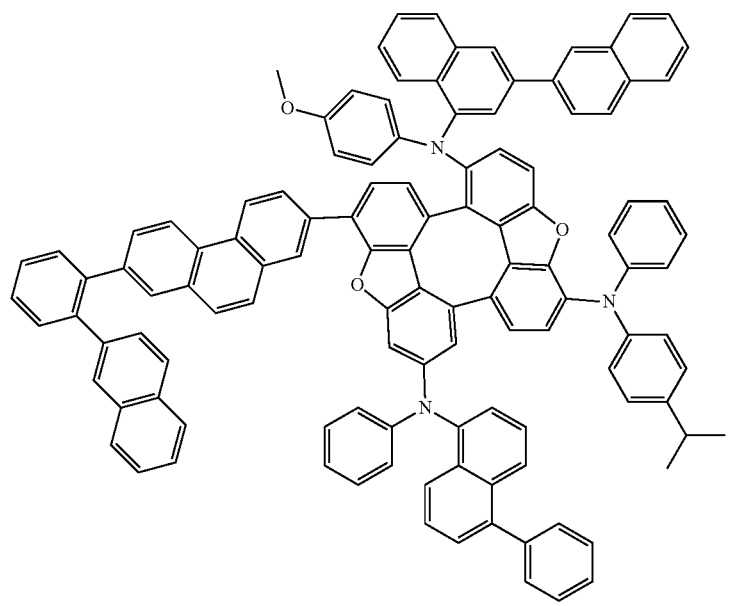

57
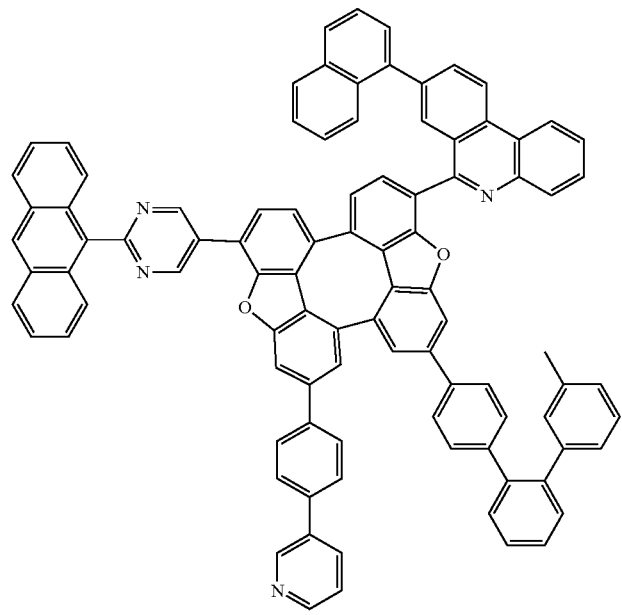
58
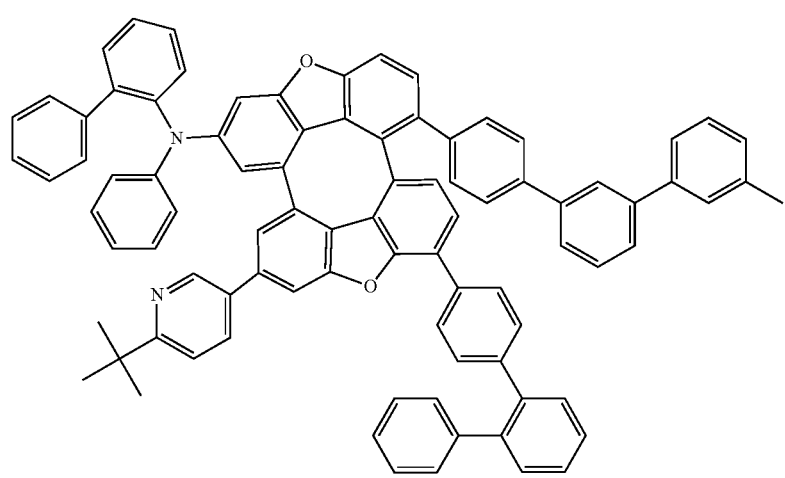

59
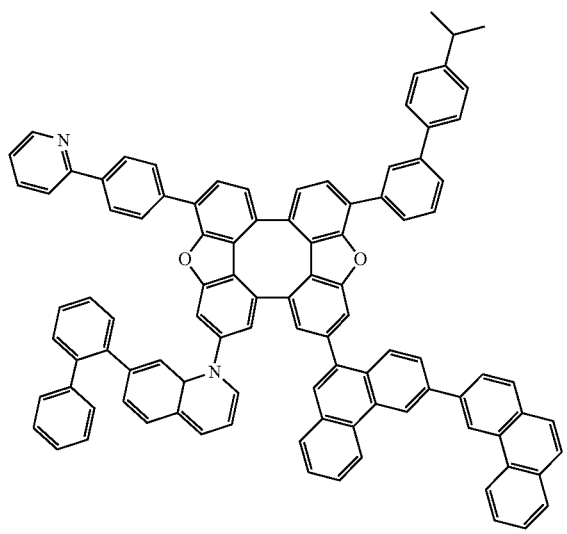
60
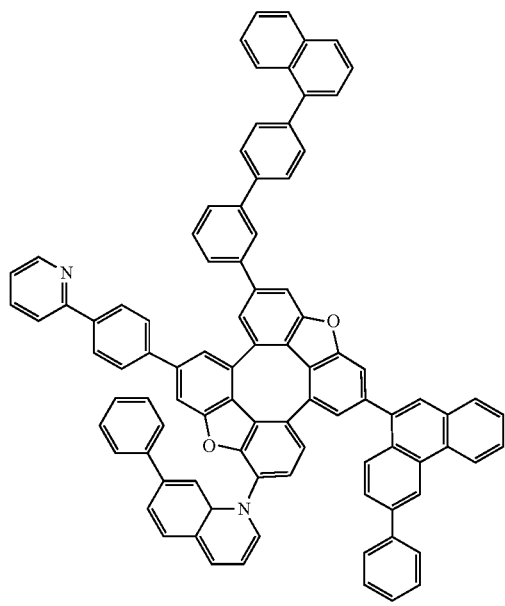
61
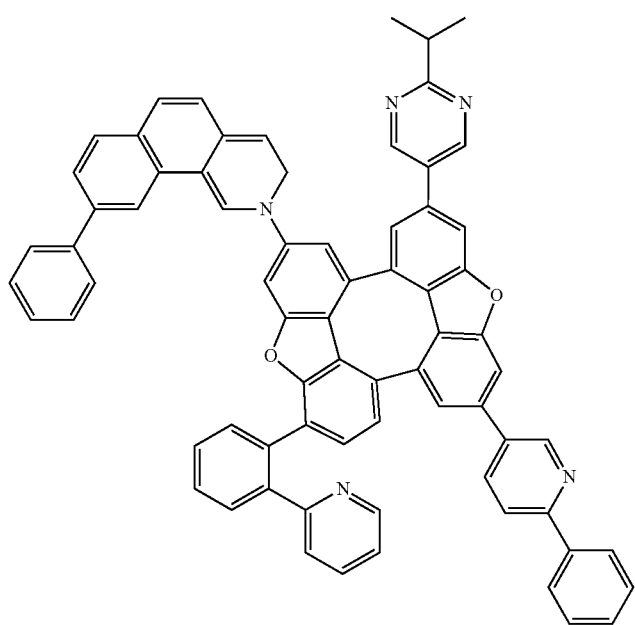

-continued
62
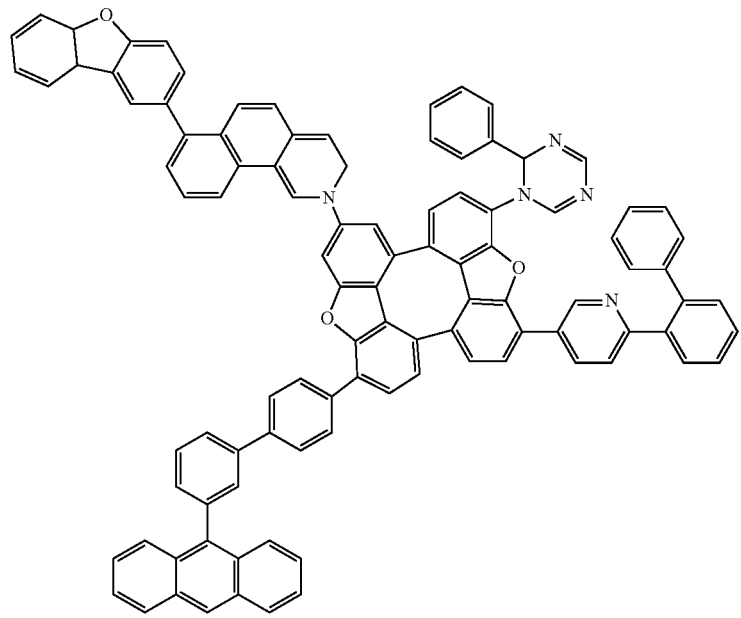
63
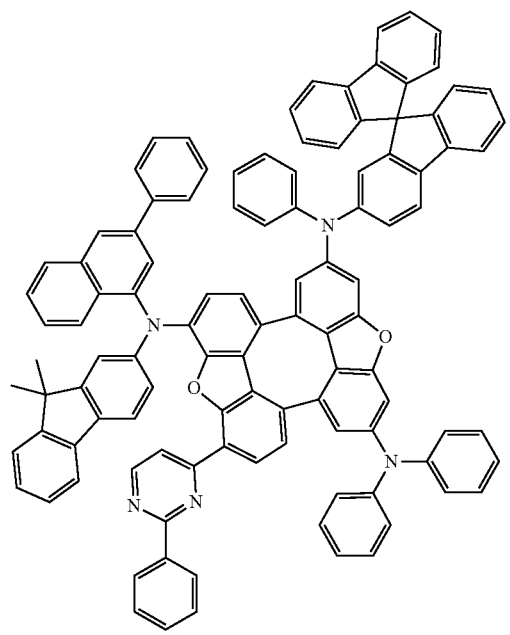
64
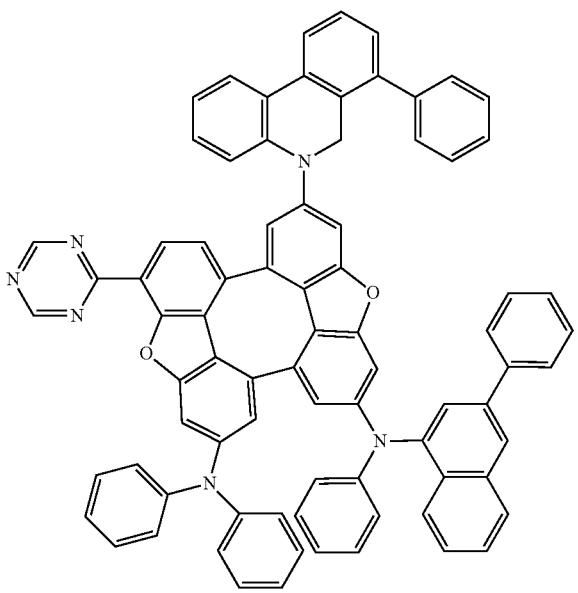

-continued
65
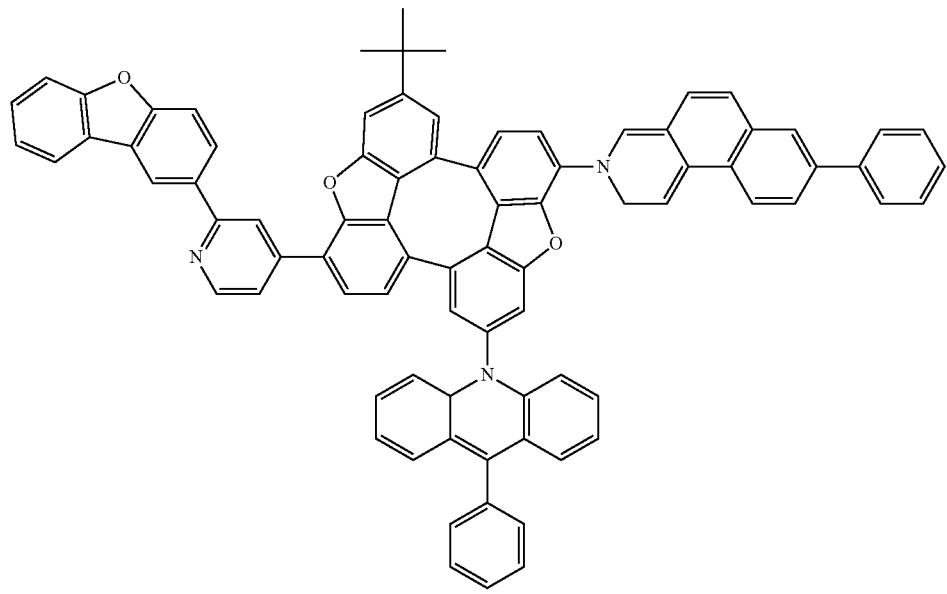
66
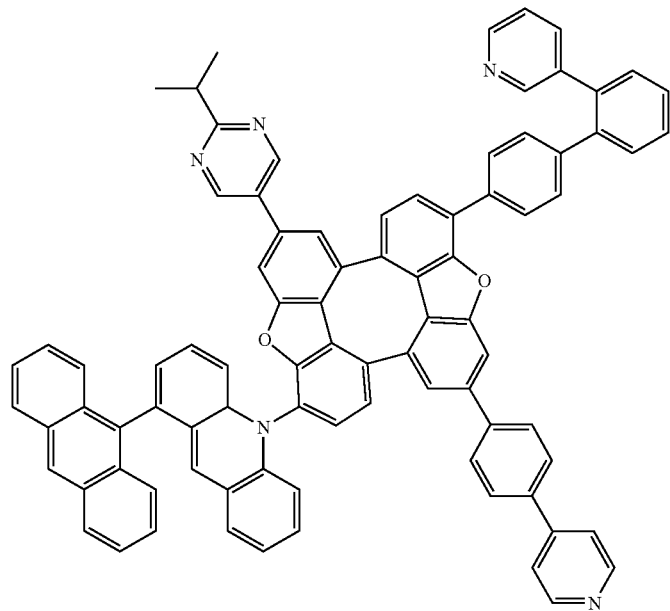

185
186
-continued
67
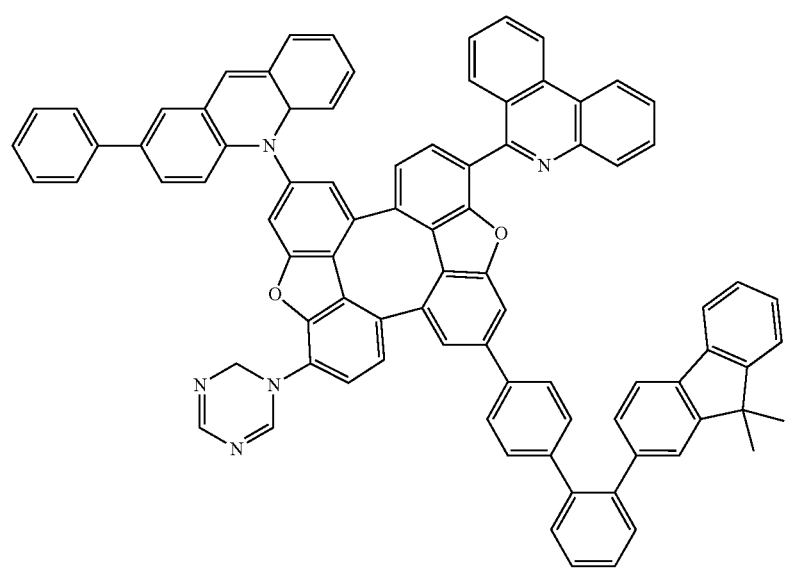
68
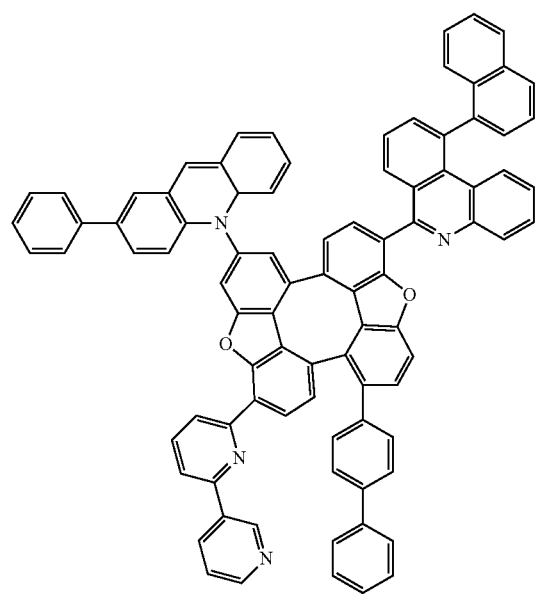
69
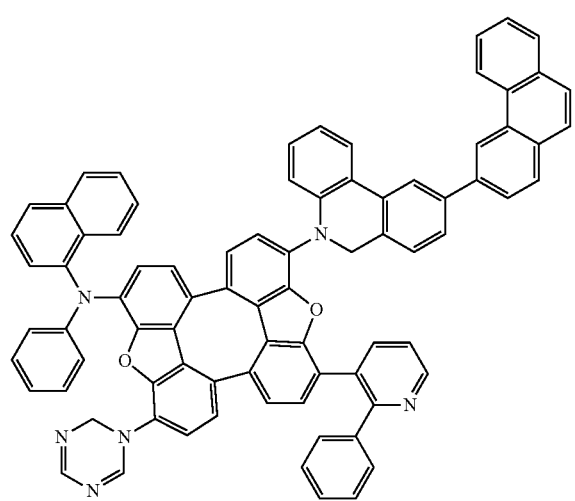

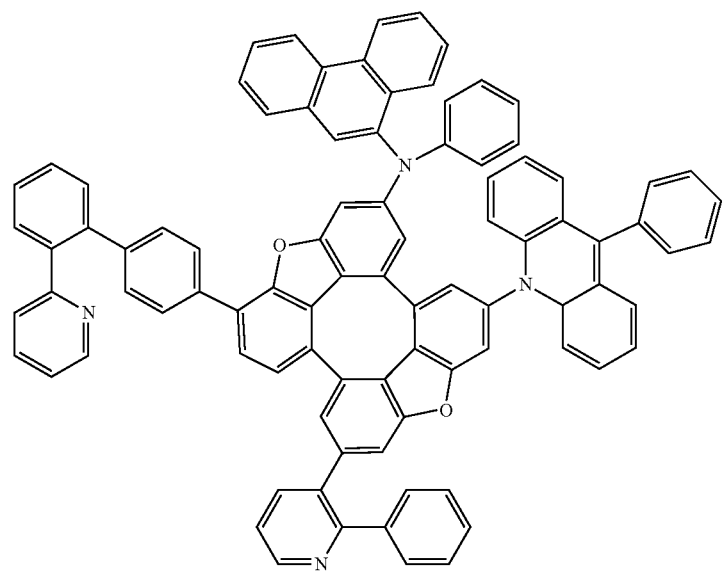

72
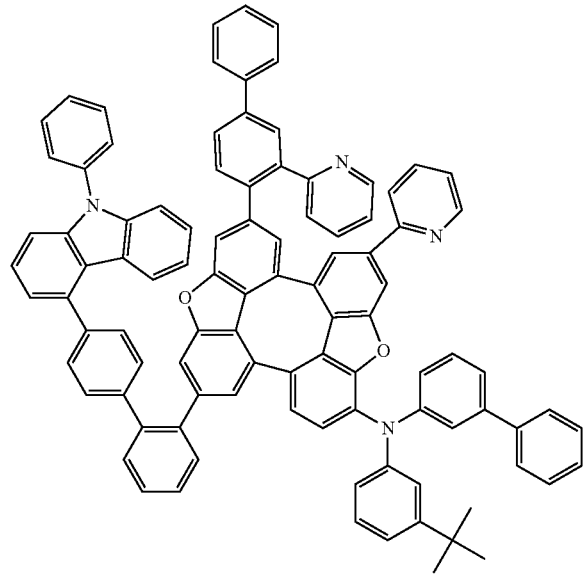
73
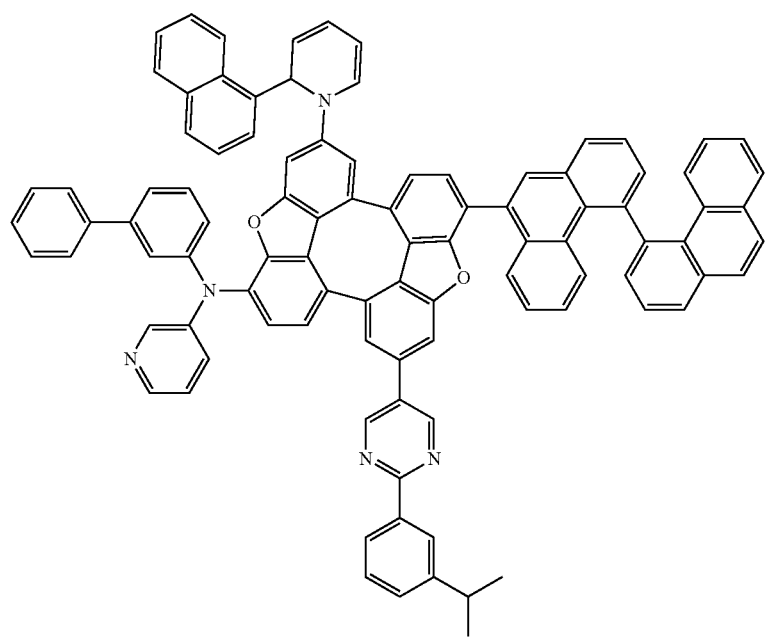

-continued
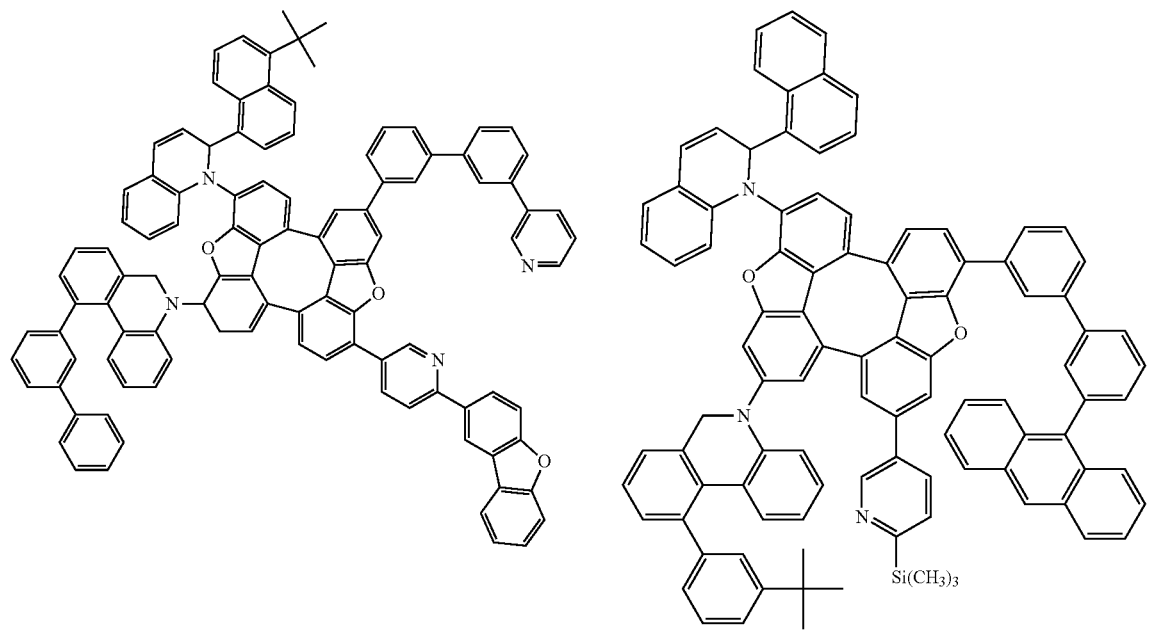
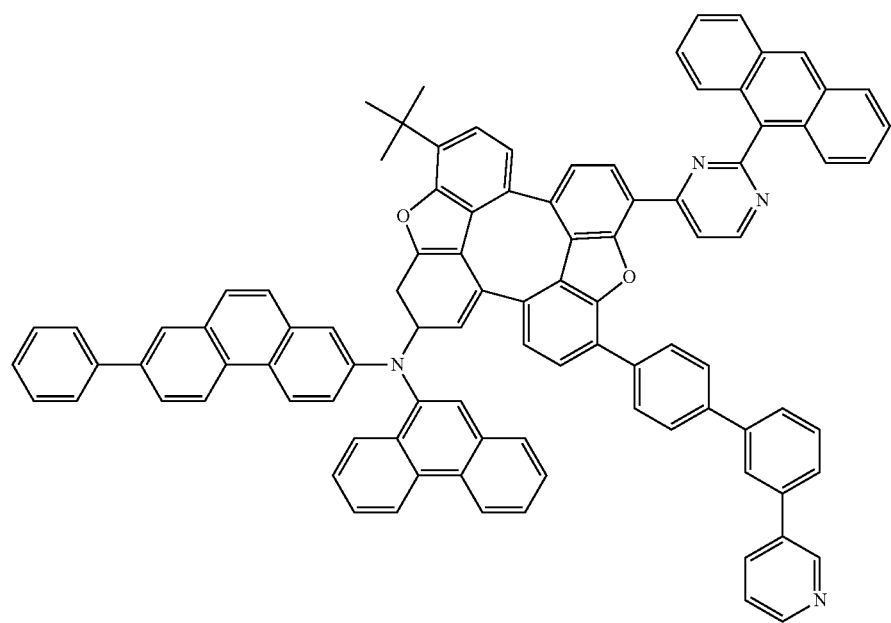

-continued
77
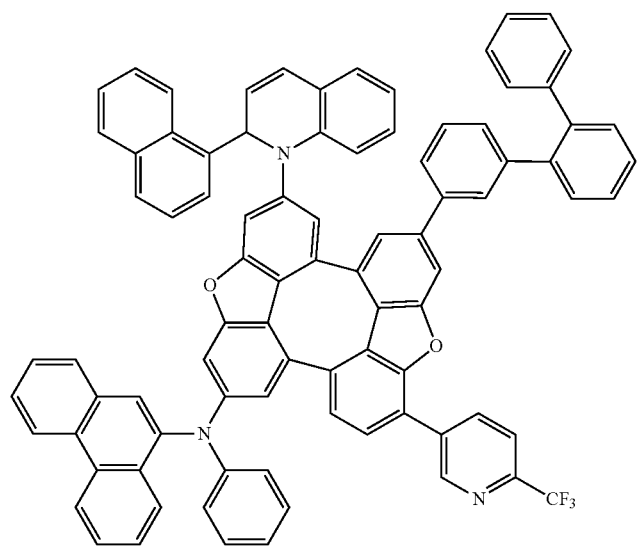
78
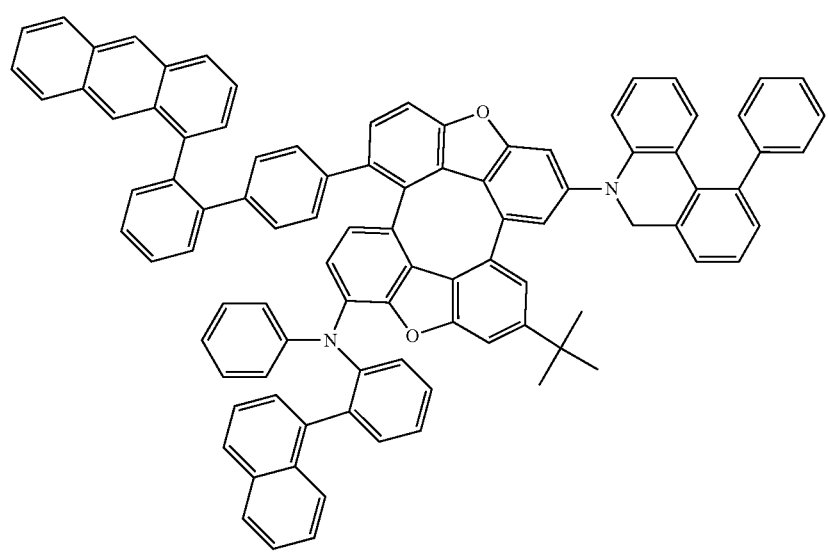

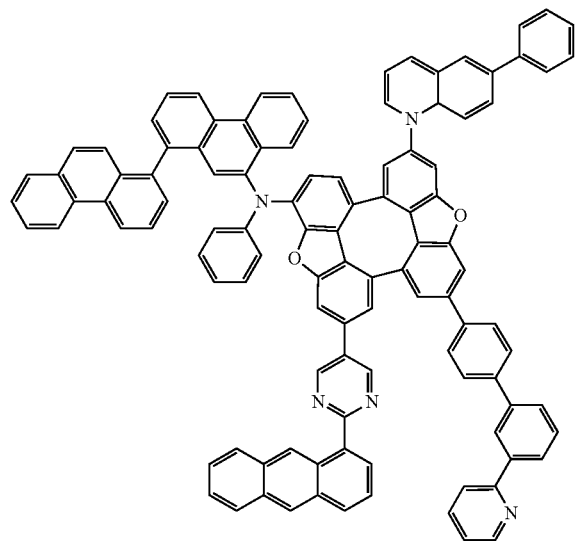
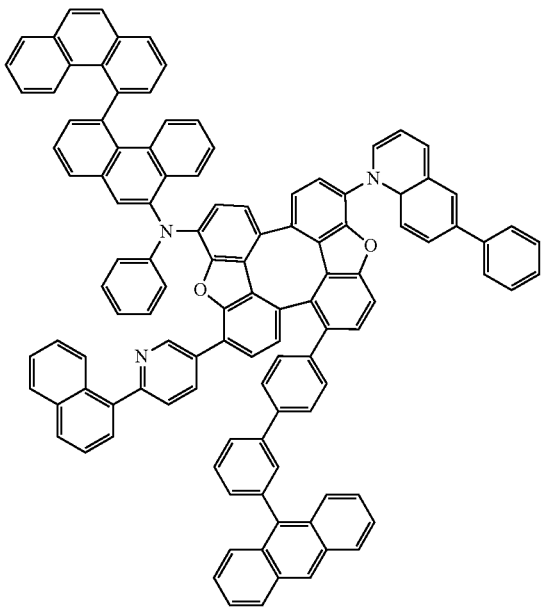
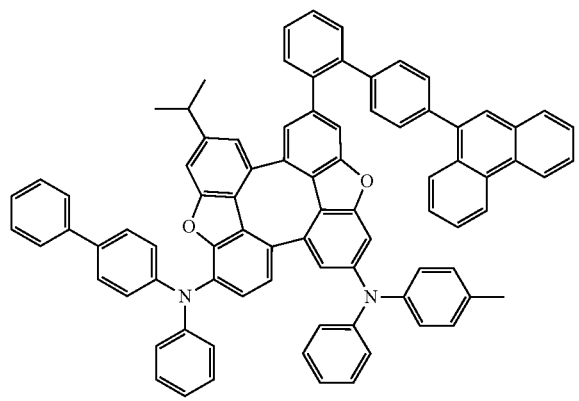
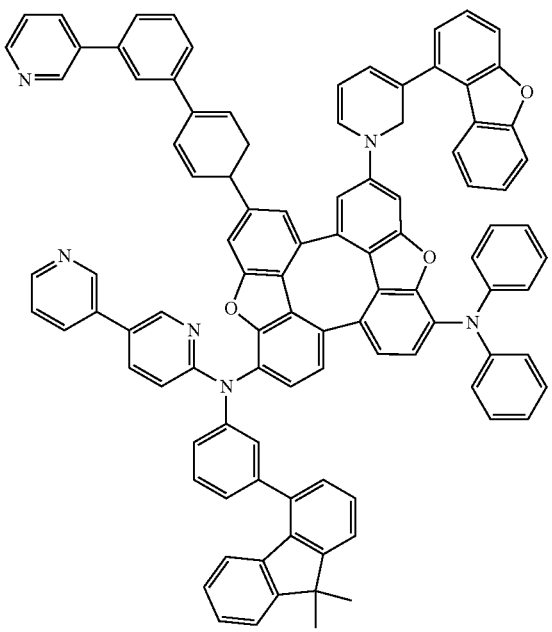

197
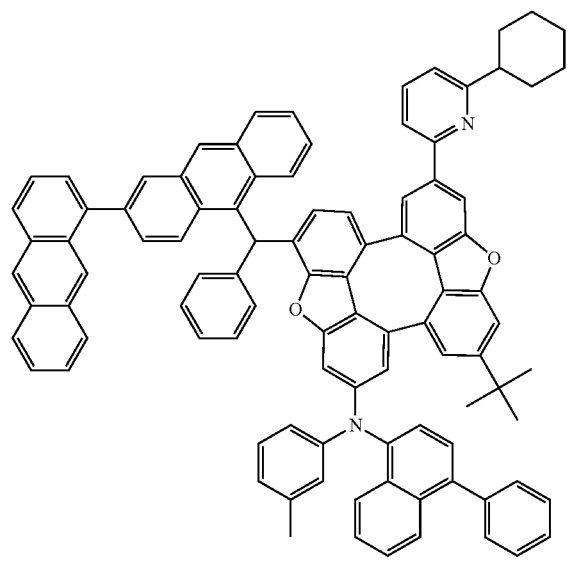
198
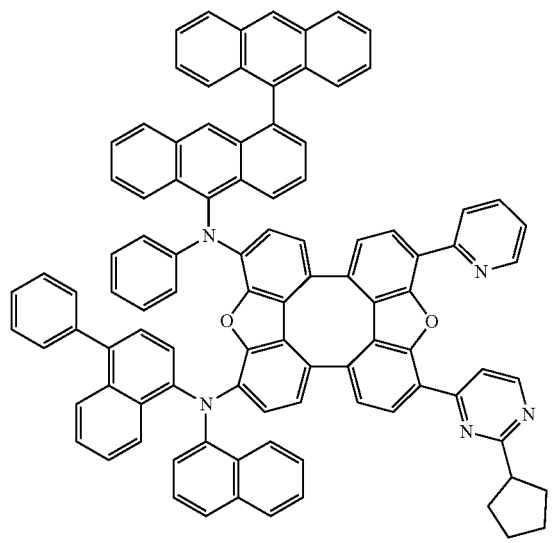
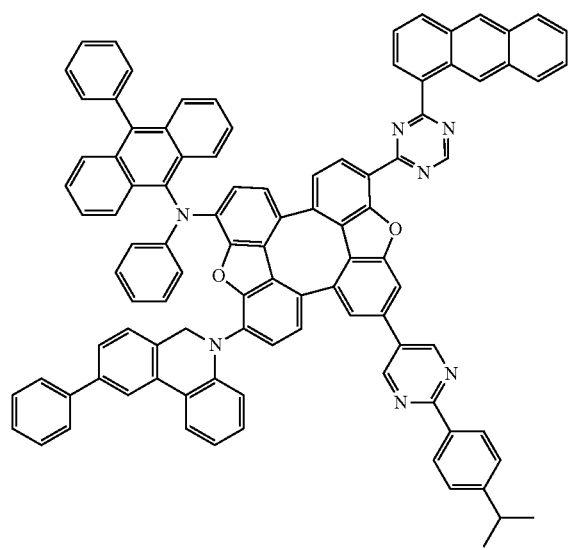
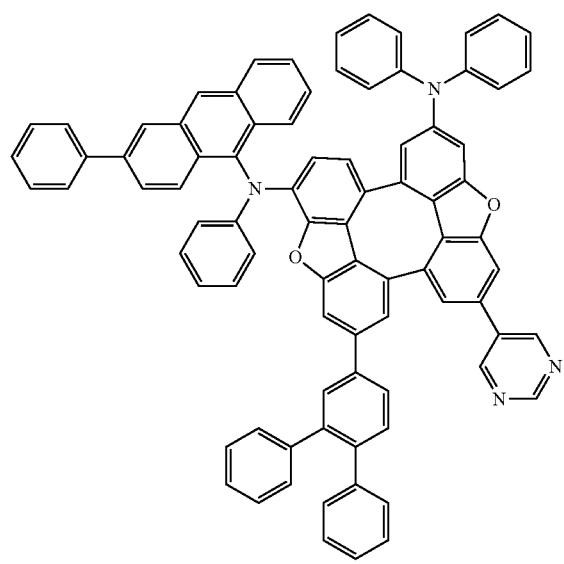

-continued
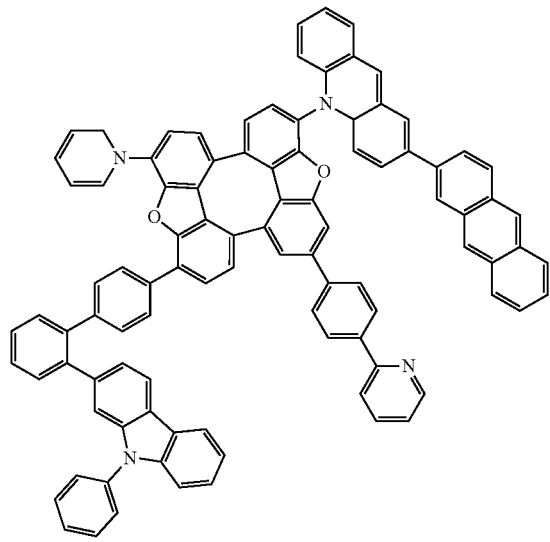
87
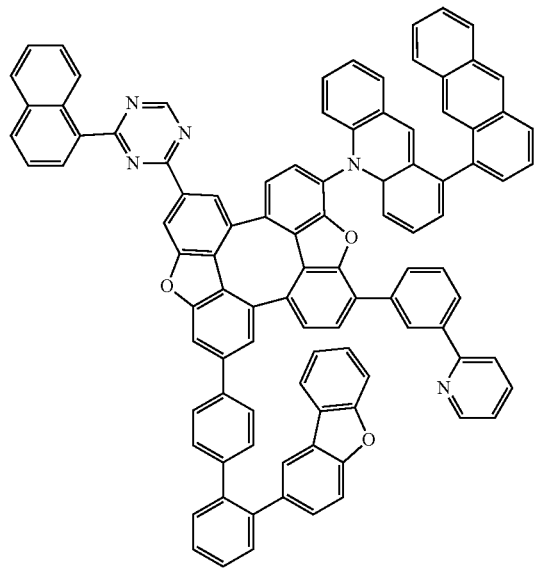
88
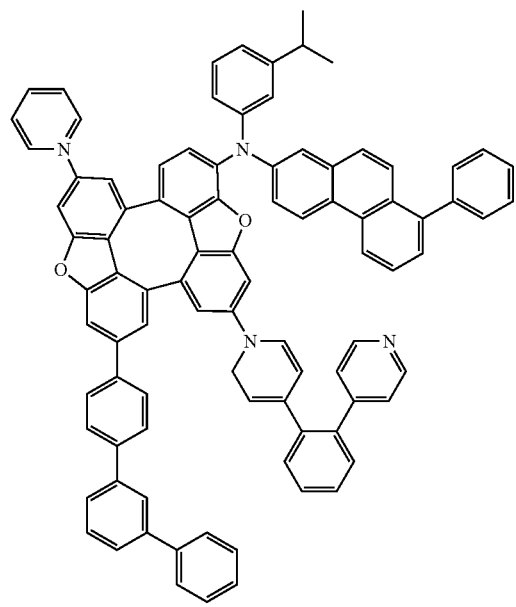
89
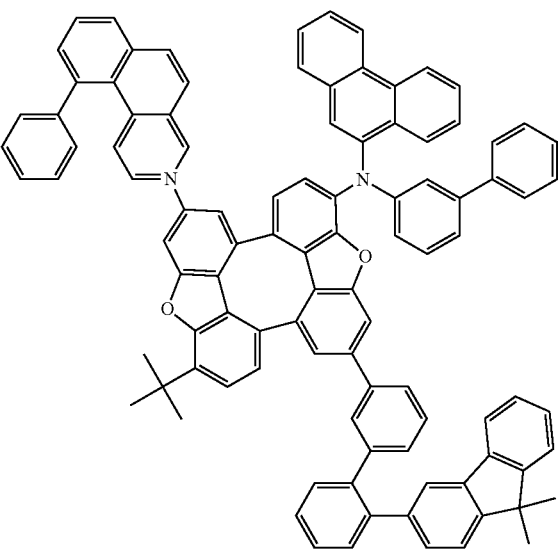
90

201 202
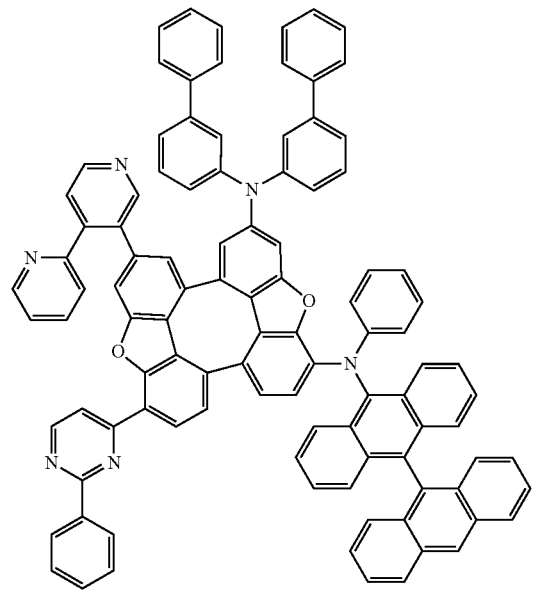 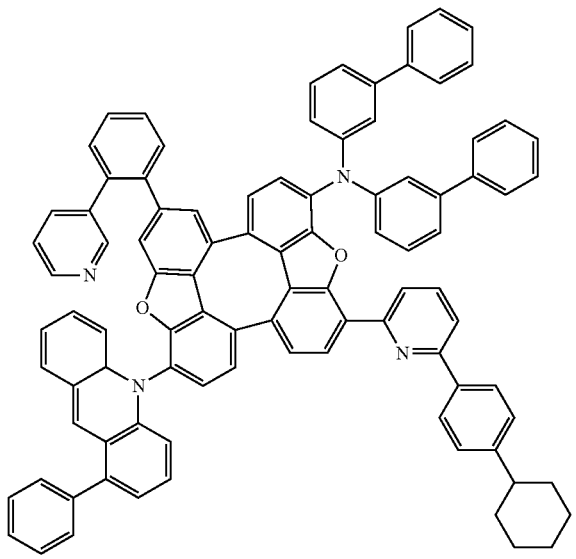
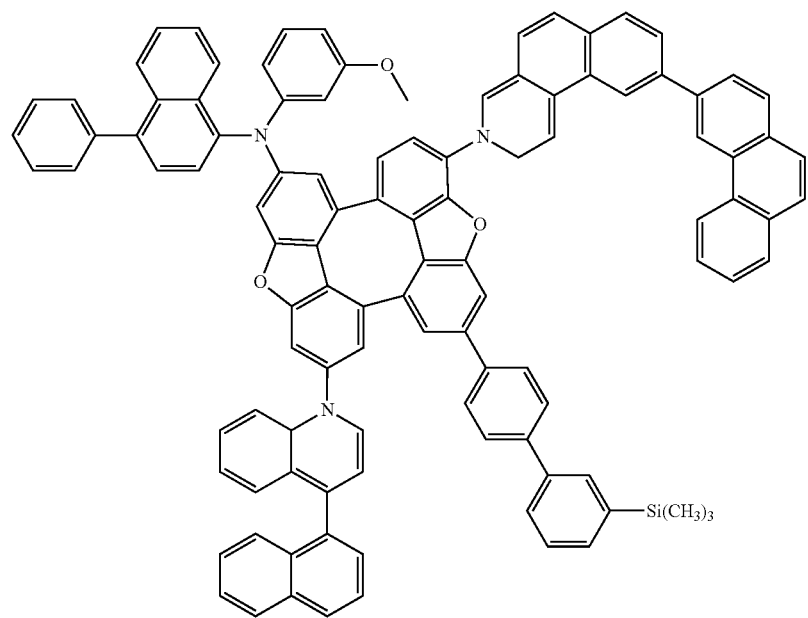

94
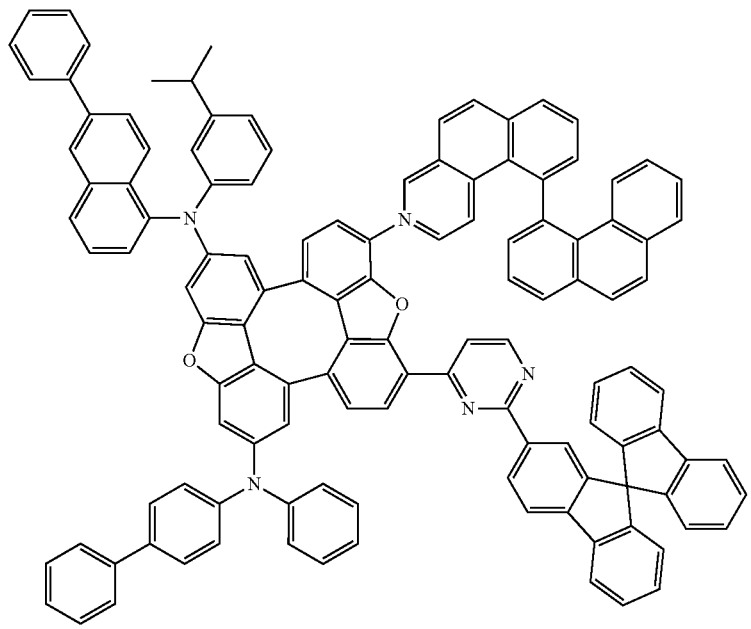
95
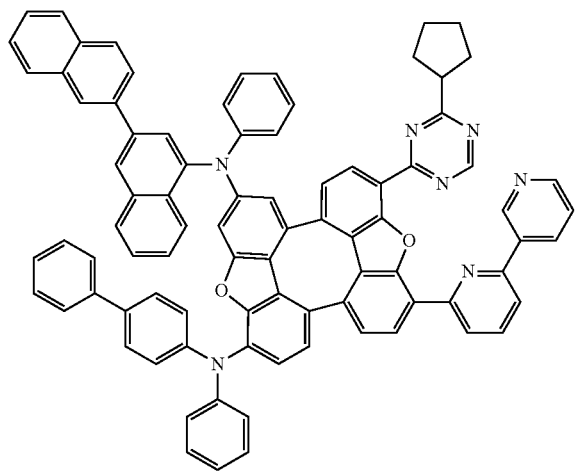
96
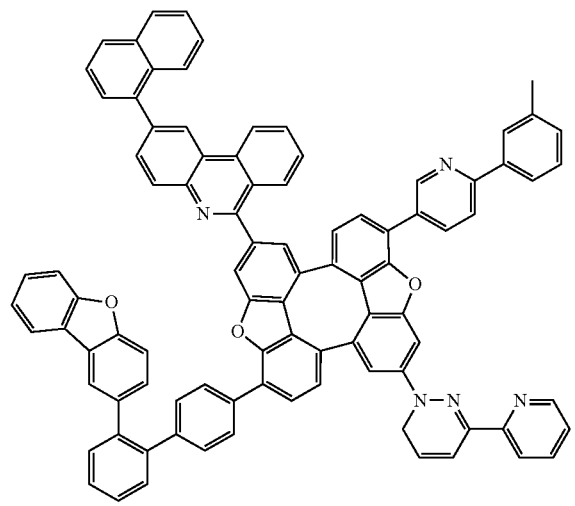

-continued
97
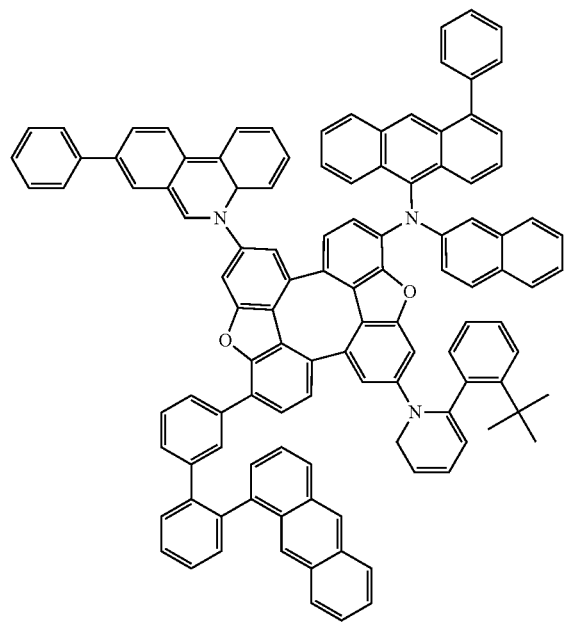
98
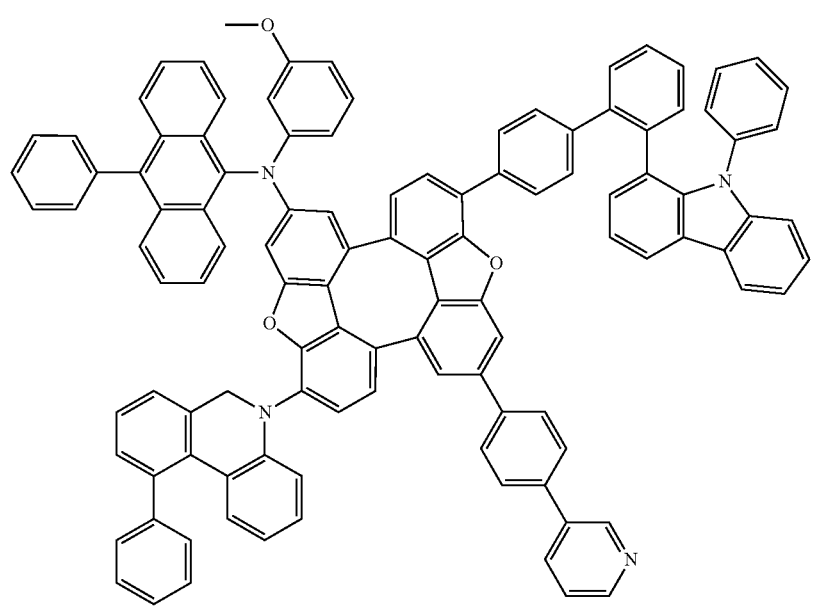

-continued
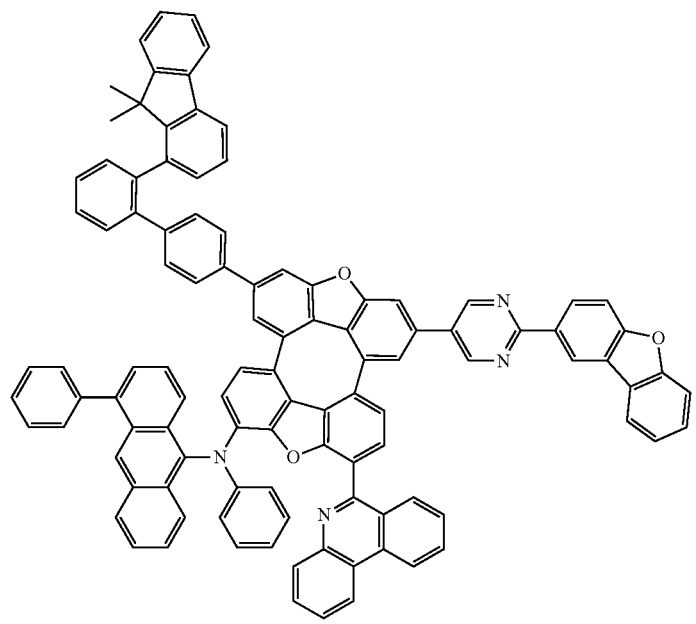
99
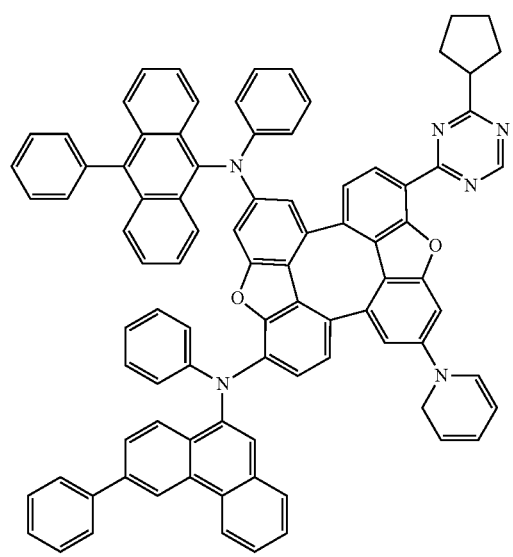
100
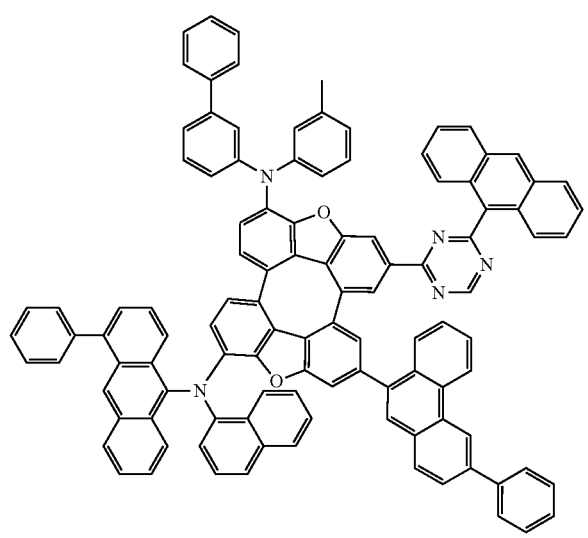
101

-continued
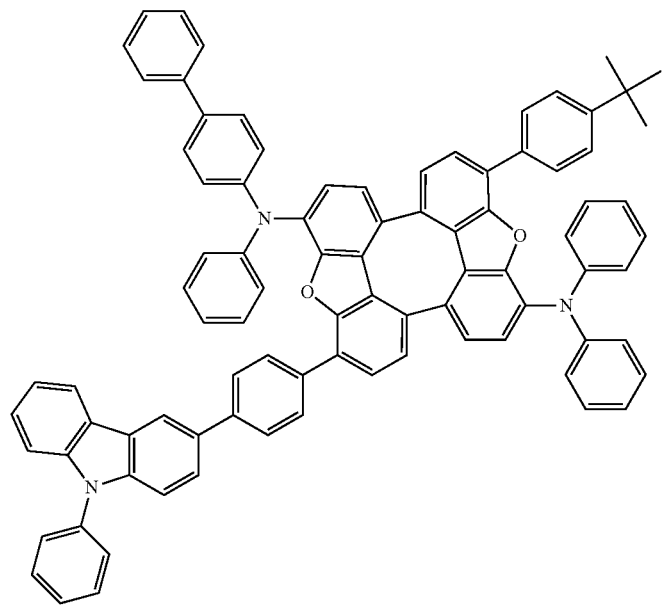
102
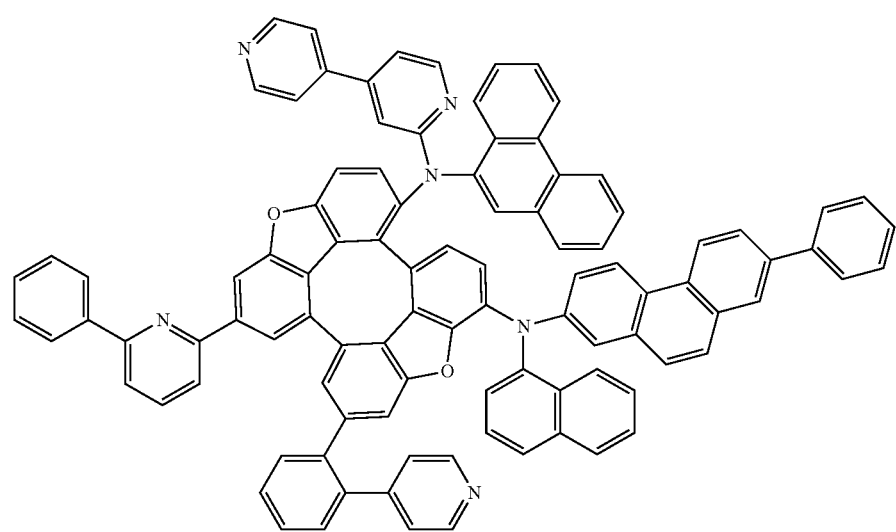
103

-continued
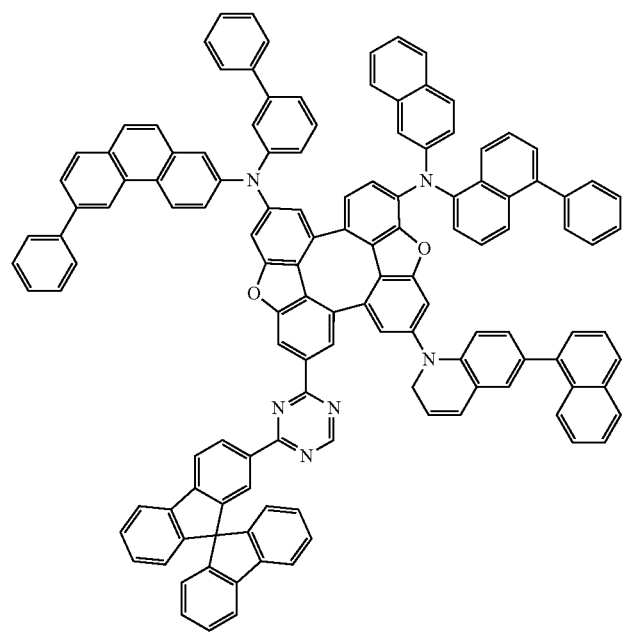
104
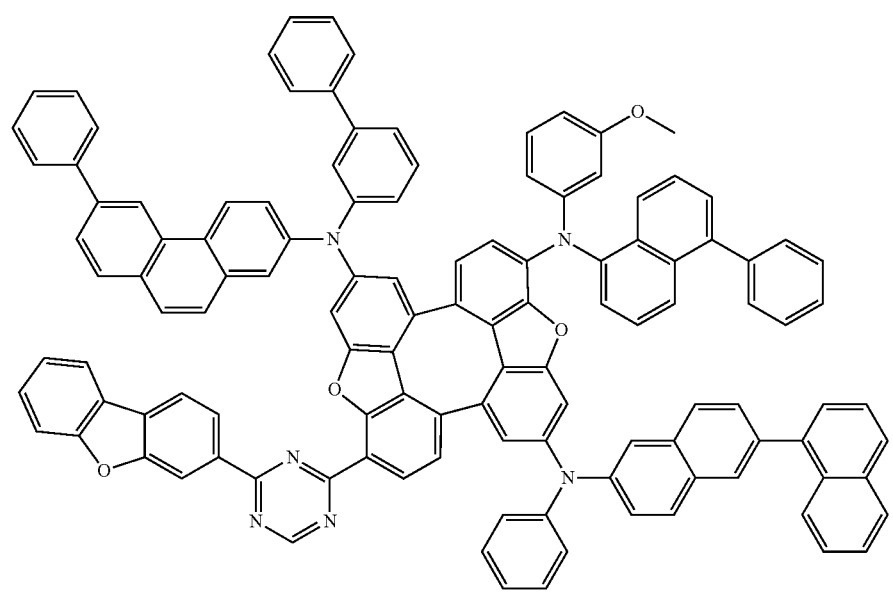
105

-continued
213
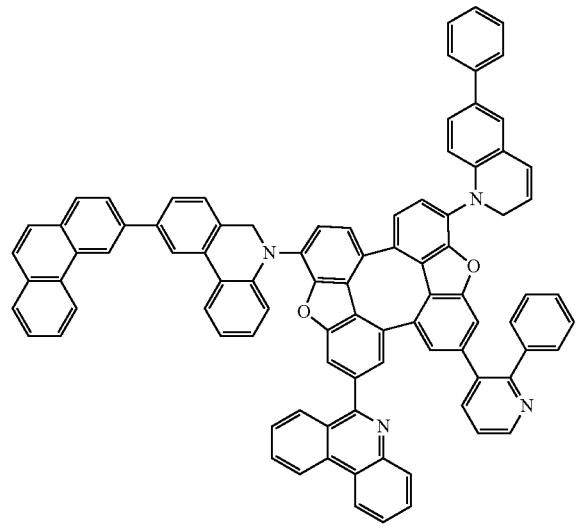
214
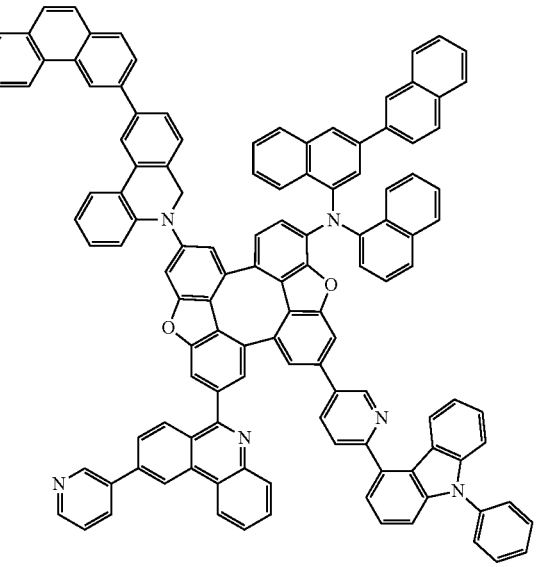
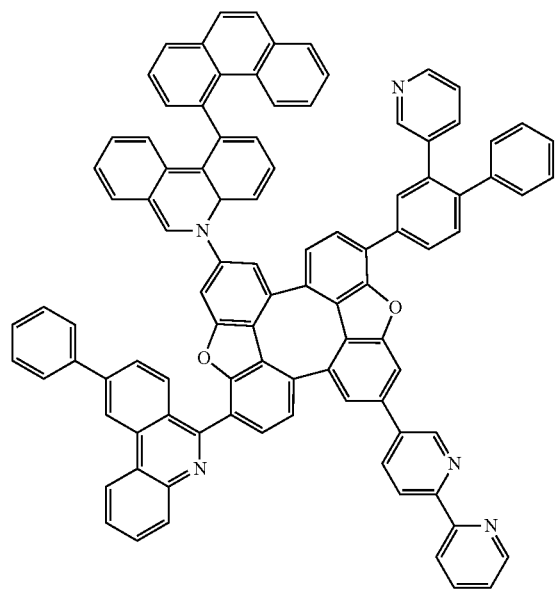
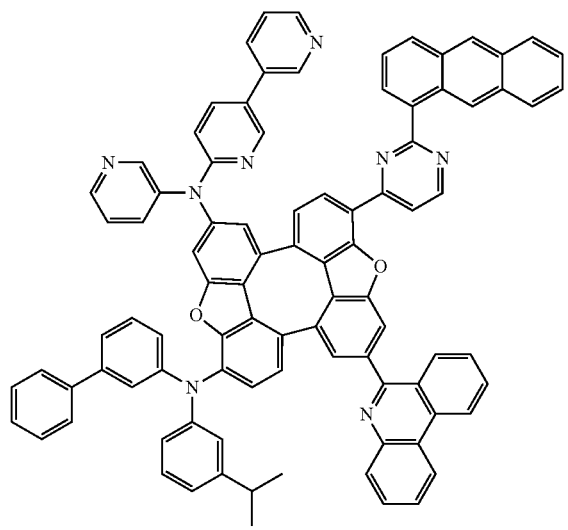

215
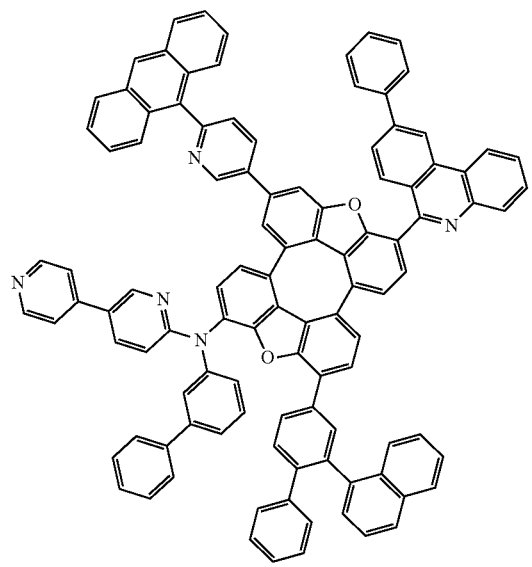
216
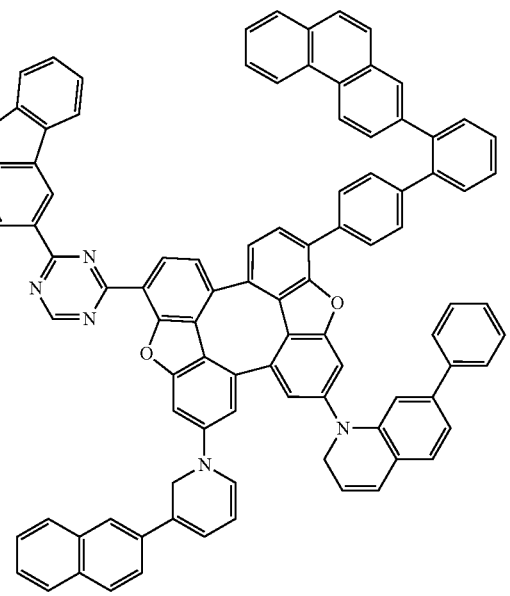
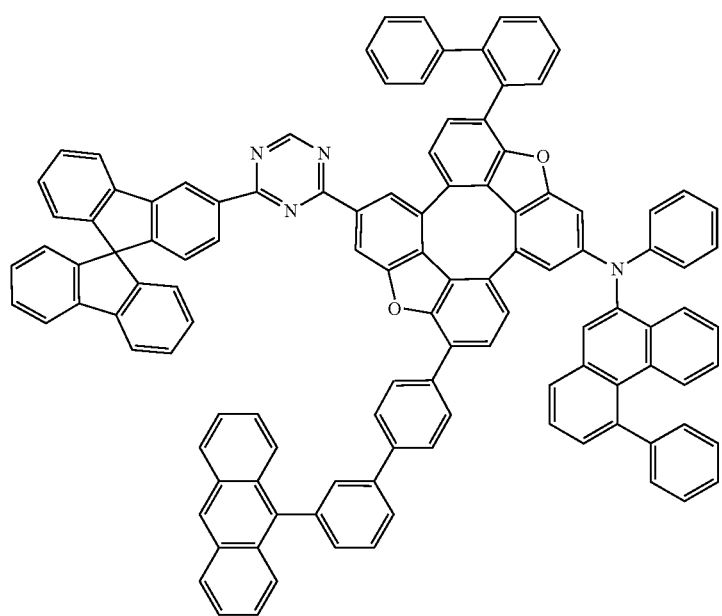

113
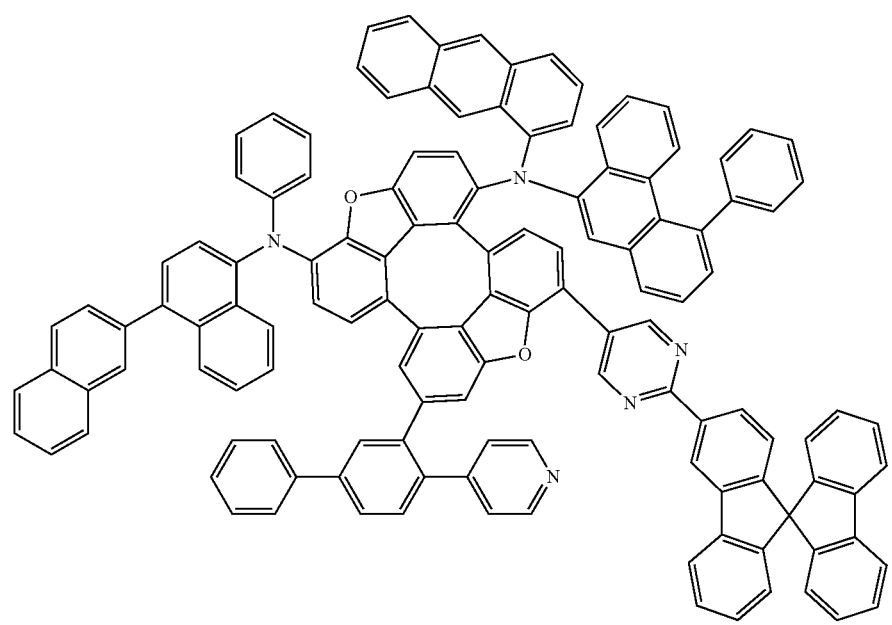
114
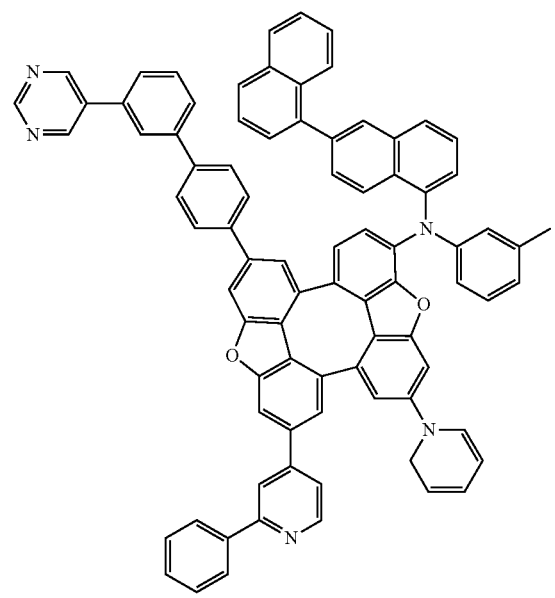
115
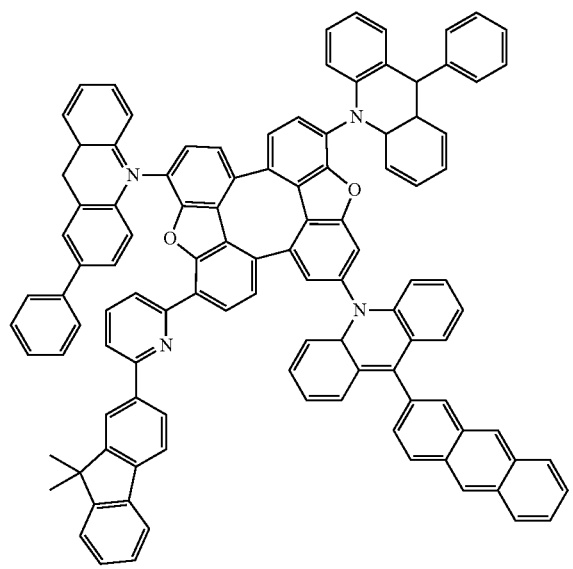

-continued
116
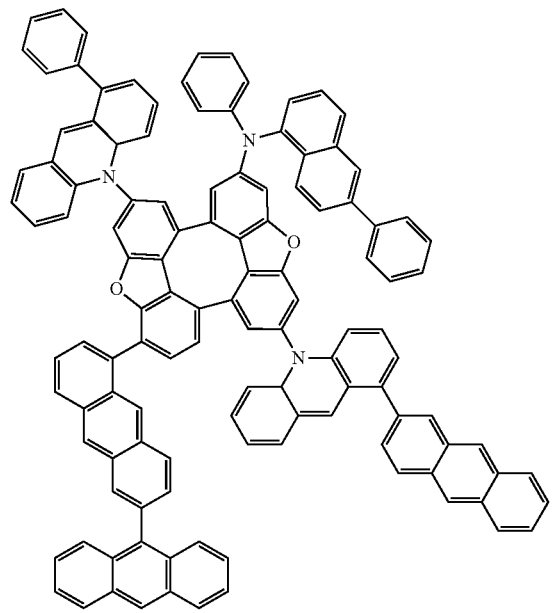
117
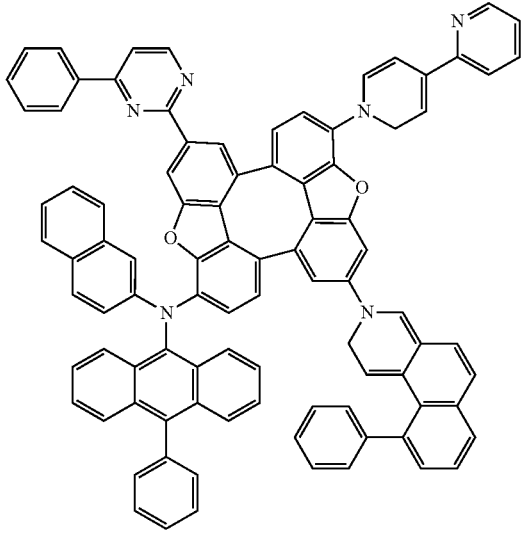
118
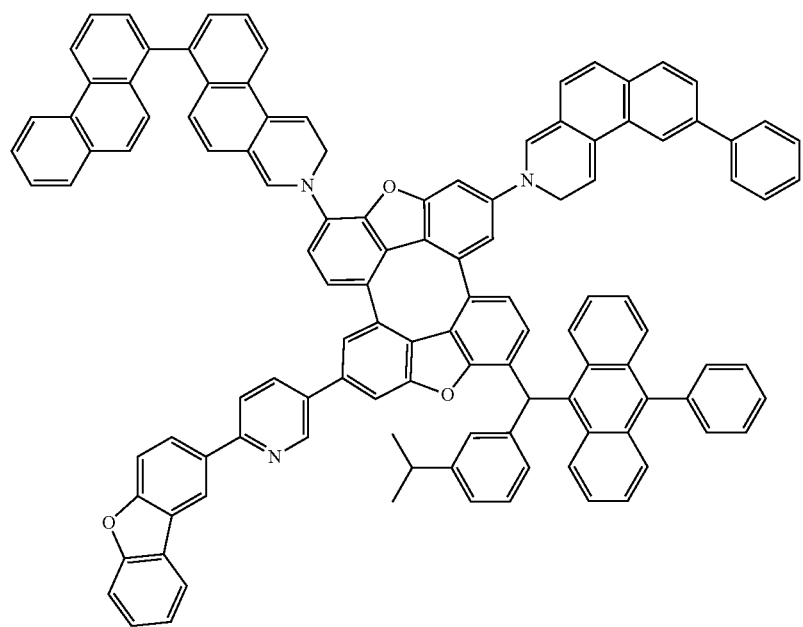

-continued
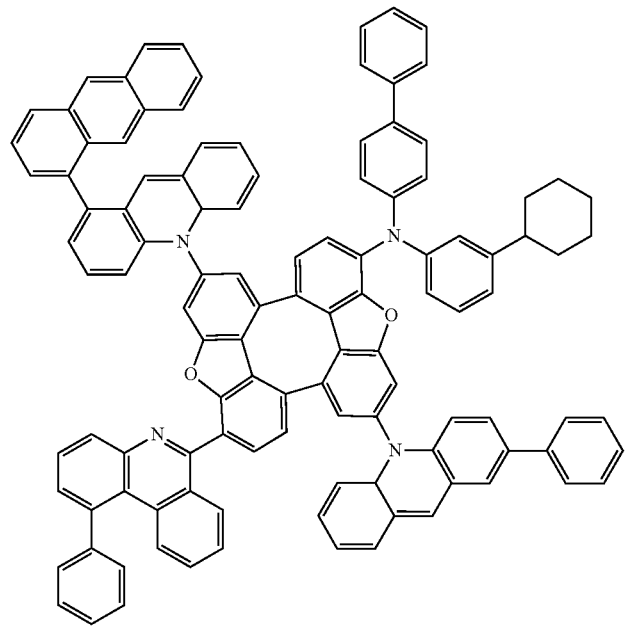
119
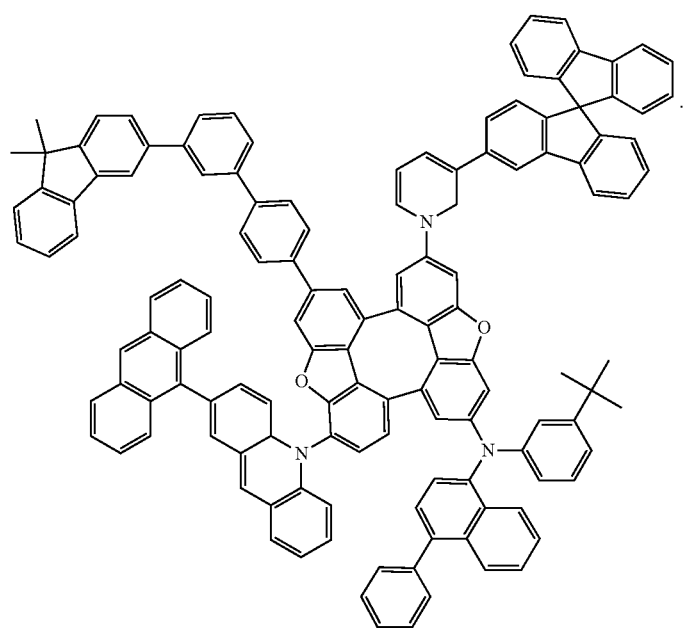
120

7. An organic electroluminescent device, comprising the organic electroluminescent compound,
wherein the organic electroluminescent compound has the following structural formula:

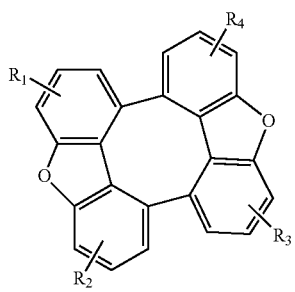

wherein $R_1$, $R_2$ and $R_4$ are, each independently, selected from a group consisting of hydrogen, a C1-C20 linear or branched alkyl group, a substituted or unsubstituted N-(phenylmethyl)imino group, a phenyl group, phenylamine, diphenylamine, phenyl pyridinylamine, bipyridinylamine, phenyl naphthylamine, binaphthylamine, phenyl phenanthrylamine, biphenanthrylamine, phenyl anthrylamine, bianthrylamine, phenanthridine, biphenyl, a pyridyl group, a pyrimidinyl group, a quinolyl group and a triazinyl group;

$R_3$ is selected from a group consisting of hydrogen, a C1-C10 linear or branched alkyl group, a substituted or unsubstituted N-(phenylmethyl)imino group, a phenyl group, phenylamine, diphenylamine, phenyl pyridinylamine, bipyridinylamine, phenyl naphthylamine, binaphthylamine, phenyl phenanthrylamine, biphenanthrylamine, phenyl anthrylamine, bianthrylamine, phenanthridine, biphenyl, a pyridyl group, a pyrimidinyl group, a quinolyl group and a triazinyl group;

wherein $R_1$, $R_2$, $R_3$ and $R_4$ being all hydrogen or C4 branched alkyl group is excluded.

8. The organic electroluminescent device according to claim 7, wherein among $R_1$, the N-(phenylmethyl)imino group, the phenyl group, phenylamine, diphenylamine, phenyl pyridinylamine, bipyridinylamine, phenyl naphthylamine, binaphthylamine, phenyl phenanthrylamine, biphenanthrylamine, phenyl anthrylamine, bianthrylamine, phenanthridine, biphenyl, the pyridyl group, the pyrimidinyl group, the quinolyl group or the triazinyl group, at least one hydrogen atom thereof is substituted with a C1-C20 linear or branched alkyl group, a C3-C24 cyclic alkyl group, a C1-C20 alkoxyl group, halogen, CN, $CF_3$, $Si(CH_3)_3$, or a C6-C50 aryl group.

9. The organic electroluminescent device according to claim 7, wherein among $R_2$, the N-(phenylmethyl)imino group, the phenyl group, phenylamine, diphenylamine, phenyl pyridinylamine, bipyridinylamine, phenyl naphthylamine, binaphthylamine, phenyl phenanthrylamine, biphenanthrylamine, phenyl anthrylamine, bianthrylamine, phenanthridine, biphenyl, the pyridyl group, the pyrimidinyl group, the quinolyl group and the triazinyl group, at least one hydrogen atom thereof is substituted with a C1-C20 linear or branched alkyl group, a C3-C24 cyclic alkyl group, a C1-C20 alkoxyl group, halogen, CN, $CF_3$, $Si(CH_3)_3$, a naphthyl group, an anthryl group, a phenanthryl group, dibenzofuran, a fluorenyl group, a carbazolyl group, spiro fluorene, or a heteroaryl group having 5-20 non-H atoms.

10. The organic electroluminescent device according to claim 7, wherein among $R_3$, the N-(phenylmethyl)imino group, the phenyl group, phenylamine, diphenylamine, phenyl pyridinylamine, bipyridinylamine, phenyl naphthylamine, binaphthylamine, phenyl phenanthrylamine, biphenanthrylamine, phenyl anthrylamine, bianthrylamine, phenanthridine, biphenyl, the pyridyl group, the pyrimidinyl group, the quinolinyl group or the triazinyl group, at least one hydrogen atom thereof is substituted with a C1-C10 linear or branched alkyl group, a C3-C12 cyclic alkyl group, a C1-C10 alkoxyl group, halogen, CN, $CF_3$, $Si(CH_3)_3$, or a C6-C30 aryl group.

11. The organic electroluminescent device according to claim 7, wherein among $R_4$, the N-(phenylmethyl)imino group, the phenyl group, phenylamine, diphenylamine, phenyl pyridinylamine, bipyridinylamine, phenyl naphthylamine, binaphthylamine, phenyl phenanthrylamine, biphenanthrylamine, phenyl anthrylamine, bianthrylamine, phenanthridine, biphenyl, the pyridyl group, the pyrimidinyl group, the quinolyl group and the triazinyl group, at least one hydrogen atom thereof is substituted with a C1-C10 linear or branched alkyl group, a C3-C12 cyclic alkyl group, a C1-C10 alkoxyl group, halogen, CN, $CF_3$, $Si(CH_3)_3$, a naphthyl group, an anthryl group, a phenanthryl group, dibenzofuran, a fluorenyl group, a carbazolyl group, spiro fluorene, or a heteroaryl group having 5-20 non-H atoms.

12. The organic electroluminescent device according to claim 7, wherein the organic electroluminescent compound is any one of following compounds:

225
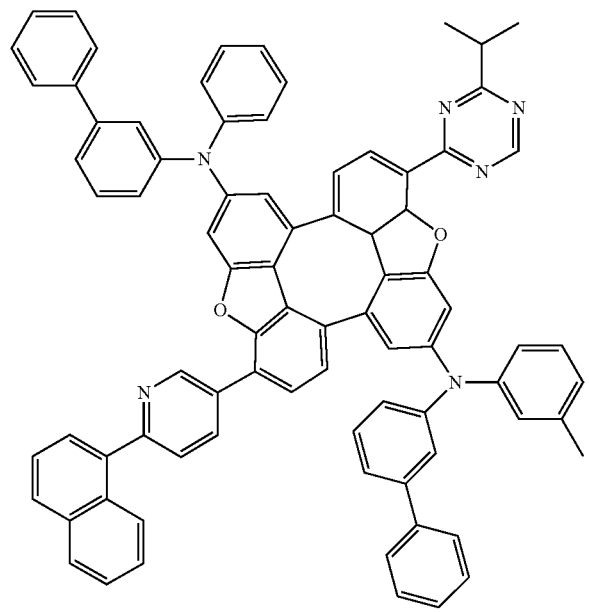
226
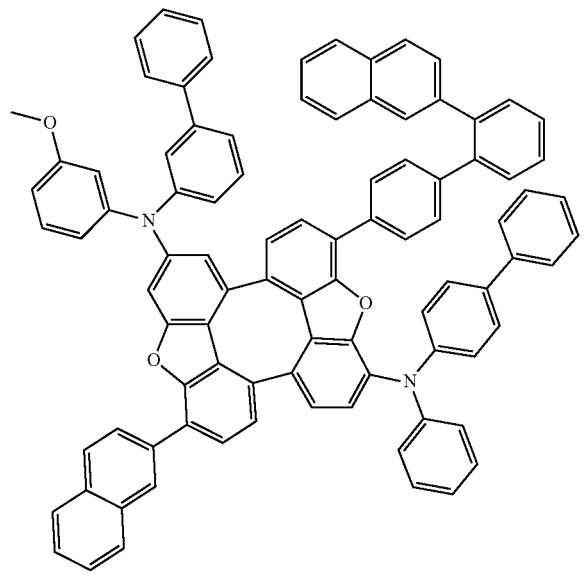
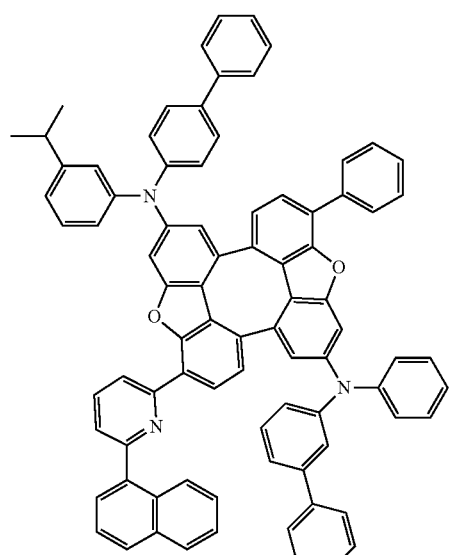
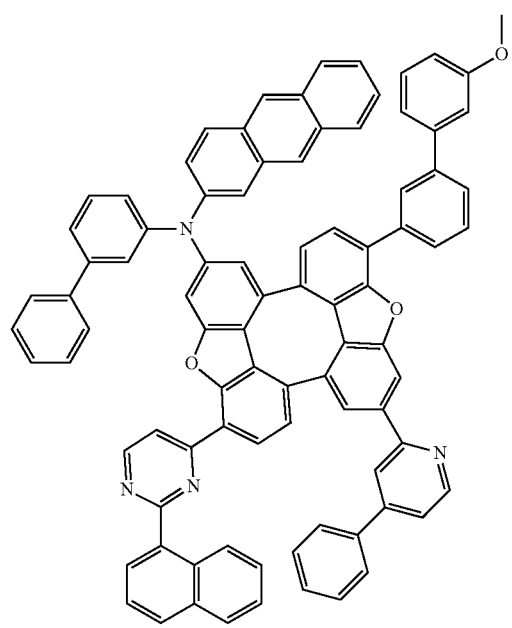

227
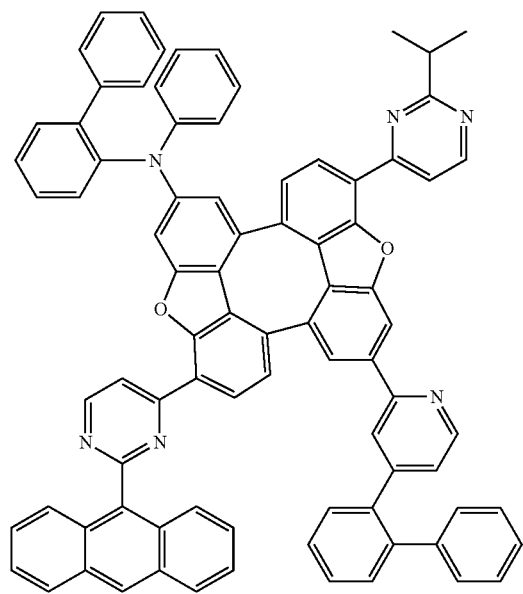
228
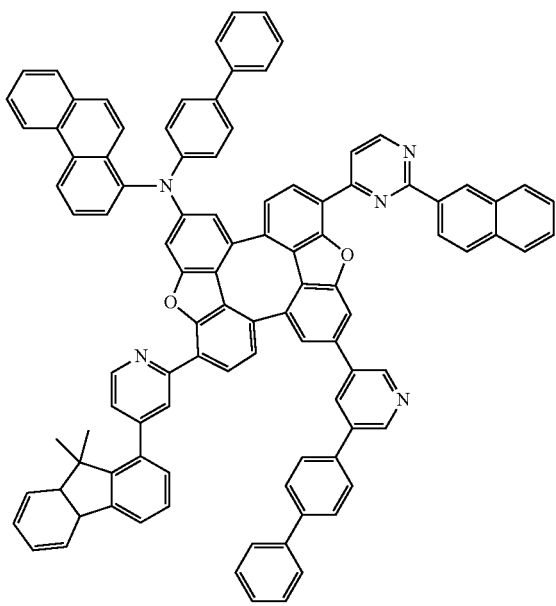
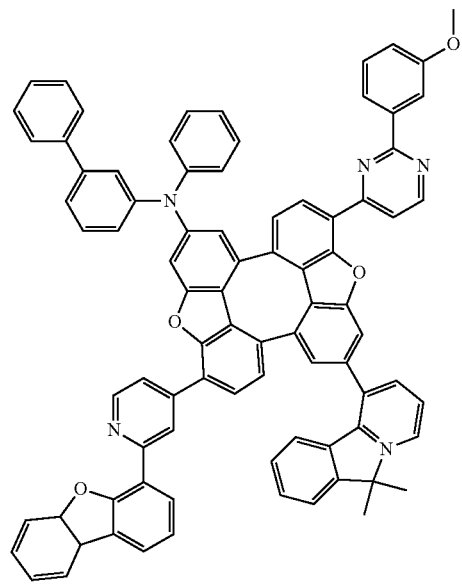
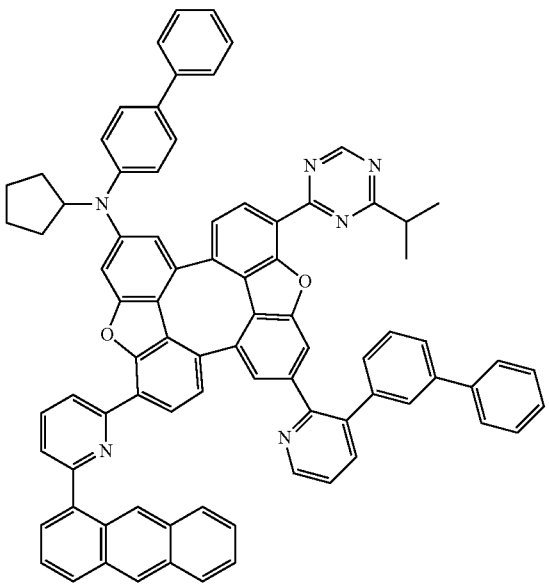

9
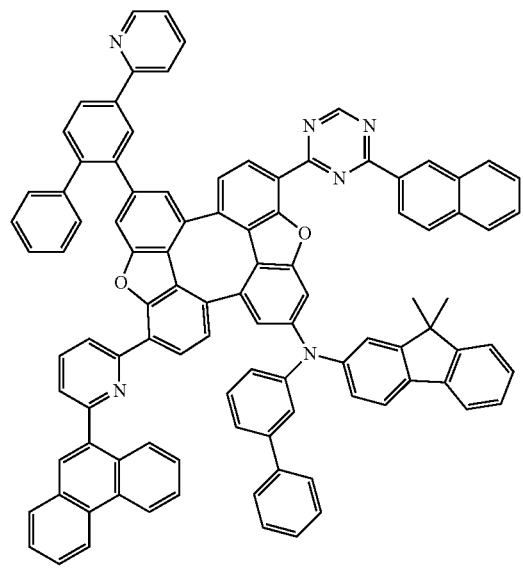
10
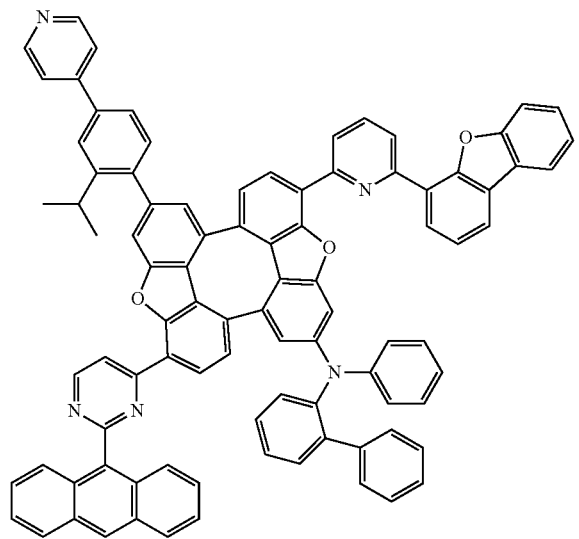
11
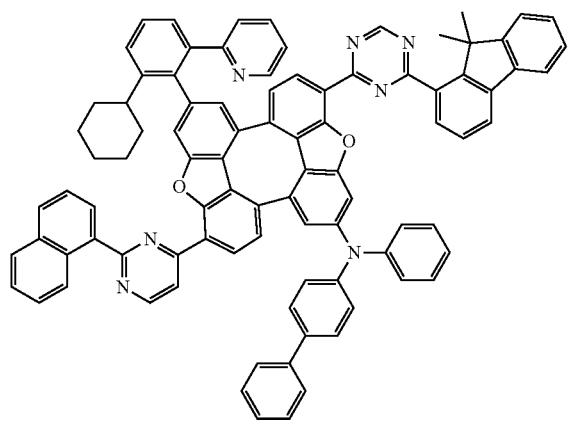
12
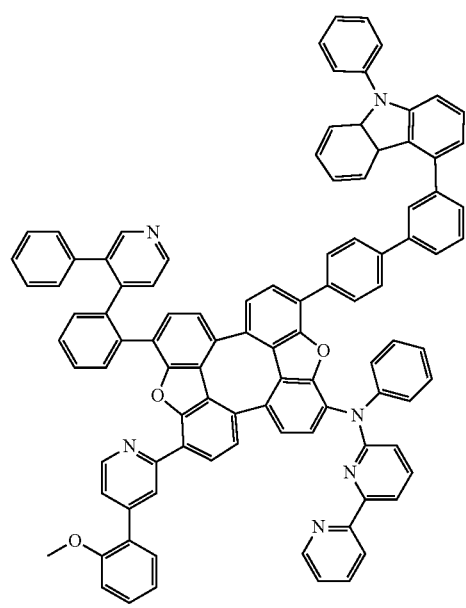

-continued
13
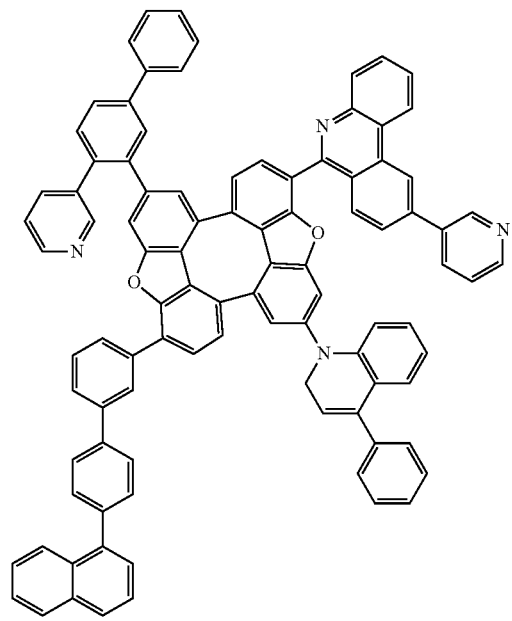
14
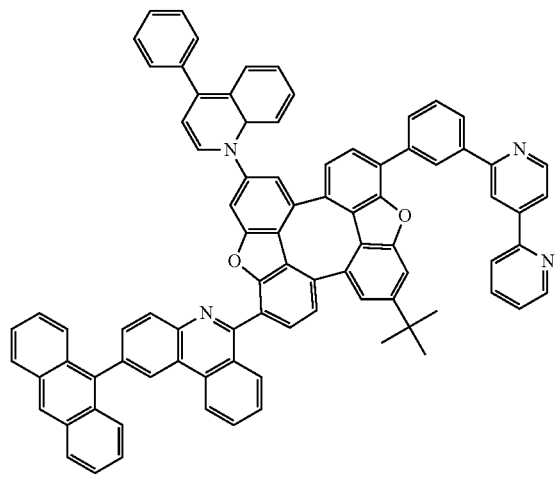
15
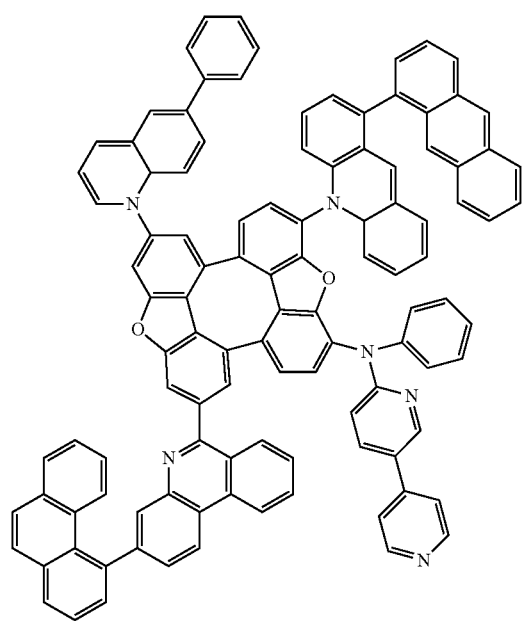
16
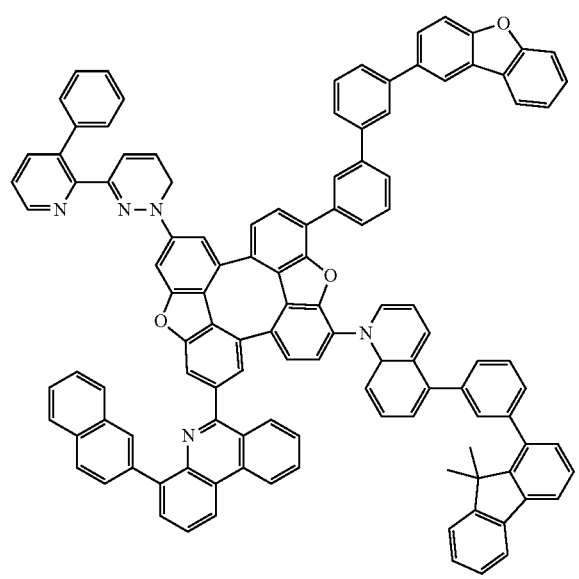

-continued
17
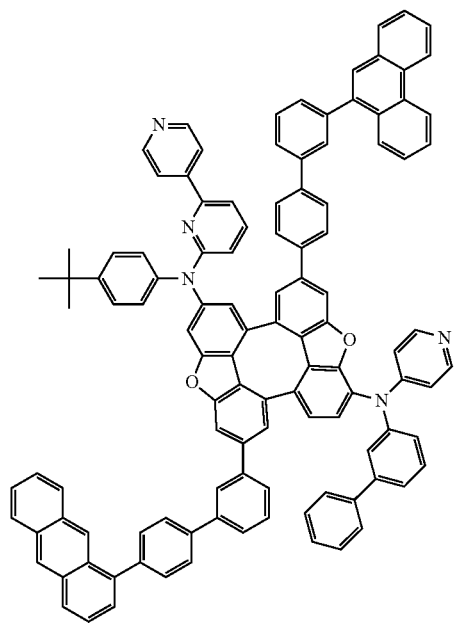
18
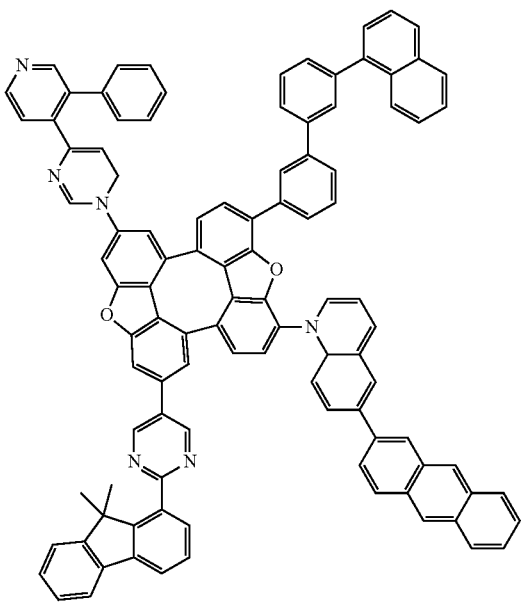
19
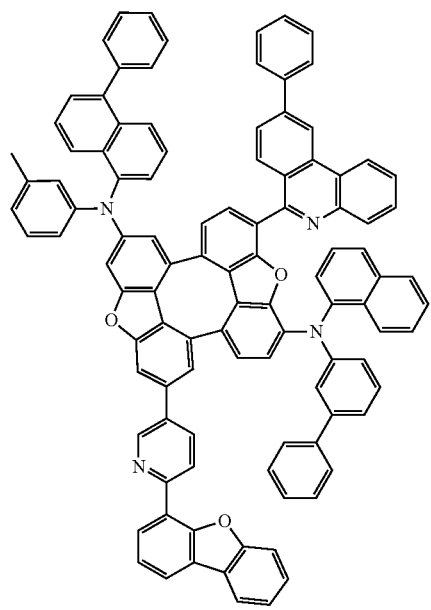
20
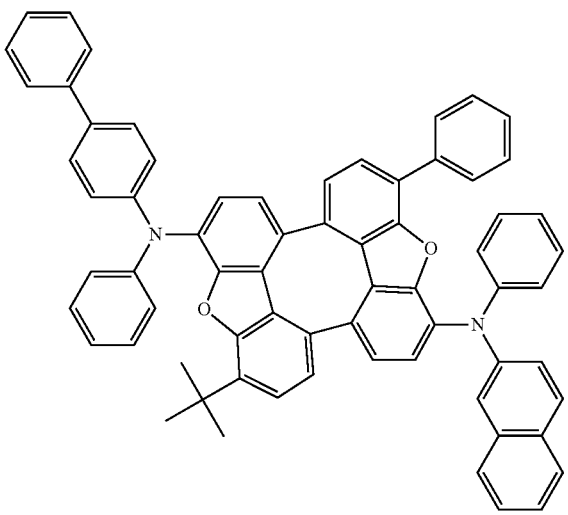

-continued
21
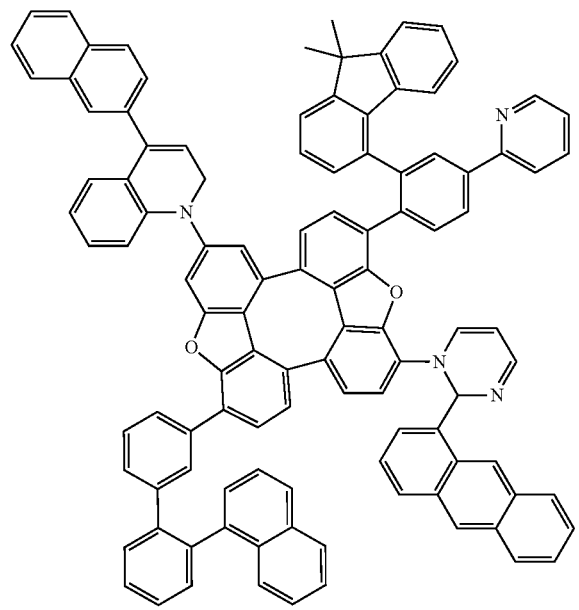
22
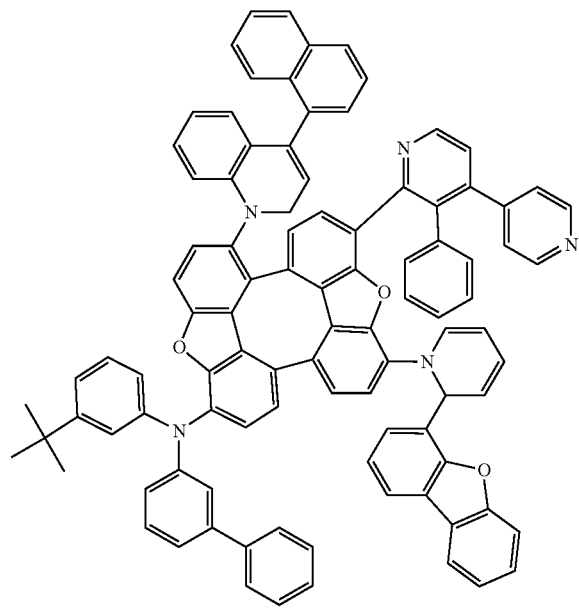
23
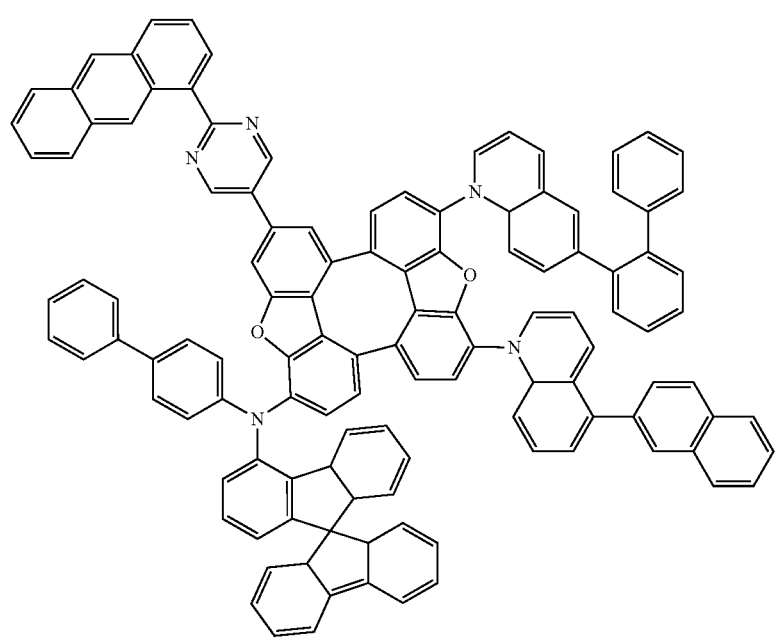

-continued
24
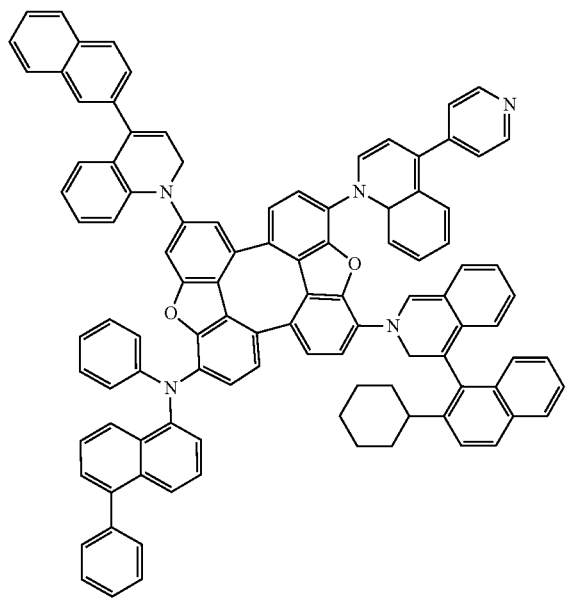
25
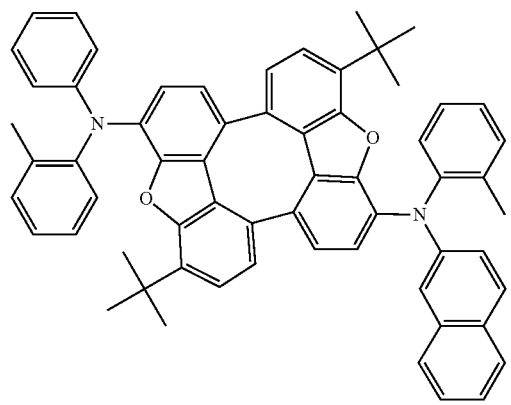
26
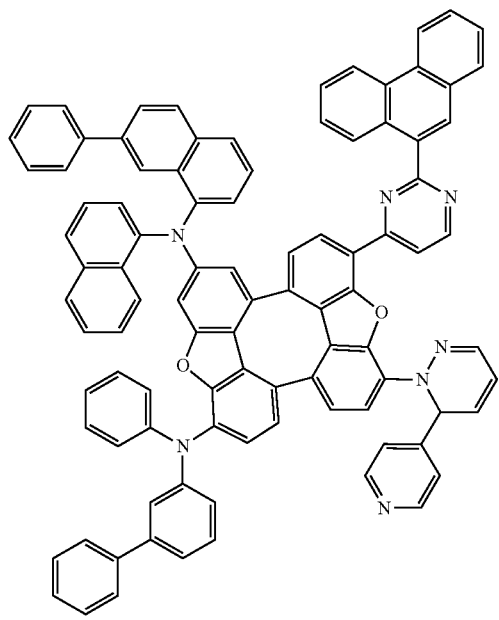
27
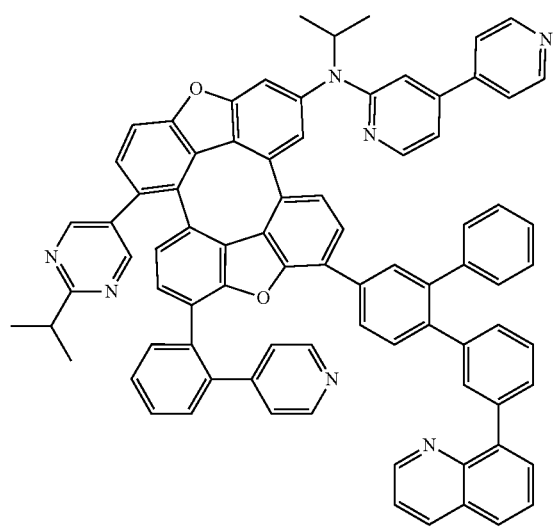

-continued
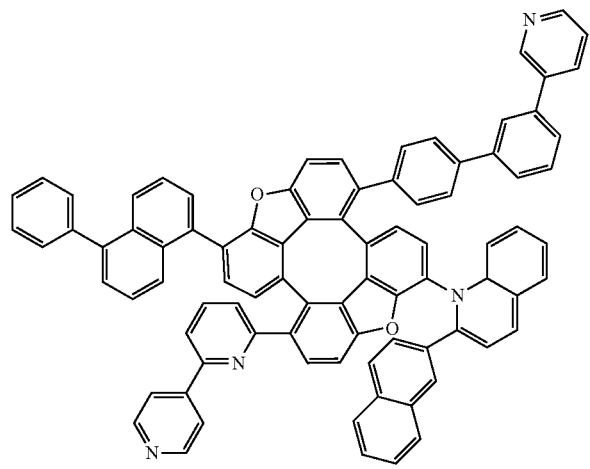
28
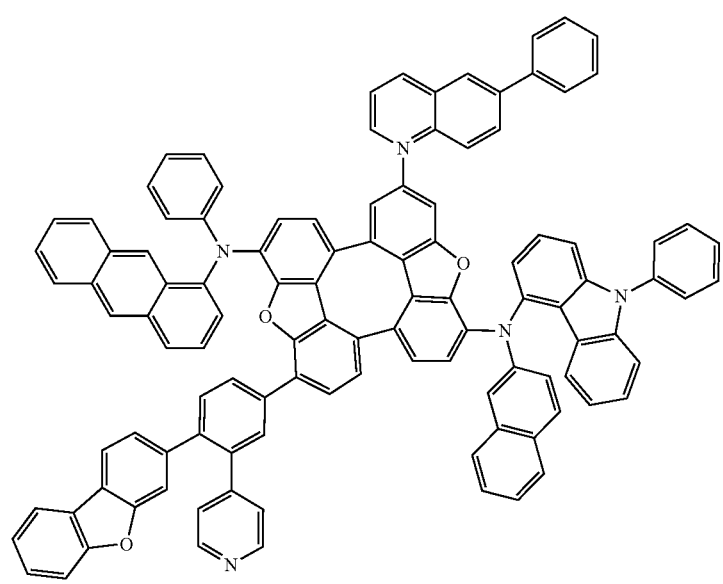
29
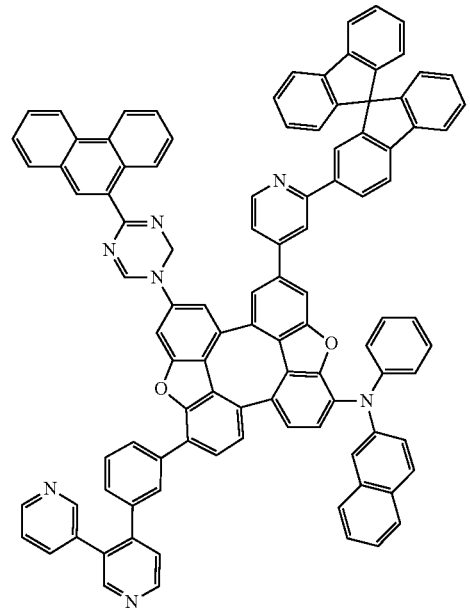
30
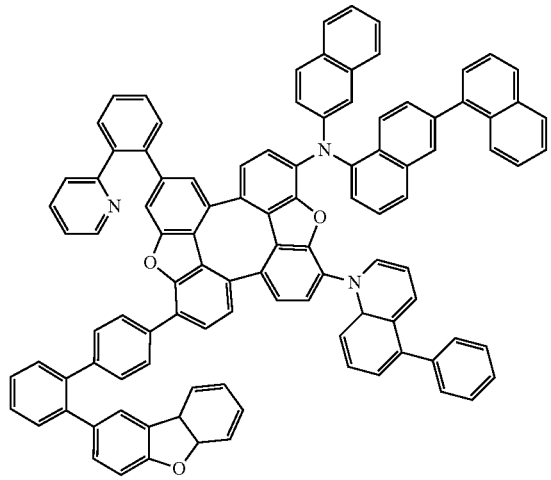
31

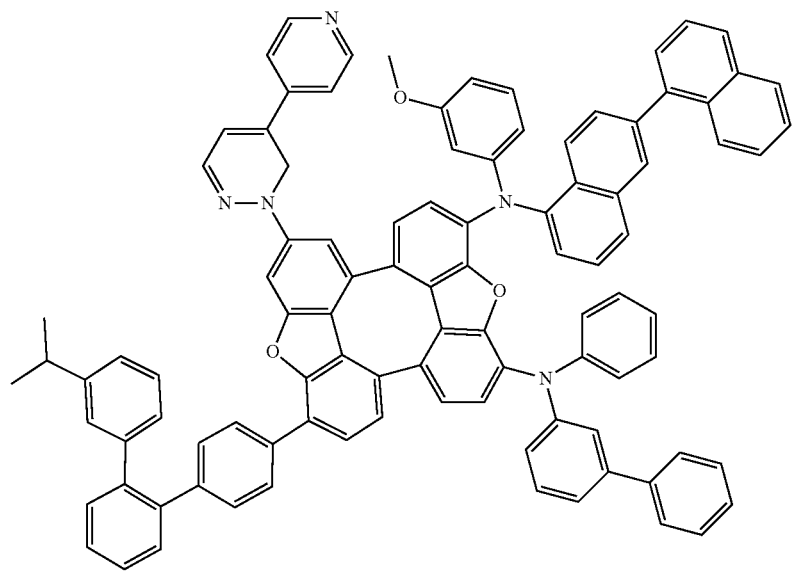
32
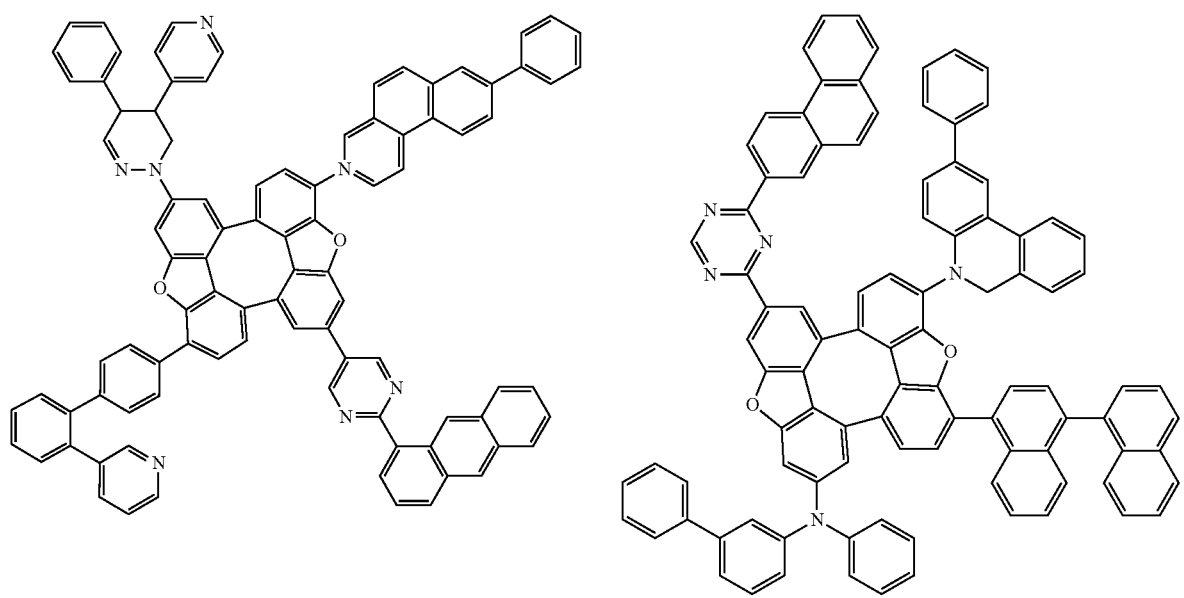
33
34

-continued
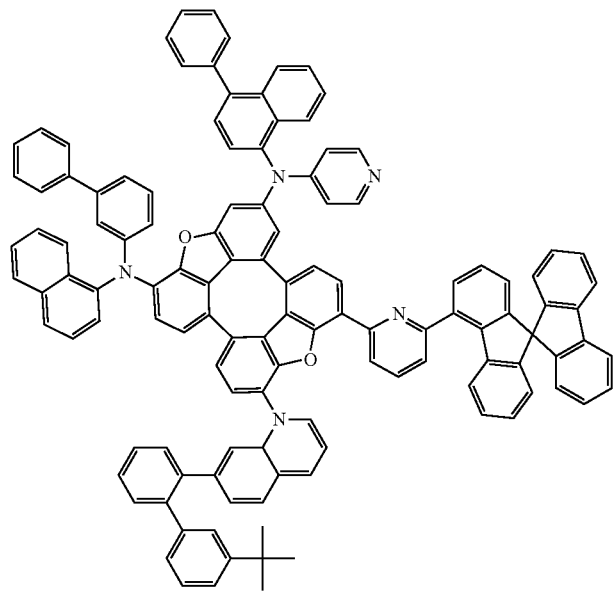
35
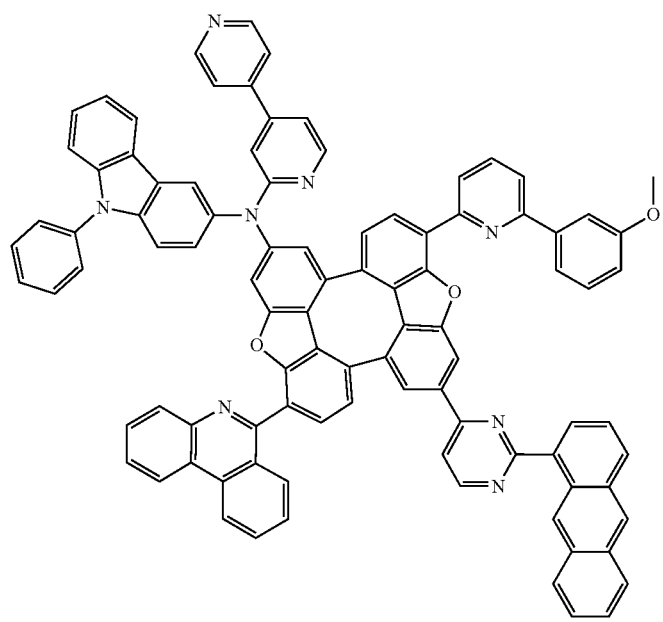
36

-continued
37
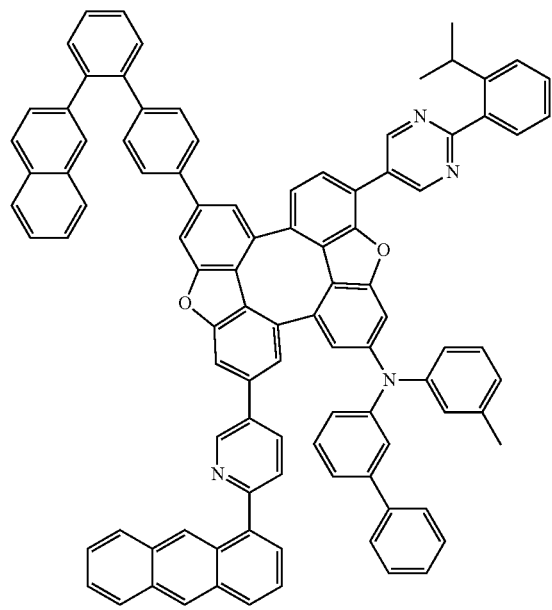
38
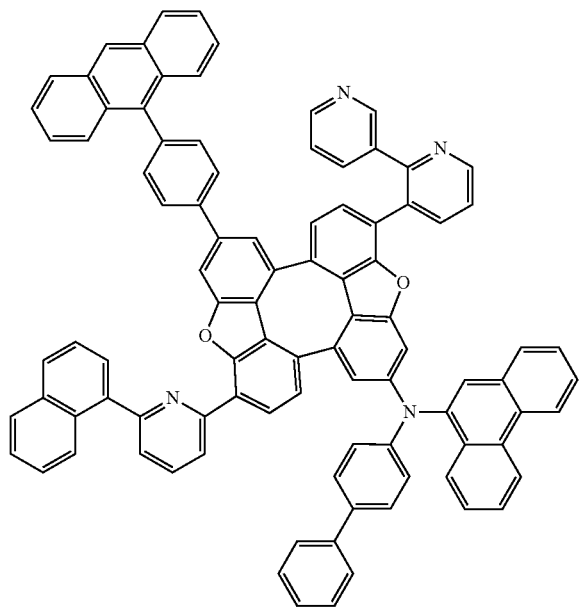
39
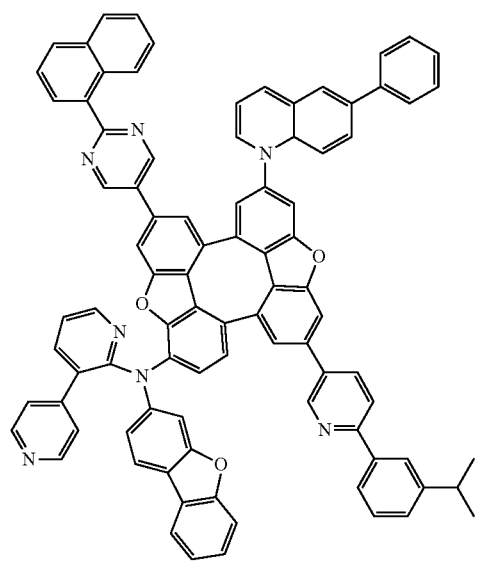
40
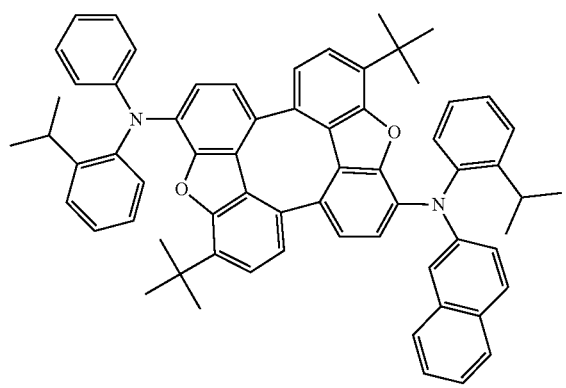

-continued
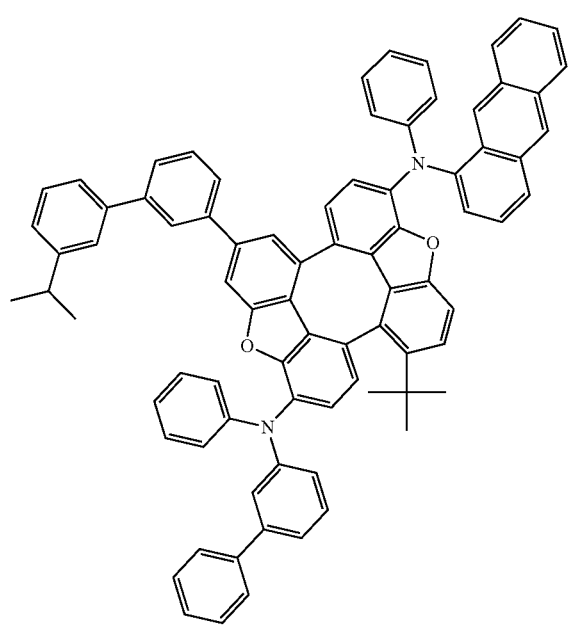
41
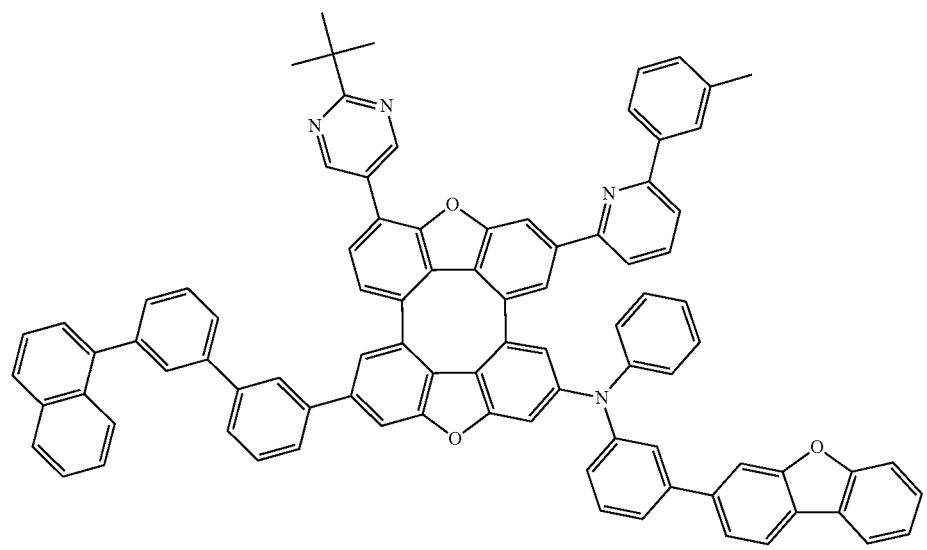
42

-continued
43
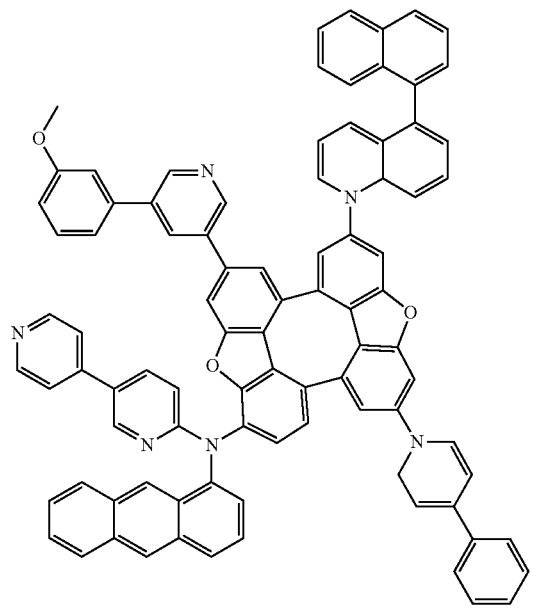
44
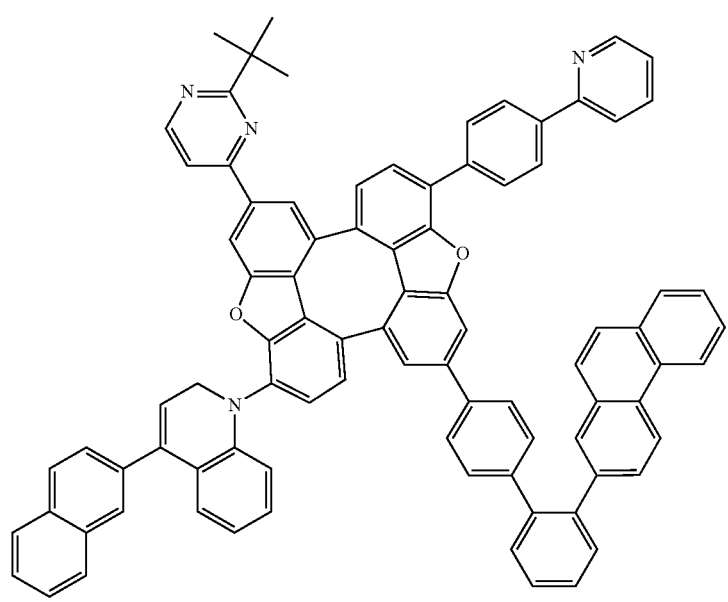

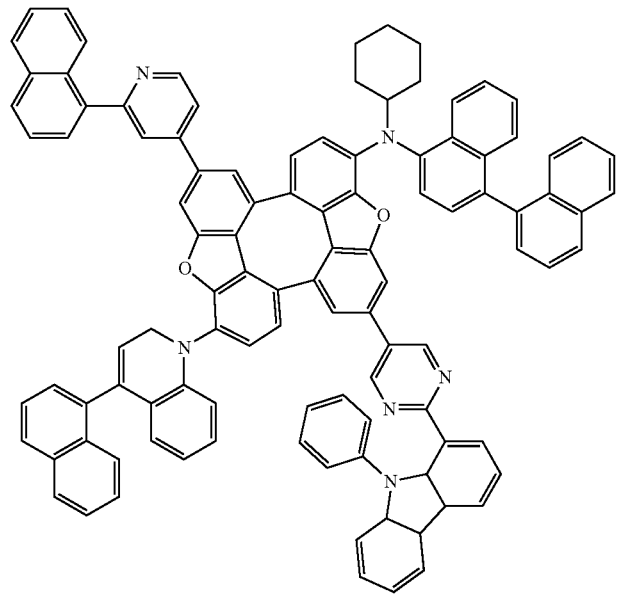
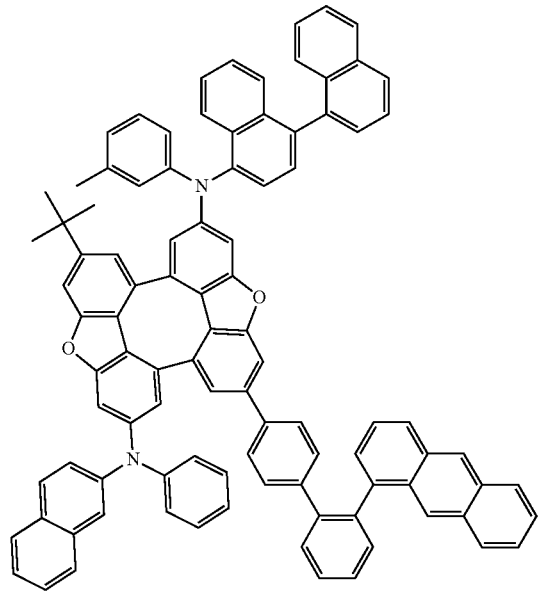
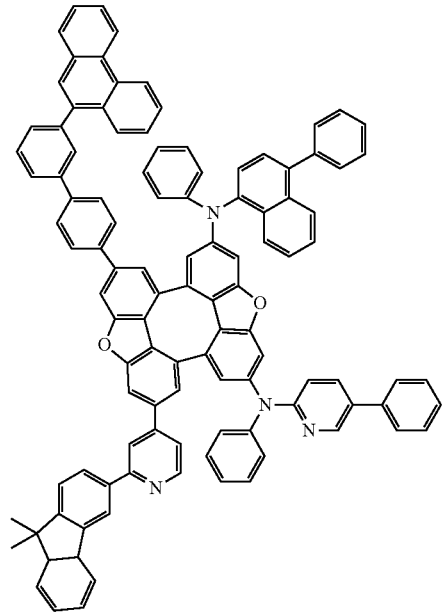

-continued
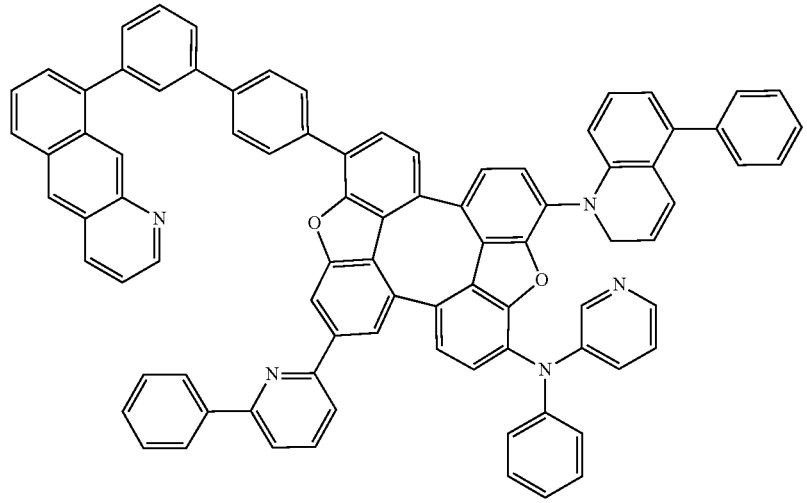
48
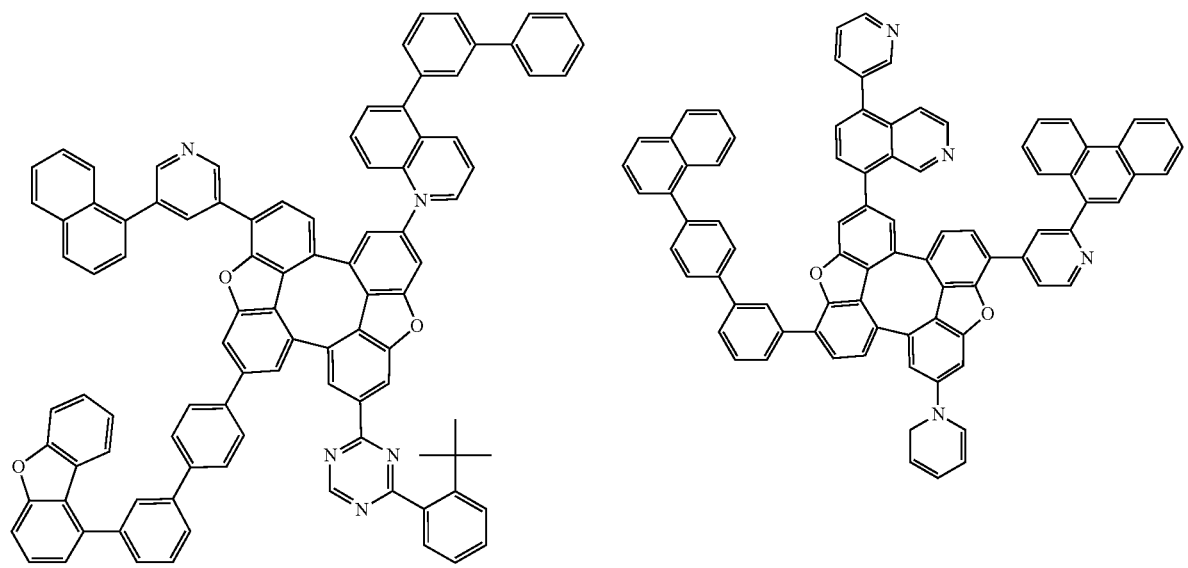
49 50
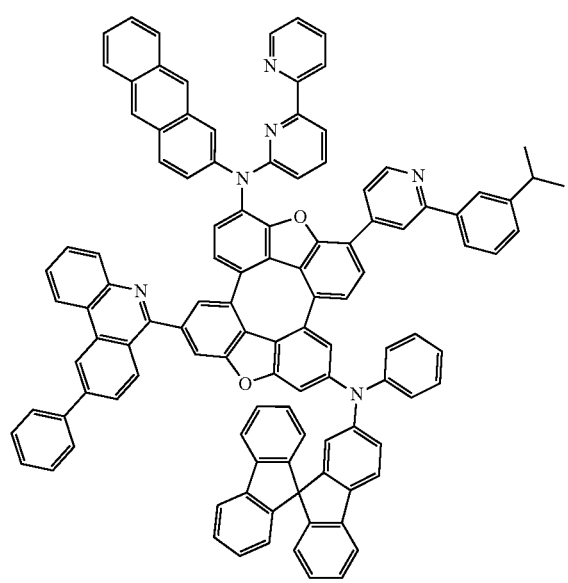
51

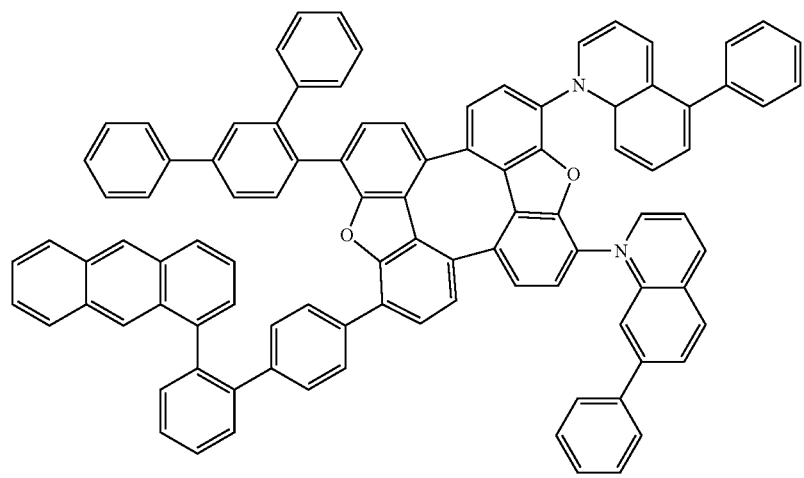
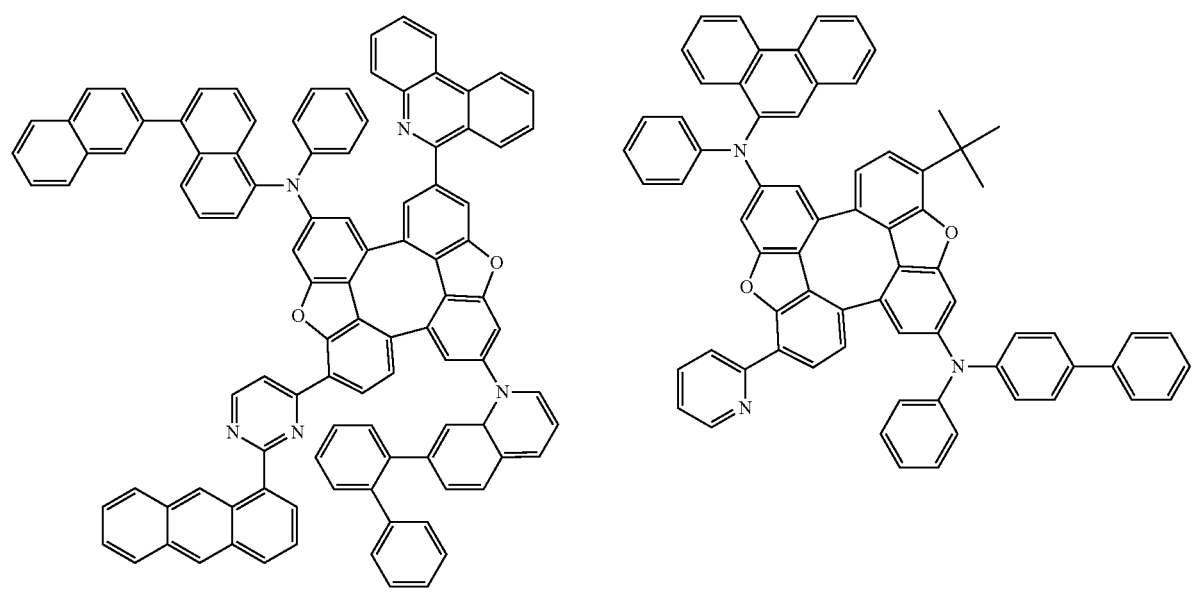

55
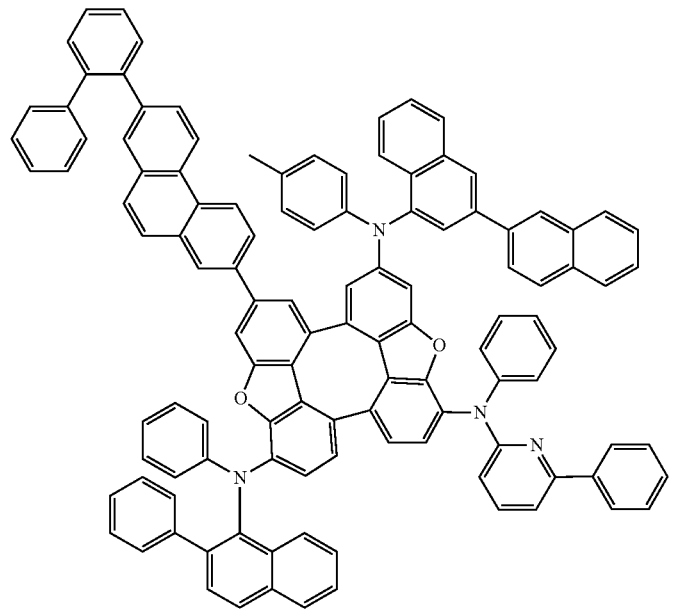
56
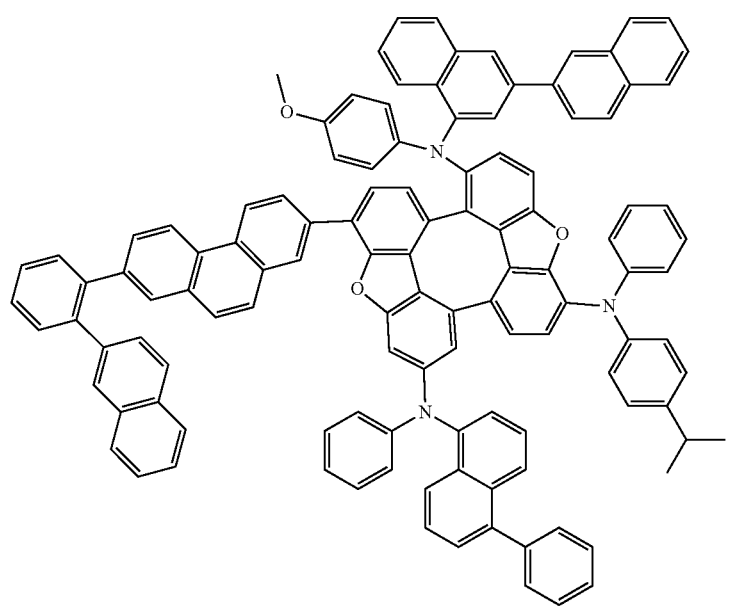

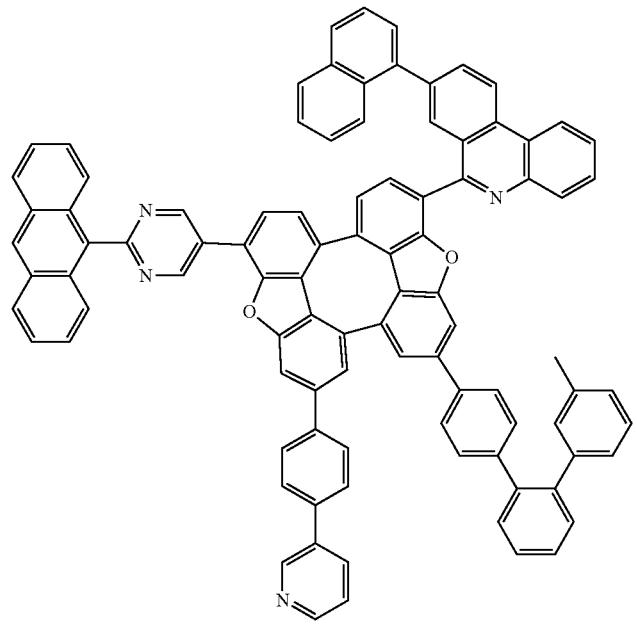
57
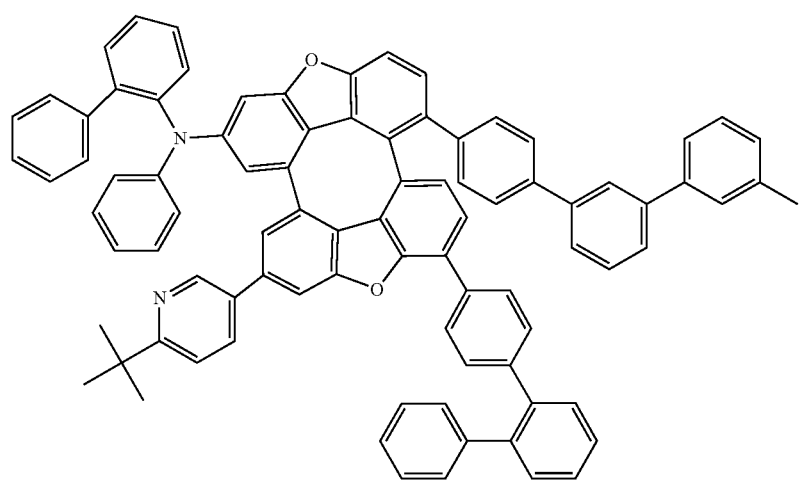
58

261 262
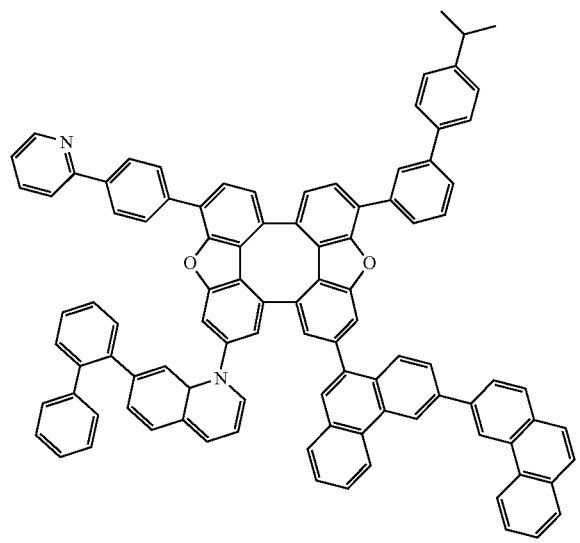
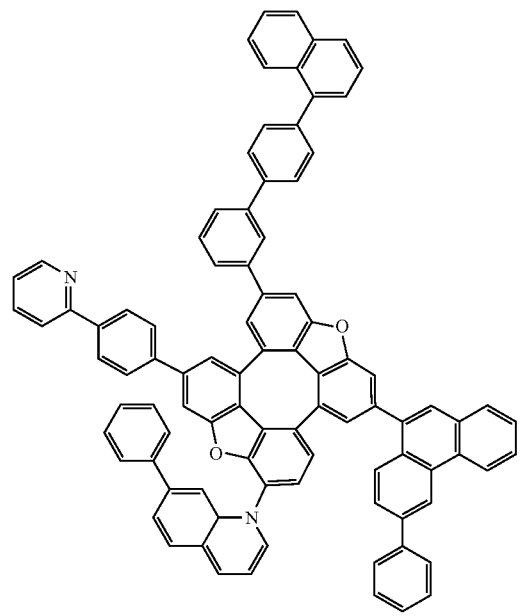
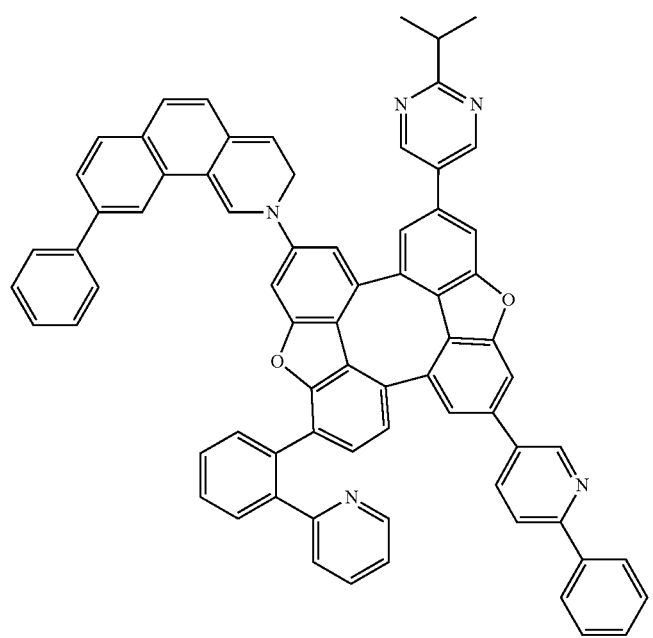

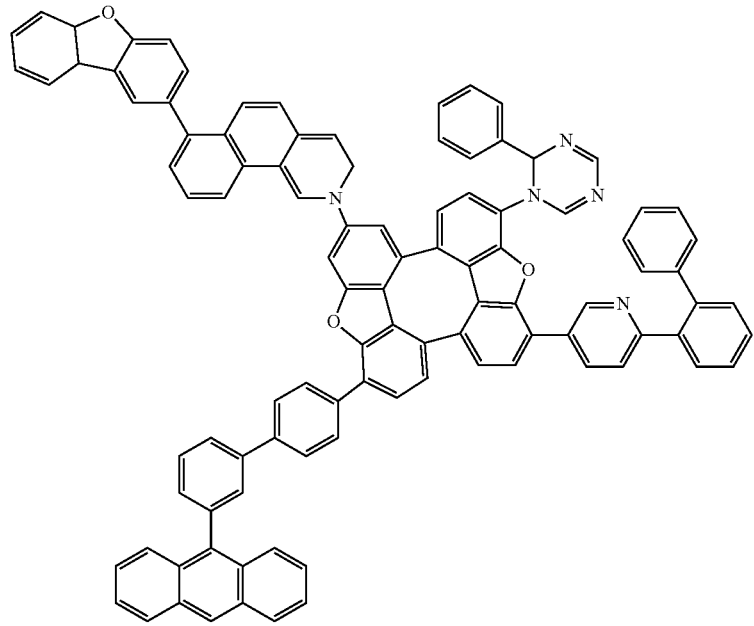
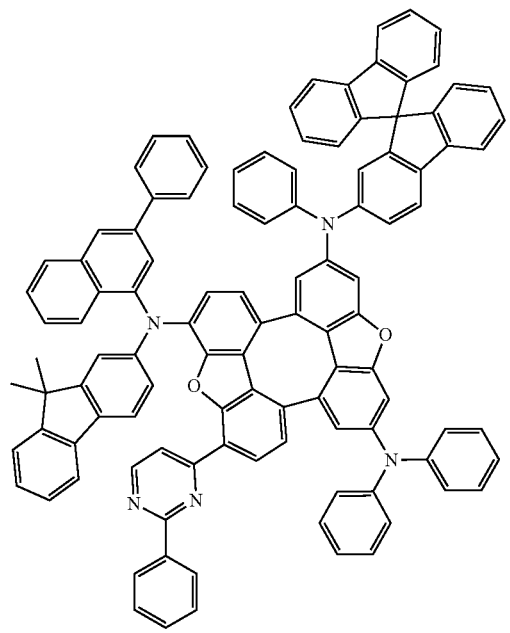
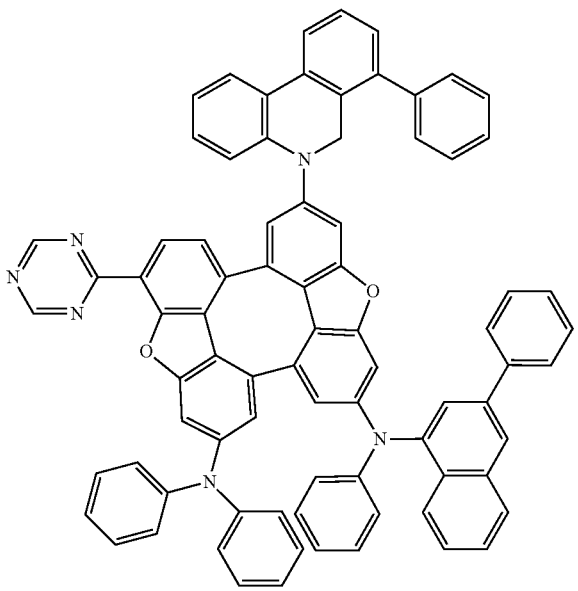

-continued
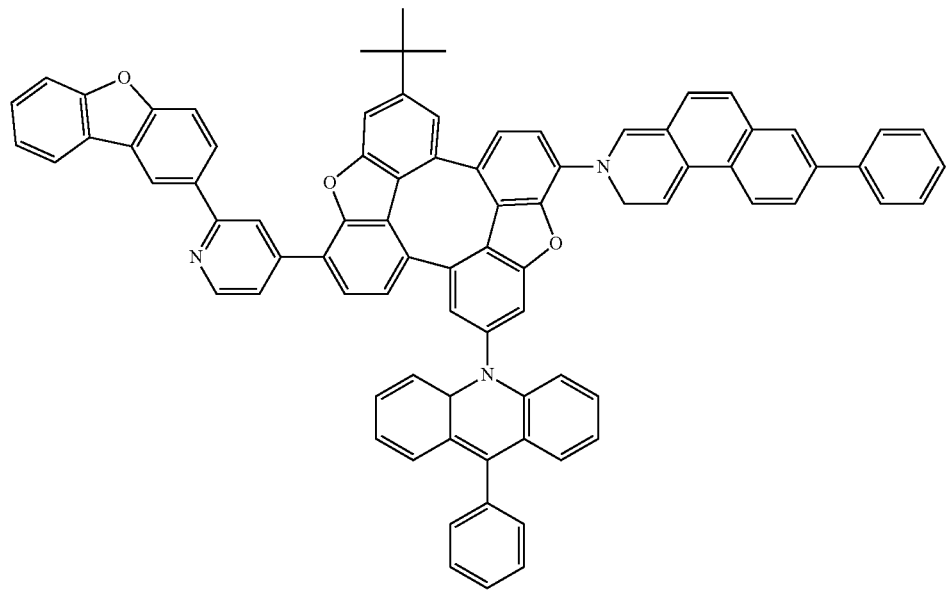
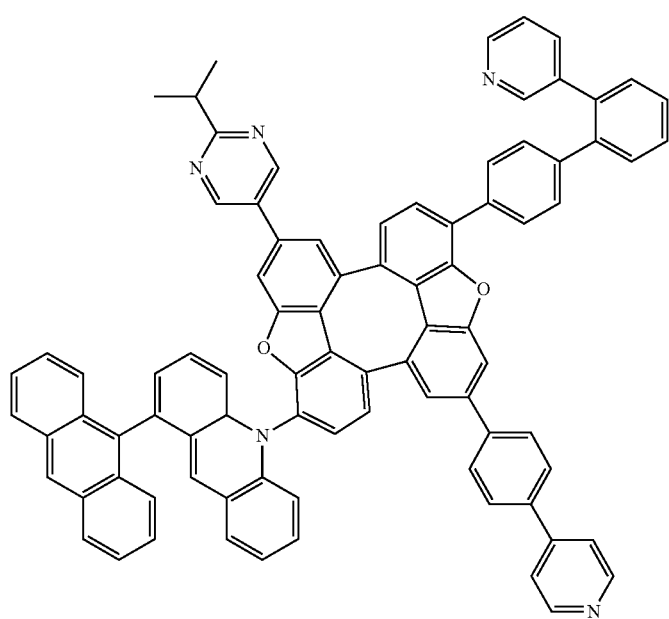

267
-continued
67
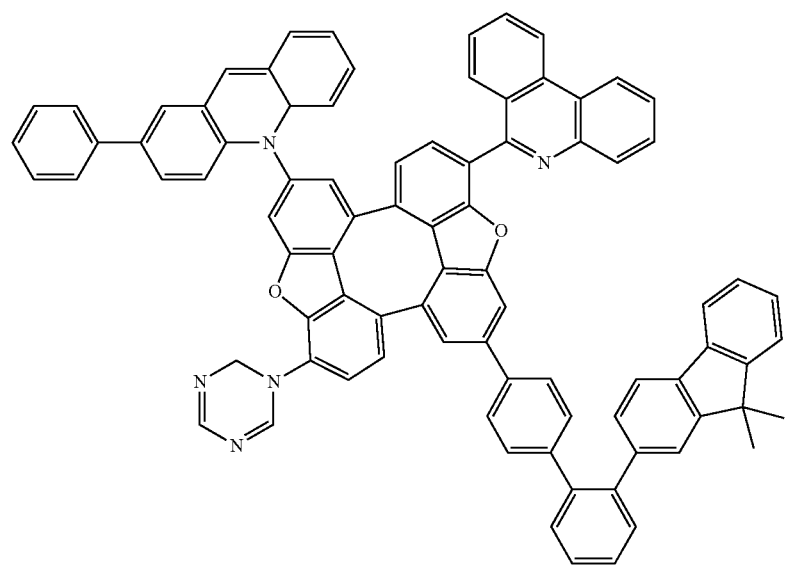
68
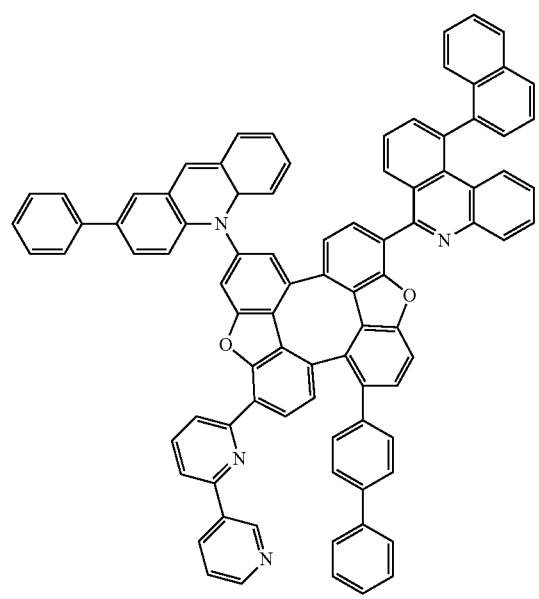
69
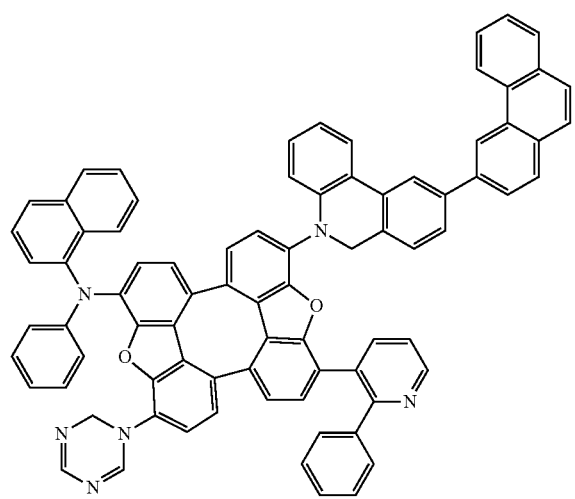

70
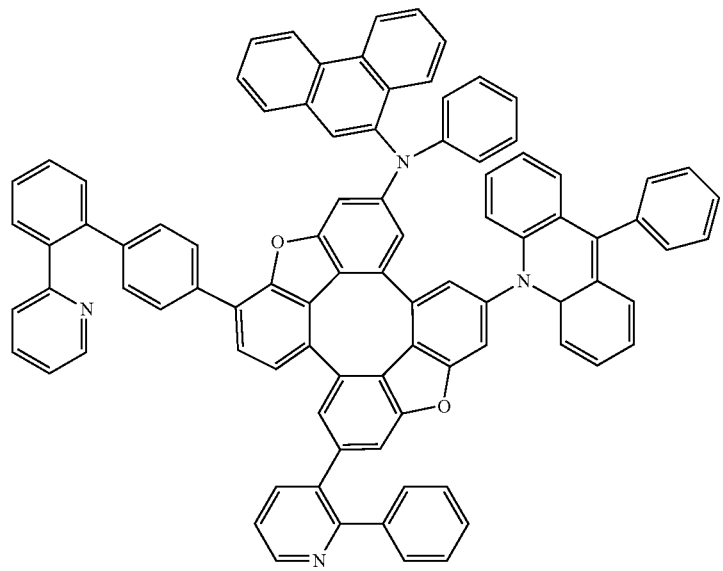
71
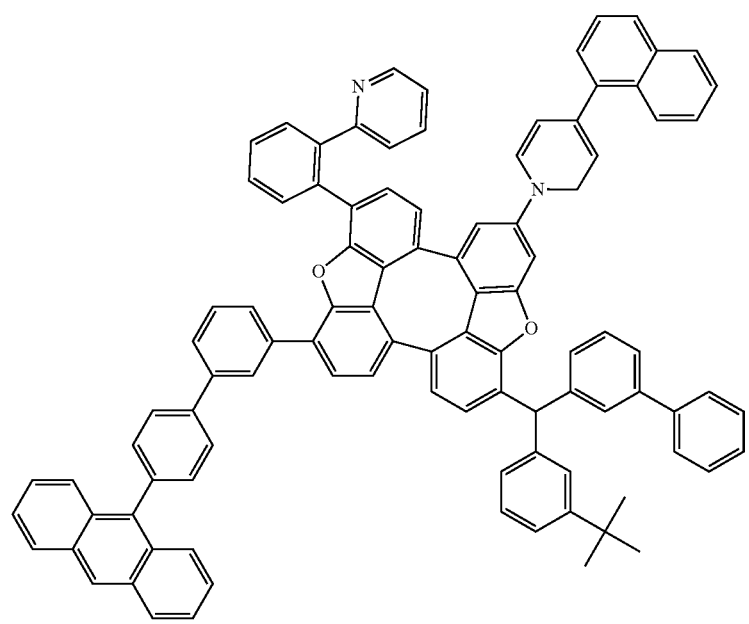

72
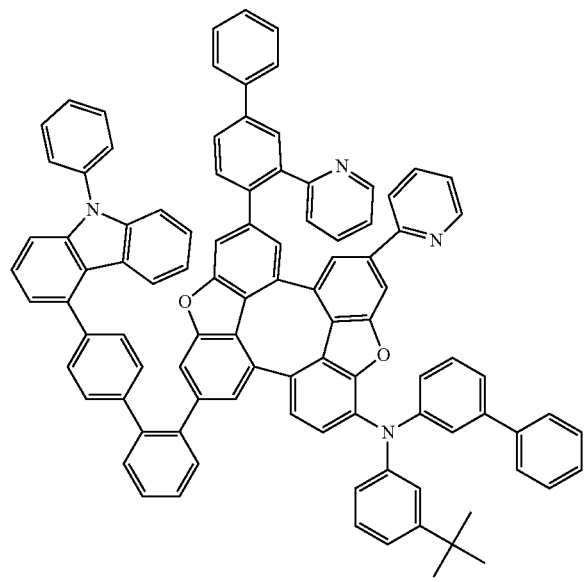
73
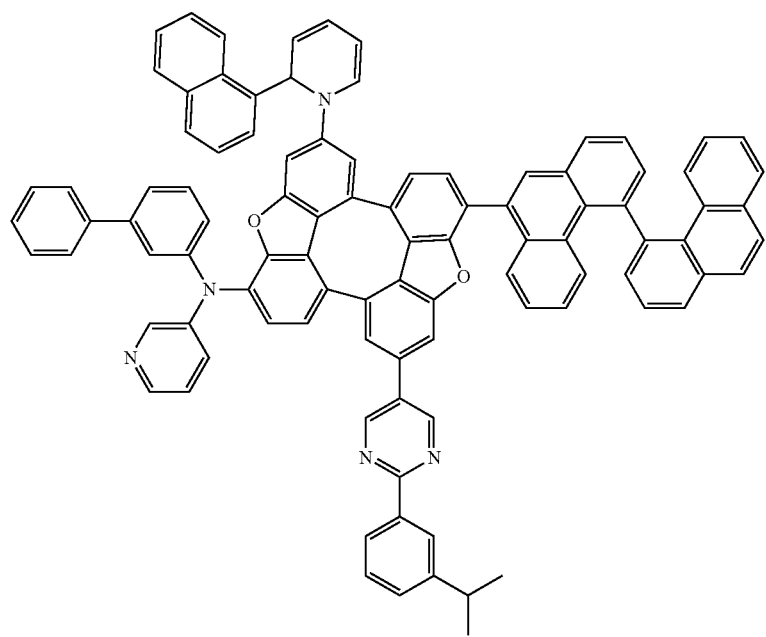

74
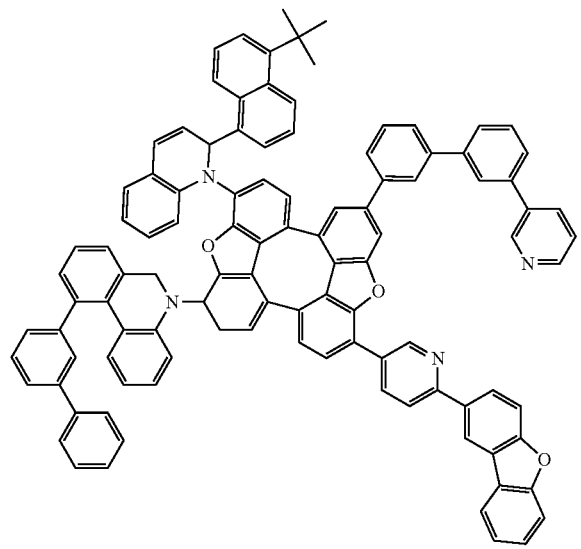
75
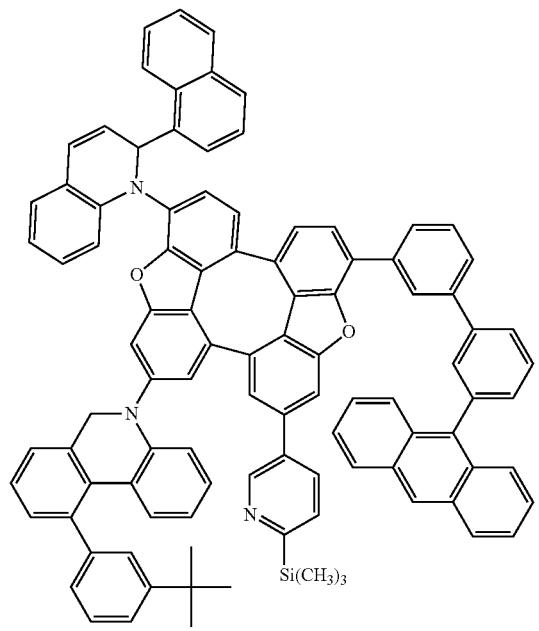
76
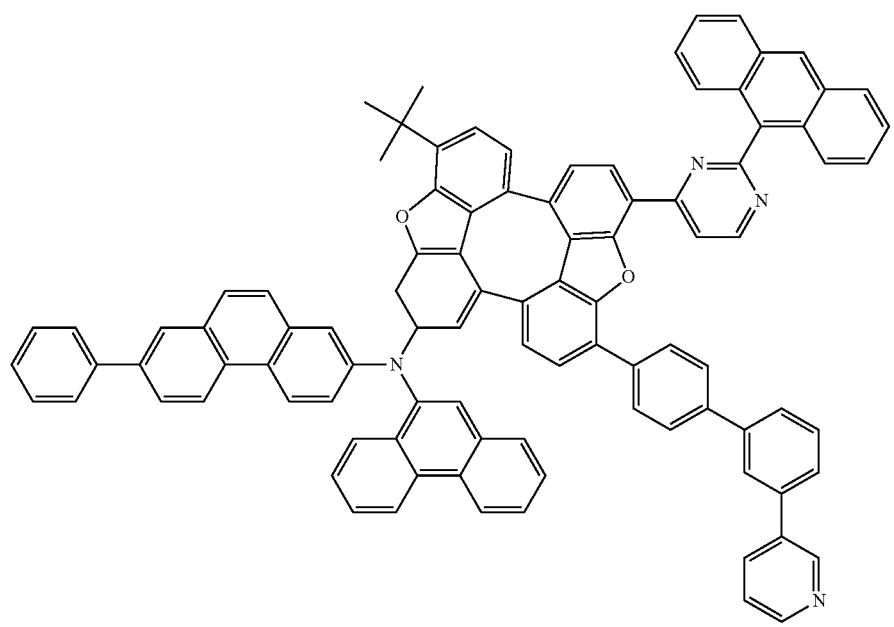

-continued
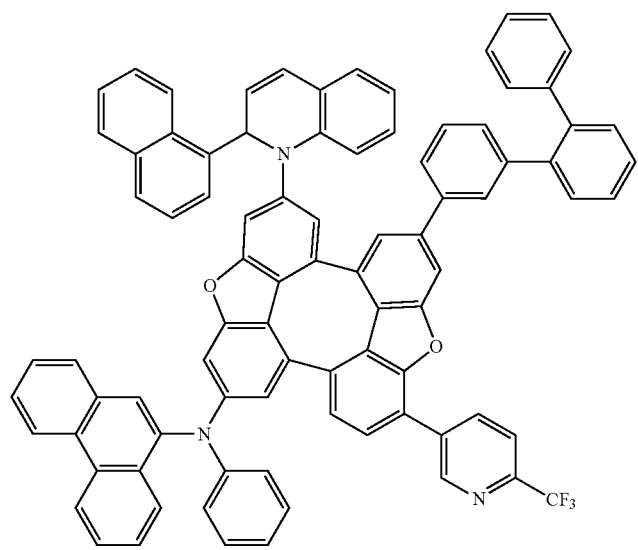
77
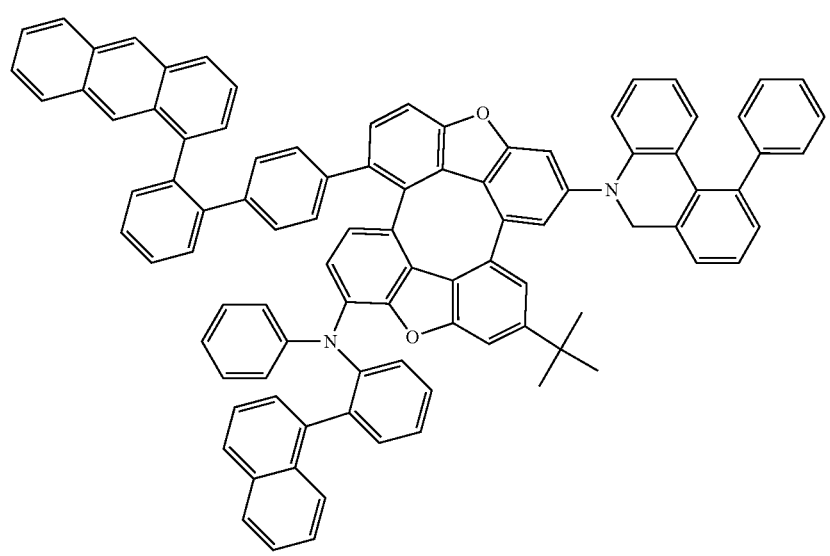
78

79
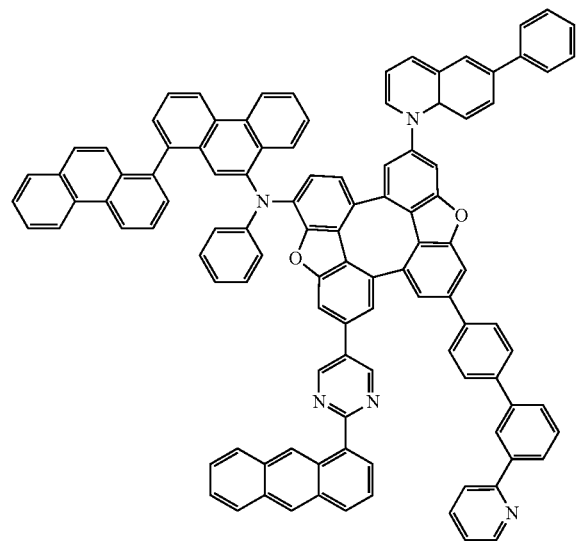
80
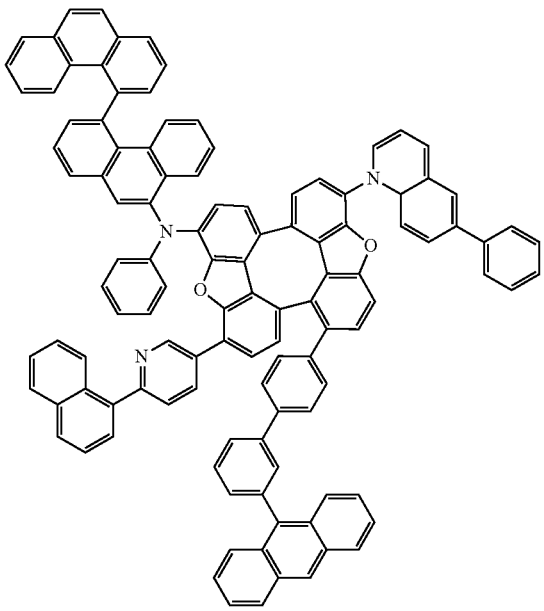
81
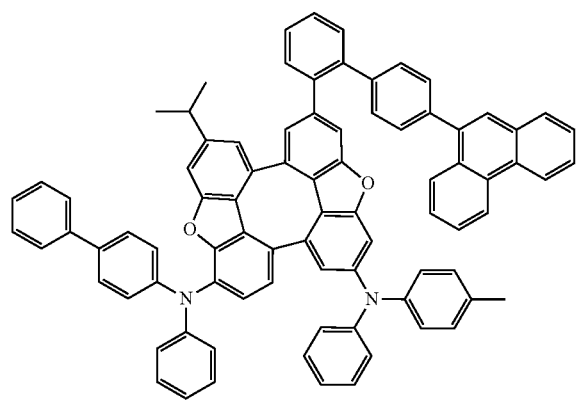
82
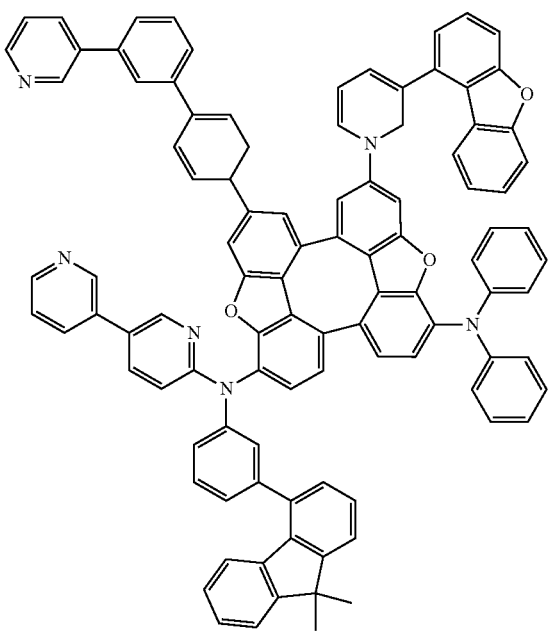

83
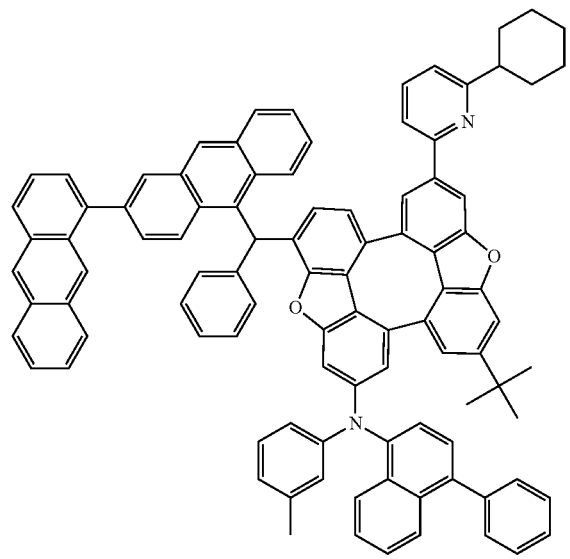
84
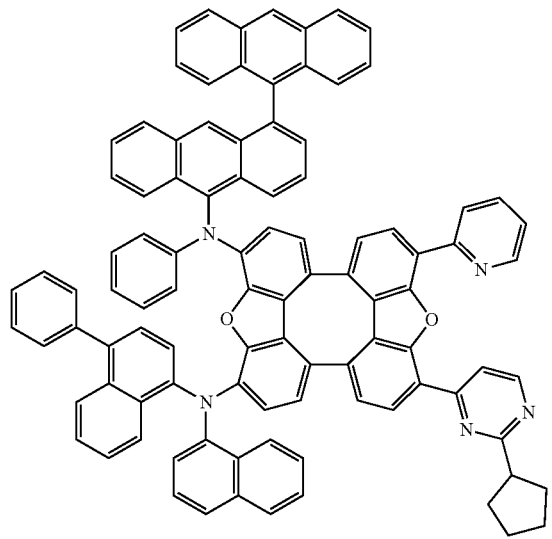
85
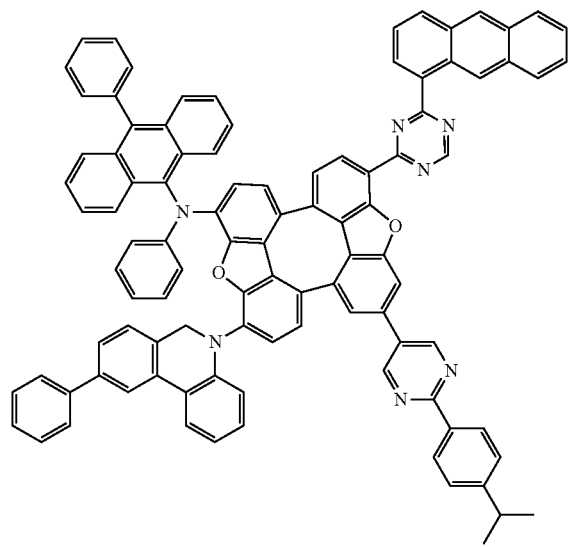
86
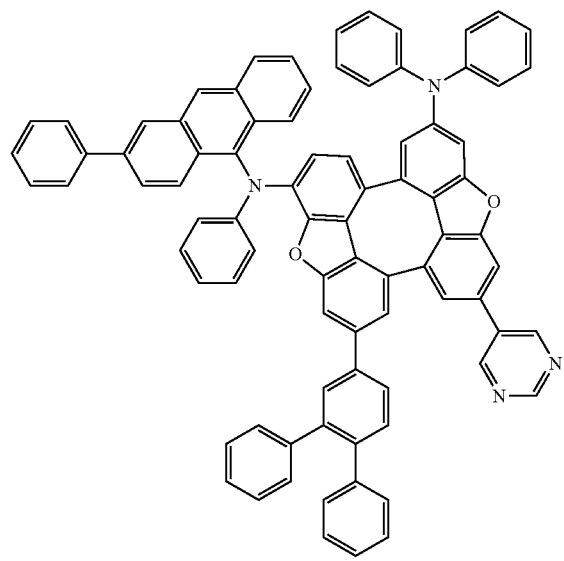

281
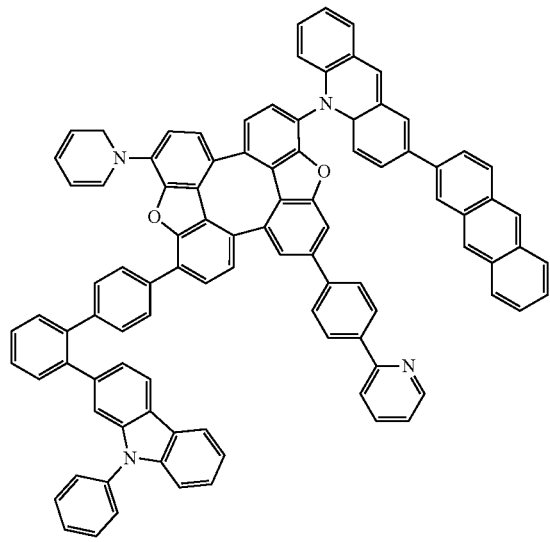
282
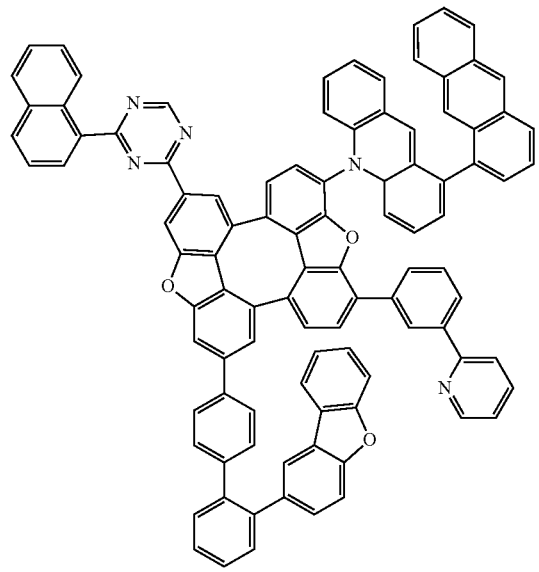
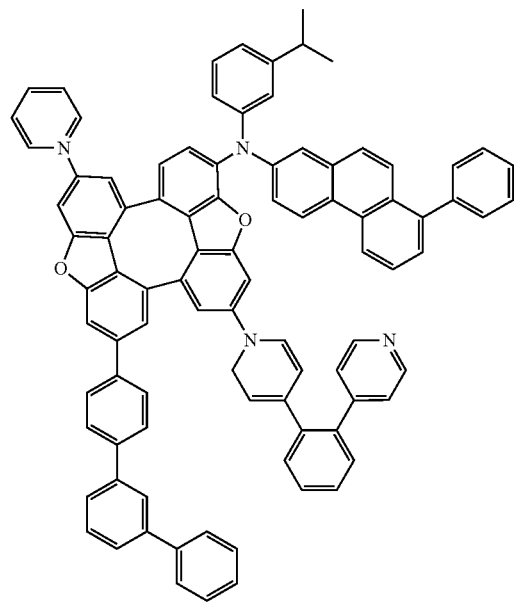
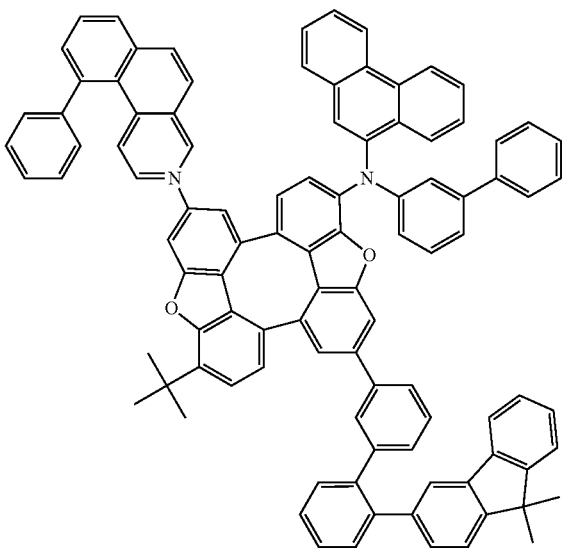

-continued
91
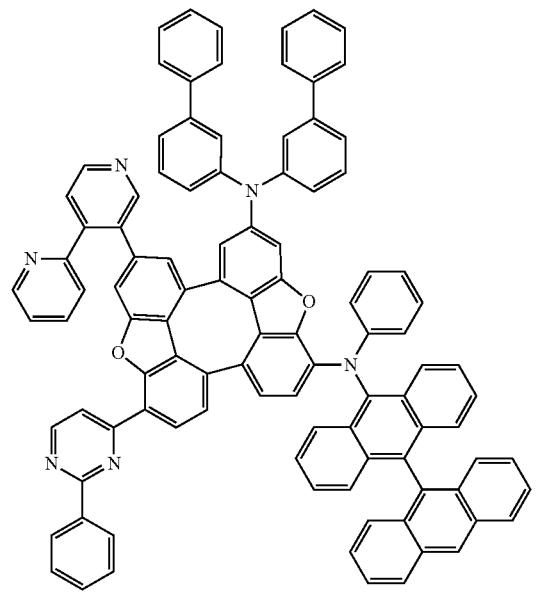
92
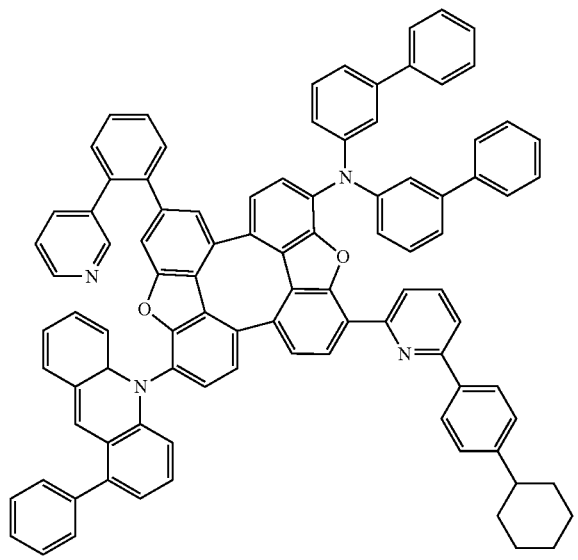
93
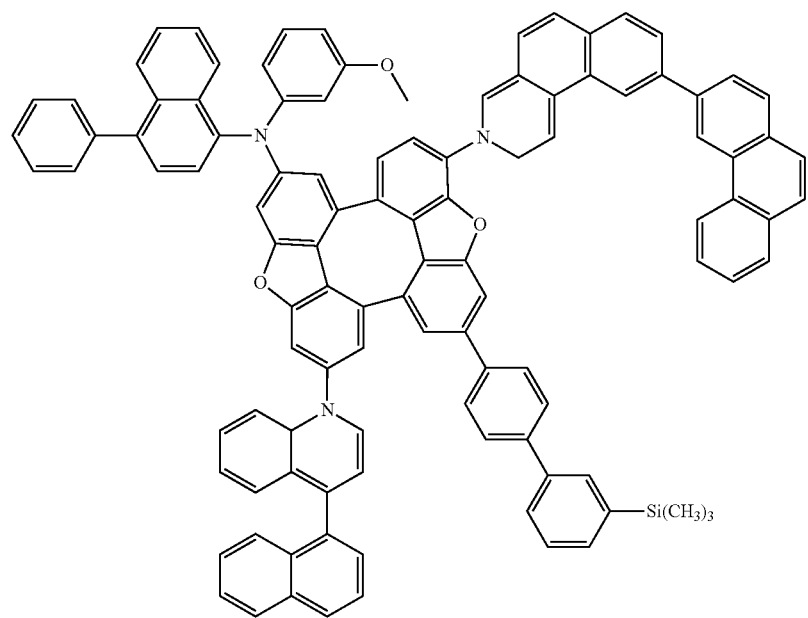

-continued
94
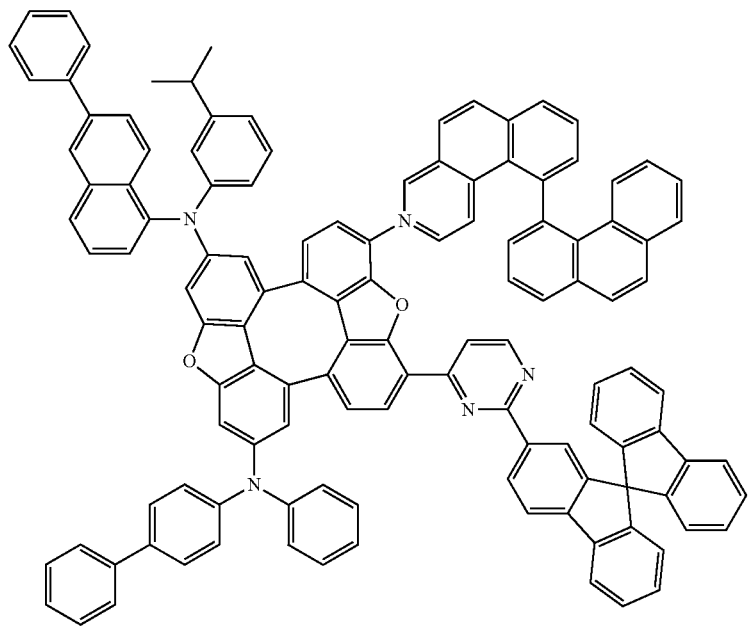
95
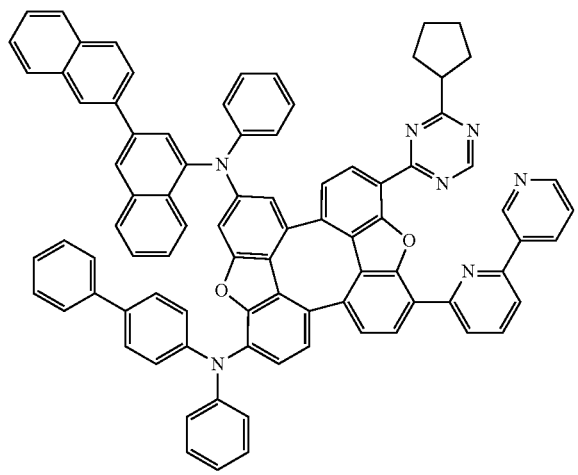
96
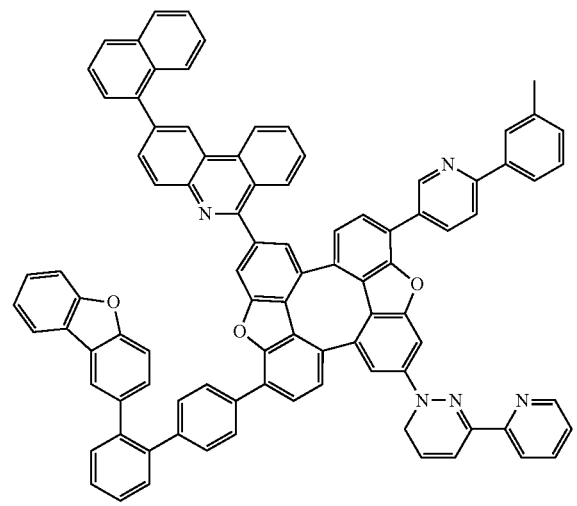

97
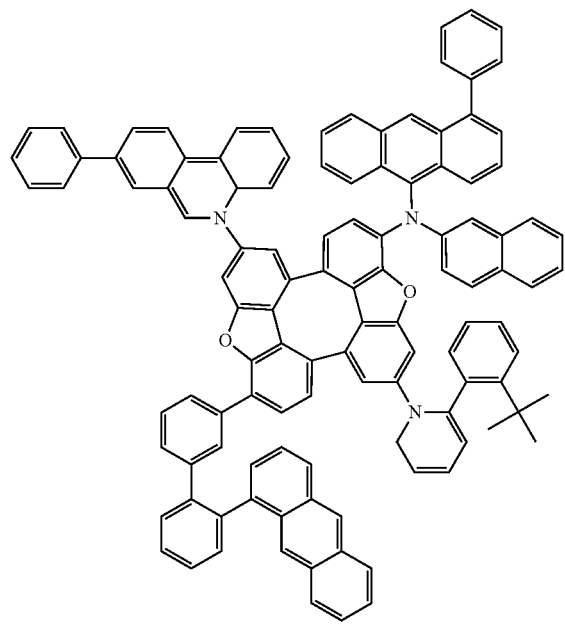
98
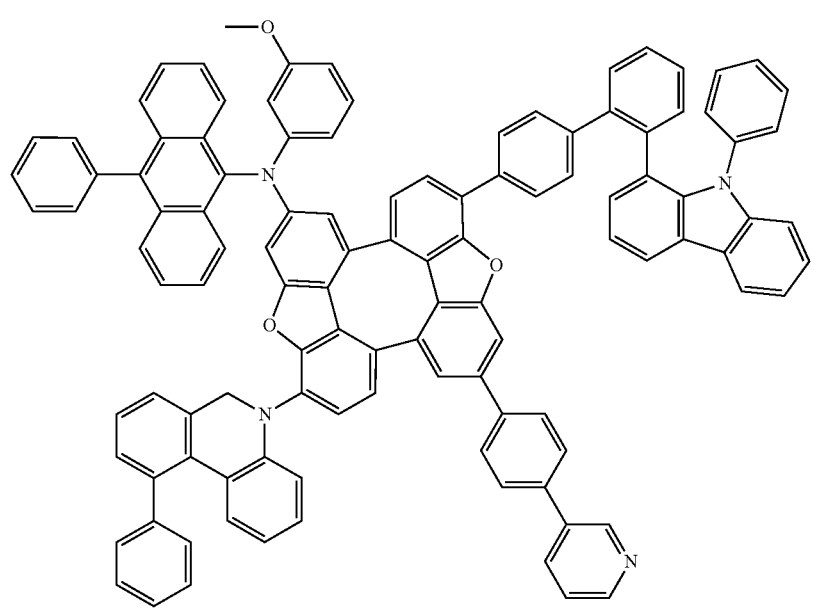

289 290
-continued
99
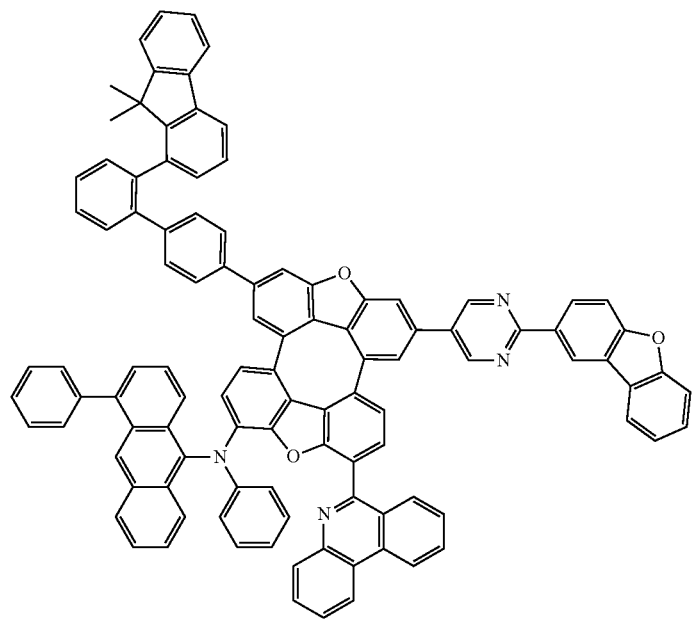
100
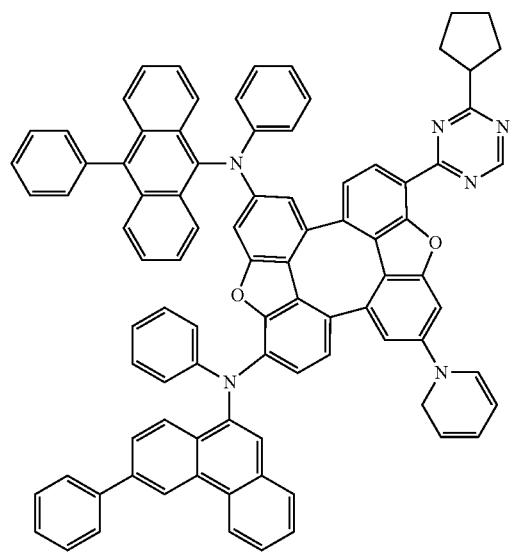
101
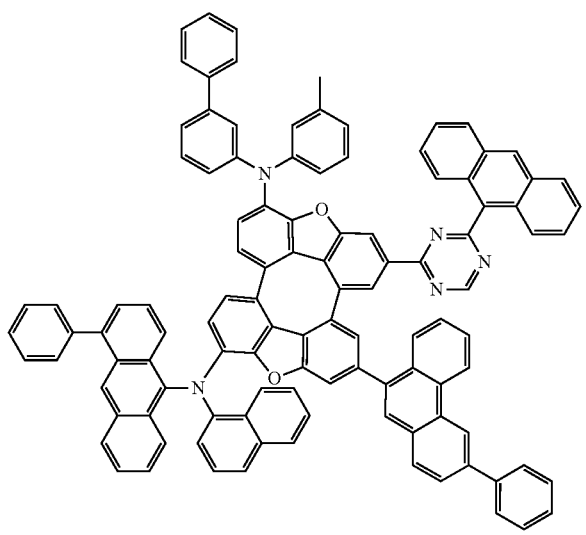

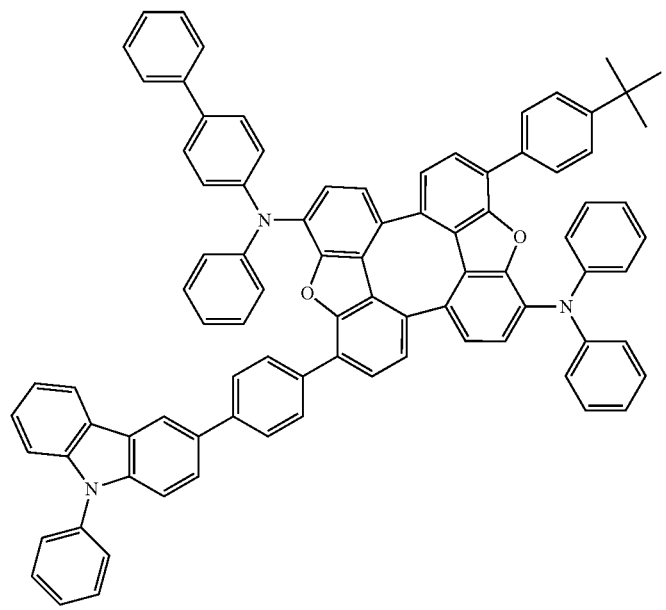
102
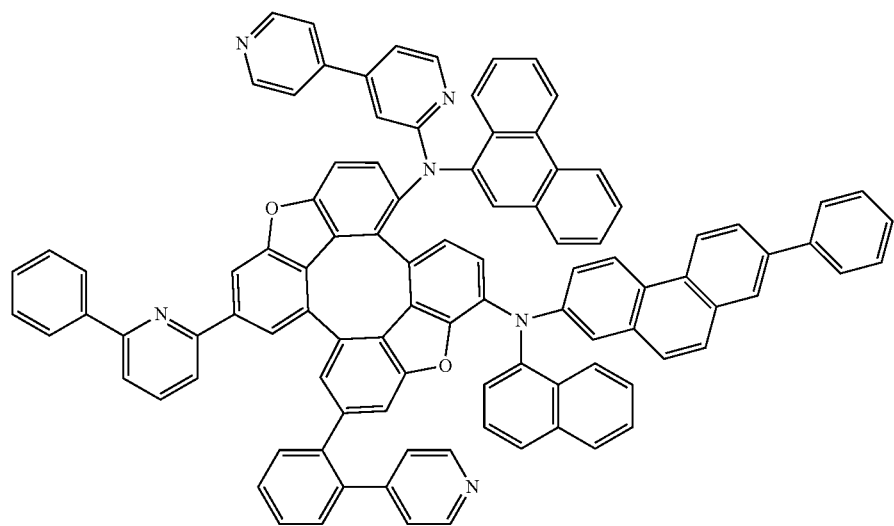
103

-continued
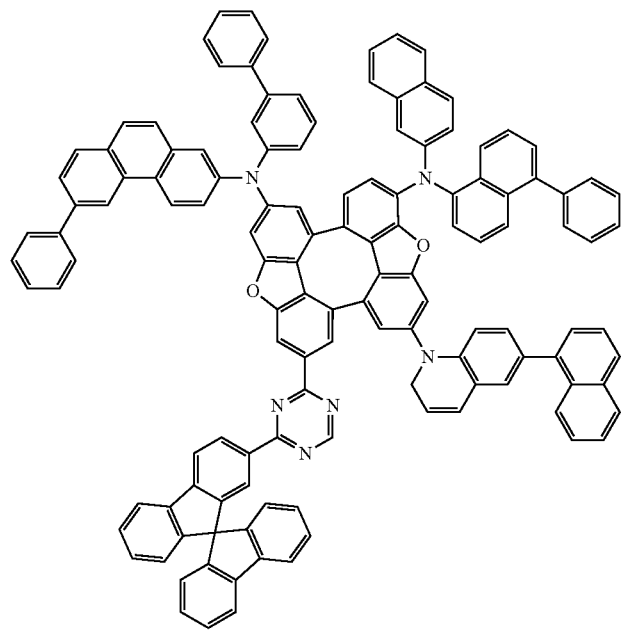
104
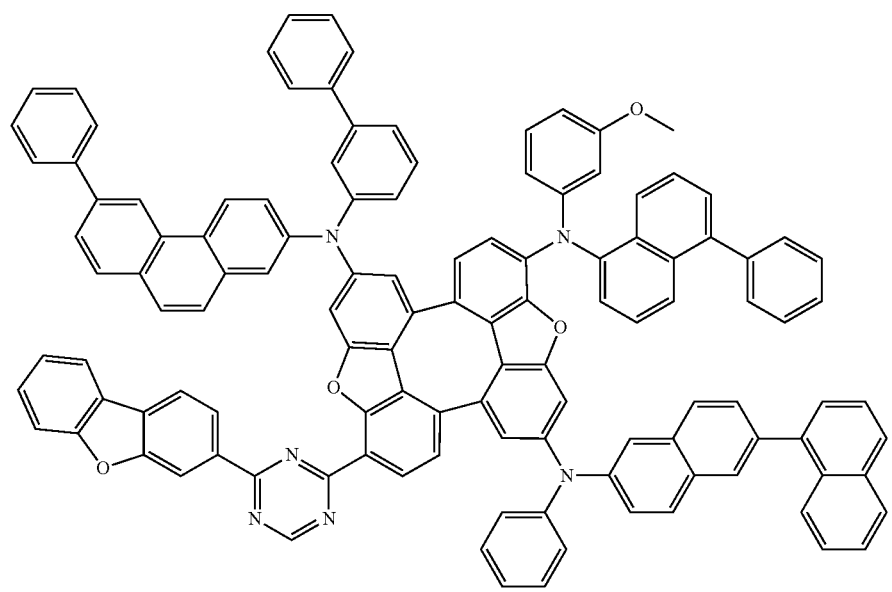
105

-continued
106
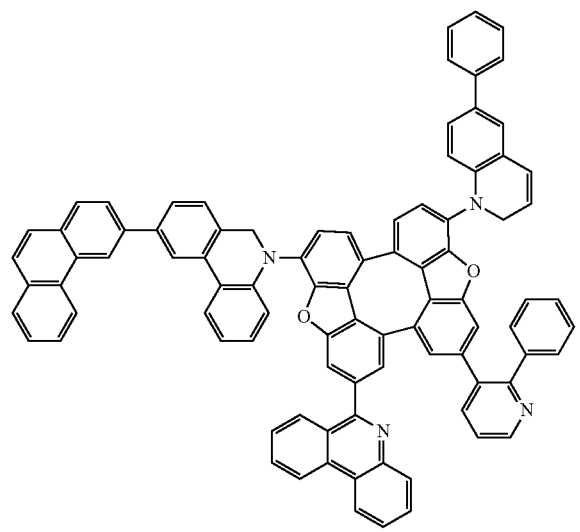
107
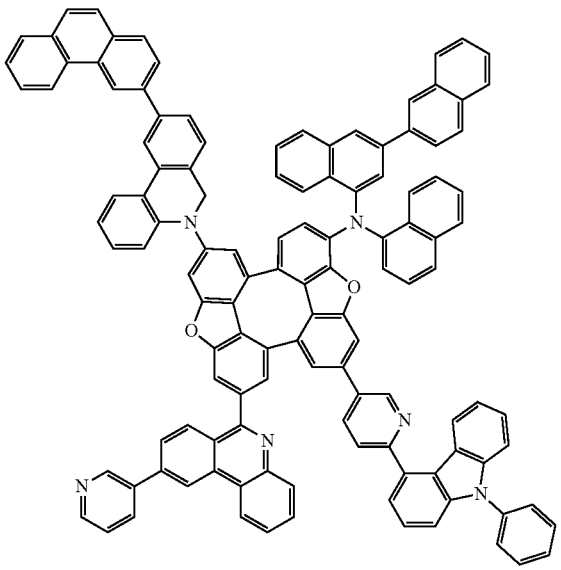
108
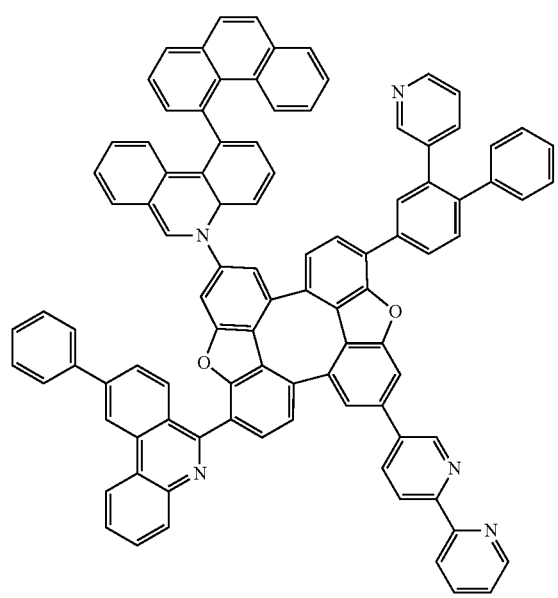
109
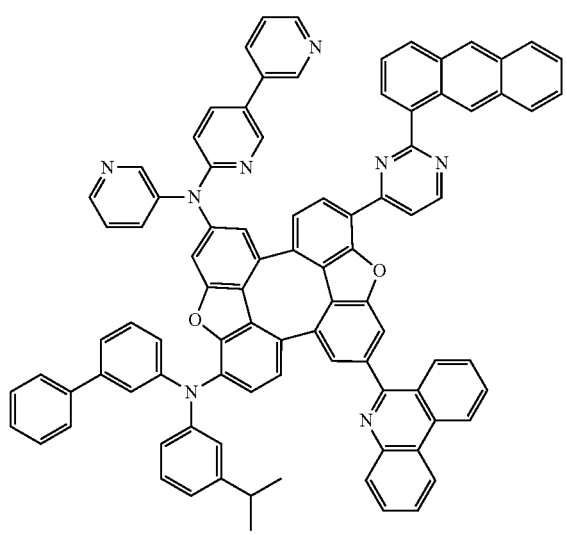

-continued
297
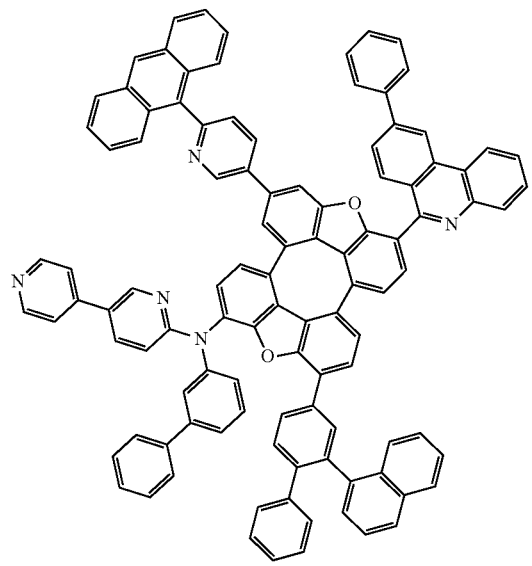
298
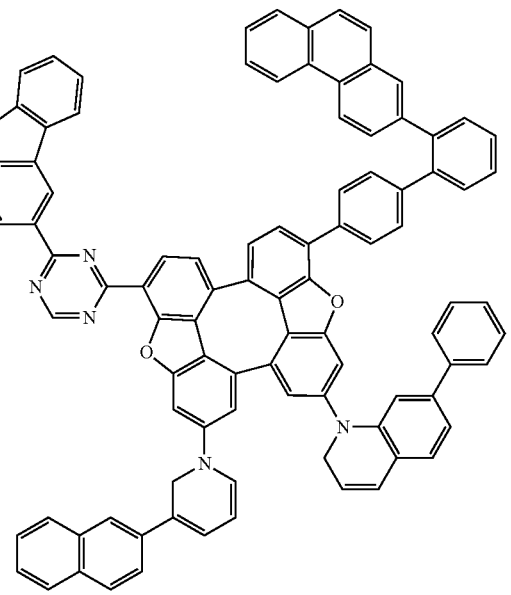
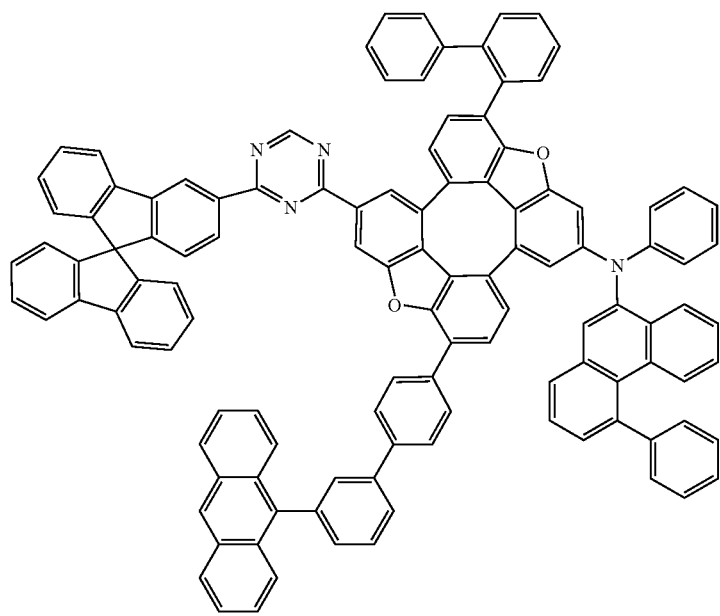

-continued
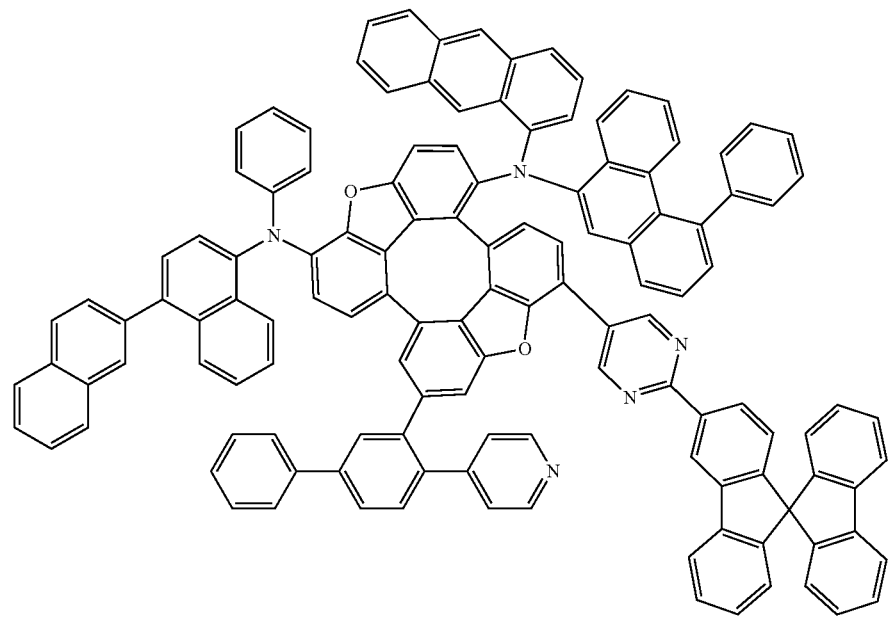
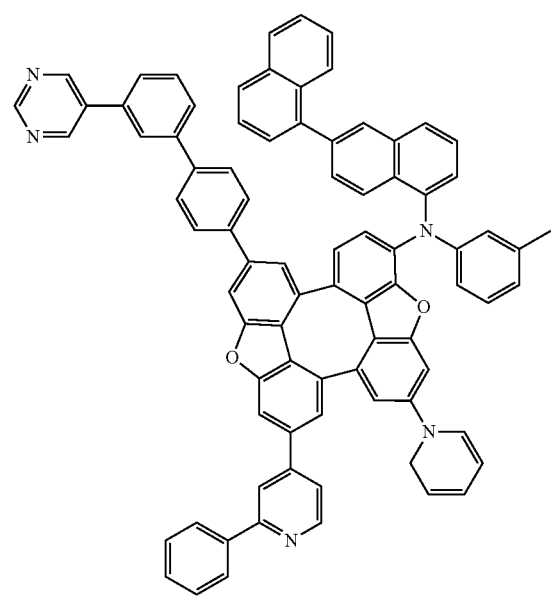

116
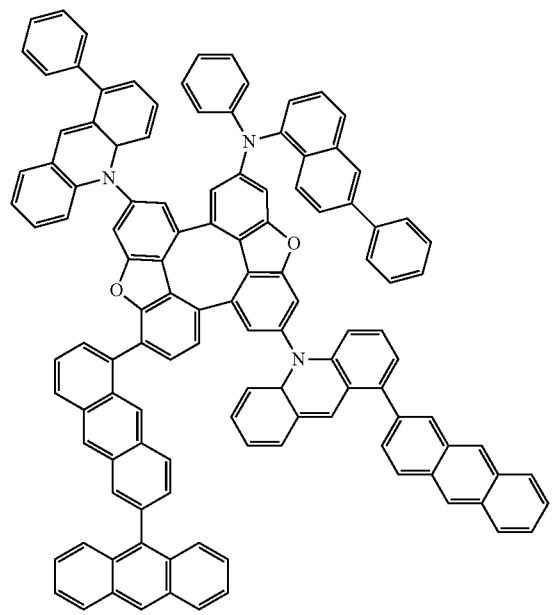
117
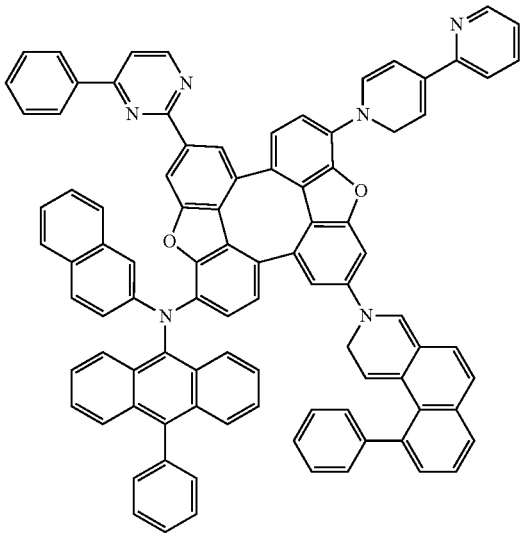
118
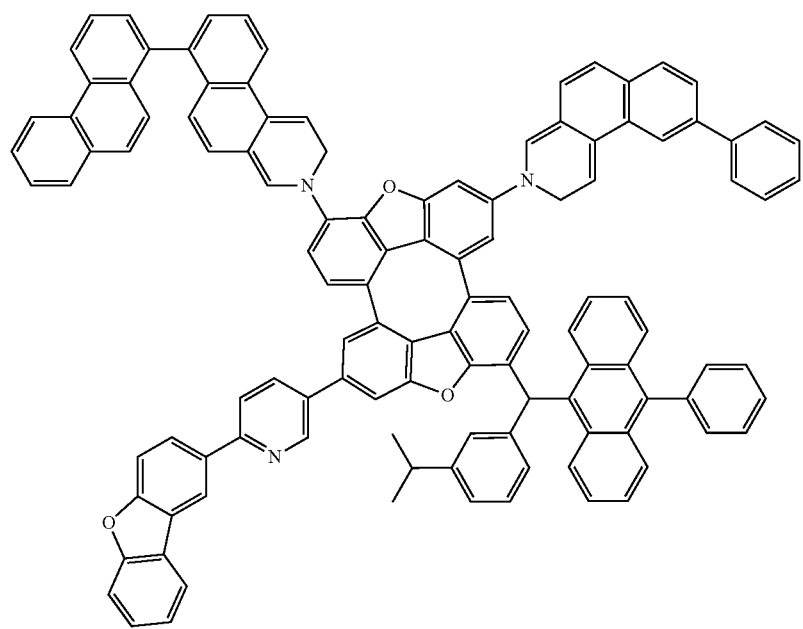

-continued
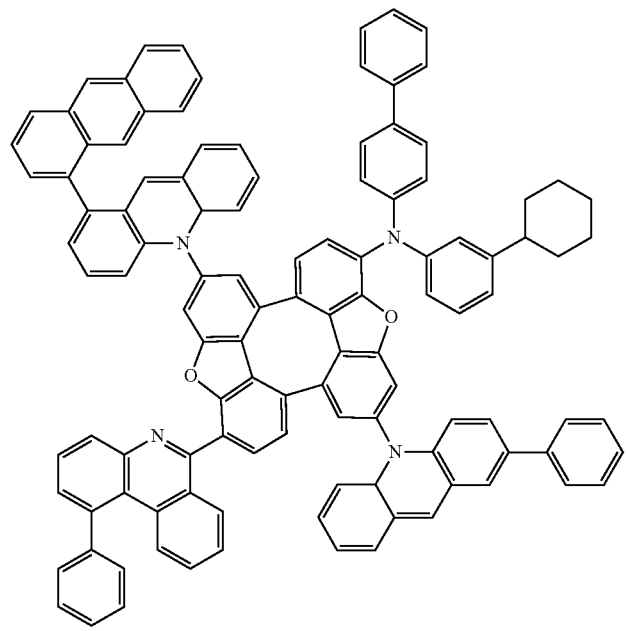
119
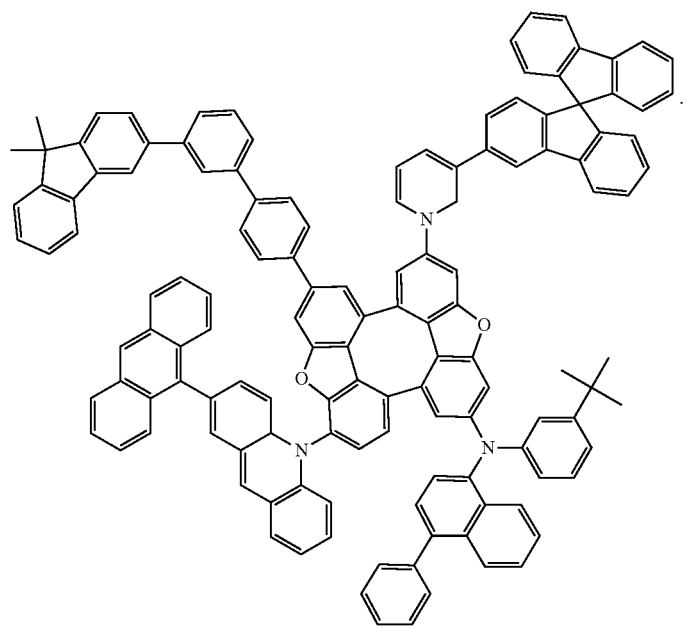
120
* * * * *